US009670286B2

(12) United States Patent
Chang et al.

(10) Patent No.: US 9,670,286 B2
(45) Date of Patent: *Jun. 6, 2017

(54) DISEASE THERAPY BY INDUCING IMMUNE RESPONSE TO TROP-2 EXPRESSING CELLS

(71) Applicant: IBC Pharmaceuticals, Inc., Morris Plains, NJ (US)

(72) Inventors: Chien-Hsing Chang, Downingtown, PA (US); David M. Goldenberg, Mendham, NJ (US); Edmund A. Rossi, Woodland Park, NJ (US); Diane Rossi, Woodland Park, NJ (US)

(73) Assignee: IBC Pharmaceuticals, Inc., Morris Plains, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/169,903

(22) Filed: Jun. 1, 2016

(65) Prior Publication Data

US 2016/0264678 A1 Sep. 15, 2016

Related U.S. Application Data

(60) Division of application No. 14/600,560, filed on Jan. 20, 2015, now Pat. No. 9,382,329, which is a continuation-in-part of application No. 14/106,737, filed on Dec. 14, 2013, which is a continuation-in-part of application No. 13/966,450, filed on Aug. 14, 2013, now Pat. No. 9,315,567.

(60) Provisional application No. 61/942,752, filed on Feb. 21, 2014, provisional application No. 62/049,826, filed on Sep. 12, 2014, provisional application No. 61/807,998, filed on Apr. 3, 2013, provisional application No. 61/733,268, filed on Dec. 4, 2012, provisional application No. 61/682,965, filed on Aug. 14, 2012.

(51) Int. Cl.

| C07K 16/28 | (2006.01) |
|---|---|
| C07K 16/30 | (2006.01) |
| A61K 38/21 | (2006.01) |
| A61K 47/48 | (2006.01) |
| A61K 39/395 | (2006.01) |
| A61K 31/4745 | (2006.01) |
| A61K 45/06 | (2006.01) |
| C07K 16/44 | (2006.01) |
| A61K 39/00 | (2006.01) |

(52) U.S. Cl.
CPC .......... *C07K 16/30* (2013.01); *A61K 31/4745* (2013.01); *A61K 38/21* (2013.01); *A61K 38/212* (2013.01); *A61K 39/3955* (2013.01); *A61K 39/39558* (2013.01); *A61K 45/06* (2013.01); *A61K 47/486* (2013.01); *A61K 47/48215* (2013.01); *A61K 47/48384* (2013.01); *A61K 47/48569* (2013.01); *A61K 47/48592* (2013.01); *A61K 47/48615* (2013.01); *C07K 16/2803* (2013.01); *C07K 16/2809* (2013.01); *C07K 16/2833* (2013.01); *C07K 16/2863* (2013.01); *C07K 16/2887* (2013.01); *C07K 16/3007* (2013.01); *C07K 16/44* (2013.01); *A61K 2039/505* (2013.01); *A61K 2039/507* (2013.01); *C07K 2317/24* (2013.01); *C07K 2317/31* (2013.01); *C07K 2317/54* (2013.01); *C07K 2317/55* (2013.01); *C07K 2317/622* (2013.01); *C07K 2317/73* (2013.01); *C07K 2317/77* (2013.01)

(58) Field of Classification Search
None
See application file for complete search history.

(56) References Cited

U.S. PATENT DOCUMENTS

| 4,046,722 A | 9/1977 | Rowland |
|---|---|---|
| 4,359,457 A | 11/1982 | Neville et al. |

(Continued)

FOREIGN PATENT DOCUMENTS

| DE | 10034607 | 2/2002 |
|---|---|---|
| EP | 0253202 | 1/1988 |

(Continued)

OTHER PUBLICATIONS

Abbas et al., Cellular and Molecular Immunology, W.B. Saunders Comp. 1991, p. 43.
Alto et al., "Bioinformatic design of A-kinase anchoring protein-in silico: a potent and selective peptide antagonist of type II protein kinase A anchoring" Proc. Natl. Acad. Sci USA Apr. 15, 2003; 100(8):4445-50.
Backer et al., "Self-Assembled "Dock and Lock" System for Linking Payloads to Targeting Proteins" Bioconjugate Chem., 2006, 17(4):912-919.

(Continued)

*Primary Examiner* — Karen Canella
(74) *Attorney, Agent, or Firm* — Richard A. Nakashima

(57) ABSTRACT

The present invention concerns compositions and methods of use of bispecific antibodies comprising at least one binding site for Trop-2 (EGP-1) and at least one binding site for CD3. The bispecific antibodies are of use for inducing an immune response against a Trop-2 expressing tumor, such as carcinoma of the esophagus, pancreas, lung, stomach, colon, rectum, urinary bladder, breast, ovary, uterus, kidney or prostate. The methods may comprising administering the bispecific antibody alone, or with one or more therapeutic agents such as antibody-drug conjugates, interferons (preferably interferon-α), and/or checkpoint inhibitor antibodies. The bispecific antibody is capable of targeting effector T cells, NK cells, monocytes or neutrophils to induce leukocyte-mediated cytotoxicity of Trop-2$^+$ cancer cells. The cytotoxic immune response is enhanced by co-administration of interferon, checkpoint inhibitor antibody and/or ADC.

14 Claims, 36 Drawing Sheets

(56) References Cited

U.S. PATENT DOCUMENTS

| | | | |
|---|---|---|---|
| 4,699,784 A | 10/1987 | Shih et al. |
| 4,868,109 A | 9/1989 | Lansdorp et al. |
| 4,935,498 A | 6/1990 | Sessler et al. |
| 5,112,954 A | 5/1992 | Abrams et al. |
| 5,122,368 A | 6/1992 | Greenfield et al. |
| 5,185,254 A | 2/1993 | Linnenbach |
| 5,530,101 A | 6/1996 | Queen et al. |
| 5,693,762 A | 12/1997 | Queen et al. |
| 5,708,146 A | 1/1998 | Willner et al. |
| 5,770,198 A | 6/1998 | Coller et al. |
| 5,776,427 A | 7/1998 | Thorpe et al. |
| 5,824,701 A | 10/1998 | Greenwald et al. |
| 5,859,205 A | 1/1999 | Adair et al. |
| 5,871,945 A | 2/1999 | Lockerbie et al. |
| 6,017,514 A | 1/2000 | Epstein et al. |
| 6,120,995 A | 9/2000 | Waldman et al. |
| 6,156,754 A | 12/2000 | Lerchen et al. |
| 6,176,842 B1 | 1/2001 | Tachibana et al. |
| 6,180,377 B1 | 1/2001 | Morgan et al. |
| 6,214,345 B1 | 4/2001 | Firestone et al. |
| 6,261,537 B1 | 7/2001 | Klaveness et al. |
| 6,306,393 B1 | 10/2001 | Goldenberg et al. |
| 6,342,219 B1 | 1/2002 | Thorpe et al. |
| 6,524,854 B1 | 2/2003 | Monia et al. |
| 6,558,669 B1 | 5/2003 | Govindan et al. |
| 6,632,926 B1 | 10/2003 | Chen et al. |
| 6,653,104 B2 | 11/2003 | Goldenberg et al. |
| 6,716,821 B2 | 4/2004 | Zhao et al. |
| 6,962,702 B2 | 11/2005 | Hansen et al. |
| 6,989,140 B2 | 1/2006 | Tidmarsh et al. |
| 7,060,506 B2 | 6/2006 | Craig |
| 7,115,261 B1 | 10/2006 | Lode et al. |
| 7,122,636 B1 | 10/2006 | Hsei et al. |
| 7,238,785 B2 | 7/2007 | Govindan et al. |
| 7,288,249 B2 | 10/2007 | Carter et al. |
| 7,312,318 B2 | 12/2007 | Hansen et al. |
| 7,387,772 B1 | 6/2008 | Hansen et al. |
| 7,521,056 B2 | 4/2009 | Chang et al. |
| 7,527,787 B2 | 5/2009 | Chang et al. |
| 7,534,866 B2 | 5/2009 | Chang et al. |
| 7,550,143 B2 | 6/2009 | Chang et al. |
| 7,585,491 B2 | 9/2009 | Govindan et al. |
| 7,591,994 B2 | 9/2009 | Govindan et al. |
| 7,666,400 B2 | 2/2010 | Chang et al. |
| 7,858,070 B2 | 12/2010 | Chang et al. |
| 7,871,622 B2 | 1/2011 | Chang et al. |
| 7,901,680 B2 | 3/2011 | Chang et al. |
| 7,906,121 B2 | 3/2011 | Chang et al. |
| 7,981,398 B2 | 7/2011 | Chang et al. |
| 7,999,083 B2 | 8/2011 | Govindan et al. |
| 8,003,111 B2 | 8/2011 | Chang et al. |
| 8,034,352 B2 | 10/2011 | Chang et al. |
| 8,080,250 B1 | 12/2011 | Govindan et al. |
| 8,119,101 B2 | 2/2012 | Byrd et al. |
| 8,158,129 B2 | 4/2012 | Chang et al. |
| 8,163,291 B2 | 4/2012 | Chang et al. |
| 8,211,440 B2 | 7/2012 | Chang et al. |
| 8,246,960 B2 | 8/2012 | Chang et al. |
| 8,268,317 B2 | 9/2012 | Govindan et al. |
| 8,268,319 B2 | 9/2012 | Govindan et al. |
| 8,277,817 B2 | 10/2012 | Chang et al. |
| 8,282,934 B2 | 10/2012 | Chang et al. |
| 8,349,332 B2 | 1/2013 | Chang et al. |
| 8,420,086 B2 | 4/2013 | Govindan et al. |
| 8,425,912 B2 | 4/2013 | Govindan et al. |
| 8,435,540 B2 | 5/2013 | Chang et al. |
| 8,475,794 B2 | 7/2013 | Chang et al. |
| 8,481,041 B2 | 7/2013 | Chang et al. |
| 8,491,914 B2 | 7/2013 | Chang et al. |
| 8,551,480 B2 | 10/2013 | Chang et al. |
| 8,562,988 B2 | 10/2013 | Chang et al. |
| 8,597,659 B2 | 12/2013 | Chang et al. |
| 8,617,558 B2 | 12/2013 | Govindan et al. |
| 8,741,300 B2 | 6/2014 | Govindan et al. |
| 8,759,496 B2 | 6/2014 | Govindan et al. |
| 8,834,886 B2 | 9/2014 | Govindan et al. |
| 8,877,202 B2 | 11/2014 | Govindan et al. |
| 8,877,901 B2 | 11/2014 | Govindan et al. |
| 2001/0034363 A1 | 10/2001 | Li et al. |
| 2002/0041847 A1 | 4/2002 | Goldenberg et al. |
| 2003/0096249 A1 | 5/2003 | Westphal et al. |
| 2003/0133972 A1 | 7/2003 | Danthi et al. |
| 2003/0162709 A1 | 8/2003 | Rossi et al. |
| 2003/0198595 A1 | 10/2003 | Goldenberg et al. |
| 2003/0198956 A1 | 10/2003 | Makowski et al. |
| 2003/0232420 A1 | 12/2003 | Braun et al. |
| 2004/0001825 A1 | 1/2004 | Govindan et al. |
| 2004/0018587 A1 | 1/2004 | Makowski et al. |
| 2004/0126361 A1 | 7/2004 | Saifer et al. |
| 2005/0002945 A1 | 1/2005 | McBride et al. |
| 2005/0003403 A1 | 1/2005 | Rossi et al. |
| 2005/0048588 A1* | 3/2005 | Calenoff ............... A61K 38/02 435/7.23 |
| 2005/0053606 A1 | 3/2005 | Kufe et al. |
| 2005/0220758 A1 | 10/2005 | Zobel et al. |
| 2006/0142506 A1 | 6/2006 | Breitenkamp et al. |
| 2006/0193865 A1 | 8/2006 | Govindan et al. |
| 2006/0210475 A1 | 9/2006 | Goldenberg et al. |
| 2007/0086942 A1 | 4/2007 | Chang et al. |
| 2007/0212350 A1 | 9/2007 | Govindan et al. |
| 2007/0264265 A1 | 11/2007 | Goldenberg et al. |
| 2007/0274998 A1 | 11/2007 | Utku |
| 2008/0166363 A1 | 7/2008 | Govindan et al. |
| 2008/0213256 A1 | 9/2008 | Kufer et al. |
| 2009/0111143 A1 | 4/2009 | Goldenberg et al. |
| 2010/0303827 A1 | 12/2010 | Sharma et al. |
| 2011/0020273 A1 | 1/2011 | Chang et al. |
| 2011/0064754 A1 | 3/2011 | Taylor et al. |
| 2011/0070156 A1 | 3/2011 | Govindan et al. |
| 2011/0143417 A1 | 6/2011 | Chang et al. |
| 2011/0158905 A1 | 6/2011 | Goldenberg et al. |
| 2011/0160159 A1 | 6/2011 | Ryan |
| 2011/0165161 A1 | 7/2011 | Lin et al. |
| 2011/0189083 A1 | 8/2011 | Chang et al. |
| 2011/0305631 A1 | 12/2011 | Govindan et al. |
| 2012/0082617 A1 | 4/2012 | Govindan et al. |
| 2012/0093769 A1 | 4/2012 | Chang et al. |
| 2012/0196346 A1 | 8/2012 | Chang et al. |
| 2012/0276100 A1 | 11/2012 | Chang et al. |
| 2012/0276608 A1 | 11/2012 | Chang et al. |
| 2012/0328564 A1 | 12/2012 | Govindan et al. |
| 2013/0078183 A1 | 3/2013 | Chang et al. |
| 2013/0090458 A1 | 4/2013 | Govindan et al. |
| 2013/0109073 A1 | 5/2013 | Chang et al. |
| 2013/0164816 A1 | 6/2013 | Chang et al. |
| 2013/0177526 A1 | 7/2013 | Govindan et al. |
| 2013/0177532 A1 | 7/2013 | Chang et al. |
| 2013/0216561 A1 | 8/2013 | Govindan et al. |
| 2013/0217091 A1 | 8/2013 | Chang et al. |
| 2013/0295005 A1 | 11/2013 | Chang et al. |
| 2014/0004078 A1 | 1/2014 | Govindan et al. |
| 2014/0050660 A1 | 2/2014 | Chang et al. |
| 2014/0058067 A1 | 2/2014 | Govindan et al. |
| 2014/0170063 A1 | 6/2014 | Govindan et al. |
| 2014/0219914 A1 | 8/2014 | Govindan et al. |
| 2014/0227180 A1 | 8/2014 | Govindan et al. |
| 2014/0286860 A1 | 9/2014 | Govindan et al. |

FOREIGN PATENT DOCUMENTS

| | | | |
|---|---|---|---|
| EP | 0306943 | 3/1989 | |
| WO | 98/12227 | 3/1998 | |
| WO | 98/42378 | 10/1998 | |
| WO | 99/54440 | 10/1999 | |
| WO | 00/68248 | 11/2000 | |
| WO | 00/69914 | 11/2000 | |
| WO | 0076551 | 12/2000 | |
| WO | 0124763 | 4/2001 | |
| WO | WO03070234 | * 8/2003 | ............ A61K 31/13 |
| WO | 03106495 | 12/2003 | |
| WO | 2004054622 | 7/2004 | |
| WO | 2006/107617 | 10/2006 | |
| WO | 2006/107786 | 10/2006 | |
| WO | 2007/046893 | 4/2007 | |

(56) References Cited

FOREIGN PATENT DOCUMENTS

| WO | 2007/075270 | 7/2007 |
|---|---|---|
| WO | 2007112193 A1 | 10/2007 |
| WO | 2007123995 | 11/2007 |
| WO | 2009000194 | 8/2009 |
| WO | 2010093395 | 8/2010 |
| WO | 2011/025904 | 3/2011 |
| WO | 2014092804 | 6/2014 |

OTHER PUBLICATIONS

Baillie et al., "Compartmentalisation of phospodiesterases and protein kinase A: opposites attract" FEBS Letters 2005; 579:3264-3270.
Banky et al., "Dimerization/Docking Domain of the Type Iα Regulatory Subunit of cAMP-dependent Protein Kinase" J. Biol. Chem. 273:35048-55, 1998.
Basu et al., "Structure-Function Engineering of Interferon-β-1b for Improving Stability, Solubility, Potency, Immunogenicity, and Pharmacokinetic Properties by Site-Selective Mono-PEGylation" Bioconjugate Chem. 2006; 17:618-630.
Belardelli et al., "Interferon-alpha in tumor immunity and immunotherapy" Cytokine Growth Factor Rev. 13(2):119-134 (2002).
Belardelli et al., "International Meeting on Cancer Vaccines: How Can We Enhance Efficacy of Therapeutic Vaccines?" Cancer Res. 64:6827-6830 (2004).
Belardelli et al., "The neglected role of type I interferon in the T-cell response: implications for its clinical use" Immunol. Today 17(8):369-72 (1996).
Biron et al., "Natural killer cells in antiviral defense: function and regulation by innate cytokines" Annu. Rev. Immunol. 17:189-220 (1999).
Brunda et al., "Modulation of Murine Natural Killer Cell Activity in Vitro and in Vivo by Recombinant Human Interferons" Cancer Res. 44:597-601 (1984).
Burns-Hamuro et al., "Distinct interaction modes of an AKAP bound to two regulatory subunit isoforms of protein kinase A revealed by amide hydrogen/deuterium exchange" Protein Science (2005), 14:2982-2992.
Carr et al., "Interaction of the Regulatory Subunit (RII) of cAMP-dependent Protein Kinase with RII-anchoring Proteins Occurs through an Amphipathic Helix Binding Motif" J. Biol. Chem. 266:14188-92 (1991).
Carr et al., "Identification of Sperm-specific Proteins That Interact with A-kinase Anchoring Proteins in a Manner Similar to the Type II Regulatory Subunit of PKA" J. Biol. Chem. 276(20):17332-17338 (2001).
Carrero et al., "Lymphocytes are detrimental during the early innate immune response against *Listeria monocytogenes*" J. Exp. Med. 203(4):933-940 (2006).
Chang et al., "The Dock and Lock Method: A Novel Platform Technology for Building Multivalent, Multifunctional Structures of Defined Composition with Retained Bioactivity" Clin. Cancer Res. Sep. 15, 2007;13(18 Suppl), pp. 5586-5591.
Chmura et al., "Antibodies with infinite affinity" Proc. Natl. Acad. Sci. USA 98(15):8480-8484 (2001).
Colledge et al., "AKAPs: from structure to function" Trends Cell Biol. 6:216-21 (1999).
Corbin et al., "Regulation of Adenosine 3',5'-Monophosphate-dependent Protein Kinase" J. Biol. Chem. 248:1813-21 (1973).
Dhalluin et al., "Structural and Biophysical Characterization of the 40 kDa PEG-Interferon-α2a and Its Individual Positional Isomers" Bioconjugate Chem. 2005;16:504-517.
Dodart et al., "Immunotherapy for Alzheimer's Disease: will vaccination work?" Trends Mol. Med. 9(3):85-87 (2003).
Doherty et al., "Site-Specific PEGylation of Engineered Cysteine Analogues of Recombinant Human Granulocyte-Macrophage Colony-Stimulating Factor" Bioconjugate Chem. 2005;16:1291-1298.

Ferrantini et al., "IFN-α1 Gene Expression into a Metastatic Murine Adenocarcinoma (TS/A) Results in CD8+ T Cell-Mediated Tumor Rejection and Development of Antitumor Immunity" J. Immunol. 153:4604-15 (1994).
Ferrantini et al., "Interferon-α and cancer: Mechanisms of action and new perspectives of clinical use" Biochimie 89: 884-893 (2007).
Foser et al., "Improved biological and transcriptional activity of monopegylated interferon-α-2a isomers" The Pharmacogenomics J 3:312-319 (2003).
Gillies et al., "High-level expression of chimeric antibodies using adapted cDNA variable region cassettes" J. Immunol. Methods 125 (1989) 191-202.
Glennie et al., "Mechanisms of killing by anti-CD20 monoclonal antibodies" Mol. Immunol. 44:3823-3837 (2007).
Gold et al., "A Novel Bispecific, Trivalent Antibody Construct for Targeting Pancreatic Carcinoma", Cancer Res. 68:4819-26, 2008.
Gold et al., "Molecular Basis of AKAP Specificity for PKA Regulatory Subunits" Mol. Cell Nov. 3, 2006;24(3):383-95.
Goldenberg et al., "Multifunctional Antibodies by the Dock-and-Lock Method for Improved Cancer Imaging and Therapy by Pretargeting" J. Nucl. Med. 49:158-63, 2008.
Goldenberg et al., "Properties and structure-function relationships of veltuzumab (hA20), a humanized anti-CD20 monoclonal antibody" Blood 113:1062-70 (2009).
Goodson et al., "Site-Directed PEGylation of Recombinant Interleukin-2 at its Glycosylation Site" Nat. Biotechnology Apr. 1990;8(4):343-6.
Grace et al., "Site of Pegylation and Polyethylene Glycol Molecule Size Attenuate Interferon-α Antiviral and Antiproliferative Activities through the JAK/STAT Signaling Pathway" J. Biol. Chem. 2005;280(8):6327-6336.
Grimley et al., "Prolonged STAT1 Activation Related to the Growth Arrest of Malignant Lymphoma Cells by Interferon-α" Blood 91(8):3017-27 (1998).
Gutterman et al., "Leukocyte Interferon-Induced Tumor Regression in Human Metastatic Breast Cancer, Multiple Myeloma, and Malignant Lymphoma" Ann. Intern. Med. 93(3):399-406 (1980).
Gutterman et al., "Cytokine therapeutics: Lessons from interferon α" Proc. Natl. Acad. Sci. USA 91:1198-205 (1994).
Harris et al., "Effect of pegylation on pharmaceuticals" Nat. Rev. Drug. Discov. 2:214-221 (2003).
Hausken et al. "Mutational Analysis of the A-Kinase Anchoring Protein (AKAP)-binding Site on RII" J. Biol. Chem. 271:29016-22 (1996).
Hodneland et al., Selective immobilization of proteins to self-assembled monolayers presenting active site-directed capture ligands, Proc. Natl. Acad. Sci. USA 2002; 99:5048-5052.
Huang et al., "Targeting IFN-α to B Cell Lymphoma by a Tumor-Specific Antibody Elicits Potent Antitumor Activities" J. Immunol. 179:6881-88 (2007).
Hundsrucker et al., "High-affinity AKAP7δ-protein kinase A interaction yields novel protein kinase A-anchoring disruptor peptides" Biochem. J. (2006) 396, 297-306.
Kimby et al., "Long-term molecular remissions in patients with indolent lymphoma treated with rituximab as a single agent or in combination with interferon alpha-2a: A randomized phase II study from the Nordic Lymphoma Group" Leuk. Lymphoma 49(1):102-112 (2008).
Kinderman et al., "A Dynamic Mechanism for AKAP Binding to RII Isoforms of cAMP-Dependent Protein Kinase" Mol. Cell 24(3):397-408 (2006).
Kinstler et al., "Characterization and Stability of N-terminally PEGylated rhG-CSF" Pharm. Res. 1996;13(7):996-1002.
Kramer et al., "Cell and virus sensitivity studies with recombinant human alpha interferons" J. Interferon. Res. 3(4):425-35 (1983).
Le Bon et al., "Type I Interferons Potently Enhance Humoral Immunity and Can Promote Isotype Switching by Stimulating Dendritic Cells in Vivo" Immunity 14:461-470 (2001).
Lee et al., "Solid-Phase PEGylation of Recombinant Interferon α-2a for Site-Specific Modification: Process Performance, Characterization, and in Vitro Bioactivity" Bioconjugate Chem. 2007; 18:1728-34.

(56) References Cited

OTHER PUBLICATIONS

Lohmann et al., "High-affinity binding of the regulatory subunit (RII) of cAMP-dependent protein kinase to microtubule-associated and other cellular proteins" Proc. Natl. Acad. Sci. USA 81:6723-27 (1984).
Luft et al., "Type I IFNs Enhance the Terminal Differentiation of Dendritic Cells" J. Immunol. 161:1947-1953 (1998).
Mason, Anthony J., "Functional Analysis of the Cysteine Residues of Activin A" Mol. Endocrinol. 8:325-32 (1994).
Allard et al., "Targeting CD73 enhances the antitumor activity of anti-PD-1 and anti-CTLA-4 mAbs", Clin Cancer Res. Oct. 15, 2013;19(20):5626-35.
Amann et al., "Antitumor activity of an EpCAM/CD3-bispecific BiTE antibody during long-term treatment of mice in the absence of T-cell anergy and sustained cytokine release", J Immunother. Jun. 2009;32(5):452-64.
Baeuerle et al., "Bispecific T-cell engaging antibodies for cancer therapy", Cancer Res. Jun. 15, 2009;69(12):4941-4.
Bargou et al., "Tumor regression in cancer patients by very low doses of a T cell-engaging antibody", Science. Aug. 15, 2008;321(5891):974-7.
Bassan et al., "Toward victory in adult ALL: blinatumomab joins in", Blood. Dec. 20, 2012;120(26):5094-5.
Beum et al., "Binding of rituximab, trastuzumab, cetuximab, or mAb T101 to cancer cells promotes trogocytosis mediated by THP-1 cells and monocytes", J Immunol. Dec. 1, 2008;181(11):8120-32.
Callahan et al., "At the bedside: CTLA-4- and PD-1-blocking antibodies in cancer immunotherapy", J Leukoc Biol. Jul. 2013;94(1):41-53.
Cardillo et al., "Targeting both IGF-1R and mTOR synergistically inhibits growth of renal cell carcinoma in vitro", BMC Cancer. Apr. 1, 2013;13:170.
Chang et al., "A new method to produce monoPEGylated dimeric cytokines shown with human interferon-α2b", Bioconjug Chem. Oct. 21, 2009;20(10)1899-907.
Chang et al., "A novel class of anti-HIV agents with multiple copies of enfuvirtide enhances inhibition of viral replication and cellular transmission in vitro", PLoS One. 2012;7(7):e41235.
Chang et al., "Evaluation of a novel hexavalent humanized anti-IGF-1R antibody and its bivalent parental IgG in diverse cancer cell lines", PLoS One. 2012;7(8):e44235.
Cubas et al., "Trop2: a possible therapeutic target for late stage epithelial carcinomas", Biochim Biophys Acta. Dec. 2009;1796(2):309-14.
Flieger et al., "A bispecific single-chain antibody directed against EpCAM/CD3 in combination with the cytokines interferon alpha and interleukin-2 efficiently retargets T and CD3+CD56+ natural-killer-like T lymphocytes to EpCAM-expressing tumor cells", Cancer Immunol Immunother. Oct. 2000;49(8):441-8.
Gleason et al., "Bispecific and trispecific killer cell engagers directly activate human NK cells through CD16 signaling and induce cytotoxicity and cytokine production", Mol Cancer Ther. Dec. 2012;11(12):2674-84.
Goldenberg et al., "Cancer Imaging and Therapy with Bispecific Antibody Pretargeting", Update Cancer Ther. Mar. 2007;2(1):19-31.
Govindan et al., "Designing immunoconjugates for cancer therapy", Expert Opin Biol Ther. Jul. 2012;12(7):873-90.
Intlekofer et al., "At the bench: preclinical rationale for CTLA-4 and PD-1 blockade as cancer immunotherapy", J Leukoc Biol. Jul. 2013;94(1):25-39.
Kipriyanov et al., "Synergistic antitumor effect of bispecific CD19×CD3 and CD19×CD16 diabodies in a preclinical model of non-Hodgkin's lymphoma", J Immunol. Jul. 1, 2002;169(1):137-44.
Kyi et al., "Checkpoint blocking antibodies in cancer immunotherapy", FEBS Lett. Jan. 21, 2014;588(2):368-76.
Liu et al., "Trop-2-targeting tetrakis-ranpimase has potent antitumor activity against triple-negative breast cancer", Mol Cancer. Mar. 10, 2014;13:53.
Lum et al., "Targeted T-cell Therapy in Stage IV Breast Cancer: A Phase I Clinical Trial", Clin Cancer Res. May 15, 2015;21(10):2305-14.
Moore et al., "Application of dual affinity retargeting molecules to achieve optimal redirected T-cell killing of B-cell lymphoma", Blood. Apr. 28, 2011;117(17):4542-51.
Morales-Kastresana et al., "Combined immunostimulatory monoclonal antibodies extend survival in an aggressive transgenic hepatocellular carcinoma mouse model", Clin Cancer Res. Nov. 15, 2013;19(22):6151-62.
Nagorsen et al., Immunotherapy of lymphoma and leukemia with T-cell engaging BiTE antibody blinatumomab, Leuk Lymphoma. Jun. 2009;50(6):886-91.
Nitta et al., Preliminary trial of specific targeting therapy against malignant glioma, Lancet. Feb. 17, 1990;335(8686):368-71.
Oberst et al., "CEA/CD3 bispecific antibody MEDI-565/AMG 211 activation of T cells and subsequent killing of human tumors is independent of mutations commonly found in colorectal adenocarcinomas", MAbs. 2014;6(6):1571-84.
Pegram et al., "Inhibitory effects of combinations of HER-2/neu antibody and chemotherapeutic agents used for treatment of human breast cancers", Oncogene. Apr. 1, 1999;18(13):2241-51.
Peng et al., "The CEA/CD3-bispecific antibody MEDI-565 (MT111) binds a nonlinear epitope in the full-length but not a short splice variant of CEA", PLoS One. 2012;7(5):e36412.
Podojil et al., "Targeting the B7 family of co-stimulatory molecules: successes and challenges", BioDrugs. Feb. 2013;27(1):1-13.
Portell et al., "Clinical and pharmacologic aspects of blinatumomab in the treatment of B-cell acute lymphoblastic leukemia", Clin Pharmacol. Apr. 12, 2013;5(Suppl 1):5-11.
Portner et al., "T and NK cells of B cell NHL patients exert cytotoxicity against lymphoma cells following binding of bispecific tetravalent antibody CD19×CD3 or CD19×CD16", Cancer Immunol Immunother. Oct. 2012;61(10):1869-75.
Robinson, R., "RNAi therapeutics: how likely, how soon?", PLoS Biol. Jan. 2004;2(1):E28.
Rossi et al., "Novel T-cell redirecting trivalent bispecific antibodies", Cancer Res Apr. 15, 2013; vol. 73 (8 Supplement), Abstr #4747.
Rossi et al., "Hexavalent bispecific antibodies represent a new class of anticancer therapeutics: 1. Properties of anti-CD20/CD22 antibodies in lymphoma", Blood. Jun. 11, 2009;113(24):6161-71.
Rossi et al., "CD20-targeted tetrameric interferon-alpha, a novel and potent immunocytokine for the therapy of B-cell lymphomas", Blood. Oct. 29, 2009;114(18):3864-71.
Rossi et al., "The dock-and-lock method combines recombinant engineering with site-specific covalent conjugation to generate multifunctional structures", Bioconjug Chem. Mar. 21, 2012;23(3):309-23.
Rossi et al., "Complex and defined biostructures with the dock-and-lock method", Trends Pharmacol Sci. Sep. 2012;33(9):474-81.
Rossi et al., "A new class of bispecific antibodies to redirect T cells for cancer immunotherapy", MAbs. Mar.-Apr. 2014;6(2):381-91.
Rossi et al., "Redirected T-cell killing of solid cancers targeted with an anti-CD3/Trop-2-bispecific antibody is enhanced in combination with interferon-α", Mol Cancer Ther. Oct. 2014;13(10):2341-51.
Rossi et al., "A New Platform for Trivalent Bispecific Antibodies Used for T-Cell Redirected Killing of B-Cell Malignancies", Nov. 15, 2013; Blood: 122 (21).
Rossi et al., "A novel Trop-2/CD3 trivalent bispecific antibody effectively redirects T cells to kill target human pancreatic and gastric cancer cells", Proceedings of the 105th Annual Meeting of the American Association for Cancer Research; Apr. 5-9, 2014; San Diego, CA; Cancer Res 2014;74(19 Suppl):Abstract # 2655.
Sharkey et al., "Improved cancer therapy and molecular imaging with multivalent, multispecific antibodies", Cancer Biother Radiopharm. Feb. 2010;25(1):1-12.
Shubert et al., "A recombinant triplebody with specificity for CD19 and HLA-DR mediates preferential binding to antigen double-positive cells by dual-targeting", MAbs. Jan.-Feb. 2012;4(1):45-56.
Topalian et al., "Targeting the PD-1/B7-H1(PD-L1) pathway to activate anti-tumor immunity", Curr Opin Immunol. Apr. 2012;24(2):207-12.

(56) References Cited

OTHER PUBLICATIONS

Topp et al., "Long-term follow-up of hematologic relapse-free survival in a phase 2 study of blinatumomab in patients with MRD in B-lineage ALL", Blood. Dec. 20, 2012;120(26):5185-7.
Traunecker et al., "Bispecific single chain molecules (Janusins) target cytotoxic lymphocytes on HIV infected cells", EMBO J. Dec. 1991;10(12):3655-9.
Vallera et al., "A bispecific recombinant immunotoxin, DT2219, targeting human CD19 and CD22 receptors in a mouse xenograft model of B-cell leukemia/lymphoma", Clin Cancer Res. May 15, 2005;11(10):3879-88.
Veri et al., "Therapeutic control of B cell activation via recruitment of Fcgamma receptor IIb (CD32B) inhibitory function with a novel bispecific antibody scaffold", Arthritis Rheum. Jul. 2010;62(7):1933-43.
Wei et al., "Disulfide-stabilized diabody antiCD19/antiCD3 exceeds its parental antibody in tumor-targeting activity", Cell Oncol (Dordr). Dec. 2012;35(6):423-34.
Zhou et al., "A fully human CD19/CD3 bi-specific antibody triggers potent and specific cytotoxicity by unstimulated T lymphocytes against non-Hodgkin's lymphoma", Biotechnol Lett. Jul. 2012;34(7):1183-91.
Kufer et al., "A revival of bispecific antibodies", Trends Biotechnol. May 2004;22(5):238-44.
Matarrese et al., "Type I Interferon Gene Transfer Sensitizes Melanoma Cells to Apoptosis via a Target Activity on Mitochondrial Function" Am. J. Pathol. 2002, 160(4):1507-1520.
Mecchia et al., "Type I consensus interferon (CIFN) gene transfer into human melanoma cells up-regulates p53 and enhances cisplatin-induced apoptosis: implications for new therapeutic strategies with IFN-alpha" Gene Ther. (2000) 7, 167-179.
Newlon et al., "A Novel Mechanism of PKA Anchoring Revealed by Solution Structures of Anchoring Complexes" EMBO J. 2001:20:1651-1662.
Newlon et al., "The molecular basis for protein kinase A anchoring revealed by solution NMR" Nature Struct. Biol. 1999; 3:222-227.
Ngo et al., "Computational Complexity, Protein Structure Prediction, and the Levinthal Paradox", The Protein Folding Problem and Tertiary Structure Prediction, Ch. 14, pp. 492-495, (Mertz & Le Grand, Eds.), Birkhauser Boston, 1994.
Osborn et al., "Pharmacokinetic and Pharmacodynamic Studies of a Human Serum Albumin-Interferon-α Fusion Protein in Cynomolgus Monkeys" J. Pharmacol. Exp. Ther. 303(2):540-548 (2002).
Oyen et al., "Human testis cDNA for the regulatory subunit RIIα of cAMP-dependent protein kinase encodes an alternate amino-terminal region" FEBS Letters 246:57-64, 1989.
Ozzello et al., "Conjugation of interferon alpha to a humanized monoclonal antibody (HuBrE-3vl) enhances the selective localization and antitumor effects of interferon in breast cancer xenografts" Breast Cancer Res. Treat. 48: 135-147 (1998).
Paquette et al., "Interferon-α and granulocyte-macrophage colony-stimulating factor differentiate peripheral blood monocytes into potent antigen-presenting cells" J. Leukoc. Biol. 64:358-367; 1998.
Pelham et al., "Interferon-α conjugation to human osteogenic sarcoma monoclonal antibody 791T/36" Cancer Immunol. Immuother. 1983;15(3):210-216.
Pepinsky et al., "Improved Pharmacokinetic Properties of a Polyethylene Glycol-Modified Form of Interferon-β-1a with Preserved in Vitro Bioactivity" Pharmacol. Exp. Ther. 2001; 297(3):1059-1066.
Pilling et al., "Interferon-β mediates stromal cell rescue of T cells from apoptosis" Eur. J. Immunol. 29:1041-1050 (1999).
Rabjohn et al., "Molecular Cloning and Epitope Analysis of the Peanut Allergen Ara h 3" J. Clinical Investigation 103(04):535-542 (1999).
Raefsky et al., "Studies of Interferon as a regulator of hematopoietic cells proliferation" J. Immunol. 135(4):2507-2512 (1985).
Rihova, B., "Receptor-mediated targeted drug or toxin delivery", Adv Drug Deliv Rev. Feb. 2, 1998;29(3):273-289.

Rose et al., "Structural basis of dimerization, coactivator recognition and MODY3 mutations in HNF-1α" Nature Struct. Biol. 2000; 7:744-748.
Rosendahl et al., "A Long-Acting, Highly Potent Interferon α-2 Conjugate Created Using Site-Specific PEGylation" Bioconjugate Chem. 2005;16:200-207.
Rossi et al., "Novel Designs of Multivalent Anti-CD20 Humanized Antibodies as Improved Lymphoma Therapeutics" Cancer Res. 68:8384-92 (2008).
Rossi et al., "Stably tethered multifunctional structures of defined composition made by the dock and lock method for use in cancer targeting" Proc. Natl. Acad. Sci. Epub Apr. 24, 2006, vol. 103, No. 18, pp. 6841-6846.
Rossi et al., "Optimization of Multivalent Bispecific Antibodies and Immunocytokines with Improved in Vivo Properties", Bioconjug Chem. Jan. 16, 2013;24(1):63-71.
Rubin, KM., "Management of primary cutaneous and metastatic melanoma", Semin Oncol Nurs. Aug. 2013;29(3):195-205.
Rustandi et al., "The Ca2+-Dependent Interaction of S100B(ββ) with a Peptide Derived from p53", Biochemistry 1998; 37: 1951-1960.
Sabaawy et al., "Enhancement of 5-fluorouracil cytotoxicity on human colon cancer cells by retrovirus-mediated interferon-α gene transfer" Int. J. Oncol. Jun. 1999; 14(6):1143-51.
Salles et al., "Rituximab combined with chemotherapy and interferon in follicular lymphoma patients: results of the Gela-Goelams FL2000 study" Blood 2008; 112:4824-4831.
Santini et al., "Type I Interferon as a Powerful Adjuvant for Monocyte-derived Dendritic Cell Development and Activity in Vivo and in Hu-PBL-SCID Mice" J. Exp. Med. 191(10):1777-1788 (2000).
Scott et al., "Type II Regulatory Subunit Dimerization Determines the Subcellular Localization of the cAMP-dependent Protein Kinase" J. Biol. Chem. 265:21561-66 (1990).
Scott et al., "Cyclic nucleotide-dependent protein kinases" Pharmacol. Ther. 1991;50(1):123-45.
Seffernick et al., "Melamine Deaminase and Atrazine Chlorohydrolase: 98 Percent Identical but Functionally Different" J. Bacteriol. 183(8):2405-2410 (2001).
Sharkey et al., "Improved Therapeutic Results by Pretargeted Radioimmunotherapy of Non-Hodgkin's Lymphoma with a New Recombinant, Trivalent, Anti-CD20, Bispecific Antibody" Cancer Res. 68:5282-90 (2008).
Sharkey et al., "Metastatic Human Colonic Carcinoma: Molecular Imaging with Pretargeted SPECT and PET in a Mouse Model" Radiology 246:497-507 (2008).
Sharkey et al., "A new Tri-Fab bispecific antibody for pretargeting Trop-2-expressing epithelial cancers", J Nucl Med. Oct. 2012;53(10):1625-32.
Sidky et al., "Inhibition of Angiogenesis by Interferons: Effects on Tumor- and Lymphocyte-induced Vascular Responses" Cancer Res. 47:5155-5161, Oct. 1, 1987.
Stein et al., "Characterization of a New Humanized Anti-CD20 Monoclonal Antibody, IMMU-106, and Its Use in Combination with the Humanized Anti-CD22 Antibody, Epratuzumab, for the Therapy of Non-Hodgkin's Lymphoma" Clin. Cancer Res. vol. 10, 2868-2878, Apr. 15, 2004.
Stein et al., "Characterization of a humanized IgG4 anti-HLA-DR monoclonal antibody that lacks effector cell functions but retains direct antilymphoma activity and increases the potency of rituximab" Blood 2006;108:2736-2744.
Stokka et al., "Characterization of A-kinase-anchoring disruption using a solution-based assay" Biochem. J. (2006) 400, 493-499.
Stryer et al., "Levels of Structure in Protein Architecture", Biochemistry, 3rd Ed., pp. 31-33, W.H. Freeman & Co., New York, 1988.
Takaoka et al., "Integration of interferon-α/β signalling to p53 responses in tumour suppression and antiviral defence" Nature Jul. 31, 2003;424(6948):516-23.
Taylor, S., "cAMP-dependent Protein Kinase" J. Biol. Chem. 1989;264(15):8443-8446.

(56) References Cited

OTHER PUBLICATIONS

Tretola et al., "CD133, Trop-2 and alpha2beta1 integrin surface receptors as markers of putative human prostate cancer stem cells", Am J Transl Res. Mar. 15, 2010;2(2):135-44.
Varughese et al., "Cervical carcinomas overexpress human trophoblast cell-surface marker (Trop-2) and are highly sensitive to immunotherapy with hRS7, a humanized monoclonal anti-Trop-2 antibody", Am J Obstet Gynecol. Dec. 2011;205(6):567.e1-7.
Walsh et al., "An Adenosine 3', 5'-Monophosphate-dependant Protein Kinase from Rabbit Skeletal Muscle" J. Biol. Chem. 243(13):3763-3774 (1968).
Weck et al., "Comparison of the Antiviral Activities of Various Cloned Human Interferon-α Subtypes in Mammalian Cell Cultures" J. Gen. Virol. (1981), 57, 233-237.
Winkler et al., "Changing the Antigen Binding Specificity by Single Point Mutations of an Anti-p24 (HIV-1) Antibody" J. Immunol. 165:4505-14 (2000).
Witkowski et al., "Conversion of a β-Ketoacyl Synthase to a Malonyl Decarboxylase by Replacement of the Active-Site Cysteine with Glutamine" Biochemistry 38(36):11643-50 (1999).
Wong et al., "AKAP Signalling Complexes: Focal Points in Space and Time" Nat. Rev. Mol. Cell Biol. 12:959-70 (2004).
Zhu et al., "Inhibition of tumor growth and metastasis by targeting tumor-associated angiogenesis with antagonists to the receptors of vascular endothelial growth factor" Invest. New Drugs 17:195-212, 1999.
Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11(9):1936-47.
Arlen et al., "The use of specific monoclonal antibodies to target immunogenic tumor membrane proteins in patients with recurrent pancreatic and colon cancer", Curr Drug Deliv. Jan. 2012;9(1):52-6.
Bamrungphon et al. "A new mucin antibody/enzyme-linked lectin-sandwich assay of serum MUC5AC mucin for the diagnosis of cholangiocarcinoma", Cancer Lett. Mar. 18, 2007;247(2):301-8.
Brennan et al., "Novel agents for the treatment of pancreatic cancer", JOP. Mar. 10, 2014;15(2):110-3.
Bu et al. "Altered expression of MUC2 and MUC5AC in progression of colorectal carcinoma", World J Gastroenterol. Aug. 28, 2010;16(32):4089-94.
Burkard et al., "Validating cancer drug targets through chemical genetics", Biochim Biophys Acta. Dec. 2010;1806(2):251-7.
Burke et al., "Design, synthesis, and biological evaluation of antibody-drug conjugates comprised of potent camptothecin analogues", Bioconjug Chem. Jun. 2009;20(6):1242-50.
Burnham et al., "Invasion of HeLa cells by group B streptococcus requires the phosphoinositide-3-kinase signalling pathway and modulates phosphorylation of host-cell Akt and glycogen synthase kinase-3", Microbiology. Dec. 2007;153(Pt 12):4240-52.
Cunningham et al., "Cetuximab monotherapy and cetuximab plus irinotecan in irinotecan-refractory metastatic colorectal cancer", N Engl J Med. Jul. 22, 2004;351(4):337-45.
Edelman et al., "The covalent structure of an entire gammaG immunoglobulin molecule", Proc Natl Acad Sci U S A. May 1969;63(1):78-85.
Feldmann et al., "Design of effective immunotherapy for human autoimmunity", Nature. Jun. 2, 2005;435(7042):612-9.
Forgue-Lafitte et al., "Abnormal expression of M1/MUC5AC mucin in distal colon of patients with diverticulitis, ulcerative colitis and cancer", Int J Cancer. Oct. 1, 2007;121(7):1543-9.
Fukuda et al., "Evaluation of novel platinum complexes, inhibitors of topoisomerase I and II in non-small cell lung cancer (NSCLC) sublines resistant to cisplatin", Anticancer Res. Mar.-Apr. 1995;15(2):393-8.
Garcia-Giron et al., "Phase II trial of fortnightly irinotecan (CPT-11) in the treatment of colorectal cancer patients resistant to previous fluoropyrimidine-based chemotherapy", Clin Transl Oncol. Jul. 2005;7(6):244-9.

Gomez-Manzano et al., "Delta-24 increases the expression and activity of topoisomerase I and enhances the antiglioma effect of irinotecan", Clin Cancer Res. Jan. 15, 2006;12(2):556-62.
Govindan et al., "New antibody conjugates in cancer therapy", ScientificWorldJournal. Oct. 12, 2010;10:2070-89.
Govindan et al., "Milatuzumab-SN-38 conjugates for the treatment of CD74+ cancers", Mol Cancer Ther. Jun. 2013;12(6):968-78.
Gura, T., "Systems for identifying new drugs are often faulty", Science. Nov. 7, 1997;278(5340):1041-2.
Haab et al., "Glycosylation variants of mucins and CEACAMs as candidate biomarkers for the diagnosis of pancreatic cystic neoplasms", Ann Surg. May 2010;251(5):937-45.
Han et al., "Combination of MUC5ac and WT-1 immunohistochemistry is useful in distinguishing pancreatic ductal carcinoma from ovarian serous carcinoma in effusion cytology", Diagn Cytopathol. May 2010;38(5):333-6.
He et al., "Synthesis and biological evaluation of bis and monocarbonate prodrugs of 10-hydroxycamptothecins", Bioorg Med Chem. Aug. 1, 2004;12(15):4003-8.
Ho et al., "Methylation status of promoters and expression of MUC2 and MUC5AC mucins in pancreatic cancer cells", Int J Oncol. Feb. 2003;22(2):273-9.
Ho et al., "Secretion of MUC5AC mucin from pancreatic cancer cells in response to forskolin and VIP", Biochem Biophys Res Commun. Jun. 14, 2002;294(3):680-6.
Horwitz et al., "Antiviral action of camptothecin", Antimicrob Agents Chemother. Nov. 1972;2(5):395-401.
Hoshi et al., "Tumor-associated MUC5AC stimulates in vivo tumorigenicity of human pancreatic cancer", Int J Oncol. Mar. 2011;38(3):619-27.
Kaiser, J., "Cancer. First pass at cancer genome reveals complex landscape", Science. Sep. 8, 2006;313(5792):1370.
Kanno et al., "The expression of MUC4 and MUC5AC is related to the biologic malignancy of intraductal papillary mucinous neoplasms of the pancreas", Pancreas. Nov. 2006;33(4):391-6.
Kufe et al., Non-Intercalating Topoisomerase-Targeting Drugs, Holland-Frei Cancer Medicine, Hamilton (ON), BC Decker (2003).
Kufe et al., Topoisomerase Biology, 6th Ed., Holland-Frei Cancer Medicine, Hamilton (ON), BC Decker (2003).
Kunze et al., "Tumor-associated neoexpression of the pS2 peptide and MUC5AC mucin in primary adenocarcinomas and signet ring cell carcinomas of the urinary bladder", Histol Histopathol. May 2008;23(5):539-48.
Luka et al., "Development of a serum biomarker assay that differentiates tumor-associated MUC5AC (NPC-1C Antigen) from normal MUC5AC", J Biomed Biotechnol. 2011;2011:934757.
Mahato et al., "Prodrugs for improving tumor targetability and efficiency", Adv Drug Deliv Rev. Jul. 18, 2011;63(8):659-70.
Matsumura et al., "Preclinical and clinical studies of NK012, an SN-38-incorporating polymeric micelles, which is designed based on EPR effect", Adv Drug Deliv Rev. Mar. 18, 2011;63(3):184-92.
Maurin et al. "Progression of tumors arising from large ACF is associated with the MUC5AC expression during rat colon MNNG carcinogenis", Int J Cancer. Feb. 1, 2007;120(3):477-83.
Patel et al., "Anti-tumor activity of a novel monoclonal antibody, NPC-1C, optimized for recognition of tumor antigen MUC5AC variant in preclinical models", Cancer Immunol Immunother Jun. 2013;62(6):1011-9.
Reis et al. "Immunohistochemical study of MUC5AC expression in human gastric carcinomas using a novel monoclonal antibody", Int J Cancer. Feb. 20, 1997;74(1):112-21.
Silsirivanit et al., "A novel serum carbohydrate marker on mucin 5AC: values for diagnostic and prognostic indicators for cholangiocarcinoma", Cancer. Aug. 1, 2011;117(15):3393-403.
Stanford University Environmental Health and Safety (Information on Azide Compounds, Dec. 2, 2008).
Talmadge et al., "Murine models to evaluate novel and conventional therapeutic strategies for cancer", Am J Pathol. Mar. 2007;170(3):793-804.
Thurber et al., "Antibody tumor penetration: transport opposed by systemic and antigen-mediated clearance", Adv Drug Deliv Rev. Sep. 2008;60(12):1421-34.

(56) References Cited

OTHER PUBLICATIONS

Van Noort and Amor, "Cell Biology of Autoimmune Disease", vol. 178, pp. 127-206; International Rev. of Cytology, 1998.
Wongkham et al. "Serum MUC5AC mucin as a potential marker for cholangiocarcinoma", Cancer Lett. May 30, 2003;195(1):93-9.
Cardillo et al., "Therapeutic Advantage of 90Yttrium-versus 131Iodine-labeled PAM4 Antibody in Experimental Pancreatic Cancer" Clin. Cancer Res. 7(10):3186-3192, Oct. 2001.
Cardillo et al., "Combined Gemcitabine and Radioimmunotherapy for the Treatment of Pancreatic Cancer" Int. J. Cancer: 97(3):386-392 (2002).
Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.
Carter et al., Chemotherapy of Cancer; 2nd Edition; John Wiley & Sons, New York, 1981; Appendix C.
Clark et al., "Antibody humanization: a case of the Emeror's new clothes?" Immunol. Today 21(8):397-402 (2000).
Dall'Acqua et al., "Antibody Engineering" Curr. Opin. Struct. Biol., Aug. 1998; 8(4):443-50.
Daniel et al., "Mapping of Linear Antigenic Sites on the S Glycoprotein of a Neurotropic Murine Coronavirus with Synthetic Peptides: A Combination of Nine Prediction Algorithms Fails to Identify Relevant Epitopes and Peptide Immunogenicity Is Drastically Influenced by the Nature of the Protein Carrier" Virology 202, 540-549 (1994).
El Sewedy et al., "Cloning of the murine TROP2 gene: conservation of a PIP2-binding sequence in the cytoplasmic domain of TROP-2", Int J Cancer. Jan. 19, 1998;75(2):324-30.
Emery et al., "Humanised monoclonal antibodies for therapeutic applications" Exp. Opin. Invest. Drugs (1994) 3(3):241-251.
Frolich et al., "The anti-CD74 humanized monoclonal antibody, milatuzumab, which targets the invariant chain of MHC II complexes, alters B-cell proliferation, migration, and adhesion molecule expression", Arthritis Res Ther. Mar. 9, 2012;14(2):R54.
Gold et al., "Radioimmunotherapy of Experimental Pancreatic Cancer with 131I-Labeled Monoclonal Antibody PAM4" Int. J. Cancer: 71(4):660-667 (1997).
Gold et al., "Chimerization and CDR-grafted humanization of PAM4, a murine monoclonal anti-pancreatic cancer antibody" Proc AACR 1993; 34:480, abstract 2866.
Gold et al., "Characterization of Monoclonal Antibody PAM4 Reactive with a pancreatic Cancer Mucin" Int. J. Cancer 57(2): 204-210 (1994).
Gold et al., "Localization of pancreatic cancer with radiolabeled monoclonal antibody PAM4" Crit. Rev. Oncol. Hematol. Jul.-Aug. 2001;39(1-2):147-154.
Gold et al., "PAM4-reactive MUC1 is a biomarker for early pancreatic adenocarcinoma", Clin Cancer Res. Dec. 15, 2007;13(24):7380-7.
Govindan et al., "CEACAM5-targeted therapy of human colonic and pancreatic cancer xenografts with potent abetuzumab-SN-38 immunoconjugates", Clin Cancer Res. Oct. 1, 2009;15(19):6052-61.
Govindan et al., "Preclinical therapy of breast cancer with a radioiodinated humanized anti-EGP-1 monoclonal antibody: advantage of a residualizing iodine radiolabel", Breast Cancer Res Treat. Mar. 2004;84(2):173-82.
Greenspan et al., "Defining epitopes: It's not as easy as it seems" Nat. Biotech. 17:936-937 (1999).
Ho et al., "Antisense Oligonucleaotides as Therapeutics for Malignant Diseases" Semin. Oncol. 24(2):187-202 (1997).
Jiang et al., "A Novel Peptide Isolated from a Phage Display Peptide Library with Trastuzumab Can Mimic Antigen Epitope of HER-2", J. Biol. Chem. Feb. 2005;280(6):4656-4662.
Jones, DT "Critically assessing the state-of-the-art in protein structure prediction" Pharmacogenomics J.; 1:126-134, 2001.

Karacay et al., "A Pretargeting Bispecific Antibody Method for Improved Imaging and Therapy of Pancreatic Cancer" J. Nucl. Med., vol. 43, No. 5(Suppl.), May 2002, p. 369P, No. 1484.
Kipriyanov et al., "Generation of Recombinant Antibodies" Mol. Biotechnol., vol. 12, Sep. 1999; pp. 173-201.
Klivenyi et al., "Gallium-68 Chelate Imaging of Human Colon Carcinoma Xenografts Pretargeted with Bispecific Anti-CD44V6/Anti-Gallium Chelate Antibodies" J. Nucl. Med. 39(10): pp. 1769-1776, Oct. 1998.
Krontiris and Capizzi, Internal Medicine, Chapters 71-72, pp. 699-729; 4th Edition, Jay Stein (Ed.), Elsevier Science, 1994.
Linnenbach et al., "Sequence investigation of the major gastrointestinal tumor-associated antigen gene family, GA733", Proc Natl Acad Sci U S A. Jan. 1989;86(1):27-31.
Mariani et al., "Initial Tumor Targeting, Biodistribution, and Pharmacokinetic Evaluation of the Monoclonal Antibody PAM4 in Patients with Pancreatic Cancer" Cancer Res. Suppl. 55, 5911s-5915s, Dec. 1, 1995.
Price et al., "Summary Report on the ISOBM TD-4 Workshop: Analysis of 56 Monoclonal Antibodies against the MUC1 Mucin" Tumor Biol. 1998, 19(Suppl. 1):1-20.
Schuhmacher et al., "Pretargeting of human mammary carcinoma xenografts with bispecific anti-MUC1/anti-Ga chelate antibodies and immunoscintigraphy with PET" Nucl. Med. Biol. 28 (2001) 821-828.
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Sharkey et al., "Epratuzumab-SN-38: a new antibody-drug conjugate for the therapy of hematologic malignancies", Mol Cancer Ther. Jan. 2012;11(1):224-34.
Skolnick et al., "From genes to protein structure and function: novel applications of computational approaches in the genomic era" Trends Biotechnol. 2000; 18:34-39.
Stancovski et al., "Mechanistic aspects of the opposing effects of monoclonal antibodies to the ERBB2 receptor on tumor growth", Proc Natl Acad Sci U S A. Oct. 1, 1991;88(19):8691-5.
Stein et al., "Radioimmunotherapy of a human lung cancer xenograft with monoclonal antibody RS7: evaluation of (177)Lu and comparison of its efficacy with that of (90)Y and residualizing (131)I", J Nucl Med. Jun. 2001;42(6):967-74.
Stein et al., "Improved iodine radiolabels for monoclonal antibody therapy", Cancer Res. Jan. 1, 2003;63(1):111-8.
Stein et al., "Successful therapy of a human lung cancer xenograft using MAb RS7 labeled with residualizing radioiodine", Crit Rev Oncol Hematol. Jul.-Aug. 2001;39(1-2):173-80.
Stein et al., "Targeting human cancer xenografts with monoclonal antibodies labeled using radioiodinated, diethylenetriaminepentaacetic acid-appended peptides", Clin Cancer Res. Oct. 1999;5(10 Suppl):3079s-3087s.
Stein et al., "Advantage of yttrium-90-labeled over iodine-131-labeled monoclonal antibodies in the treatment of a human lung carcinoma xenograft", Cancer Dec. 15, 1997;80(12 Suppl):2636-41.
Steinfeld et al., "Epratuzumab (humanised anti-CD22 antibody) in autoimmune diseases", Expert Opin Biol Ther. Sep. 2006;6(9):943-9.
Tosatto et al., "Large-Scale Prediction of Protein Structure and Function from Sequence" Curr. Pharm. Des., 12, 2006, 2067-2086.
Walker et al., "Improved Cellular Delivery of Antisense Oligonucleotides Using Transferrin Receptor Antibody-Oligonucleotide Conjugates" Pharm. Res., 12(10):1548-53, (1995).
Yazawa et al., "Immunotherapy using unconjugated CD19 monoclonal antibodies in animal models for B lymphocyte malignancies and autoimmune disease", Proc Natl Acad Sci U S A. Oct. 18, 2005;102(42):15178-83.
Alberts et al., Molecular Biology of the Cell, 3rd Ed., pp. 1216-1218, Garland Publishing, Inc. (1994).
Basu et al., "The epithelial/carcinoma antigen EGP-1, recognized by monoclonal antibody RS7-3G11, is phosphorylated on serine 303" Int. J. Cancer 62(4):472-479 (1995).

(56) References Cited

OTHER PUBLICATIONS

Bendig et al., "Humanization of Rodent Monoclonal Antibodies by CDR Grafting" Methods: A Companion to Methods in Enzymology 8:83-93-93 (1995).
Bennouna et al., "Therapeutic strategies for colorectal cancer in Europe and the United States: focus on chemotherapy for advanced colorectal cancer" Int. J. Clin. Oncol. (2002) 7:236-244.
Cao et al., "Bispecific Antibodies as Novel Bioconjugates" Bioconj. Chem. Nov.-Dec. 1998;9(6):635-44.
Chari et al., "Immunoconjugates Containing Novel Maytansinoids: Promising Anticancer Drugs" Cancer Res. Jan. 1, 1992;52(1):127-31.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Hatzakis et al., "Synthesis and single enzyme activity of a clicked lipase-BSA hetero-dimer" Chem. Commun., 2006, 2012-2014.
Heindel et al., "A Novel Heterobifunctional Linker for Formyl to Thiol Coupling" Bioconjugate Chem. 1991, 2, 427-430.
Huang et al., "The *Rana catesbeiana* rcr Gene Encoding a Cytotoxic Ribonuclease" J. Biol. Chem. 273(11):6395-6401 (1998).
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Leung et al., "Chimerization of LL2, a Rapidly Internalizing Antibody Specific for B Cell Lymphoma" Hybridoma 13(6):469-476 (1994).
Miller et al., "Development of Taxoids with Enhanced Toxicity and Solubility" Poster Presentation, 224th ACS Nat. Meeting, Aug. 18-22, 2002, Boston, MA.
Moon et al., "Antibody Conjugates of 7-Ethyl-10-hydroxycamptothecin (SN-38) for Targeted Cancer Chemotherapy" J. Med. Chem. 2008, 51, 6916-6926.
Morrison et al., "Chimeric human antibody molecules: Mouse antigen-binding domains with human constant region domains" Proc. Natl. Acad. Sci, USA 81:6851-6855 (1984).
Newton et al., "Potent and specific antitumor effects of an anti-CD22-targeted cytotoxic ribonuclease: potential for the treatment of non-Hodgkin lymphoma" Blood, 97(2):528-35 (2001).
Paul, W. Fundamental Immunology, 3rd Ed., p. 242; pp. 292-295, Raven Press, New York (1993).
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Qu et al., "Humanization of Immu31, an α-Fetoprotein-specific Antibody" Clin. Cancer Res. 5(10 Suppl):3094s-3100s (1999).

Reddy et al., "Elimination of Fc Receptor-Dependent Effector Functions of a Modified IgG4 Monoclonal Antibody to Human CD4", J. Immunol. 164:1925-1933 (2000).
Ripani et al., "Human Trop-2 is a tumor-associated calcium signal transducer", Int J Cancer. May 29, 1998;76(5):671-6.
Rowlinson-Busza et al., "Targeted delivery of biologic and other antineoplastic agents" Curr. Opin. Oncol. Dec. 1992;4(6):1142-1148.
Rudikoff et al., "Single amino acid substitution altering antigen-binding specificity" Proc. Natl. Acad. Sci. USA 79:1979-1983 (1982).
Schoonjans et al., "FAB chains as an Efficient Heterodimerization Scaffold for the Production of Recombinant Bispecific and Trispecific Antibody Derivatives" J. Immunol. 165(12):7050-7057 (2000).
Shih et al., "In Vitro and in Vivo Reactivity of an Internalizing Antibody, RS7, with Human Breast Cancer" Cancer Res. 55(23 Suppl.):5857s-5863s (1995).
Shih et al., "The Processing and Fate of Antibodies and Their Radiolabels Bound to the Surface of Tumor Cells in Vitro: A Comparison of Nine Radiolabels" J. Nucl. Med. 1994; 35:899-908.
Stein et al., "Therapy of a Breast Cancer Xenograft Using Humanized RS7 Labeled with Residualizing Iodine" Proc. Am. Assoc. Cancer Res. vol. 43, pp. 88-89, Mar. 2002 (Abstract).
Stein et al., "Comparative Biodistribution and Radioimmunotherapy of Monoclonal Antibody RS7 and its F(ab')2 in Nude Mice Bearing Human Tumor Xenografts" Cancer 73:816-823 (1994).
Stein et al., "Effects of Radiolabeling Monoclonal Antibodies with a Residualizing Iodine Radiolabel on the Accretion of Radioisotope in Tumors" Cancer Res. 55(14):3132-3139 (1995).
Stein et al., "Specificity and properties of MAb RS7-3G11 and the antigen defined by this pancarcinoma monoclonal antibody" Int. J. Cancer 55(6):938-946 (1993).
Stein et al., "Characterization of cluster 13: the epithelial/carcinoma antigen recognized by MAb RS7" Int. J. Cancer 57(S8):98-102 (1994).
Stein et al., "Murine Monoclonal Antibodies Raised against Human Non-Small Cell Carcinoma of the Lung: Specificity and Tumor Targeting" Cancer Res. 50(4):1330-1336 (1990).
Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).
Suzawa et al., "Enhanced tumor cell selectivity of adriamycin-monoclonal antibody conjugate via a poly(ethylene glycol)-based cleavable linker" J. Control. Release 79:229-242 (2002).
Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.
Walker et al., "Synthesis of an Immunoconjugate of Camptothecin" Bioorg. Med. Chem. Lett. 12(2):217-219 (2002).

\* cited by examiner

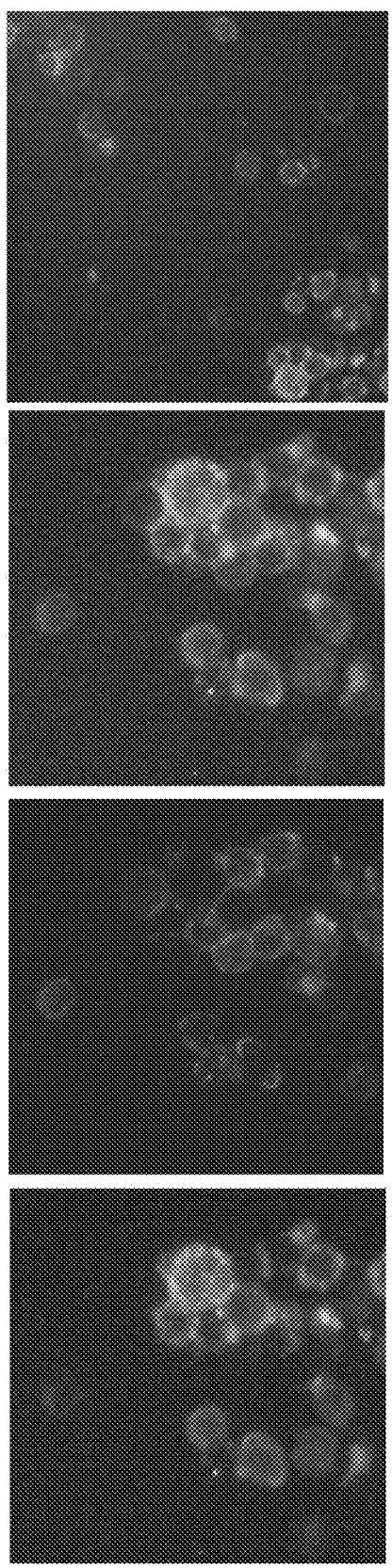

*Figure from Moore et al. *Blood* 2011, 117:4542-4551.

Immunological synapse formation between Capan-1 pancreatic adenocarcinoma cells (MUC5AC+Trop2+CD19-) and Jurkat T cells
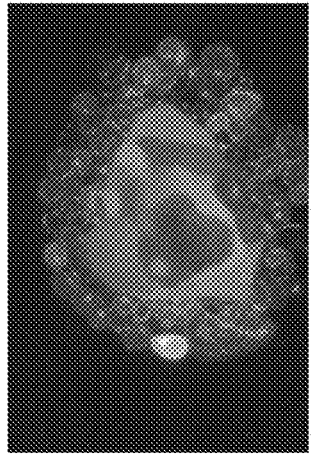
FIG. 6C (E1)-3s
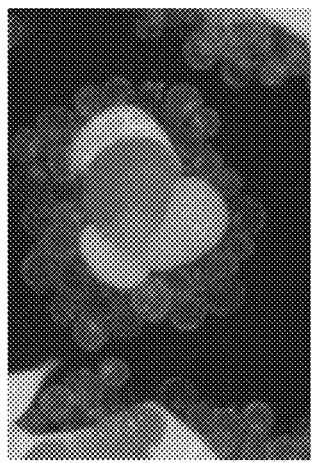
FIG. 6B (M1)-3s
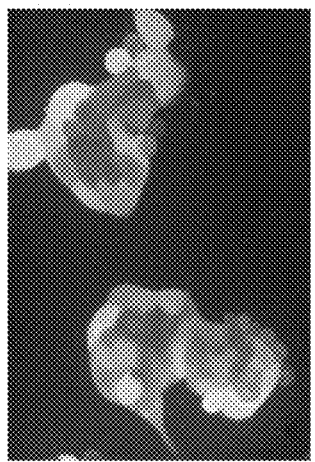
FIG. 6A (19)-3s

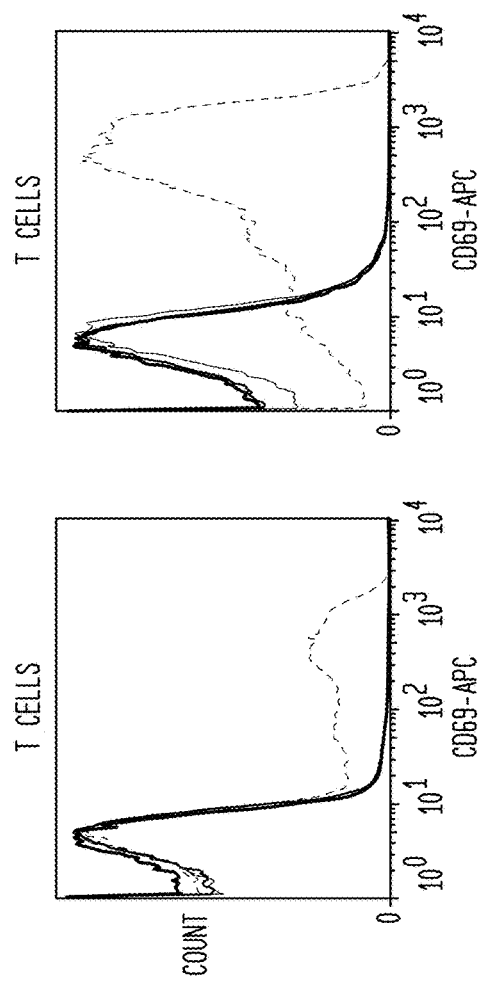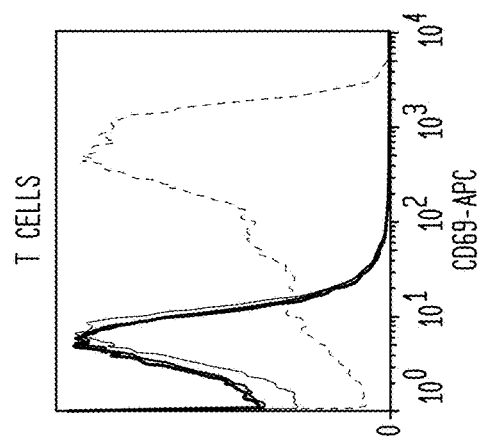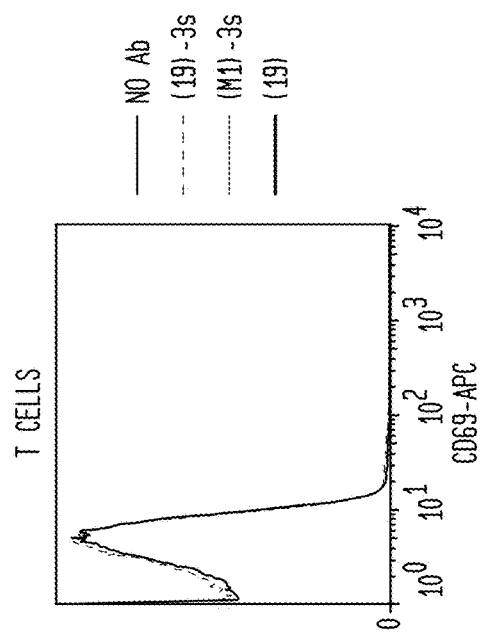

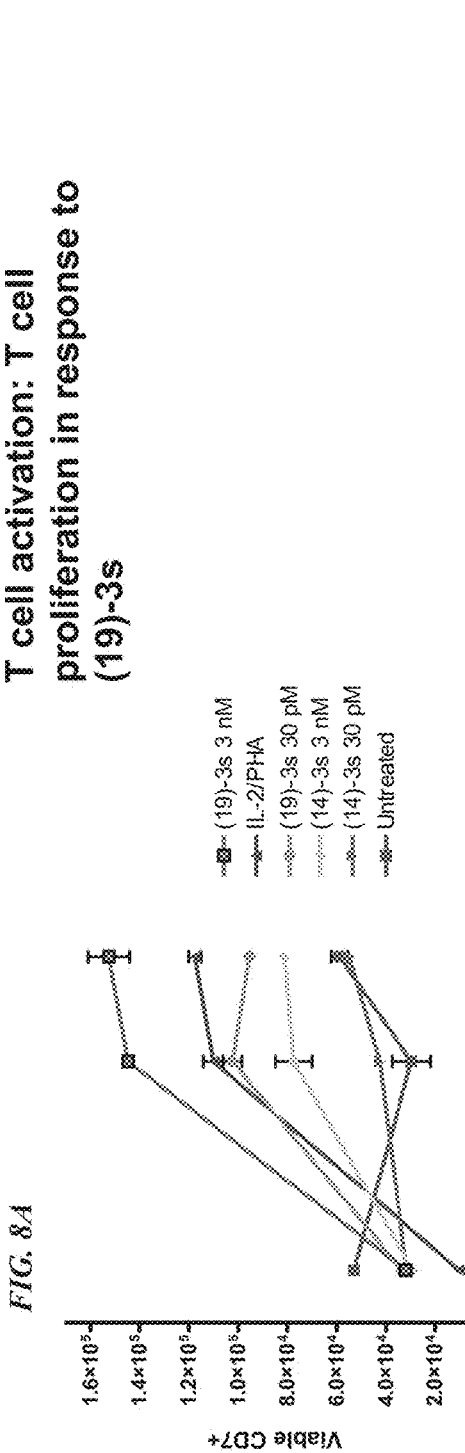
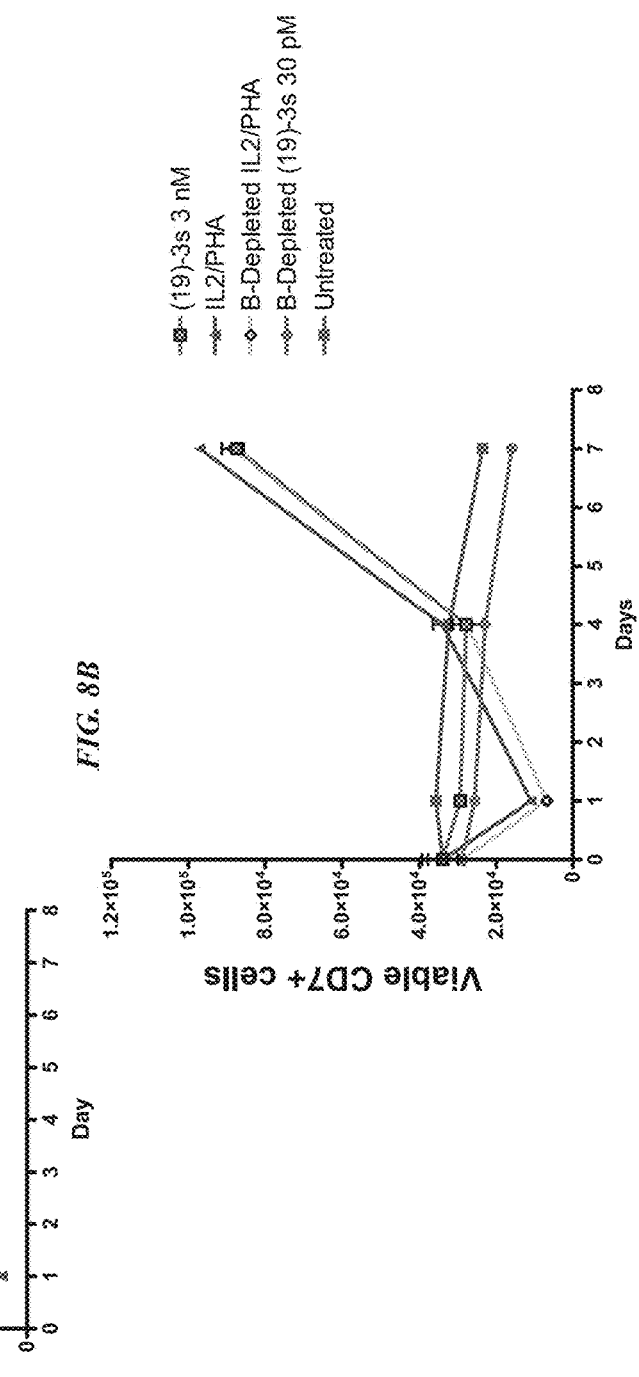
FIG. 8A
FIG. 8B

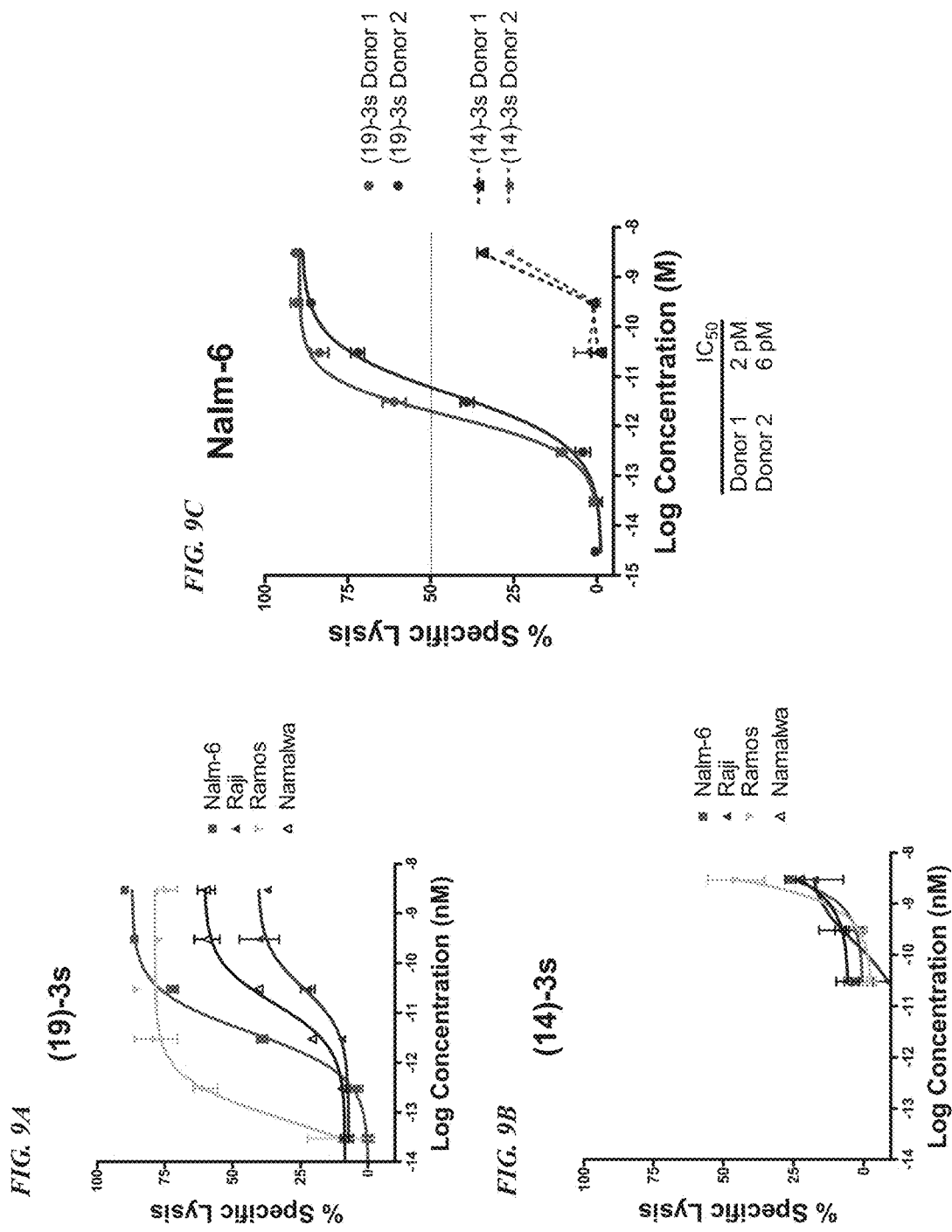

FIG. 12

|  |  |  | Expression* | IC50 (pM) | Max lysis (%) |
|---|---|---|---|---|---|
| (20)-3s | CD20 | Daudi | 1 | <0.3 | ~90 |
| (19)-3s | CD19 | Daudi | 1 | 1 | ~60 |
| (22)-3s | CD22 | Daudi | 1 | ~5 | ~60 |
| (20)-3s | CD20 | Nalmawa | 0.11 | 30 | 53 |
| (19)-3s | CD19 | Namalwa | 1.67 | 63 | 60 |
| (22)-3s | CD22 | Namalwa | 0.06 | ND | 42 |
| (20)-3s | CD20 | Jeko-1 | 1.02 | 1 | 90 |
| (19)-3s | CD19 | Jeko-1 | 1.93 | 3000 | 50 |
| (20)-3s | CD20 | Ramos | TBD | TBD | TBD |
| (19)-3s | CD19 | Ramos | 0.84 | 0.17 | 79 |
| (20)-3s | CD20 | Nalm6 | TBD | TBD | TBD |
| (19)-3s | CD19 | Nalm6 | 0.75 | 6 | ~93 |
| (20)-3s | CD20 | Raji | TBD | TBD | TBD |
| (19)-3s | CD19 | Raji | 2.55 | >3000 | 41 |
| (C2)-3s |  | Daudi |  |  |  |
|  |  | Jeko-1 |  | 20 | 88 |

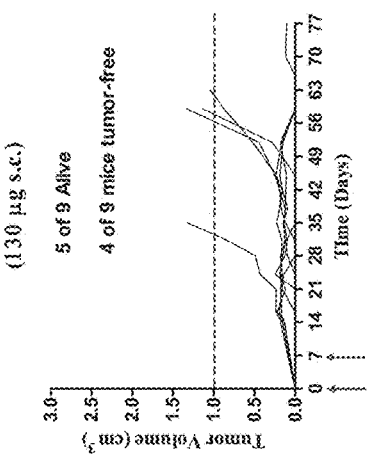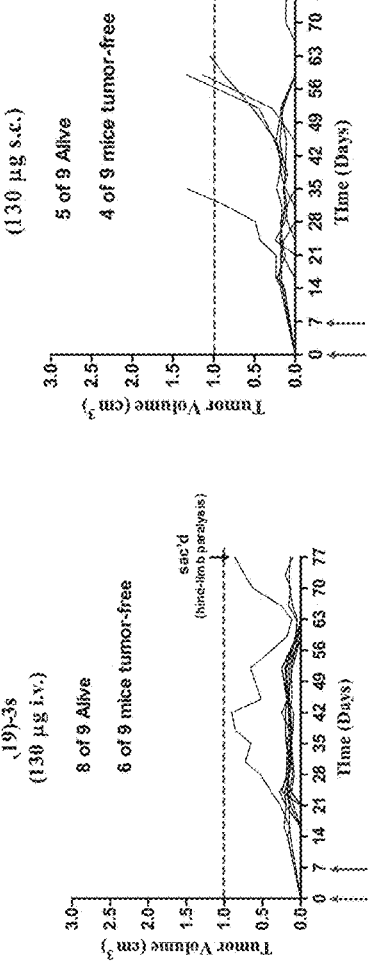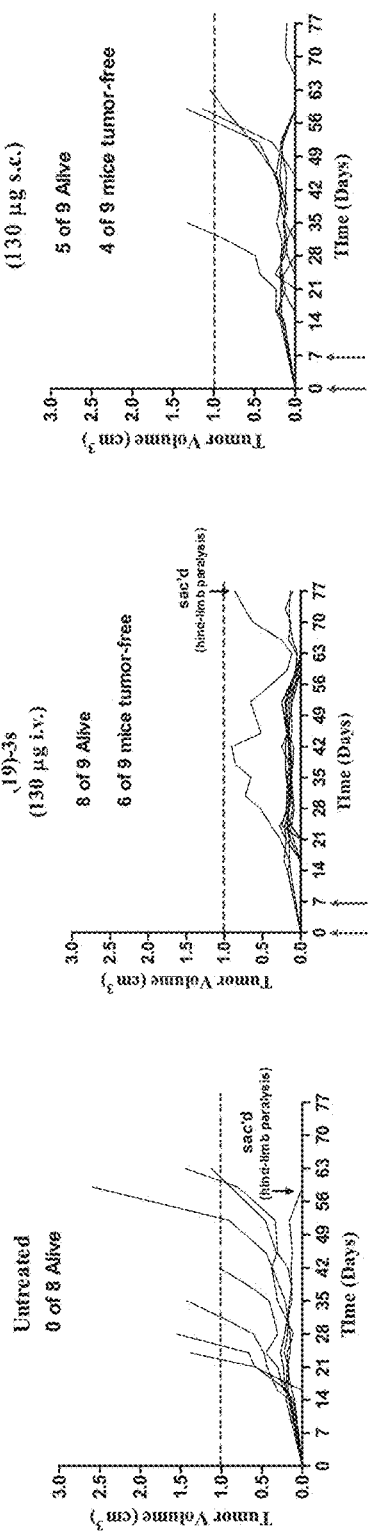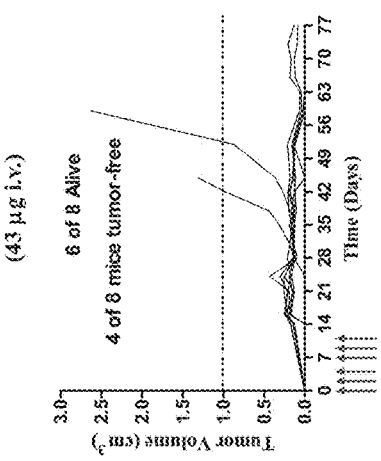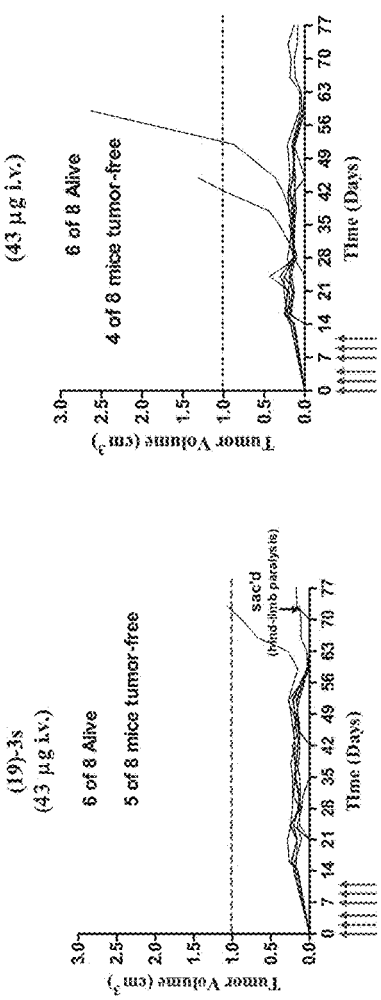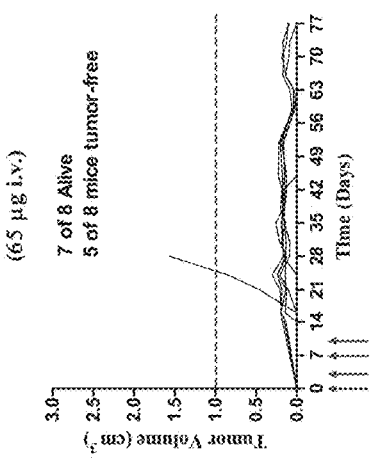

FIG. 23A BxPC3
FIG. 23B Capan-1
FIG. 23C NCI-N87

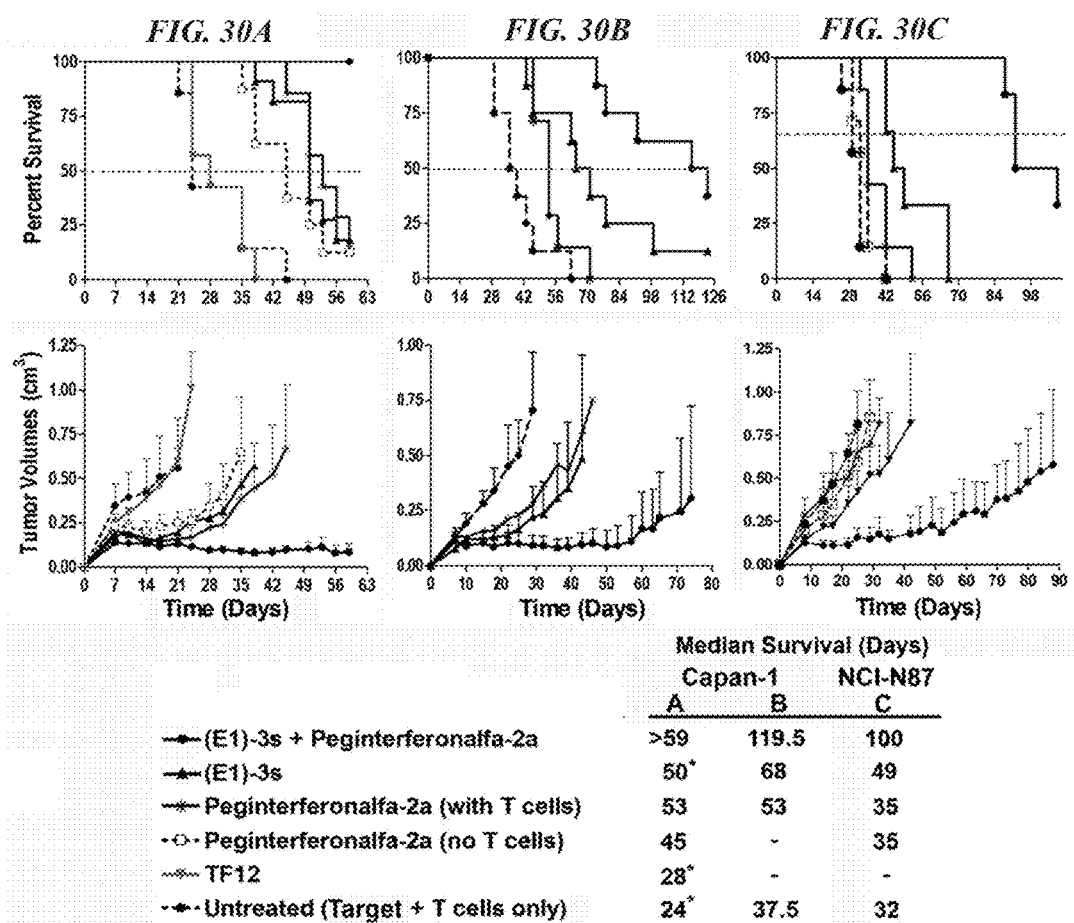

SEQUENCE LISTING

```
<160> NUMBER OF SEQ ID NOS: 120

<210> SEQ ID NO 1
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 2
<211> LENGTH: 45
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Cys Gly His Ile Gln Ile Pro Pro Gly Leu Thr Glu Leu Leu Gln Gly
1               5                   10                  15

Tyr Thr Val Glu Val Leu Arg Gln Gln Pro Pro Asp Leu Val Glu Phe
            20                  25                  30

Ala Val Glu Tyr Phe Thr Arg Leu Arg Glu Ala Arg Ala
        35                  40                  45

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Ile Glu Tyr Leu Ala Lys Gln Ile Val Asp Asn Ala Ile Gln Gln
1               5                   10                  15

Ala

<210> SEQ ID NO 4
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 4

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 5
<211> LENGTH: 50
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Ser Leu Arg Glu Cys Glu Leu Tyr Val Gln Lys His Asn Ile Gln Ala
1               5                   10                  15

Leu Leu Lys Asp Ser Ile Val Gln Leu Cys Thr Ala Arg Pro Glu Arg
            20                  25                  30

Pro Met Ala Phe Leu Arg Glu Tyr Phe Glu Arg Leu Glu Lys Glu Glu
        35                  40                  45

Ala Lys
    50

<210> SEQ ID NO 6
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Met Ser Cys Gly Gly Ser Leu Arg Glu Cys Glu Leu Tyr Val Gln Lys
1               5                   10                  15

His Asn Ile Gln Ala Leu Leu Lys Asp Ser Ile Val Gln Leu Cys Thr
            20                  25                  30

Ala Arg Pro Glu Arg Pro Met Ala Phe Leu Arg Glu Tyr Phe Glu Arg
        35                  40                  45

Leu Glu Lys Glu Glu Ala Lys
    50                  55

<210> SEQ ID NO 7
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Gly Phe Glu Glu Leu Ala Trp Lys Ile Ala Lys Met Ile Trp Ser
1               5                   10                  15

Asp Val Phe Gln Gln Gly Cys
            20

<210> SEQ ID NO 8
<211> LENGTH: 51
<212> TYPE: PRT
<213> ORGANISM: Homo sapiens

<400> SEQUENCE: 8
```

```
Ser Leu Arg Glu Cys Glu Leu Tyr Val Gln Lys His Asn Ile Gln Ala
1               5                   10                  15

Leu Leu Lys Asp Val Ser Ile Val Gln Leu Cys Thr Ala Arg Pro Glu
            20                  25                  30

Arg Pro Met Ala Phe Leu Arg Glu Tyr Phe Glu Lys Leu Glu Lys Glu
            35                  40                  45

Glu Ala Lys
        50

<210> SEQ ID NO 9
<211> LENGTH: 54
<212> TYPE: PRT
<213> ORGANISM: Homo sapiens

<400> SEQUENCE: 9

Ser Leu Lys Gly Cys Glu Leu Tyr Val Gln Leu His Gly Ile Gln Gln
1               5                   10                  15

Val Leu Lys Asp Cys Ile Val His Leu Cys Ile Ser Lys Pro Glu Arg
            20                  25                  30

Pro Met Lys Phe Leu Arg Glu His Phe Glu Lys Leu Glu Lys Glu Glu
            35                  40                  45

Asn Arg Gln Ile Leu Ala
        50

<210> SEQ ID NO 10
<211> LENGTH: 44
<212> TYPE: PRT
<213> ORGANISM: Homo sapiens

<400> SEQUENCE: 10

Ser His Ile Gln Ile Pro Pro Gly Leu Thr Glu Leu Leu Gln Gly Tyr
1               5                   10                  15

Thr Val Glu Val Gly Gln Gln Pro Pro Asp Leu Val Asp Phe Ala Val
            20                  25                  30

Glu Tyr Phe Thr Arg Leu Arg Glu Ala Arg Arg Gln
            35                  40

<210> SEQ ID NO 11
<211> LENGTH: 44
<212> TYPE: PRT
<213> ORGANISM: Homo sapiens

<400> SEQUENCE: 11

Ser Ile Glu Ile Pro Ala Gly Leu Thr Glu Leu Leu Gln Gly Phe Thr
1               5                   10                  15

Val Glu Val Leu Arg His Gln Pro Ala Asp Leu Leu Glu Phe Ala Leu
            20                  25                  30

Gln His Phe Thr Arg Leu Gln Gln Glu Asn Glu Arg
            35                  40

<210> SEQ ID NO 12
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 12

Thr His Ile Gln Ile Pro Pro Gly Leu Thr Glu Leu Leu Gln Gly Tyr
```

```
                1               5                  10                  15
Thr Val Glu Val Leu Arg Gln Gln Pro Pro Asp Leu Val Glu Phe Ala
            20                  25                  30
Val Glu Tyr Phe Thr Arg Leu Arg Glu Ala Arg Ala
            35                  40

<210> SEQ ID NO 13
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Lys Ile Gln Ile Pro Pro Gly Leu Thr Glu Leu Leu Gln Gly Tyr
1               5                  10                  15
Thr Val Glu Val Leu Arg Gln Gln Pro Pro Asp Leu Val Glu Phe Ala
            20                  25                  30
Val Glu Tyr Phe Thr Arg Leu Arg Glu Ala Arg Ala
            35                  40

<210> SEQ ID NO 14
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Arg Ile Gln Ile Pro Pro Gly Leu Thr Glu Leu Leu Gln Gly Tyr
1               5                  10                  15
Thr Val Glu Val Leu Arg Gln Gln Pro Pro Asp Leu Val Glu Phe Ala
            20                  25                  30
Val Glu Tyr Phe Thr Arg Leu Arg Glu Ala Arg Ala
            35                  40

<210> SEQ ID NO 15
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Ser His Ile Asn Ile Pro Pro Gly Leu Thr Glu Leu Leu Gln Gly Tyr
1               5                  10                  15
Thr Val Glu Val Leu Arg Gln Gln Pro Pro Asp Leu Val Glu Phe Ala
            20                  25                  30
Val Glu Tyr Phe Thr Arg Leu Arg Glu Ala Arg Ala
            35                  40

<210> SEQ ID NO 16
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16
```

Ser His Ile Gln Ile Pro Pro Ala Leu Thr Glu Leu Leu Gln Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
            35                  40

<210> SEQ ID NO 17
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Ser His Ile Gln Ile Pro Pro Gly Leu Ser Glu Leu Leu Gln Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
            35                  40

<210> SEQ ID NO 18
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Ser His Ile Gln Ile Pro Pro Gly Leu Thr Asp Leu Leu Gln Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
            35                  40

<210> SEQ ID NO 19
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Ser His Ile Gln Ile Pro Pro Gly Leu Thr Glu Leu Leu Asn Gly Tyr
1               5                   10                  15

Thr Val Glu Val Leu Arg Gln Gln Pro Pro Asp Leu Val Glu Phe Ala
                20                  25                  30

Val Glu Tyr Phe Thr Arg Leu Arg Glu Ala Arg Ala
            35                  40

<210> SEQ ID NO 20
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

```
Ser His Ile Gln Ile Pro Pro Gly Leu Thr Glu Leu Leu Gln Ala Tyr
1               5                   10                  15

Thr Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40
```

<210> SEQ ID NO 21
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

```
Ser His Ile Gln Ile Pro Pro Gly Leu Thr Glu Leu Leu Gln Gly Tyr
1               5                   10                  15

Ser Val Glu Val Leu Arg Gln Gln Pro Pro Asp Leu Val Glu Phe Ala
            20                  25                  30

Val Glu Tyr Phe Thr Arg Leu Arg Glu Ala Arg Ala
        35                  40
```

<210> SEQ ID NO 22
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

```
Ser His Ile Gln Ile Pro Pro Gly Leu Thr Glu Leu Leu Gln Gly Tyr
1               5                   10                  15

Thr Val Asp Val Leu Arg Gln Gln Pro Pro Asp Leu Val Glu Phe Ala
            20                  25                  30

Val Glu Tyr Phe Thr Arg Leu Arg Glu Ala Arg Ala
        35                  40
```

<210> SEQ ID NO 23
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

```
Ser His Ile Gln Ile Pro Pro Gly Leu Thr Glu Leu Leu Gln Gly Tyr
1               5                   10                  15

Thr Val Glu Val Leu Lys Gln Gln Pro Pro Asp Leu Val Glu Phe Ala
            20                  25                  30

Val Glu Tyr Phe Thr Arg Leu Arg Glu Ala Arg Ala
        35                  40
```

<210> SEQ ID NO 24
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide -continued

```
<400> SEQUENCE: 24

Ser His Ile Gln Ile Pro Pro Gly Leu Thr Glu Leu Leu Gln Gly Tyr
1               5                   10                  15

Thr Val Glu Val Leu Arg Asn Gln Pro Pro Asp Leu Val Glu Phe Ala
            20                  25                  30

Val Glu Tyr Phe Thr Arg Leu Arg Glu Ala Arg Ala
        35                  40

<210> SEQ ID NO 25
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Ser His Ile Gln Ile Pro Pro Gly Leu Thr Glu Leu Leu Gln Gly Tyr
1               5                   10                  15

Thr Val Glu Val Leu Arg Gln Asn Pro Pro Asp Leu Val Glu Phe Ala
            20                  25                  30

Val Glu Tyr Phe Thr Arg Leu Arg Glu Ala Arg Ala
        35                  40

<210> SEQ ID NO 26
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser His Ile Gln Ile Pro Pro Gly Leu Thr Glu Leu Leu Gln Gly Tyr
1               5                   10                  15

Thr Val Glu Val Leu Arg Gln Gln Pro Pro Glu Leu Val Glu Phe Ala
            20                  25                  30

Val Glu Tyr Phe Thr Arg Leu Arg Glu Ala Arg Ala
        35                  40

<210> SEQ ID NO 27
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Asp Phe Ala
            20                  25                  30

Val Glu Tyr Phe Thr Arg Leu Arg Glu Ala Arg Ala
        35                  40

<210> SEQ ID NO 28
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 28

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Leu
            20                  25                  30

Val Glu Tyr Phe Thr Arg Leu Arg Glu Ala Arg Ala
        35                  40

<210> SEQ ID NO 29
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ile
            20                  25                  30

Val Glu Tyr Phe Thr Arg Leu Arg Glu Ala Arg Ala
        35                  40

<210> SEQ ID NO 30
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Val
            20                  25                  30

Val Glu Tyr Phe Thr Arg Leu Arg Glu Ala Arg Ala
        35                  40

<210> SEQ ID NO 31
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Ser His Ile Gln Ile Pro Pro Gly Leu Thr Glu Leu Leu Gln Gly Tyr
1               5                   10                  15

Thr Val Glu Val Leu Arg Gln Gln Pro Pro Asp Leu Val Glu Phe Ala
            20                  25                  30

Val Asp Tyr Phe Thr Arg Leu Arg Glu Ala Arg Ala
        35                  40

<210> SEQ ID NO 32
<211> LENGTH: 17
<212> TYPE: PRT
<213> ORGANISM: Artificial Sequence
<220> FEATURE:
<223> OTHER INFORMATION: Description of Artificial Sequence: Synthetic

```
                          peptide

<400> SEQUENCE: 32

Asn Ile Glu Tyr Leu Ala Lys Gln Ile Val Asp Asn Ala Ile Gln Gln
1               5                   10                  15

Ala

<210> SEQ ID NO 33
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Leu Glu Tyr Leu Ala Lys Gln Ile Val Asp Asn Ala Ile Gln Gln
1               5                   10                  15

Ala

<210> SEQ ID NO 34
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Val Glu Tyr Leu Ala Lys Gln Ile Val Asp Asn Ala Ile Gln Gln
1               5                   10                  15

Ala

<210> SEQ ID NO 35
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Gln Ile Asp Tyr Leu Ala Lys Gln Ile Val Asp Asn Ala Ile Gln Gln
1               5                   10                  15

Ala

<210> SEQ ID NO 36
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gln Ile Glu Phe Leu Ala Lys Gln Ile Val Asp Asn Ala Ile Gln Gln
1               5                   10                  15

Ala

<210> SEQ ID NO 37
<211> LENGTH: 17
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 37

Gln Ile Glu Thr Leu Ala Lys Gln Ile Val Asp Asn Ala Ile Gln Gln
1               5                   10                  15

Ala

<210> SEQ ID NO 38
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

Gln Ile Glu Ser Leu Ala Lys Gln Ile Val Asp Asn Ala Ile Gln Gln
1               5                   10                  15

Ala

<210> SEQ ID NO 39
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Gln Ile Glu Tyr Ile Ala Lys Gln Ile Val Asp Asn Ala Ile Gln Gln
1               5                   10                  15

Ala

<210> SEQ ID NO 40
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Gln Ile Glu Tyr Val Ala Lys Gln Ile Val Asp Asn Ala Ile Gln Gln
1               5                   10                  15

Ala

<210> SEQ ID NO 41
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

Gln Ile Glu Tyr Leu Ala Arg Gln Ile Val Asp Asn Ala Ile Gln Gln
1               5                   10                  15

Ala

<210> SEQ ID NO 42
<211> LENGTH: 17
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 42

Gln Ile Glu Tyr Leu Ala Lys Asn Ile Val Asp Asn Ala Ile Gln Gln
1               5                   10                  15

Ala

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 43

Gln Ile Glu Tyr Leu Ala Lys Gln Ile Val Glu Asn Ala Ile Gln Gln
1               5                   10                  15

Ala

<210> SEQ ID NO 44
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Gln Ile Glu Tyr Leu Ala Lys Gln Ile Val Asp Gln Ala Ile Gln Gln
1               5                   10                  15

Ala

<210> SEQ ID NO 45
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gln Ile Glu Tyr Leu Ala Lys Gln Ile Val Asp Asn Ala Ile Asn Gln
1               5                   10                  15

Ala

<210> SEQ ID NO 46
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Gln Ile Glu Tyr Leu Ala Lys Gln Ile Val Asp Asn Ala Ile Gln Asn
1               5                   10                  15

Ala

<210> SEQ ID NO 47
<211> LENGTH: 17
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 47

Gln Ile Glu Tyr Leu Ala Lys Gln Ile Val Asp Asn Ala Ile Gln Gln
1               5                   10                  15

Leu

<210> SEQ ID NO 48
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Gln Ile Glu Tyr Leu Ala Lys Gln Ile Val Asp Asn Ala Ile Gln Gln
1               5                   10                  15

Ile

<210> SEQ ID NO 49
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Gln Ile Glu Tyr Leu Ala Lys Gln Ile Val Asp Asn Ala Ile Gln Gln
1               5                   10                  15

Val

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

Gln Ile Glu Tyr Val Ala Lys Gln Ile Val Asp Tyr Ala Ile His Gln
1               5                   10                  15

Ala

<210> SEQ ID NO 51
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Gln Ile Glu Tyr Lys Ala Lys Gln Ile Val Asp His Ala Ile His Gln
1               5                   10                  15

Ala

<210> SEQ ID NO 52
<211> LENGTH: 17
```

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

Gln Ile Glu Tyr His Ala Lys Gln Ile Val Asp His Ala Ile His Gln
1               5                   10                  15

Ala

<210> SEQ ID NO 53
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Ile Glu Tyr Val Ala Lys Gln Ile Val Asp His Ala Ile His Gln
1               5                   10                  15

Ala

<210> SEQ ID NO 54
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Pro Leu Glu Tyr Gln Ala Gly Leu Leu Val Gln Asn Ala Ile Gln Gln
1               5                   10                  15

Ala Ile

<210> SEQ ID NO 55
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Leu Leu Ile Glu Thr Ala Ser Ser Leu Val Lys Asn Ala Ile Gln Leu
1               5                   10                  15

Ser Ile

<210> SEQ ID NO 56
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Leu Ile Glu Glu Ala Ala Ser Arg Ile Val Asp Ala Val Ile Glu Gln
1               5                   10                  15

Val Lys

<210> SEQ ID NO 57
```

```
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Ala Leu Tyr Gln Phe Ala Asp Arg Phe Ser Glu Leu Val Ile Ser Glu
1               5                   10                  15

Ala Leu

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Leu Glu Gln Val Ala Asn Gln Leu Ala Asp Gln Ile Ile Lys Glu Ala
1               5                   10                  15

Thr

<210> SEQ ID NO 59
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Phe Glu Glu Leu Ala Trp Lys Ile Ala Lys Met Ile Trp Ser Asp Val
1               5                   10                  15

Phe

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Glu Leu Val Arg Leu Ser Lys Arg Leu Val Glu Asn Ala Val Leu Lys
1               5                   10                  15

Ala Val

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 61

Thr Ala Glu Glu Val Ser Ala Arg Ile Val Gln Val Val Thr Ala Glu
1               5                   10                  15

Ala Val
```

```
<210> SEQ ID NO 62
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 62

Gln Ile Lys Gln Ala Ala Phe Gln Leu Ile Ser Gln Val Ile Leu Glu
1               5                   10                  15

Ala Thr

<210> SEQ ID NO 63
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Leu Ala Trp Lys Ile Ala Lys Met Ile Val Ser Asp Val Met Gln Gln
1               5                   10                  15

<210> SEQ ID NO 64
<211> LENGTH: 24
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 64

Asp Leu Ile Glu Glu Ala Ala Ser Arg Ile Val Asp Ala Val Ile Glu
1               5                   10                  15

Gln Val Lys Ala Ala Gly Ala Tyr
            20

<210> SEQ ID NO 65
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Leu Glu Gln Tyr Ala Asn Gln Leu Ala Asp Gln Ile Ile Lys Glu Ala
1               5                   10                  15

Thr Glu

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Phe Glu Glu Leu Ala Trp Lys Ile Ala Lys Met Ile Trp Ser Asp Val
1               5                   10                  15

Phe Gln Gln Cys
            20
```

```
<210> SEQ ID NO 67
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Gln Ile Glu Tyr Leu Ala Lys Gln Ile Pro Asp Asn Ala Ile Gln Gln
1               5                   10                  15

Ala

<210> SEQ ID NO 68
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Lys Gly Ala Asp Leu Ile Glu Glu Ala Ala Ser Arg Ile Val Asp Ala
1               5                   10                  15

Val Ile Glu Gln Val Lys Ala Ala Gly
            20                  25

<210> SEQ ID NO 69
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Lys Gly Ala Asp Leu Ile Glu Glu Ala Ala Ser Arg Ile Pro Asp Ala
1               5                   10                  15

Pro Ile Glu Gln Val Lys Ala Ala Gly
            20                  25

<210> SEQ ID NO 70
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Pro Glu Asp Ala Glu Leu Val Arg Leu Ser Lys Arg Leu Val Glu Asn
1               5                   10                  15

Ala Val Leu Lys Ala Val Gln Gln Tyr
            20                  25

<210> SEQ ID NO 71
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Glu Asp Ala Glu Leu Val Arg Thr Ser Lys Arg Leu Val Glu Asn
```

```
1               5                   10                  15
Ala Val Leu Lys Ala Val Gln Gln Tyr
            20                  25

<210> SEQ ID NO 72
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 72

Pro Glu Asp Ala Glu Leu Val Arg Leu Ser Lys Arg Asp Val Glu Asn
1               5                   10                  15

Ala Val Leu Lys Ala Val Gln Gln Tyr
            20                  25

<210> SEQ ID NO 73
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 73

Pro Glu Asp Ala Glu Leu Val Arg Leu Ser Lys Arg Leu Pro Glu Asn
1               5                   10                  15

Ala Val Leu Lys Ala Val Gln Gln Tyr
            20                  25

<210> SEQ ID NO 74
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 74

Pro Glu Asp Ala Glu Leu Val Arg Leu Ser Lys Arg Leu Pro Glu Asn
1               5                   10                  15

Ala Pro Leu Lys Ala Val Gln Gln Tyr
            20                  25

<210> SEQ ID NO 75
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 75

Pro Glu Asp Ala Glu Leu Val Arg Leu Ser Lys Arg Leu Val Glu Asn
1               5                   10                  15

Ala Val Glu Lys Ala Val Gln Gln Tyr
            20                  25

<210> SEQ ID NO 76
<211> LENGTH: 25
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 76

Glu Glu Gly Leu Asp Arg Asn Glu Glu Ile Lys Arg Ala Ala Phe Gln
1               5                   10                  15

Ile Ile Ser Gln Val Ile Ser Glu Ala
            20                  25

<210> SEQ ID NO 77
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 77

Leu Val Asp Asp Pro Leu Glu Tyr Gln Ala Gly Leu Leu Val Gln Asn
1               5                   10                  15

Ala Ile Gln Gln Ala Ile Ala Glu Gln
            20                  25

<210> SEQ ID NO 78
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gln Tyr Glu Thr Leu Leu Ile Glu Thr Ala Ser Ser Leu Val Lys Asn
1               5                   10                  15

Ala Ile Gln Leu Ser Ile Glu Gln Leu
            20                  25

<210> SEQ ID NO 79
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

Leu Glu Lys Gln Tyr Gln Glu Gln Leu Glu Glu Val Ala Lys Val
1               5                   10                  15

Ile Val Ser Met Ser Ile Ala Phe Ala
            20                  25

<210> SEQ ID NO 80
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 80

Asn Thr Asp Glu Ala Gln Glu Glu Leu Ala Trp Lys Ile Ala Lys Met
1               5                   10                  15

Ile Val Ser Asp Ile Met Gln Gln Ala
            20                  25
```

```
<210> SEQ ID NO 81
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 81

Val Asn Leu Asp Lys Lys Ala Val Leu Ala Glu Lys Ile Val Ala Glu
1               5                   10                  15

Ala Ile Glu Lys Ala Glu Arg Glu Leu
            20                  25

<210> SEQ ID NO 82
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 82

Asn Gly Ile Leu Glu Leu Glu Thr Lys Ser Ser Lys Leu Val Gln Asn
1               5                   10                  15

Ile Ile Gln Thr Ala Val Asp Gln Phe
            20                  25

<210> SEQ ID NO 83
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 83

Thr Gln Asp Lys Asn Tyr Glu Asp Glu Leu Thr Gln Val Ala Leu Ala
1               5                   10                  15

Leu Val Glu Asp Val Ile Asn Tyr Ala
            20                  25

<210> SEQ ID NO 84
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 84

Glu Thr Ser Ala Lys Asp Asn Ile Asn Ile Glu Glu Ala Ala Arg Phe
1               5                   10                  15

Leu Val Glu Lys Ile Leu Val Asn His
            20                  25

<210> SEQ ID NO 85
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85
```

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 86
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 86

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
     50                  55                  60

Leu Ser Ser Val Val Thr Val Pro Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Arg Val Glu Pro Lys Ser Cys Asp Lys Thr His Thr Cys Pro Pro Cys
             100                 105                 110

Pro Ala Pro Glu Leu Leu Gly Gly Pro Ser Val Phe Leu Phe Pro Pro
             115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 87
<211> LENGTH: 44
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (2)..(2)
<223> OTHER INFORMATION: His, Lys or Arg
<220> FEATURE:
<221> NAME/KEY: MOD_RES
<222> LOCATION: (4)..(4)
<223> OTHER INFORMATION: Gln or Asn
<220> FEATURE:
```

```
<221> NAME/KEY: MOD_RES
<222> LOCATION: (8)..(8)
<223> OTHER INFORMATION: Gly or Ala
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (11)..(11)
<223> OTHER INFORMATION: Glu or Asp
<220> FEATURE:
<221> NAME/KEY: MOD_RES
<222> LOCATION: (14)..(14)
<223> OTHER INFORMATION: Gln or Asn
<220> FEATURE:
<221> NAME/KEY: MOD_RES
<222> LOCATION: (15)..(15)
<223> OTHER INFORMATION: Gly or Ala
<220> FEATURE:
<221> NAME/KEY: MOD_RES
<222> LOCATION: (17)..(17)
<223> OTHER INFORMATION: Thr or Ser
<220> FEATURE:
<221> NAME/KEY: MOD_RES
<222> LOCATION: (19)..(19)
<223> OTHER INFORMATION: Glu or Asp
<220> FEATURE:
<221> NAME/KEY: MOD_RES
<222> LOCATION: (22)..(22)
<223> OTHER INFORMATION: Arg or Lys
<220> FEATURE:
<221> NAME/KEY: MOD_RES
<222> LOCATION: (23)..(24)
<223> OTHER INFORMATION: Gln or Asn
<220> FEATURE:
<221> NAME/KEY: MOD_RES
<222> LOCATION: (27)..(27)
<223> OTHER INFORMATION: Asp or Glu
<220> FEATURE:
<221> NAME/KEY: MOD_RES
<222> LOCATION: (30)..(30)
<223> OTHER INFORMATION: Glu or Asp
<220> FEATURE:
<221> NAME/KEY: MOD_RES
<222> LOCATION: (32)..(32)
<223> OTHER INFORMATION: Ala, Leu, Ile or Val
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (41)..(41)
<223> OTHER INFORMATION: Glu or Asp
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (43)..(43)
<223> OTHER INFORMATION: Arg or Lys
<220> FEATURE:
<221> NAME/KEY: MOD_RES
<222> LOCATION: (44)..(44)
<223> OTHER INFORMATION: Ala, Leu, Ile or Val
```

```
<400> SEQUENCE: 87

Xaa Xaa Ile Xaa Ile Pro Pro Xaa Leu Xaa Xaa Leu Leu Xaa Xaa Tyr
1               5                   10                  15

Xaa Val Xaa Val Leu Xaa Xaa Xaa Pro Pro Xaa Leu Val Xaa Phe Xaa
            20                  25                  30

Val Xaa Tyr Phe Xaa Xaa Leu Xaa Xaa Xaa Xaa
        35                  40

<210> SEQ ID NO 88
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln or Asn
<220> FEATURE:
<221> NAME/KEY: MOD_RES
<222> LOCATION: (2)..(2)
<223> OTHER INFORMATION: Ile, Leu or Val
<220> FEATURE:
<221> NAME/KEY: MOD_RES
<222> LOCATION: (3)..(3)
<223> OTHER INFORMATION: Glu or Asp
<220> FEATURE:
<221> NAME/KEY: MOD_RES
<222> LOCATION: (4)..(4)
<223> OTHER INFORMATION: Tyr, Phe, Thr or Ser
<220> FEATURE:
<221> NAME/KEY: MOD_RES
<222> LOCATION: (5)..(5)
<223> OTHER INFORMATION: Leu, Ile or Val
<220> FEATURE:
<221> NAME/KEY: MOD_RES
<222> LOCATION: (7)..(7)
<223> OTHER INFORMATION: Lys or Arg
<220> FEATURE:
<221> NAME/KEY: MOD_RES
<222> LOCATION: (8)..(8)
<223> OTHER INFORMATION: Gln or Asn
<220> FEATURE:
<221> NAME/KEY: MOD_RES
<222> LOCATION: (11)..(11)
<223> OTHER INFORMATION: Asp or Glu
<220> FEATURE:
<221> NAME/KEY: MOD_RES
<222> LOCATION: (12)..(12)
<223> OTHER INFORMATION: Asn or Gln
<220> FEATURE:
<221> NAME/KEY: MOD_RES
<222> LOCATION: (15)..(16)
<223> OTHER INFORMATION: Gln or Asn
<220> FEATURE:
<221> NAME/KEY: MOD_RES
<222> LOCATION: (17)..(17)
<223> OTHER INFORMATION: Ala, Leu, Ile or Val

<400> SEQUENCE: 88

Xaa Xaa Xaa Xaa Xaa Ala Xaa Xaa Ile Val Xaa Xaa Ala Ile Xaa Xaa
1               5                   10                  15

Xaa

<210> SEQ ID NO 89
<211> LENGTH: 44
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: MOD_RES
<222> LOCATION: (1)..(1)
<223> OTHER INFORMATION: Ser or Thr
<220> FEATURE:
<221> NAME/KEY: MOD_RES
<222> LOCATION: (4)..(4)
<223> OTHER INFORMATION: Gln or Asn
<220> FEATURE:
<221> NAME/KEY: MOD_RES
<222> LOCATION: (10)..(10)
<223> OTHER INFORMATION: Thr or Ser
<220> FEATURE:
<221> NAME/KEY: MOD_RES
<222> LOCATION: (18)..(18)
<223> OTHER INFORMATION: Val, Ile, Leu or Ala
<220> FEATURE:
<221> NAME/KEY: MOD_RES
<222> LOCATION: (23)..(23)
<223> OTHER INFORMATION: Gln or Asn
<220> FEATURE:
<221> NAME/KEY: MOD_RES
<222> LOCATION: (33)..(33)
<223> OTHER INFORMATION: Val, Ile, Leu or Ala
<220> FEATURE:
<221> NAME/KEY: MOD_RES
<222> LOCATION: (34)..(34)
<223> OTHER INFORMATION: Glu or Asp
<220> FEATURE:
<221> NAME/KEY: MOD_RES
<222> LOCATION: (37)..(37)
<223> OTHER INFORMATION: Thr or Ser
<220> FEATURE:
<221> NAME/KEY: MOD_RES
<222> LOCATION: (38)..(38)
<223> OTHER INFORMATION: Arg or Lys
<220> FEATURE:
<221> NAME/KEY: MOD_RES
<222> LOCATION: (40)..(40)
<223> OTHER INFORMATION: Arg or Lys
<220> FEATURE:
<221> NAME/KEY: MOD_RES
<222> LOCATION: (42)..(42)
<223> OTHER INFORMATION: Ala, Leu, Ile or Val
<220> FEATURE:
<221> NAME/KEY: MOD_RES
<222> LOCATION: (44)..(44)
<223> OTHER INFORMATION: Ala, Leu, Ile or Val

<400> SEQUENCE: 89

Xaa His Ile Xaa Ile Pro Pro Gly Leu Xaa Glu Leu Leu Gln Gly Tyr
1               5                   10                  15

Thr Xaa Glu Val Leu Arg Xaa Gln Pro Pro Asp Leu Val Glu Phe Ala
            20                  25                  30

Xaa Xaa Tyr Phe Xaa Xaa Leu Xaa Glu Xaa Arg Xaa
        35                  40

<210> SEQ ID NO 90
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 90

Lys Ala Ser Gln Ser Val Asp Tyr Asp Gly Asp Ser Tyr Leu Asn
1               5                   10                  15

<210> SEQ ID NO 91
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 91

Asp Ala Ser Asn Leu Val Ser
1               5

<210> SEQ ID NO 92
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 92

Gln Gln Ser Thr Glu Asp Pro Trp Thr
1               5

<210> SEQ ID NO 93
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Ser Tyr Trp Met Asn
1               5

<210> SEQ ID NO 94
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Gln Ile Trp Pro Gly Asp Gly Asp Thr Asn Tyr Asn Gly Lys Phe Lys
1               5                   10                  15

Gly

<210> SEQ ID NO 95
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Arg Glu Thr Thr Thr Val Gly Arg Tyr Tyr Tyr Ala Met Asp Tyr
1               5                   10                  15

<210> SEQ ID NO 96
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96
```

-continued

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser
            115
```

<210> SEQ ID NO 97
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 97

```
Gly Gly Gly Gly Ser Gly Gly Gly Gly Ser Gly Gly Gly Gly Ser
1               5                   10                  15
```

<210> SEQ ID NO 98
<211> LENGTH: 107
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

```
Asp Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Lys Arg
            100                 105
```

<210> SEQ ID NO 99
<211> LENGTH: 5
<212> TYPE: PRT
<213> ORGANISM: Artificial Sequence
<220> FEATURE:
<223> OTHER INFORMATION: Description of Artificial Sequence: Synthetic peptide

```
<400> SEQUENCE: 99

Gly Gly Gly Gly Ser
1               5

<210> SEQ ID NO 100
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

His His His His His His Gly Gly Gly Ser Gly
1               5                   10

<210> SEQ ID NO 101
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Cys Gly Gln Ile Glu Tyr Leu Ala Lys Gln Ile Val Asp Asn Ala Ile
1               5                   10                  15

Gln Gln Ala Gly Cys
            20

<210> SEQ ID NO 102
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Pro Lys Ser Cys
1

<210> SEQ ID NO 103
<211> LENGTH: 55
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Gly Ser Gly Gly Gly Ser Gly Gly Gly Ser His Ile Gln Ile
1               5                   10                  15

Pro Pro Gly Leu Thr Glu Leu Leu Gln Gly Tyr Thr Val Glu Val Leu
            20                  25                  30

Arg Gln Gln Pro Pro Asp Leu Val Glu Phe Ala Val Glu Tyr Phe Thr
        35                  40                  45

Arg Leu Arg Glu Ala Arg Ala
    50                  55

<210> SEQ ID NO 104
<211> LENGTH: 29
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 104

Gly Ser Gly Gly Gly Gly Ser Gly Gly Gly Gly Ser Gln Ile Glu Tyr
1               5                   10                  15

Leu Ala Lys Gln Ile Val Asp Asn Ala Ile Gln Gln Ala
            20                  25

<210> SEQ ID NO 105
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 105

His His His His His His
1               5

<210> SEQ ID NO 106
<211> LENGTH: 1579
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 106
```

| | | | | | |
|---|---|---|---|---|---|
| tctagacaca | ggccgccatc | atgggatgga | gctgtatcat | cctcttcttg | gtagcaacag | 60 |
| ctacaggtgt | ccactccgac | attcagctga | cccagtctcc | atcctccctg | tctgcatctg | 120 |
| taggagacag | agtcagcatc | acctgcaagg | ccagtcagga | tgtgagtatt | gctgtagcct | 180 |
| ggtatcagca | gaaaccaggg | aaagccccta | agctcctgat | ctactcggca | tcctaccggt | 240 |
| acactggagt | ccctgatagg | ttcagtggca | gtggatctgg | gacagatttc | actctcacca | 300 |
| tcagcagtct | gcaacctgaa | gattttgcag | tttattactg | tcagcaacat | tatattactc | 360 |
| cgctcacgtt | cggtgctggg | accaaggtgg | agatcaaagg | tggaggaggg | tccggtggag | 420 |
| gagggtctgg | tggaggaggg | agccaggtcc | agctgcagca | atctgggtct | gagttgaaga | 480 |
| agcctggggc | ctcagtgaag | gtttcctgca | aggcttctgg | atacaccttc | acaaactatg | 540 |
| gaatgaactg | ggtgaagcag | gcccctggac | aagggcttaa | atggatgggc | tggataaaca | 600 |
| cctacactgg | agagccaaca | tatactgatg | acttcaaggg | acggtttgcc | ttctccttgg | 660 |
| acacctctgt | cagcacggca | tatctccaga | tcagcagcct | aaaggctgac | gacactgccg | 720 |
| tgtatttctg | tgcaagaggg | gggttcggta | gtagctactg | gtacttcgat | gtctggggcc | 780 |
| aagggtccct | ggtcaccgtc | tcctcaggtg | gcggagggtc | cgatatcaag | ctgcagcagt | 840 |
| ctggagcaga | gctcgctcga | ccaggagcta | gtgtgaagat | gtcatgtaaa | acaagtggct | 900 |
| atactttcac | ccggtacact | atgcactggg | tcaagcagcg | cccaggacag | ggtctggaat | 960 |
| ggatcggcta | cattaacccc | agcagggat | ataccaacta | caatcagaag | ttcaaggata | 1020 |
| aagccaccct | gactaccgac | aagtcctcta | gtacagctta | tatgcagctg | tcaagcctca | 1080 |
| cttccgagga | ctctgcagtg | tattactgcg | ccagatatta | cgacgatcat | tattgtctgg | 1140 |
| attactgggg | ccagggaaca | actctcacag | tgtcctctgt | cgaaggtggc | agtggagggt | 1200 |
| caggtggcag | cggagggtcc | ggtggagtgg | acgatatcca | gctgacccag | tctcctgcca | 1260 |
| ttatgagcgc | ttccccaggc | gagaaggtga | caatgacttg | ccgggccagt | tcaagcgtca | 1320 |

-continued

```
gctatatgaa ttggtatcag cagaagtctg gaaccagtcc taaacgatgg atctatgaca    1380
catctaaagt ggcaagcggg gtcccataca ggttctctgg gagtggttca ggcactagct    1440
attccctgac catttcctct atggaggccg aagatgcagc cacctattac tgtcagcagt    1500
ggagttcaaa tccactcacc ttcggagcag gcactaaact ggaactcaag caccaccacc    1560
accaccacta aggcggccg                                                 1579
```

<210> SEQ ID NO 107
<211> LENGTH: 497
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

```
Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys Gly Gly Gly Gly Ser
            100                 105                 110

Gly Gly Gly Gly Ser Gly Gly Gly Ser Gln Val Gln Leu Gln Gln
        115                 120                 125

Ser Gly Ser Glu Leu Lys Lys Pro Gly Ala Ser Val Lys Val Ser Cys
130                 135                 140

Lys Ala Ser Gly Tyr Thr Phe Thr Asn Tyr Gly Met Asn Trp Val Lys
145                 150                 155                 160

Gln Ala Pro Gly Gln Gly Leu Lys Trp Met Gly Trp Ile Asn Thr Tyr
                165                 170                 175

Thr Gly Glu Pro Thr Tyr Thr Asp Asp Phe Lys Gly Arg Phe Ala Phe
            180                 185                 190

Ser Leu Asp Thr Ser Val Ser Thr Ala Tyr Leu Gln Ile Ser Ser Leu
        195                 200                 205

Lys Ala Asp Asp Thr Ala Val Tyr Phe Cys Ala Arg Gly Gly Phe Gly
    210                 215                 220

Ser Ser Tyr Trp Tyr Phe Asp Val Trp Gly Gln Gly Ser Leu Val Thr
225                 230                 235                 240

Val Ser Ser Gly Gly Gly Gly Ser Asp Ile Lys Leu Gln Gln Ser Gly
                245                 250                 255

Ala Glu Leu Ala Arg Pro Gly Ala Ser Val Lys Met Ser Cys Lys Thr
            260                 265                 270

Ser Gly Tyr Thr Phe Thr Arg Tyr Thr Met His Trp Val Lys Gln Arg
        275                 280                 285

Pro Gly Gln Gly Leu Glu Trp Ile Gly Tyr Ile Asn Pro Ser Arg Gly
    290                 295                 300
```

```
Tyr Thr Asn Tyr Asn Gln Lys Phe Lys Asp Lys Ala Thr Leu Thr Thr
305                 310                 315                 320

Asp Lys Ser Ser Ser Thr Ala Tyr Met Gln Leu Ser Ser Leu Thr Ser
                325                 330                 335

Glu Asp Ser Ala Val Tyr Tyr Cys Ala Arg Tyr Tyr Asp Asp His Tyr
            340                 345                 350

Cys Leu Asp Tyr Trp Gly Gln Gly Thr Thr Leu Thr Val Ser Ser Val
        355                 360                 365

Glu Gly Gly Ser Gly Gly Ser Gly Gly Ser Gly Gly Ser Gly Gly Val
    370                 375                 380

Asp Asp Ile Gln Leu Thr Gln Ser Pro Ala Ile Met Ser Ala Ser Pro
385                 390                 395                 400

Gly Glu Lys Val Thr Met Thr Cys Arg Ala Ser Ser Ser Val Ser Tyr
                405                 410                 415

Met Asn Trp Tyr Gln Gln Lys Ser Gly Thr Ser Pro Lys Arg Trp Ile
            420                 425                 430

Tyr Asp Thr Ser Lys Val Ala Ser Gly Val Pro Tyr Arg Phe Ser Gly
        435                 440                 445

Ser Gly Ser Gly Thr Ser Tyr Ser Leu Thr Ile Ser Ser Met Glu Ala
    450                 455                 460

Glu Asp Ala Ala Thr Tyr Tyr Cys Gln Gln Trp Ser Ser Asn Pro Leu
465                 470                 475                 480

Thr Phe Gly Ala Gly Thr Lys Leu Glu Leu Lys His His His His His
                485                 490                 495

His

<210> SEQ ID NO 108
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Asp Ile Gln Leu Thr Gln Ser Pro Ser Ser Leu Ser Ala Ser Val Gly
1               5                   10                  15

Asp Arg Val Ser Ile Thr Cys Lys Ala Ser Gln Asp Val Ser Ile Ala
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Asp Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln His Tyr Ile Thr Pro Leu
                85                  90                  95

Thr Phe Gly Ala Gly Thr Lys Val Glu Ile Lys
            100                 105

<210> SEQ ID NO 109
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 109

Gly Gly Gly Gly Ser Gly Gly Gly Ser Gly Gly Gly Ser
1               5                   10                  15

<210> SEQ ID NO 110
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Gln Val Gln Leu Gln Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Lys Trp Met
            35                  40                  45

Gly Trp Ile Asn Thr Tyr Thr Gly Glu Pro Thr Tyr Thr Asp Asp Phe
        50                  55                  60

Lys Gly Arg Phe Ala Phe Ser Leu Asp Thr Ser Val Ser Thr Ala Tyr
65                  70                  75                  80

Leu Gln Ile Ser Ser Leu Lys Ala Asp Asp Thr Ala Val Tyr Phe Cys
                85                  90                  95

Ala Arg Gly Gly Phe Gly Ser Ser Tyr Trp Tyr Phe Asp Val Trp Gly
            100                 105                 110

Gln Gly Ser Leu Val Thr Val Ser Ser
        115                 120

<210> SEQ ID NO 111
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Gly Gly Gly Gly Ser
1               5

<210> SEQ ID NO 112
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Asp Ile Lys Leu Gln Gln Ser Gly Ala Glu Leu Ala Arg Pro Gly Ala
1               5                   10                  15

Ser Val Lys Met Ser Cys Lys Thr Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80
```

```
Met Gln Leu Ser Ser Leu Thr Ser Glu Asp Ser Ala Val Tyr Tyr Cys
                85                  90                  95

Ala Arg Tyr Tyr Asp Asp His Tyr Cys Leu Asp Tyr Trp Gly Gln Gly
            100                 105                 110

Thr Thr Leu Thr Val Ser Ser
        115

<210> SEQ ID NO 113
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Val Glu Gly Gly Ser Gly Gly Ser Gly Gly Ser Gly Gly Ser Gly Gly
1               5                   10                  15

Val Asp

<210> SEQ ID NO 114
<211> LENGTH: 104
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 114

Asp Ile Gln Leu Thr Gln Ser Pro Ala Ile Met Ser Ala Ser Pro Gly
1               5                   10                  15

Glu Lys Val Thr Met Thr Cys Arg Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Ser Ser Asn Pro Leu Thr
                85                  90                  95

Phe Gly Ala Gly Thr Lys Leu Glu
            100

<210> SEQ ID NO 115
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Ala Ser Gln Asp Val Ser Ile Ala Val Ala
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Description of Artificial Sequence: Synthetic
```

```
                        peptide

<400> SEQUENCE: 116

Ser Ala Ser Tyr Arg Tyr Thr
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln His Tyr Ile Thr Pro Leu Thr
1               5

<210> SEQ ID NO 118
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Asn Tyr Gly Met Asn
1               5

<210> SEQ ID NO 119
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Trp Ile Asn Thr Tyr Thr Gly Glu Pro Thr Tyr Thr Asp Asp Phe Lys
1               5                   10                  15

Gly

<210> SEQ ID NO 120
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Gly Gly Phe Gly Ser Ser Tyr Trp Tyr Phe Asp Val
1               5                   10
```

DISEASE THERAPY BY INDUCING IMMUNE RESPONSE TO TROP-2 EXPRESSING CELLS

CROSS REFERENCE TO RELATED APPLICATIONS

This application is a continuation of U.S. patent application Ser. No. 14/600,560 (now issued U.S. Pat. No. 9,382,329), which claimed the benefit under 35 U.S.C. 119(e) of provisional U.S. Patent Application No. 61/942,752, filed Feb. 21, 2014, and 62/049,826, filed Sep. 12, 2104. U.S. Ser. No. 14/600,560 was a continuation-in-part of U.S. patent application Ser. No. 14/106,737, filed Dec. 14, 2013, which was a continuation-in-part of U.S. patent application Ser. No. 13/966,450 (now U.S. issued U.S. Pat. No. 9,315,567), filed Aug. 14, 2013, which claimed the benefit under 35 U.S.C. 119(e) of provisional U.S. Patent Applications 61/682,965, filed Aug. 14, 2012; 61/733,268, filed Dec. 4, 2012, and 61/807,998, filed Apr. 3, 2013. Each priority application is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Dec. 29, 2014, is named IBC140US1_SL and is 62,950 bytes in size.

FIELD

The present invention concerns compositions and methods of use of bispecific antibodies targeting Trop-2 and CD3, that are capable of inducing an immune response against Trop-2 expressing cells, such as Trop-2$^+$ cancer cells. Preferably, the bispecific antibody is administered in combination with one or more other therapeutic agents, such as an antibody-drug conjugate, an interferon such as such as interferon-$\alpha$, interferon-$\beta$ or interferon-$\lambda$, or a checkpoint inhibitor antibody. More preferably, the bispecific antibody is an anti-Trop-2×anti-CD3 antibody that is administered in combination with interferon-$\alpha$. Most preferably, the anti-Trop-2 antibody is a hRS7 antibody. The compositions and methods are of use to treat Trop-2$^+$ tumors, such as carcinomas of the esophagus, pancreas, lung, stomach, colon and rectum, urinary bladder, breast, ovary, uterus, kidney and prostate, more preferably pancreatic cancer or gastric cancer. In preferred embodiments, the bispecific antibody is made as a DOCK-AND-LOCK™ complex, in which the components are attached together using the binding interaction between dimerization and docking domain (DDD) moieties from human protein kinase A (PKA) regulatory subunits and anchor domain (AD) moieties from AKAPs (A-kinase anchor proteins). However, other methods of making bispecific antibody complexes are known and may be used. The bispecific antibody redirects effector T cells, monocytes, NK cells or neutrophils to target diseased cells or tissues and induces an immune response against the target.

BACKGROUND

Use of bispecific antibodies (bsAbs) to redirect effector T cells for the targeted killing of tumor cells has shown considerable promise both pre-clinically and clinically (see, e.g., Topp et al., 2012, *Blood* 120:5185-87; Bargou et al., 2008, *Science* 321:974-77). The bispecific antibodies developed to date contain a first binding site specific to CD3 for T-cell recruitment and activation and a second binding site for a targeted disease-associated antigen, such as CD19 (Bassan, 2012, *Blood* 120:5094-95). The bispecific antibody brings CD3$^+$ T cells into direct contact with targeted disease cells and induces cell-mediated cytotoxicity (Bassan, 2012). Anti-CD3×anti-CD19 bispecific antibodies have been reported to produce a complete and durable molecular remission at very low concentrations in approximately 70% of adult patients with MRD$^+$ ALL (Topp et al., 2012, *Blood* 120:5185-87). Bispecific antibodies recognizing gliomas and the CD3 epitope on T cells have been successfully used in treating brain tumors in human patients (Nitta, et al. *Lancet* 1990; 355:368-371).

Leukocyte redirecting bsAbs are not limited to T cells. The bispecific killer engagers (BiKEs) comprising scFvs against the NK cell antigen CD16 and a tumor-associated antigen (e.g., CD19, CD22, CD33) have also shown potent anti-cancer activity (e.g., Miller, Hematology Soc Hematol Educ Pogram 2013:247-53). Other alternatives include trispecific killer engagers (TriKEs), such as anti-CD16×anti-CD19×anti-CD22 (Miller, 2013; Gleason et al., 2012, Mol Cancer Ther 11:2674-84). An anti-CD16×anti-CD33 BiKE was used to treat AML and myelodysplastic syndrome (Miller, 2013; Wiernik et al., 2013, Clin Cancer Res 19:3844-55). In refractory AML, a CD16×CD33 BiKE led to potent tumor cell killing and cytokine production by NK cells. Inhibition of ADAM17 enhanced the CD16×CD33 BiKE response (Miller, 2013). Other trispecific, trivalent constructs, for example against CD16/CD19/HLA-DR, have been reported (Schubert et al., 2012, mAbs 4:45-56).

Numerous methods to produce bispecific antibodies are known (see, e.g. U.S. Pat. No. 7,405,320). Bispecific antibodies can be produced by the quadroma method, which involves the fusion of two different hybridomas, each producing a monoclonal antibody recognizing a different antigenic site (Milstein and Cuello, *Nature* 1983; 305:537-540). The fused hybridomas are capable of synthesizing two different heavy chains and two different light chains, which can associate randomly to give a heterogeneous population of 10 different antibody structures of which only one of them, amounting to ⅛ of the total antibody molecules, will be bispecific, and therefore must be further purified from the other forms. Fused hybridomas are often less stable cytogenetically than the parent hybridomas, making the generation of a production cell line more problematic.

Another method for producing bispecific antibodies uses heterobifunctional cross-linkers to chemically tether two different monoclonal antibodies, so that the resulting hybrid conjugate will bind to two different targets (Staerz, et al. *Nature* 1985; 314:628-631; Perez, et al. *Nature* 1985; 316:354-356). Bispecific antibodies generated by this approach are essentially heteroconjugates of two IgG molecules, which diffuse slowly into tissues and are rapidly removed from the circulation. Bispecific antibodies can also be produced by reduction of each of two parental monoclonal antibodies to the respective half molecules, which are then mixed and allowed to reoxidize to obtain the hybrid structure (Staerz and Bevan. *Proc Natl Acad Sci USA* 1986; 83:1453-1457). An alternative approach involves chemically cross-linking two or three separately purified Fab' fragments using appropriate linkers. All these chemical methods are undesirable for commercial development due to high manufacturing cost, laborious production process, extensive purification steps, low yields (<20%), and heterogeneous products.

Discrete $V_H$ and $V_L$ domains of antibodies produced by recombinant DNA technology may pair with each other to form a dimer (recombinant Fv fragment) with binding capability (U.S. Pat. No. 4,642,334). However, such non-covalently associated molecules are not sufficiently stable under physiological conditions to have any practical use. Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFv-based agents of multivalency and multispecificity by varying the linker length were disclosed in U.S. Pat. No. 5,844,094, U.S. Pat. No. 5,837,242 and WO 98/44001. Common problems that have been frequently associated with generating scFv-based agents of multivalency and multispecificity are low expression levels, heterogeneous products, instability in solution leading to aggregates, instability in serum, and impaired affinity.

Several bispecific antibodies targeting CD3 and CD19 are in clinical development. An scFv-based bispecific antibody construct, known as BITE® (Bispecific T-cell Engager), employs a single polypeptide containing 2 antigen-binding specificities, each contributed by a cognate VH and VL, linked in tandem via a flexible linker (see, e.g., Nagorsen et al., 2009, *Leukemia & Lymphoma* 50:886-91; Amann et al., 2009, *J Immunother* 32:453-64; Baeuerle and Reinhardt, 2009, *Cancer Res* 69:4941-44). Another bispecific antibody called DART® (Dual-Affinity Re-Targeting) utilizes a disulfide-stabilized diabody design (see, e.g., Moore et al., 2011, *Blood* 117:4542-51; Veri et al., 2010, *Arthritis Rheum* 62:1933-43). Both BITE® and DART® exhibit fast blood clearance due to their small size (~55 kDa), which requires frequent administration to maintain therapeutic levels of the bispecific antibodies.

Interferons are critical role players in the antitumor and antimicrobial host defense, and have been extensively explored as therapeutic agents for cancer and infectious disease (Billiau et al., 2006, Cytokine Growth Factor Rev 17:381-409; Pestka et al., 2004, Immunol Rev 202:8-32). Despite considerable efforts with type I and II interferons (IFN-α/β and γ), their use in clinic settings have been limited because of the short circulation half-life, systemic toxicity, and suboptimal responses in patients (Pestka et al., 2004, Immunol Rev 202:8-32; Miller et al., 2009, Ann N Y Acad Sci 1182:69-79). The discovery of the IFN-λ family in early 2003 brought an exciting new opportunity to develop alternative IFN agents for these unmet clinical indications (Kotenko et al., 2003, Nat Immunol 4:69-77; Sheppard et al., 2003, Nat Immunol 4:63-8).

The therapeutic effectiveness of IFNs has been validated to date by the approval of IFN-α2 for treating hairy cell leukemia, chronic myelogenous leukemia, malignant melanoma, follicular lymphoma, condylomata *acuminata*, AIDs-related Kaposi sarcoma, and chronic hepatitis B and C; IFN-β for treating multiple sclerosis; and IFN-γ for treating chronic granulomatous disease and malignant osteopetrosis. Despite a vast literature on this group of autocrine and paracrine cytokines, their functions in health and disease are still being elucidated, including more effective and novel forms being introduced clinically (Pestka, 2007, J. Biol. Chem 282:20047-51; Vilcek, 2006, Immunity 25:343-48). The effects of combination of various interferons with antibody-based therapies also remain under investigation.

Antibody-drug conjugates (ADCs) are a potent class of therapeutic constructs that allow targeted delivery of cytotoxic agents to target cells, such as cancer cells. Because of the targeting function, these compounds show a much higher therapeutic index compared to the same systemically delivered agents. ADCs have been developed as intact antibodies or antibody fragments, such as scFvs. The antibody or fragment is linked to one or more copies of drug via a linker that is stable under physiological conditions, but that may be cleaved once inside the target cell. ADCs approved for therapeutic use include gemtuzumab ozogamicin for AML (subsequently withdrawn from the market), brentuximab vedotin for ALCL and Hodgkin lymphoma, and trastuzumab emtansine for HER2-positive metastatic breast cancer (Verma et al., 2012, N Engl J Med 367:1783-91; Bross et al., 2001, Clin Cancer Res 7:1490-96; Francisco et al., 2003, Blood 102:1458-65). Numerous other candidate ADCs are currently in clinical testing, such as inotuzumab ozogamicin (Pfizer), glembatumomab vedotin (Celldex Therapeutics), SAR3419 (Sanofi-Aventis), SAR56658 (Sanofi-Aventis), AMG-172 (Amgen), AMG-595 (Amgen), BAY-94-9343 (Bayer), BIIB015 (Biogen Idec), BT062 (Biotest), SGN-75 (Seattle Genetics), SGN-CD19A (Seattle Genetics), vorsetuzumab mafodotin (Seattle Genetics), ABT-414 (AbbVie), ASG-5ME (Agensys), ASG-22ME (Agensys), ASG-16M8F (Agensys), IMGN-529 (ImmunoGen), IMGN-853 (ImmunoGen), MDX-1203 (Medarex), MLN-0264 (Millenium), RG-7450 (Roche/Genentech), RG-7458 (Roche/Genentech), RG-7593 (Roche/Genentech), RG-7596 (Roche/Genentech), RG-7598 (Roche/Genentech), RG-7599 (Roche/Genentech), RG-7600 (Roche/Genentech), RG-7636 (Roche/Genentech), anti-PSMA ADC (Progenics), lorvotuzumab mertansine (ImmunoGen), milatuzumab-doxorubicin (Immunomedics), IMMU-130 (Immunomedics), IMMU-132 (Immunomedics) and antibody conjugates of pro-2-pyrrolinodoxorubicin. (See, e.g., Li et al., 2013, Drug Disc Ther 7:178-84; Firer & Gellerman, J Hematol Oncol 5:70; Beck et al., 2010, Discov Med 10:329-39; Mullard, 2013, Nature Rev Drug Discovery 12:329, Provisional U.S. Patent Application 61/761,845.) Because of the potential of ADCs to act as potent anti-cancer agents with reduced systemic toxicity, they may be used either alone or as an adjunct therapy to reduce tumor burden.

Another promising approach to immunotherapy concerns use of antagonistic antibodies against immune checkpoint proteins (e.g., Pardoll, 2012, Nature Reviews Cancer 12:252-64). Immune checkpoints function as endogenous inhibitory pathways for immune system function that act to maintain self-tolerance and to modulate the duration and extent of immune response to antigenic stimulation (Pardoll, 2012). However, it appears that tumor tissues and possibly certain pathogens may co-opt the checkpoint system to reduce the effectiveness of host immune response, resulting in tumor growth and/or chronic infection (see, e.g., Pardoll, 2012, Nature Reviews Cancer 12:252-64; Nirschl & Drake, 2013, Clin Cancer Res 19:4917-24). Checkpoint molecules include CTLA4 (cytotoxic T lymphocyte antigen-4), PD1 (programmed cell death protein 1), PD-L1 (programmed cell death ligand 1), LAG-3 (lymphocyte activation gene-3), TIM-3 (T cell immunoglobulin and mucin protein-3) and several others (Pardoll, 2012, Nature Reviews Cancer 12:252-64; Nirschl & Drake, 2013, Clin Cancer Res 19:4917-24). Antibodies against several of the checkpoint proteins (CTLA4, PD1, PD-L1) are in clinical trials and has shown unexpected efficacy against tumors that were resistant to standard treatments.

A need exists for methods and compositions to generate improved bispecific antibody complexes with longer $T_{1/2}$, better pharmacokinetic properties, increased in vivo stability and/or improved in vivo efficacy. A further need exists for combination therapies to improve efficacy of treatments directed to inducing immune response against various diseases, such as Trop-2+ cancer.

SUMMARY

The present invention relates to bispecific antibodies of use to treat diseases involving Trop-2+ cells, such as Trop-2+ cancer cells. Trop-2 is overexpressed in numerous types of solid tumors, such as carcinomas of the esophagus, pancreas, lung, stomach, colon and rectum, urinary bladder, breast, ovary, uterus, cervix, kidney and prostate. Preferably, the bispecific antibody is of use to treat gastric cancer or pancreatic cancer. Administration of the bispecific antibody induces an immune response to cells that are Trop-2+. Although Trop-2 is also expressed in some normal tissues (e.g., Stepan et al., 2011, J Histochem Cytochem 59:701-10), the Examples below demonstrate that anti-Trop-2 antibodies may be administered in vivo in both animal model systems and human subjects, with only tolerable toxicities. In other preferred embodiments, administration of bispecific antibody to a subject induces an immune response against Trop-2+ cancer cells without elevating levels of cytokines that would induce cytokine release syndrome (CRS). In alternative preferred embodiments, the bispecific antibody induces trogocytosis of cell surface antigens between Trop-2+ cancer cells and T cells.

In preferred embodiments, the bispecific antibody contains binding sites for Trop-2 and for CD3. However, other T cell or leukocyte antigens may be targeted besides CD3. Exemplary T-cell antigens are selected from the group consisting of CD2, CD3, CD4, CD5, CD6, CD8, CD25, CD28, CD30, CD40, CD40L, CD44, CD45, CD69 and CD90. Exemplary antigens expressed on NK cells are selected from the group consisting of CD8, CD16, CD56, CD57, ADAM17, KIR and CD137. Exemplary monocyte antigens are selected from the group consisting of CD74, HLA-DR alpha chain, CD14, CD16, CD64 and CD89. Exemplary neutrophil antigens are selected from the group consisting of CEACAM6, CEACAM8, CD16b, CD32a, CD89, CD177, CD11a, CD11b and SLC44A2. Preferably the T-cell antigen is CD3, or the NK cell antigen is CD16.

In alternative embodiments, other tumor-associated antigens besides Trop-2 may be targeted. Tumor-associated antigens that may be targeted include, but are not limited to, alpha-fetoprotein (AFP), α-actinin-4, A3, antigen specific for A33 antibody, ART-4, B7, Ba 733, BAGE, BrE3-antigen, CA125, CAMEL, CAP-1, carbonic anhydrase IX, CASP-8/m, CCCL19, CCCL21, CD1, CD1a, CD2, CD3, CD4, CD5, CD8, CD11A, CD14, CD15, CD16, CD18, CD19, CD20, CD21, CD22, CD23, CD25, CD29, CD30, CD32b, CD33, CD37, CD38, CD40, CD40L, CD44, CD45, CD46, CD52, CD54, CD55, CD59, CD64, CD66a-e, CD67, CD70, CD70L, CD74, CD79a, CD79b, CD80, CD83, CD95, CD126, CD132, CD133, CD138, CD147, CD154, CDC27, CDK-4/m, CDKN2A, CTLA4, CXCR4, CXCR7, CXCL12, HIF-1α, colon-specific antigen-p (CSAp), CEA (CEACAM5), CEACAM6, c-Met, DAM, EGFR, EGFRvIII, EGP-1 (TROP-2), EGP-2, ELF2-M, Ep-CAM, fibroblast growth factor (FGF), Flt-1, Flt-3, folate receptor, G250 antigen, GAGE, gp100, GRO-β, HLA-DR, HM1.24, human chorionic gonadotropin (HCG) and its subunits, HER2/neu, HMGB-1, hypoxia inducible factor (HIF-1), HSP70-2M, HST-2, Ia, IGF-1R, IFN-γ, IFN-α, IFN-β, IFN-λ, IL-4R, IL-6R, IL-13R, IL-15R, IL-17R, IL-18R, IL-2, IL-6, IL-8, IL-12, IL-15, IL-17, IL-18, IL-23, IL-25, insulin-like growth factor-1 (IGF-1), KC4-antigen, KS-1-antigen, KS1-4, Le-Y, LDR/FUT, macrophage migration inhibitory factor (MIF), MAGE, MAGE-3, MART-1, MART-2, NY-ESO-1, TRAG-3, mCRP, MCP-1, MIP-1A, MIP-1B, MIF, MUC1, MUC2, MUC3, MUC4, MUC5ac, MUC13, MUC16, MUM-1/2, MUM-3, NCA66, NCA95, NCA90, PAM4 antigen, pancreatic cancer mucin, PD1 receptor, placental growth factor, p53, PLAGL2, prostatic acid phosphatase, PSA, PRAME, PSMA, PlGF, ILGF, ILGF-1R, IL-6, IL-25, RS5, RANTES, T101, SAGE, S100, survivin, survivin-2B, TAC, TAG-72, tenascin, TRAIL receptors, TNF-α, Tn antigen, Thomson-Friedenreich antigens, tumor necrosis antigens, VEGFR, ED-B fibronectin, WT-1, 17-1A-antigen, complement factors C3, C3a, C3b, C5a, C5, an angiogenesis marker, bcl-2, bcl-6, Kras, an oncogene marker and an oncogene product (see, e.g., Sensi et al., Clin Cancer Res 2006, 12:5023-32; Parmiani et al., J Immunol 2007, 178:1975-79; Novellino et al. Cancer Immunol Immunother 2005, 54:187-207).

Exemplary anti-TAA antibodies that may be used include, but are not limited to, hA19 (anti-CD19, U.S. Pat. No. 7,109,304), hR1 (anti-IGF-1R, U.S. patent application Ser. No. 12/722,645, filed Mar. 12, 2010), hPAM4 (anti-MUC5ac, U.S. Pat. No. 7,282,567), hA20 (anti-CD20, U.S. Pat. No. 7,251,164), hIMMU31 (anti-AFP, U.S. Pat. No. 7,300,655), hLL1 (anti-CD74, U.S. Pat. No. 7,312,318), hLL2 (anti-CD22, U.S. Pat. No. 7,074,403), hMu-9 (anti-CSAp, U.S. Pat. No. 7,387,773), hL243 (anti-HLA-DR, U.S. Pat. No. 7,612,180), hMN-14 (anti-CEACAM5, U.S. Pat. No. 6,676,924), hMN-15 (anti-CEACAM6, U.S. Pat. No. 7,541,440), hRS7 (anti-EGP-1, U.S. Pat. No. 7,238,785), hMN-3 (anti-CEACAM6, U.S. Pat. No. 7,541,440), Ab124 and Ab125 (anti-CXCR4, U.S. Pat. No. 7,138,496), the Examples section of each cited patent or application incorporated herein by reference.

Alternative antibodies that may be used for treatment of various disease states include, but are not limited to, abciximab (anti-glycoprotein IIb/IIIa), alemtuzumab (anti-CD52), bevacizumab (anti-VEGF), cetuximab (anti-EGFR), gemtuzumab (anti-CD33), ibritumomab (anti-CD20), panitumumab (anti-EGFR), rituximab (anti-CD20), tositumomab (anti-CD20), trastuzumab (anti-ErbB2), lambrolizumab (anti-PD1 receptor), nivolumab (anti-PD1 receptor), ipilimumab (anti-CTLA4), abagovomab (anti-CA-125), adecatumumab (anti-EpCAM), atlizumab (anti-IL-6 receptor), benralizumab (anti-CD125), obinutuzumab (GA101, anti-CD20), CC49 (anti-TAG-72), AB-PG1-XG1-026 (anti-PSMA, U.S. patent application Ser. No. 11/983,372, deposited as ATCC PTA-4405 and PTA-4406), D2/B (anti-PSMA, WO 2009/130575), tocilizumab (anti-IL-6 receptor), basiliximab (anti-CD25), daclizumab (anti-CD25), efalizumab (anti-CD11a), GA101 (anti-CD20; Glycart Roche), atalizumab (anti-α4 integrin), omalizumab (anti-IgE); anti-TNF-α antibodies such as CDP571 (Ofei et al., 2011, Diabetes 45:881-85), MTNFAI, M2TNFAI, M3TNFAI, M3TNFABI, M302B, M303 (Thermo Scientific, Rockford, Ill.), infliximab (Centocor, Malvern, Pa.), certolizumab pegol (UCB, Brussels, Belgium), anti-CD40L (UCB, Brussels, Belgium), adalimumab (Abbott, Abbott Park, Ill.), BENLYSTA® (Human Genome Sciences); anti-CD38 antibodies such as MOR03087 (MorphoSys AG), MOR202 (Celgene), HuMax-CD38 (Genmab) or daratumumab (Johnson & Johnson).

Preferably, the bispecific antibody is administered in combination with one or more other therapeutic agents, such as antibodies, antibody fragments, peptides, drugs, toxins, chemotherapeutic agents, enzymes, nucleases, hormones, immunomodulators, antisense oligonucleotides, small interfering RNA (siRNA), chelators, boron compounds, photoactive agents, dyes, and radioisotopes. More preferably, the additional therapeutic agent is an antibody-drug conjugate, an interferon such as such as interferon-α, interferon-β or interferon-λ, or an antagonistic checkpoint inhibitor antibody. Most preferably, the therapeutic agent is interferon-α.

An exemplary design for a leukocyte redirecting bsAb disclosed in the Examples below combined an anti-CD3 scFv with an anti-CD19 F(ab)$_2$ to form a construct designated (19)-3s, which specifically targeted B cells. Other bsAbs combining anti-CD3 with antibody fragments against other tumor-associated antigens, discussed in more detail below, are of use in targeted leukocyte immunotherapy of various solid tumors. The advantages of this design include bivalent binding to tumor cells, a larger size (~130 kDa) to preclude rapid renal clearance, and potent leukocyte mediated cytotoxicity. The bsAbs mediate the formation of immunological synapses between leukocytes and cognate target cells, induce leukocyte activation and proliferation in the presence of target cells, redirect potent leukocyte mediated killing of target cells in vitro and inhibit growth of human tumors in vivo.

A preferred embodiment concerns leukocyte redirecting bispecific antibodies produced as trivalent DNL™ complexes, with longer $T_{1/2}$, better pharmacokinetic properties and increased in vivo stability. Methods for production and use of DNL™ complexes, comprising dimers of DDD moieties from human PKA regulatory subunits RIα, RIβ, RIIα or RIIβ, bound to AD moieties from AKAPs, are well known (see, e.g., U.S. Pat. Nos. 7,550,143; 7,521,056; 7,534,866; 7,527,787; 7,666,400; 7,906,118; 7,901,680; 8,003,111 and 8,034,352, the Examples section of each incorporated herein by reference.) By attaching different effector moieties, such as antibodies or antibody fragments, to the DDD and AD moieties, DNL™ complexes comprising virtually any combination of effectors may be constructed and used.

The antibodies of use can be of various isotypes, preferably human IgG1, IgG2, IgG3 or IgG4, more preferably comprising human IgG1 hinge and constant region sequences. The antibodies or fragments thereof can be chimeric human-mouse, humanized (human framework and murine hypervariable (CDR) regions), or fully human, as well as variations thereof, such as half-IgG4 antibodies (referred to as "unibodies"), as described by van der Neut Kolfschoten et al. (*Science* 2007; 317:1554-1557). More preferably, the antibodies or fragments thereof may be designed or selected to comprise human constant region sequences that belong to specific allotypes, which may result in reduced immunogenicity when administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes.

Other preferred embodiments concern compositions and/or use of leukocyte-redirecting complexes in combination with one or more checkpoint inhibitor antibodies. Such antibodies are antagonistic for checkpoint inhibitor function. Many such antibodies are known in the art, such as lambrolizumab (MK-3475, Merck), nivolumab (BMS-936558, Bristol-Myers Squibb), pidilizumab (CT-011, CureTech Ltd.), AMP-224 (Merck), MDX-1105 (Medarex), MEDI4736 (MedImmune), MPDL3280A (Genentech), BMS-936559 (Bristol-Myers Squibb), ipilimumab (Bristol-Myers Squibb) and tremelimumab (Pfizer). Anti-KIR antibodies such as lirilumab (Innate Pharma) and IPH2101 (Innate Pharma) may perform similar functions in NK cells.

Any known checkpoint inhibitor antibody may be used in combination with one or more of the other agents. Combination therapy with immunostimulatory antibodies has been reported to enhance efficacy, for example against tumor cells. Morales-Kastresana et al. (2013, Clin Cancer Res 19:6151-62) showed that the combination of anti-PD-L1 (10B5) antibody with anti-CD137 (1D8) and anti-OX40 (OX86) antibodies provided enhanced efficacy in a transgenic mouse model of hepatocellular carcinoma. Combination of anti-CTLA4 and anti-PD1 antibodies has also been reported to be highly efficacious (Wolchok et al., 2013, N Engl J Med 369:122-33). Combination of rituximab with anti-KIR antibody, such as lirilumab (Innate Pharma) or IPH2101 (Innate Pharma), was also more efficacious against hematopoietic tumors (Kohrt et al., 2012). The person of ordinary skill will realize that the subject combination therapy may include combinations with multiple antibodies that are immunostimulatory, anti-tumor or anti-infectious agent.

Another agent that may be used in combination is an interferon. Interferons of use are known in the art and may include interferon-α, interferon-β, interferon-λ1, interferon-λ2 or interferon-λ3. Preferably, the interferon is interferon-α. The subject interferon may be administered as free interferon, PEGylated interferon, an interferon fusion protein or interferon conjugated to an antibody.

In alternative embodiments, one or more of the immunomodulatory agents discussed above may be used in combination with an antibody-drug conjugate (ADC). ADCs are particularly effective for reducing tumor burden without significant systemic toxicity and may act to improve the effectiveness of the immune response induced by leukocyte retargeting bsAb, interferon and/or checkpoint inhibitor antibody. Exemplary ADCs of use may include ADCs approved for therapeutic use include gemtuzumab ozogamicin for AML (subsequently withdrawn from the market), brentuximab vedotin for ALCL and Hodgkin lymphoma, and trastuzumab emtansine for HER2-positive metastatic breast cancer (Verma et al., 2012, N Engl J Med 367:1783-91; Bross et al., 2001, Clin Cancer Res 7:1490-96; Francisco et al., 2003, Blood 102:1458-65). Numerous other candidate ADCs are currently in clinical testing, such as inotuzumab ozogamicin (Pfizer), glembatumomab vedotin (Celldex Therapeutics), SAR3419 (Sanofi-Aventis), SAR56658 (Sanofi-Aventis), AMG-172 (Amgen), AMG-595 (Amgen), BAY-94-9343 (Bayer), BIIB015 (Biogen Idec), BT062 (Biotest), SGN-75 (Seattle Genetics), SGN-CD19A (Seattle Genetics), vorsetuzumab mafodotin (Seattle Genetics), ABT-414 (AbbVie), ASG-5ME (Agensys), ASG-22ME (Agensys), ASG-16M8F (Agensys), IMGN-529 (ImmunoGen), IMGN-853 (ImmunoGen), MDX-1203 (Medarex), MLN-0264 (Millenium), RG-7450 (Roche/Genentech), RG-7458 (Roche/Genentech), RG-7593 (Roche/Genentech), RG-7596 (Roche/Genentech), RG-7598 (Roche/Genentech), RG-7599 (Roche/Genentech), RG-7600 (Roche/Genentech), RG-7636 (Roche/Genentech), anti-PSMA ADC (Progenics), lorvotuzumab mertansine (ImmunoGen), milatuzumab-doxorubicin (Immunomedics), IMMU-130 (Immunomedics) and IMMU-132 (Immunomedics). (See, e.g., Li et al., 2013, Drug Disc Ther 7:178-84; Firer & Gellerman, J Hematol Oncol 5:70; Beck et al., 2010, Discov Med 10:329-39; Mullard, 2013, Nature Rev Drug Discovery 12:329.) Preferably, where an ADC is used in combination with an immunomodulator, the ADC is administered prior to the immunomodulator.

The subject agents may be administered in combination with one or more other immunomodulators to enhance the immune response. Immunomodulators may include, but are not limited to, a cytokine, a chemokine, a stem cell growth factor, a lymphotoxin, an hematopoietic factor, a colony stimulating factor (CSF), erythropoietin, thrombopoietin, tumor necrosis factor-α (TNF), TNF-β, granulocyte-colony stimulating factor (G-CSF), granulocyte macrophage-colony stimulating factor (GM-CSF), interferon-α, interferon-β, interferon-γ, interferon-λ, stem cell growth factor designated "S1 factor", human growth hormone, N-methionyl human growth hormone, bovine growth hormone, parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, mullerian-inhibiting substance, mouse gonadotropin-associated peptide, inhibin, activin, vascular endothelial growth factor, integrin, NGF-β, platelet-growth factor, TGF-α, TGF-β, insulin-like growth factor-I, insulin-like growth factor-II, macrophage-CSF (M-CSF), IL-1, IL-1α, IL-2, IL-3, IL-4, IL-5, IL-6, IL-7, IL-8, IL-9, IL-10, IL-11, IL-12, IL-13, IL-14, IL-15, IL-16, IL-17, IL-18, IL-21, IL-25, LIF, FLT-3, angiostatin, thrombospondin, endostatin, or lymphotoxin. In certain embodiments, a leukocyte-redirecting bispecific antibody or antibody fragment may be attached to an immunomodulator, such as a cytokine. Cytokine complexes are disclosed, for example, in U.S. Pat. Nos. 7,906,118 and 8,034,3522, the Examples section of each incorporated herein by reference.

BRIEF DESCRIPTION OF THE DRAWINGS

The following drawings form part of the present specification and are included to further demonstrate certain embodiments of the present invention. The embodiments may be better understood by reference to one or more of these drawings in combination with the detailed description of specific embodiments presented herein.

FIG. 3A. Jurkat (T cells) and Daudi (B cells) were combined at a 1:1 ratio, treated with 0.1 μg/mL (19)-3s for 30 minutes and stained with anti-CD20-FITC, prior to analysis by fluorescence microscopy.

FIG. 3B. Jurkat (T cells) and Daudi (B cells) were combined at a 1:1 ratio, treated with 0.1 μg/mL (19)-3s for 30 minutes and stained with anti-CD20-FITC and anti-CD3-PE, prior to analysis by fluorescence microscopy.

FIG. 3C. The merged image of FIGS. 3A and 3B reveals synapse formation between green-stained Daudi and red-stained Jurkat cells.

FIG. 3D. Synapse formation was not evident in the absence of (19)-3s.

FIG. 6A. Synapse formation between T cells and Capan-1 pancreatic cancer cells mediated by (19)-3s control bsAb. CFSE-labeled Capan-1 cells were coincubated with PKH26-labeled Jurkat in the presence of the bsAb.

FIG. 6B. Synapse formation between T cells and Capan-1 pancreatic cancer cells mediated by (M1)-3s MUC5AC bsAb. CFSE-labeled Capan-1 cells were coincubated with PKH26-labeled Jurkat in the presence of the bsAb.

FIG. 6C. Synapse formation between T cells and Capan-1 pancreatic cancer cells mediated by (E1)-3s TROP-2 targeting bsAb. CFSE-labeled Capan-1 cells were coincubated with PKH26-labeled Jurkat in the presence of the bsAb.

FIG. 7A. T-cell activation by (19)-3s. Upregulation of CD69 expression is an early event in T-cell activation. Daudi cells combined with PBMCs were treated overnight with the indicated antibodies, and stained with anti-CD3-PE and anti-CD69-APC, prior to analysis by flow cytometry. CD69 expression was evaluated following gating of T cells by forward vs. side scattering and anti-CD3 staining. Combination of Daudi cells with an equal number of PBMCs resulted in 1.6% CD69+ T cells. Addition of 3 ng/mL (19)-3s induced 27% CD69+ T cells. Neither a control construct [(M1)-3s], which comprises the Okt3-scFv-AD2 module fused with a non-targeting F(ab)$_2$, nor the hA19-Fab-DDD2 module, induced T-cell activation.

FIG. 7B. T-cell activation by (19)-3s. Daudi cells combined with purified T cells were treated overnight with the indicated antibodies, and stained with anti-CD3-PE and anti-CD69-APC, prior to analysis by flow cytometry. CD69 expression was evaluated following gating of T cells by forward vs. side scattering and anti-CD3 staining. Treatment of Daudi and purified T cells with (M1)-3s or hA19-Fab-DDD2 did not increase the number of CD69+ T cells (<4%), compared to the untreated cell mixture. Alternatively, (19)-3s induced robust T-cell activation, producing 80% CD69+ cells.

FIG. 7C. T-cell activation by (19)-3s. Purified T cells alone were treated overnight with the indicated antibodies, and stained with anti-CD3-PE and anti-CD69-APC, prior to analysis by flow cytometry. CD69 expression was evaluated following gating of T cells by forward vs. side scattering and anti-CD3 staining. Without the addition of Daudi (target) cells, (19)-3s did not induce CD69 expression and T-cell activation. These results demonstrate that (19)-3s-mediated synapse formation between T cells and target cells is both required and sufficient for T-cell activation.

FIG. 8A. Induction of T-cell proliferation by (19)-3s. PBMCs were incubated with 3 nM or 30 pM of (19)-3s, compared to IL-2/PHA positive control and (14)-3s (non-target-binding control).

FIG. 8B. Induction of T-cell proliferation by (19)-3s. T cell proliferation was not observed in PBMCs depleted of B cells, indicating that target cells (B cells) are required for T-cell activation and proliferation.

FIG. 9A. In vitro cytotoxicity of (19)-3s T-cell redirecting bsAbs. Dose-response curves for cytotoxicity to Nalm-6, Raji, Ramos and Namalwa cancer cells were determined for the (19)-3s DNL™ bsAb complex.

FIG. 9B. In vitro cytotoxicity of (19)-3s T-cell redirecting bsAbs. Dose-response curves for cytotoxicity to Nalm-6, Raji, Ramos and Namalwa cancer cells were determined for the (14)-3s (non-targeting) DNL™ bsAb complex.

FIG. 9C. Consistent results were observed using PBMCs, or T cells, obtained from two different donors and Nalm-6 cancer cells.

FIG. 12. Summary of in vitro cytotoxicity data for T-cell redirecting bsAbs in cancer cell lines.

FIG. 14A. Effect of repeated dosing on in vivo retargeting of Raji lymphoma xenografts using (19)-3s bsAb. NOD/SCID mouse xenografts were prepared as indicated in the legend to FIG. 13. The (19)-3s was administered as indicated by the arrows. FIG. 14A shows untreated control.

FIG. 14B. Effect of repeated dosing on in vivo retargeting of Raji lymphoma xenografts using (19)-3s bsAb. The (19)-3s was administered as indicated by the arrows. Cells were treated 2× with 130 µg per dose of (19)-3s administered i.v.

FIG. 14C. Effect of repeated dosing on in vivo retargeting of Raji lymphoma xenografts using (19)-3s bsAb. The (19)-3s was administered as indicated by the arrows. Cells were treated treated 2× with 130 µg per dose of (19)-3s administered s.c.

FIG. 14D. Effect of repeated dosing on in vivo retargeting of Raji lymphoma xenografts using (19)-3s bsAb. The (19)-3s was administered as indicated by the arrows. Cells were treated treated 4× with 65 µg per dose of (19)-3s administered i.v.

FIG. 14E. Effect of repeated dosing on in vivo retargeting of Raji lymphoma xenografts using (19)-3s bsAb. The (19)-3s was administered as indicated by the arrows. Cells were treated treated 6× with 43 µg per dose of (19)-3s administered i.v.

FIG. 14F. Effect of repeated dosing on in vivo retargeting of Raji lymphoma xenografts using (19)-3s bsAb. The (19)-3s was administered as indicated by the arrows. Cells were treated treated 6× with 43 µg per dose of control (M1)-3s administered i.v.

FIG. 29A. T-cell activation. Purified T cells were mixed 5:1 with NCI-N87 cells and treated for 18 h with (E1)-3s before measuring CD69 expression by flow cytometry. Non-linear regression analysis (sigmoidal dose-response) of the percent CD69-positive $CD4^+$ (●) or $CD8^+$ (■) T cells vs the log of the molar concentration of (E1)-3s, in the presence (dashed line) or absence (solid line) of 0.1 nM peginterferonalfa-2a.

FIG. 30A. In-vivo efficacy with human pancreatic and gastric cancer xenografts. Groups of 8 mice inoculated with human T cells and Capan-1 pancreatic cancer cells were treated daily for five days with 50 μg of (E1)-3s (▲, solid black) or 60 μg TF12 (▼, gray), once weekly for four weeks with 0.6 μg of peginterferonalfa-2a (*, solid black), a combination of (E1)-3s and peginterferonalfa-2a regimens (●, solid black) or with saline (●, dashed black). An additional group was inoculated with Capan-1, but not T cells, and treated with peginterferonalfa-2a (□, dashed black). Top panel, Kaplan-Meyer survival plots. Bottom panel, mean tumor volumes (+S.D.) vs days. Data marked with an asterisk were adapted from FIG. 6C in Rossi et al. (2014, MAbs 6:381-91).

FIG. 30B. In-vivo efficacy with human pancreatic and gastric cancer xenografts. Groups of 8 mice inoculated with human T cells and Capan-1 pancreatic cancer cells were treated daily for five days with 50 µg of (E1)-3s (▲, solid black) or 60 µg TF12 (▼, gray), once weekly for four weeks with 0.6 µg of peginterferonalfa-2a (*, solid black), a combination of (E1)-3s and peginterferonalfa-2a regimens (●, solid black) or with saline (●, dashed black). An additional group was inoculated with Capan-1, but not T cells, and treated with peginterferonalfa-2a (□, dashed black). Top panel, Kaplan-Meyer survival plots. Bottom panel, mean tumor volumes (+S.D.) vs days. Data marked with an asterisk were adapted from FIG. 6C in Rossi et al. (2014, MAbs 6:381-91).

FIG. 30C. In-vivo efficacy with human pancreatic and gastric cancer xenografts. Groups of 8 mice inoculated with NCI-N87 gastric cancer cells were treated daily for five days with 50 µg of (E1)-3s (▲, solid black) or 60 µg TF12 (▼, gray), once weekly for four weeks with 0.6 µg of peginterferonalfa-2a (*, solid black), a combination of (E1)-3s and peginterferonalfa-2a regimens (●, solid black) or with saline (●, dashed black). An additional group was inoculated with Capan-1, but not T cells, and treated with peginterferonalfa-2a (□, dashed black). Top panel, Kaplan-Meyer survival plots. Bottom panel, mean tumor volumes (+S.D.) vs days. Data marked with an asterisk were adapted from FIG. 6C in Rossi et al. (2014, MAbs 6:381-91).

DETAILED DESCRIPTION

Definitions

Figure 1:
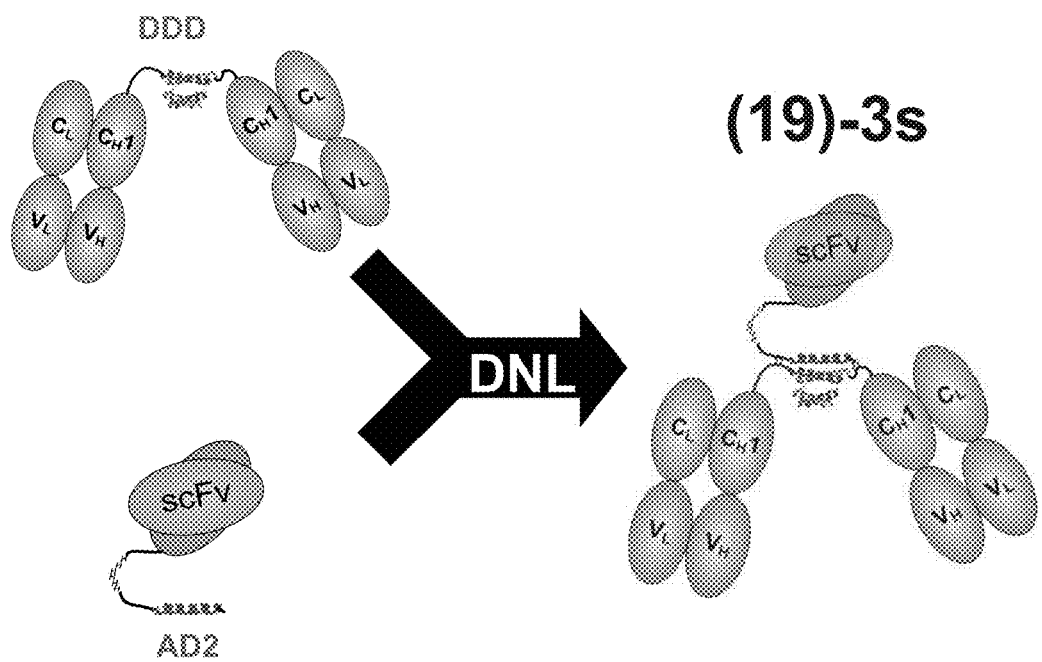
FIG. 1. Schematic diagram of formation of DOCK-AND-LOCK™ complex comprising anti-CD19 F(ab)$_2$×anti-CD3 scFv.

Unless otherwise specified, "a" or "an" means "one or more".

As used herein, the terms "and" and "or" may be used to mean either the conjunctive or disjunctive. That is, both terms should be understood as equivalent to "and/or" unless otherwise stated.

A "therapeutic agent" is an atom, molecule, or compound that is useful in the treatment of a disease. Examples of therapeutic agents include antibodies, antibody fragments, peptides, drugs, toxins, enzymes, nucleases, hormones, immunomodulators, antisense oligonucleotides, small interfering RNA (siRNA), chelators, boron compounds, photoactive agents, dyes, and radioisotopes.

An "antibody" as used herein refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment. An "antibody" includes monoclonal, polyclonal, bispecific, multispecific, murine, chimeric, humanized and human antibodies.

A "naked antibody" is an antibody or antigen binding fragment thereof that is not attached to a therapeutic or diagnostic agent. The Fc portion of an intact naked antibody can provide effector functions, such as complement fixation and ADCC (see, e.g., Markrides, *Pharmacol Rev* 50:59-87, 1998). Other mechanisms by which naked antibodies induce cell death may include apoptosis. (Vaswani and Hamilton, *Ann Allergy Asthma Immunol* 81: 105-119, 1998.)

An "antibody fragment" is a portion of an intact antibody such as F(ab')$_2$, F(ab)$_2$, Fab', Fab, Fv, scFv, dAb and the like. Regardless of structure, an antibody fragment binds with the same antigen that is recognized by the full-length antibody. For example, antibody fragments include isolated fragments consisting of the variable regions, such as the "Fv" fragments consisting of the variable regions of the heavy and light chains or recombinant single chain polypeptide molecules in which light and heavy variable regions are connected by a peptide linker ("scFv proteins"). "Single-chain antibodies", often abbreviated as "scFv" consist of a polypeptide chain that comprises a V$_H$ and a V$_L$ domain which interact to form an antigen-binding site. The V$_H$ and V$_L$ domains are usually linked by a peptide of 1 to 25 amino acid residues. Antibody fragments also include diabodies, triabodies and single domain antibodies (dAb).

A "chimeric antibody" is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A "humanized antibody" is a recombinant protein in which the CDRs from an antibody from one species; e.g., a rodent antibody, are transferred from the heavy and light variable chains of the rodent antibody into human heavy and light variable domains, including human framework region (FR) sequences. The constant domains of the antibody molecule are derived from those of a human antibody. To maintain binding activity, a limited number of FR amino acid residues from the parent (e.g., murine) antibody may be substituted for the corresponding human FR residues.

A "human antibody" is an antibody obtained from transgenic mice that have been genetically engineered to produce specific human antibodies in response to antigenic challenge. In this technique, elements of the human heavy and light chain locus are introduced into strains of mice derived from embryonic stem cell lines that contain targeted disruptions of the endogenous heavy chain and light chain loci. The transgenic mice can synthesize human antibodies specific for human antigens, and the mice can be used to produce human antibody-secreting hybridomas. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994). A human antibody also can be constructed by genetic or chromosomal transfection methods, as well as phage display technology, all of which are known in the art. (See, e.g., McCafferty et al., 1990, *Nature* 348:552-553 for the production of human antibodies and fragments thereof in vitro, from immunoglobulin variable domain gene repertoires from unimmunized donors). In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for their review, see, e.g. Johnson and Chiswell, *Current Opinion in Structural Biology* 3:5564-571 (1993). Human antibodies may also be generated by in vitro activated B cells. (See, U.S. Pat. Nos. 5,567,610 and 5,229,275).

As used herein, the term "antibody fusion protein" is a recombinantly produced antigen-binding molecule in which an antibody or antibody fragment is linked to another protein or peptide, such as the same or different antibody or antibody fragment or a DDD or AD peptide. The fusion protein may comprise a single antibody component, a multivalent or multispecific combination of different antibody components or multiple copies of the same antibody component. The fusion protein may additionally comprise an antibody or an antibody fragment and a therapeutic agent. Examples of therapeutic agents suitable for such fusion proteins include immunomodulators and toxins. One preferred toxin comprises a ribonuclease (RNase), preferably a recombinant RNase. A preferred immunomodulator might be an interferon, such as interferon-α, interferon-β or interferon-λ.

A "multispecific antibody" is an antibody that can bind simultaneously to at least two targets that are of different structure, e.g., two different antigens, two different epitopes on the same antigen, or a hapten and/or an antigen or epitope. A "multivalent antibody" is an antibody that can bind simultaneously to at least two targets that are of the same or different structure. Valency indicates how many binding arms or sites the antibody has to a single antigen or epitope; i.e., monovalent, bivalent, trivalent or multivalent. The multivalency of the antibody means that it can take advantage of multiple interactions in binding to an antigen, thus increasing the avidity of binding to the antigen. Specificity indicates how many antigens or epitopes an antibody is able to bind; i.e., monospecific, bispecific, trispecific, multispecific. Using these definitions, a natural antibody, e.g., an IgG, is bivalent because it has two binding arms but is monospecific because it binds to one epitope. Multispecific, multivalent antibodies are constructs that have more than one binding site of different specificity.

A "bispecific antibody" is an antibody that can bind simultaneously to two targets which are of different structure. Bispecific antibodies (bsAb) and bispecific antibody fragments (bsFab) may have at least one arm that specifically binds to, for example, a T cell, an NK cell, a monocyte or a neutrophil, and at least one other arm that specifically binds to an antigen produced by or associated with a diseased cell, tissue, organ or pathogen, for example a tumor-associated antigen. A variety of bispecific antibodies can be produced using molecular engineering.

An antibody preparation, or a composition described herein, is said to be administered in a "therapeutically effective amount" if the amount administered is physiologically significant. An agent is physiologically significant if its presence results in a detectable change in the physiology of a recipient subject. In particular embodiments, an antibody preparation is physiologically significant if its presence invokes an antitumor response or mitigates the signs and symptoms of an infectious disease state. A physiologically significant effect could also be the evocation of a humoral and/or cellular immune response in the recipient subject leading to growth inhibition or death of target cells.

Anti-Trop-2 Antibodies

In preferred embodiments, the subject bispecific antibody includes at least one antibody or fragment thereof that binds to Trop-2. In a more preferred embodiment, the anti-Trop-2 antibody may is a humanized RS7 antibody (see, e.g., U.S. Pat. No. 7,238,785, incorporated herein by reference in its entirety), comprising the light chain CDR sequences CDR1 (KASQDVSIAVA, SEQ ID NO:115); CDR2 (SASYRYT, SEQ ID NO:116); and CDR3 (QQHYITPLT, SEQ ID NO:117) and the heavy chain CDR sequences CDR1 (NYGMN, SEQ ID NO:118); CDR2 (WINTYTGEPTYTDDFKG, SEQ ID NO:119) and CDR3 (GGFGSSYWYFDV, SEQ ID NO:120).

The RS7 antibody was a murine $IgG_1$ raised against a crude membrane preparation of a human primary squamous cell lung carcinoma. (Stein et al., Cancer Res. 50: 1330, 1990) The RS7 antibody recognizes a 46-48 kDa glycoprotein, characterized as cluster 13. (Stein et al., Int. J. Cancer Supp. 8:98-102, 1994) The antigen was designated as EGP-1 (epithelial glycoprotein-1), but is also referred to as Trop-2.

Trop-2 is a type-I transmembrane protein and has been cloned from both human (Fornaro et al., Int J Cancer 1995; 62:610-8) and mouse cells (Sewedy et al., Int J Cancer 1998; 75:324-30). In addition to its role as a tumor-associated calcium signal transducer (Ripani et al., Int J Cancer 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5).

The growing interest in Trop-2 as a therapeutic target for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell (Fong et al., Modern Pathol 2008; 21:186-91) carcinomas. The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

Flow cytometry and immunohistochemical staining studies have shown that the RS7 MAb detects antigen on a variety of tumor types, with limited binding to normal human tissue (Stein et al., 1990). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., 1990; Stein et al., 1991).

Strong RS7 staining has been demonstrated in tumors from the lung, breast, bladder, ovary, uterus, stomach, and prostate. (Stein et al., Int. J. Cancer 55:938, 1993) The lung cancer cases comprised both squamous cell carcinomas and adenocarcinomas. (Stein et al., Int. J. Cancer 55:938, 1993) Both cell types stained strongly, indicating that the RS7 antibody does not distinguish between histologic classes of non-small-cell carcinoma of the lung.

The RS7 MAb is rapidly internalized into target cells (Stein et al., 1993). The internalization rate constant for RS7 MAb is intermediate between the internalization rate constants of two other rapidly internalizing MAbs, which have been demonstrated to be useful for immunotoxin production. (Id.) It is well documented that internalization of immunotoxin conjugates is a requirement for anti-tumor activity. (Pastan et al., Cell 47:641, 1986) Internalization of drug immunoconjugates has been described as a major factor in anti-tumor efficacy. (Yang et al., Proc. Nat'l Acad. Sci. USA 85: 1189, 1988) Thus, the RS7 antibody exhibits several important properties for therapeutic applications.

While the hRS7 antibody is preferred, other anti-Trop-2 antibodies are known and/or publicly available and in alternative embodiments may be utilized in the subject ADCs. While humanized or human antibodies are preferred for reduced immunogenicity, in alternative embodiments a chimeric antibody may be of use. As discussed below, methods of antibody humanization are well known in the art and may be utilized to convert an available murine or chimeric antibody into a humanized form.

Anti-Trop-2 antibodies are commercially available from a number of sources and include LS-C126418, LS-C178765, LS-C126416, LS-C126417 (LifeSpan BioSciences, Inc., Seattle, Wash.); 10428-MM01, 10428-MM02, 10428-R001, 10428-R030 (Sino Biological Inc., Beijing, China); MR54 (eBioscience, San Diego, Calif.); sc-376181, sc-376746, Santa Cruz Biotechnology (Santa Cruz, Calif.); MM0588-49D6, (Novus Biologicals, Littleton, Colo.); ab79976, and ab89928 (ABCAM®, Cambridge, Mass.).

Other anti-Trop-2 antibodies have been disclosed in the patent literature. For example, U.S. Publ. No. 2013/0089872 discloses anti-Trop-2 antibodies K5-70 (Accession No. FERM BP-11251), K5-107 (Accession No. FERM BP-11252), K5-116-2-1 (Accession No. FERM BP-11253), T6-16 (Accession No. FERM BP-11346), and T5-86 (Accession No. FERM BP-11254), deposited with the International Patent Organism Depositary, Tsukuba, Japan. U.S. Pat. No. 5,840,854 disclosed the anti-Trop-2 monoclonal antibody BR110 (ATCC No. HB11698). U.S. Pat. No. 7,420,040 disclosed an anti-Trop-2 antibody produced by hybridoma cell line AR47A6.4.2, deposited with the IDAC (International Depository Authority of Canada, Winnipeg, Canada) as accession number 141205-05. U.S. Pat. No. 7,420,041 disclosed an anti-Trop-2 antibody produced by hybridoma cell line AR52A301.5, deposited with the IDAC as accession number 141205-03. U.S. Publ. No. 2013/0122020 disclosed anti-Trop-2 antibodies 3E9, 6G11, 7E6, 15E2, 18B1. Hybridomas encoding a representative antibody were deposited with the American Type Culture Collection (ATCC), Accession Nos. PTA-12871 and PTA-12872. U.S. Pat. No. 8,715,662 discloses anti-Trop-2 antibodies produced by hybridomas deposited at the AID-ICLC (Genoa, Italy) with deposit numbers PD 08019, PD 08020 and PD 08021. U.S. Patent Application Publ. No. 20120237518 discloses anti-Trop-2 antibodies 77220, KM4097 and KM4590. U.S. Pat. No. 8,309,094 (Wyeth) discloses antibodies A1 and A3, identified by sequence listing. The Examples section of each patent or patent application cited above in this paragraph is incorporated herein by reference. Non-patent publication Lipinski et al. (1981, Proc Natl. Acad Sci USA, 78:5147-50) disclosed anti-Trop-2 antibodies 162-25.3 and 162-46.2.

Numerous anti-Trop-2 antibodies are known in the art and/or publicly available. As discussed below, methods for preparing antibodies against known antigens were routine in the art. The sequence of the human Trop-2 protein was also known in the art (see, e.g., GenBank Accession No. CAA54801.1). Methods for producing humanized, human or chimeric antibodies were also known. The person of ordinary skill, reading the instant disclosure in light of general knowledge in the art, would have been able to make and use the genus of anti-Trop-2 antibodies in the subject ADCs.

Anti-CD3 Antibodies

A variety of antibodies against CD3 that may be used in the claimed methods and compositions are publicly known and/or commercially available, such as from LSBio (catalog Nos. LS-B6698, LS-B8669; LS-B8765, LS-C96311, LS-C58677, etc.); ABCAM® (catalog Nos. ab5690, ab16669, ab699, ab828, ab8671, etc.); Santa Cruz Biotechnology (catalog Nos. sc-20047, sc-20080, sc-19590, sc-59008, sc-101442, etc.); and many other suppliers.

In a preferred embodiment, the amino acid sequence of the anti-CD3 moiety, used as part of a DNL™ complex, is as disclosed below in SEQ ID NO:96 to SEQ ID NO:101. However, the person of ordinary skill will realize that any known anti-CD3 antibody may be utilized in the claimed methods and compositions. Preferably, the antibody moieties of use are humanized or human.

Leukocyte Redirecting Bispecific Antibody Complexes

In preferred embodiments, the subject bispecific antibodies comprise an anti-CD3×anti-Trop-2 antibody. As discussed above, various antibodies against CD3 or Trop-2 are known in the art and any such known antibody may be utilized. However, in alternative embodiments, antibodies against other leukocyte antigens than CD3 or against other disease-associated antigens than Trop-2 may be utilized.

Exemplary T-cell antigens include CD2, CD3, CD4, CD5, CD6, CD8, CD25, CD28, CD30, CD40, CD40L, CD44, CD45, CD69 and CD90. Other exemplary antigens may be selected from CD8, CD16, CD56, CD57, ADAM17, and CD137 for NK cells; CD74, HLA-DR alpha chain, CD14, CD16, CD64 and CD89 for monocytes; and CEACAM6, CEACAM8, CD16b, CD32a, CD89, CD177, CD11a, CD11b and SLC44A2 for neutrophils. Preferably, the anti-T-cell antibody binds to CD3, or the anti-NK antibody binds to CD16. As discussed below, many examples of disease-associated antigens, such as tumor-associated antigens (TAAs) are known. An exemplary preferred TAA is Trop-2.

Certain alternative embodiments may concern an anti-CD3×anti-CD19 bispecific antibody. Various bispecific anti-CD3×anti-CD19 antibodies are known in the art and presently in clinical development, such as BITE® (Bispecific T-cell Engager) (e.g., Nagorsen et al., 2009, *Leukemia & Lymphoma* 50:886-91; Amann et al., 2009, *J Immunother* 32:453-64; Baeuerle and Reinhardt, 2009, *Cancer Res* 69:4941-44) and DART® (see, e.g., Moore et al., 2011, *Blood* 117:4542-51; Veri et al., 2010, *Arthritis Rheum* 62:1933-43). Blinatumomab is a BITE® antibody comprising $V_H$ and $V_L$ domains of anti-CD3 and anti-CD19 antibody fragments, connected with a 5-amino acid linker and expressed as a single polypeptide chain that anneals to itself to form the antigen-binding sites. It is thought that blinatumomab acts by bringing the T-cell-specific CD3 and B-cell specific CD19 antigens into close proximity, to initiate a T-cell cytotoxic response against the juxtaposed B cells, which does not require T-cell specificity to the cancer cells (e.g., Portell et al., 2013, *Clin Pharmacol* 5(Suppl 1): 5-11). Due to its short half-life, blinatumomab requires continuous intravenous infusion to be effective, (Portell et al., 2013). A phase II trial of B-cell ALL patients with persistent or relapsed minimal residual disease reported an approximately 80% rate of complete remission (Portell et al., 2013).

Doses of blinatumomab as low as 0.005 mg/m$^2$/day were reported to be effective to eliminate cancer cells in non-Hodgkin's lymphoma patients (Bargou et al., 2008, *Science* 321:974-77). Partial and complete remissions were observed starting at a dose level of 0.015 mg and all six patients tested at a dose of 0.06 mg experienced a tumor regression (Bargou et al., 2008). In vitro, blinatumomab induced 50% cell lysis of MEC-1 cells at a concentration of 10 pg/mL (Topp et al., 2012, *Blood* 120:5185-87; Bassan et al., 2012, *Blood* 120: 5094-95).

The anti-CD19 portion of blinatumomab was derived from the HD37 hybridoma (see, e.g., U.S. Pat. No. 7,575, 923, the Examples section of which is incorporated herein by reference), which is publicly available (e.g., Santa Cruz Biotechnology Cat. No. sc-18894). The anti-CD3 portion of blinatumomab was derived from the TR66 hybridoma (U.S. Pat. No. 7,575,923; Traunecker et al., 1991, *EMBO J.* 10:3655-59), also publicly available (e.g., Enzo Life Sciences, catalog No. ALX-804-822-C100).

A variety of antibodies against CD19 are publicly known and/or commercially available, such as from Santa Cruz Biotechnology (catalog Nos. sc-390244, sc-373897, sc-18894, sc-18896, etc.); ABCAM® (catalog Nos. ab25232, ab134114, ab140981, ab1255, etc.); ABBIOTEC™ (catalog Nos. 252262, 252248, 250585, 251063, etc.) and many other vendors.

In a preferred embodiment, the anti-CD19 antibody moiety is a humanized A19 antibody, comprising the light chain CDR sequences CDR1 KASQSVDYDGDSYLN (SEQ ID NO:90); CDR2 DASNLVS (SEQ ID NO:91); and CDR3 QQSTEDPWT (SEQ ID NO:92) and the heavy chain CDR sequences CDR1 SYWMN (SEQ ID NO:93); CDR2 QIWPGDGDTNYNGKFKG (SEQ ID NO:94) and CDR3 RETTTVGRYYYAMDY (SEQ ID NO:95).

Other anti-CD3×anti-CD19 bispecific antibodies are known, such as DART®, which also incorporates the anti-CD19 Fv sequences of HD37 and the anti-CD3 Fv sequences of TR66 (Moore et al., 2011, *Blood* 117:4542-51; Veri et al., 2010, *Arthritis Rheum* 62:1933-43). Moore et al. (2011) reported that DART® bispecific antibodies were more potent at inducing B cell lysis than single-chain, bispecific antibodies (BITE®) bearing identical anti-CD19 and anti-CD3 variable region sequences, with $EC_{50}$ values in the pg/mL range (Moore et al., 2011). Other anti-CD3×anti-CD19 bispecific antibodies besides DART® and BITE® have been reported (see, e.g., Wei et al., 2012, *Cell Oncol* 35:423-34; Portner et al., 2012, *Cancer Immunol Immunother* 61:1869-75; Zhou et al., 2012, *Biotechnol Lett.* 34:1183-91). In certain embodiments, any known anti-CD3× anti-CD19 bispecific antibody may be used to induce an immune response against disease-associated cells.

Catumaxomab is an anti-CD3×anti-EpCAM bispecific antibody that has been approved in Europe for treatment of malignant ascites associated with metastasizing cancer (Chames & Baty, 2009, MAbs 1:539-47). In a mouse model system, catumaxomab was able to kill tumor cells at a concentration range of 10 pM and was reported to lead to total eradication of melanoma tumors (Chames & Baty, 2009). Human clinical trials with ovarian cancer patients with malignant ascites also showed a statistically significant efficacy (Chames & Baty, 2009). However, the high immunogenicity of the rat/mouse hybrid bsAb may limit i.v. administration of the antibody (Chames & Baty, 2009). The use of anti-tumor bsAbs is not limited to anti-CD3×anti-CD19, but has also included anti-HER2×anti-CD64 (MDX-210, MDX-H210), anti-EGFR×anti-CD64 (MDX-447), anti-CD30×anti-CD16 (HRS-3/A9), anti-HER2×anti-CD3 (Her2Bi), anti-CD20×anti-CD3 (CD20Bi, Bi20), anti-EpCAM×anti-CD3 (catumaxomab, MT110), anti-HER2×anti-CD3 (ertumaxomab), and anti-NG2×anti-CD28 (rM28) (Chames & Baty, 2009).

The person of ordinary skill will realize that the subject leukocyte redirecting bispecific antibodies are not limited to anti-CD3×anti-Trop-2 constructs, but may comprise antibodies against any known disease-associated antigens attached to an anti-CD3 antibody moiety. Alternatively, antibodies against other T-cell antigens besides CD3, or other antigens expressed on NK cells, monocytes or neutrophils may also be used. Exemplary T-cell antigens include, but are not limited to, CD2, CD3, CD4, CD5, CD6, CD8, CD25, CD28, CD30, CD40, CD40L, CD44, CD45, CD69 and CD90. Other exemplary antigens may be selected from CD8, CD16, CD56, CD57, ADAM17, KIR and CD137 for NK cells; CD74, HLA-DR alpha chain, CD14, CD16, CD64 and CD89 for monocytes; and CEACAM6, CEACAM8, CD16b, CD32a, CD89, CD177, CD11a, CD11b and SLC44A2 for neutrophils. Antibodies against each of the leukocyte antigens are publicly known and/or publicly available (see, e.g., ABCAM® catalog numbers ab131276, ab139266, ab8360, ab51312, ab846, ab133616, ab75877, ab133255, ab109217, ab93278, ab17147, ab115851, ab128955, ab13463, ab85986; Santa Cruz Biotechnology catalog numbers sc-46683, sc-59047; Enzo Life Sciences, Inc. catalog number ALX-805-037-C100; Sino Biological Inc. catalog numbers 12211-RP02, 11150-R074; Millipore catalog numbers 04-1102, 04-1102, MAB1406). These and numerous other anti-leukocyte antibodies were publicly available and could have been used in the subject leukocyte redirecting bsAbs. As discussed below, numerous antibodies against a wide variety of disease-associated antigens were publicly known and/or commercially available and could have been used in the subject leukocyte redirecting bispecific antibodies. Other exemplary leukocyte redirecting bsAbs of potential use include FBTA05 (anti-CD20× anti-CD3) and TRBS07 (anti-GD2×anti-CD3).

Interferon Therapy

In various embodiments, the subject bispecific antibodies may be used in combination with one or more interferons, such as interferon-α, interferon-β or interferon-λ, preferably interferon-α. Human interferons are well known in the art and the amino acid sequences of human interferons may be readily obtained from public databases (e.g., GenBank Accession Nos. AAA52716.1; AAA52724; AAC41702.1; EAW56871.1; EAW56870.1; EAW56869.1). Human interferons may also be commercially obtained from a variety of vendors (e.g., Cell Signaling Technology, Inc., Danvers, Mass.; Genentech, South San Francisco, Calif.; EMD Millipore, Billerica, Mass.).

Interferon-α (IFNα) has been reported to have anti-tumor activity in animal models of cancer (Ferrantini et al., 1994, *J Immunol* 153:4604-15) and human cancer patients (Gutterman et al., 1980, *Ann Intern Med* 93:399-406). IFNα can exert a variety of direct anti-tumor effects, including down-regulation of oncogenes, up-regulation of tumor suppressors, enhancement of immune recognition via increased expression of tumor surface MHC class I proteins, potentiation of apoptosis, and sensitization to chemotherapeutic agents (Gutterman et al., 1994, *PNAS USA* 91:1198-205; Matarrese et al., 2002, *Am J Pathol* 160:1507-20; Mecchia et al., 2000, *Gene Ther* 7:167-79; Sabaawy et al., 1999, *Int J Oncol* 14:1143-51; Takaoka et al, 2003, *Nature* 424:516-23). For some tumors, IFNα can have a direct and potent anti-proliferative effect through activation of STAT1 (Grimley et al., 1998 *Blood* 91:3017-27). Interferon-α2b has been conjugated to anti-tumor antibodies, such as the hL243 anti-HLA-DR antibody and depletes lymphoma and myeloma cells in vitro and in vivo (Rossi et al., 2011, *Blood* 118:1877-84).

Indirectly, IFNα can inhibit angiogenesis (Sidky and Borden, 1987, *Cancer Res* 47:5155-61) and stimulate host immune cells, which may be vital to the overall antitumor response but has been largely under-appreciated (Belardelli et al., 1996, *Immunol Today* 17:369-72). IFNα has a pleiotropic influence on immune responses through effects on myeloid cells (Raefsky et al, 1985, *J Immunol* 135:2507-12; Luft et al, 1998, *J Immunol* 161:1947-53), T-cells (Carrero et al, 2006, *J Exp Med* 203:933-40; Pilling et al., 1999, *Eur J Immunol* 29:1041-50), and B-cells (Le et al, 2001, *Immunity* 14:461-70). As an important modulator of the innate immune system, IFNα induces the rapid differentiation and activation of dendritic cells (Belardelli et al, 2004, *Cancer Res* 64:6827-30; Paquette et al., 1998, *J Leukoc Biol* 64:358-67; Santini et al., 2000, *J Exp Med* 191:1777-88) and enhances the cytotoxicity, migration, cytokine production and antibody-dependent cellular cytotoxicity (ADCC) of NK cells (Biron et al., 1999, *Ann Rev Immunol* 17:189-220; Brunda et al. 1984, *Cancer Res* 44:597-601).

Interferon-β has been reported to be efficacious for therapy of a variety of solid tumors. Patients treated with 6 million units of IFN-β twice a week for 36 months showed a decreased recurrence of hepatocellular carcinoma after complete resection or ablation of the primary tumor in patients with HCV-related liver cancer (Ikeda et al., 2000, *Hepatology* 32:228-32). Gene therapy with interferon-β induced apoptosis of glioma, melanoma and renal cell carcinoma (Yoshida et al., 2004, *Cancer Sci* 95:858-65). Endogenous IFN-β has been observed to inhibit tumor growth by inhibiting angiogenesis in vivo (Jablonska et al., 2010, *J Clin Invest.* 120:1151-64.)

IFN-λs, designated as type III interferons, are a newly described group of cytokines that consist of IFN-λ1, 2, 3 (also referred to as interleukin-29, 28A, and 28B, respectively), that are genetically encoded by three different genes located on chromosome 19 (Kotenko et al., 2003, *Nat Immunol* 4:69-77; Sheppard et al., 2003, *Nat Immunol* 4:63-8). At the protein level, IFN-λ2 and -λ3 are is highly homologous, with 96% amino acid identity, while IFN-λ1 shares approximately 81% homology with IFN-λ2 and -λ3 (Sheppard et al., 2003, *Nat Immunol* 4:63-8). IFN-λs activate signal transduction via the JAK/STAT pathway similar to that induced by type I IFN, including the activation of JAK1 and TYK2 kinases, the phosphorylation of STAT proteins, and the activation of the transcription complex of IFN-stimulated gene factor 3 (ISGF3) (Witte et al., 2010, *Cytokine Growth Factor Rev* 21:237-51; Zhou et al., 2007, *J Virol* 81:7749-58).

A major difference between type III and type I IFN systems is the distribution of their respective receptor complexes. IFN-α/β signals through two extensively expressed type I interferon receptors, and the resulting systemic toxicity associated with IFN-α/β administration has limited their use as therapeutic agents (Pestka et al., 2007, *J Biol Chem* 282:20047-51). In contrast, IFN-λs signal through a heterodimeric receptor complex consisting of unique IFN-λ, receptor 1 (IFN-λR1) and IL-10 receptor 2 (IL-10R2). As previously reported (Witte et al., 2009, *Genes Immun* 10:702-14), IFN-λR1 has a very restricted expression pattern with the highest levels in epithelial cells, melanocytes, and hepatocytes, and the lowest level in primary central nervous system (CNS) cells. Blood immune system cells express high levels of a short IFN-λ receptor splice variant (sIFN-λR1) that inhibits IFN-λ action. The limited responsiveness of neuronal cells and immune cells implies that the severe toxicity frequently associated with IFN-α therapy may be absent or significantly reduced with IFN-λs (Witte et al., 2009, *Genes Immun* 10:702-14; Witte et al., 2010, *Cytokine Growth Factor Rev* 21:237-51). A recent publication reported that while IFN-α and IFN-λ induce expression of a common set of ISGs (interferon-stimulated genes) in hepatocytes, unlike IFN-α, administration of IFN-λ did not induce STAT activation or ISG expression in purified lymphocytes or monocytes (Dickensheets et al., 2013, *J Leukoc Biol.* 93, published online Dec. 20, 2012). It was suggested that IFN-λ may be superior to IFN-α for treatment of chronic HCV infection, as it is less likely to induce leukopenias that are often associated with IFN-α therapy (Dickensheets et al., 2013).

IFN-λs display structural features similar to IL-10-related cytokines, but functionally possess type I IFN-like anti-viral and anti-proliferative activity (Witte et al., 2009, *Genes Immun* 10:702-14; Ank et al., 2006, *J Virol* 80:4501-9; Robek et al., 2005, *J Virol* 79:3851-4). IFN-λ1 and -λ2 have been demonstrated to reduce viral replication or the cytopathic effect of various viruses, including DNA viruses (hepatitis B virus (Robek et al., 2005, *J Virol* 79:3851-4, Doyle et al., 2006, *Hepatology* 44:896-906) and herpes simplex virus 2 (Ank et al., 2008, *J Immunol* 180:2474-85)), ss (+) RNA viruses (EMCV; Sheppard et al., 2003, *Nat Immunol* 4:63-8) and hepatitis C virus (Robek et al., 2005, *J Virol* 79:3851-4, Doyle et al., 2006, *Hepatology* 44:896-906; Marcello et al., 2006, *Gastroenterol* 131:1887-98; Pagliaccetti et al., 2008, *J Biol Chem* 283:30079-89), ss (−) RNA viruses (vesicular stomatitis virus; Pagliaccetti et al., 2008, *J Biol Chem* 283:30079-89) and influenza-A virus (Jewell et al., 2010, *J Virol* 84:11515-22) and double-stranded RNA viruses, such as rotavirus (Pott et al., 2011, *PNAS USA* 108:7944049). IFN-λ3 has been identified from genetic studies as a key cytokine in HCV infection (Ge et al., 2009, *Nature* 461:399-401), and has also shown potent activity against EMCV (Dellgren et al., 2009, *Genes Immun* 10:125-31). A deficiency of rhinovirus-induced IFN-λ production was reported to be highly correlated with the severity of rhinovirus-induced asthma exacerbation (Contoli et al., 2006, *Nature Med* 12:1023-26) and IFN-λ therapy has been suggested as a new approach for treatment of allergic asthma (Edwards and Johnston, 2011, *EMBO Mol Med* 3:306-8; Koltsida et al., 2011, *EMBO Mot Med* 3:348-61).

The anti-proliferative activity of IFN-λs has been established in several human cancer cell lines, including neuroendocrine carcinoma BON1 (Zitzmann et al., 2006, *Biochem Biophys Res Commun* 344:1334-41), glioblastoma LN319 (Meager et al., 2005, *Cytokine* 31:109-18), immortalized keratinocyte HaCaT (Maher et al., 2008, *Cancer Biol Ther* 7:1109-15), melanoma F01 (Guenterberg et al., 2010, *Mol Cancer Ther* 9:510-20), and esophageal carcinoma TE-11 (Li et al., 2010, *Eur J Cancer* 46:180-90). In animal models, IFN-λs induce both tumor apoptosis and destruction through innate and adaptive immune responses, suggesting that local delivery of IFN-λ might be a useful adjunctive strategy in the treatment of human malignancies (Numasaki et al., 2007, *J Immunol* 178:5086-98). A Fab-linked interferon-λ was demonstrated to have potent anti-tumor and anti-viral activity in targeted cells (Liu et al., 2013, PLoS One 8:e63940).

In clinical settings, PEGylated IFN-λ1 (PEG-IFN-λ1) has been provisionally used for patients with chronic hepatitis C virus infection. In a phase Ib study (n=56), antiviral activity was observed at all dose levels (0.5-3.0 μg/kg), and viral load reduced 2.3 to 4.0 logs when PEG-IFN-λ1 was administrated to genotype 1 HCV patients who relapsed after IFN-α therapy (Muir et al., 2010, *Hepatology* 52:822-32). A phase IIb study (n=526) showed that patients with HCV genotypes 1 and 4 had significantly higher response rates to treatment with PEG-IFN-λ1 compared to PEG-IFN-α. At the same time, rates of adverse events commonly associated with type I interferon treatment were lower with PEG-IFN-λ1 than with PEG-IFN-α. Neutropenia and thrombocytopenia were infrequently observed and the rates of flu-like symptoms, anemia, and musculoskeletal symptoms decreased to about ⅓ of that seen with PEG-IFN-α treatment. However, rates of serious adverse events, depression and other common adverse events (≥10%) were similar between PEG-IFN-λ1 and PEG-IFN-α. Higher rates of hepatotoxicity were seen in the highest-dose PEG-IFN-λ1 compared with PEG-IFN-α ("Investigational Compound PEG-Interferon Lambda Achieved Higher Response Rates with Fewer Flu-like and Musculoskeletal Symptoms and Cytopenias Than PEG-Interferon Alfa in Phase IIb Study of 526 Treatment-Naive Hepatitis C Patients," Apr. 2, 2011, Press Release from Bristol-Myers Squibb).

In various embodiments, the subject leukocyte redirecting bispecific antibodies, ADCs and/or checkpoint inhibitor mAbs may be used in combination with one or more interferons, such as interferon-α, interferon-β, interferon-λ1, interferon-λ2, or interferon-λ3. When used with other agents, the interferon may be administered prior to, concurrently with, or after the other agent. When administered concurrently, the interferon may be either conjugated to or separate from the other agent.

Checkpoint Inhibitor Antibodies

Studies with checkpoint inhibitor antibodies for cancer therapy have generated unprecedented response rates in cancers previously thought to be resistant to cancer treatment (see, e.g., Ott & Bhardwaj, 2013, Frontiers in Immunology 4:346; Menzies & Long, 2013, Ther Adv Med Oncol 5:278-85; Pardoll, 2012, Nature Reviews Cancer 12:252-64; Mavilio & Lugli). Therapy with antagonistic checkpoint blocking antibodies against immune system checkpoints such as CTLA4, PD1 and PD-L1 are one of the most promising new avenues of immunotherapy for cancer and other diseases. In contrast to the majority of anti-cancer agents, checkpoint inhibitors do not target tumor cells directly, but rather target lymphocyte receptors or their ligands in order to enhance the endogenous antitumor activity of the immune system. (Pardoll, 2012, Nature Reviews Cancer 12:252-264) Because such antibodies act primarily by regulating the immune response to diseased cells, tissues or pathogens, they may be used in combination with other therapeutic modalities, such as the subject leukocyte redirecting bispecific antibodies, ADCs and/or interferons to enhance the anti-tumor effect of such agents.

It is now clear that tumors can escape immune surveillance by co-opting certain immune-checkpoint pathways, particularly in T cells that are specific for tumor antigens (Pardoll, 2012, Nature Reviews Cancer 12:252-264). Because many such immune checkpoints are initiated by ligand-receptor interactions, they can be readily blocked by antibodies against the ligands and/or their receptors (Pardoll, 2012, Nature Reviews Cancer 12:252-264). Although checkpoint inhibitor antibodies against CTLA4, PD1 and PD-L1 are the most clinically advanced, other potential checkpoint antigens are known and may be used as the target of therapeutic antibodies, such as LAG3, B7-H3, B7-H4 and TIM3 (Pardoll, 2012, Nature Reviews Cancer 12:252-264).

Programmed cell death protein 1 (PD1, also known as CD279) encodes a cell surface membrane protein of the immunoglobulin superfamily, which is expressed in B cells and NK cells (Shinohara et al., 1995, Genomics 23:704-6; Blank et al., 2007, Cancer Immunol Immunother 56:739-45; Finger et al., 1997, Gene 197:177-87; Pardoll, 2012, Nature Reviews Cancer 12:252-264). The major role of PD1 is to limit the activity of T cells in peripheral tissues during inflammation in response to infection, as well as to limit autoimmunity (Pardoll, 2012, Nature Reviews Cancer 12:252-264). PD1 expression is induced in activated T cells and binding of PD1 to one of its endogenous ligands acts to inhibit T-cell activation by inhibiting stimulatory kinases (Pardoll, 2012, Nature Reviews Cancer 12:252-264). PD1 also acts to inhibit the TCR "stop signal" (Pardoll, 2012, Nature Reviews Cancer 12:252-264). PD1 is highly expressed on $T_{reg}$ cells and may increase their proliferation in the presence of ligand (Pardoll, 2012, Nature Reviews Cancer 12:252-264).

Anti-PD1 antibodies have been used for treatment of melanoma, non-small-cell lung cancer, bladder cancer, prostate cancer, colorectal cancer, head and neck cancer, triple-negative breast cancer, leukemia, lymphoma and renal cell cancer (Topalian et al., 2012, N Engl J Med 366:2443-54; Lipson et al., 2013, Clin Cancer Res 19:462-8; Berger et al., 2008, Clin Cancer Res 14:3044-51; Gildener-Leapman et al., 2013, Oral Oncol 49:1089-96; Menzies & Long, 2013, Ther Adv Med Oncol 5:278-85). Because PD1/PD-L1 and CTLA4 act by different pathways, it is possible that combination therapy with checkpoint inhibitor antibodies against each may provide an enhanced immune response.

Exemplary anti-PD1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4).

Programmed cell death 1 ligand 1 (PD-L1, also known as CD274 and B7-H1) is a ligand for PD1, found on activated T cells, B cells, myeloid cells and macrophages. Although there are two endogenous ligands for PD1-PD-L1 and PD-L2, anti-tumor therapies have focused on anti-PD-L1 antibodies. The complex of PD1 and PD-L1 inhibits proliferation of CD8+ T cells and reduces the immune response (Topalian et al., 2012, N Engl J Med 366:2443-54; Brahmer et al., 2012, N Eng J Med 366:2455-65). Anti-PD-L1 antibodies have been used for treatment of non-small cell lung cancer, melanoma, colorectal cancer, renal-cell cancer, pancreatic cancer, gastric cancer, ovarian cancer, breast cancer, and hematologic malignancies (Brahmer et al., N Eng J Med 366:2455-65; Ott et al., 2013, Clin Cancer Res 19:5300-9; Radvanyi et al., 2013, Clin Cancer Res 19:5541; Menzies & Long, 2013, Ther Adv Med Oncol 5:278-85; Berger et al., 2008, Clin Cancer Res 14:13044-51).

Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1).

Cytotoxic T-lymphocyte antigen 4 (CTLA4, also known as CD152) is also a member of the immunoglobulin superfamily that is expressed exclusively on T-cells. CTLA4 acts to inhibit T-cell activation and is reported to inhibit helper T-cell activity and enhance regulatory T-cell immunosuppressive activity (Pardoll, 2012, Nature Reviews Cancer 12:252-264). Although the precise mechanism of action of CTL4-A remains under investigation, it has been suggested that it inhibits T cell activation by outcompeting CD28 in binding to CD80 and CD86, as well as actively delivering inhibitor signals to the T cell (Pardoll, 2012, Nature Reviews Cancer 12:252-264). Anti-CTLA4 antibodies have been used in clinical trials for treatment of melanoma, prostate cancer, small cell lung cancer, non-small cell lung cancer (Robert & Ghiringhelli, 2009, Oncologist 14:848-61; Ott et al., 2013, Clin Cancer Res 19:5300; Weber, 2007, Oncologist 12:864-72; Wada et al., 2013, J Transl Med 11:89). A significant feature of anti-CTL4A is the kinetics of anti-tumor effect, with a lag period of up to 6 months after initial treatment required for physiologic response (Pardoll, 2012, Nature Reviews Cancer 12:252-264). In some cases, tumors may actually increase in size after treatment initiation, before a reduction is seen (Pardoll, 2012, Nature Reviews Cancer 12:252-264).

Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, J Transl Med 11:89).

The person of ordinary skill will realize that methods of determining optimal dosages of checkpoint inhibitor antibodies to administer to a patient in need thereof, either alone or in combination with one or more other agents, may be determined by standard dose-response and toxicity studies that are well known in the art. In an exemplary embodiment, a checkpoint inhibitor antibody may preferably be administered at about 0.3-10 mg/kg, or the maximum tolerated dose, administered about every three weeks or about every six weeks. Alternatively, the checkpoint inhibitor antibody may be administered by an escalating dosage regimen including administering a first dosage at about 3 mg/kg, a second dosage at about 5 mg/kg, and a third dosage at about 9 mg/kg. Alternatively, the escalating dosage regimen includes administering a first dosage of checkpoint inhibitor antibody at about 5 mg/kg and a second dosage at about 9 mg/kg. Another stepwise escalating dosage regimen may include administering a first dosage of checkpoint inhibitor antibody about 3 mg/kg, a second dosage of about 3 mg/kg, a third dosage of about 5 mg/kg, a fourth dosage of about 5 mg/kg, and a fifth dosage of about 9 mg/kg. In another aspect, a stepwise escalating dosage regimen may include administering a first dosage of 5 mg/kg, a second dosage of 5 mg/kg, and a third dosage of 9 mg/kg. Exemplary reported dosages of checkpoint inhibitor mAbs include 3 mg/kg ipilimumab administered every three weeks for four doses; 10 mg/kg ipilimumab every three weeks for eight cycles; 10 mg/kg every three weeks for four cycles then every 12 weeks for a total of three years; 10 mg/kg MK-3475 every two or every three weeks; 2 mg/kg MK-3475 every three weeks; 15 mg/kg tremilimumab every three months; 0.1, 0.3, 1, 3 or 10 mg/kg nivolumab every two weeks for up to 96 weeks; 0.3, 1, 3, or 10 mg/kg BMS-936559 every two weeks for up to 96 weeks (Kyi & Postow, Oct. 23, 2013, FEBS Lett [Epub ahead of print]; Callahan & Wolchok, 2013, J Leukoc Biol 94:41-53).

These and other known agents that stimulate immune response to tumors and/or pathogens may be used in combination with leukocyte redirecting bispecific antibodies alone or in further combination with an interferon, such as interferon-α, and/or an antibody-drug conjugate for improved cancer therapy. Other known co-stimulatory pathway modulators that may be used in combination include, but are not limited to, agatolimod, belatacept, blinatumomab, CD40 ligand, anti-B7-1 antibody, anti-B7-2 antibody, anti-B7-H4 antibody, AG4263, eritoran, anti-OX40 antibody, ISF-154, and SGN-70; B7-1, B7-2, ICAM-1, ICAM-2, ICAM-3, CD48, LFA-3, CD30 ligand, CD40 ligand, heat stable antigen, B7h, OX40 ligand, LIGHT, CD70 and CD24.

In certain embodiments, anti-KIR antibodies may also be used in combination with leukocyte-redirecting bsAbs, interferons, ADCs and/or checkpoint inhibitor antibodies. NK cells mediate anti-tumor and anti-infectious agent activity by spontaneous cytotoxicity and by ADCC when activated by antibodies (Kohrt et al., 2013, Blood, [Epub ahead of print Dec. 10, 2013]). The degree of cytotoxic response is determined by a balance of inhibitory and activating signals received by the NK cells (Kohrt et al., 2013). The killer cell immunoglobulin-like receptor (KIR) mediates an inhibitory signal that decreases NK cell response. Anti-KIR antibodies, such as lirilumab (Innate Pharma) and IPH2101 (Innate Pharma) have demonstrated anti-tumor activity in multiple myeloma (Benson et al., 2012, Blood 120:4324-33). In vitro, anti-KIR antibodies prevent the tolerogenic interaction of NK cells with target cells and augments the NK cell cytotoxic response to tumor cells (Kohrt et al., 2013). In vivo, in combination with rituximab (anti-CD20), anti-KIR antibodies at a dose of 0.5 mg/kg induced enhanced NK cell-mediated, rituximab-dependent cytotoxicity against lymphoma tumors (Kohrt et al., 2013). Anti-KIR mAbs may be combined with ADCs, leukocyte-redirecting bsAbs, interferons and/or checkpoint inhibitor antibodies to potentiate cytotoxicity to tumor cells or pathogenic organisms.

General Antibody Techniques

Techniques for preparing monoclonal antibodies against virtually any target antigen are well known in the art. See, for example, Kohler and Milstein, Nature 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in *METHODS IN MOLECULAR BIOLOGY*, VOL. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art. The use of antibody components derived from humanized, chimeric or human antibodies obviates potential problems associated with the immunogenicity of murine constant regions.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 86: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_\kappa$ and $V_H$ domains of murine LL2, an anti-CD22 monoclonal antibody, with respective human κ and $IgG_1$ constant region domains.

Humanized Antibodies

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Generally, those human FR amino acid residues that differ from their murine counterparts and are located close to or touching one or more CDR amino acid residues would be candidates for substitution.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Phamacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: PHAGE DISPLAY LABORATORY MANUAL, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art (see, e.g., Pasqualini and Ruoslahti, 1996, *Nature* 380:364-366; Pasqualini, 1999, *The Quart. J. Nucl. Med.* 43:159-162).

Phage display can be performed in a variety of formats, for their review, see e.g. Johnson and Chiswell, *Current Opinion in Structural Biology* 3:5564-571 (1993). Human antibodies may also be generated by in vitro activated B cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XENOMOUSE® (e.g., Green et al., 1999, *J. Immunol. Methods* 231:11-23) from Abgenix (Fremont, Calif.). In the XENOMOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Igkappa loci, including the majority of the variable region sequences, along accessory genes and regulatory sequences. The human variable region repertoire may be used to generate antibody producing B cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Antibody Cloning and Production

Various techniques, such as production of chimeric or humanized antibodies, may involve procedures of antibody cloning and construction. The antigen-binding Vκ (variable light chain) and $V_H$ (variable heavy chain) sequences for an antibody of interest may be obtained by a variety of molecular cloning procedures, such as RT-PCR, 5'-RACE, and cDNA library screening. The V genes of an antibody from a cell that expresses a murine antibody can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci. USA*, 86: 3833 (1989)). Based on the V gene sequences, a humanized antibody can then be designed and constructed as described by Leung et al. (*Mol. Immunol.*, 32: 1413 (1995)).

cDNA can be prepared from any known hybridoma line or transfected cell line producing a murine antibody by general molecular cloning techniques (Sambrook et al., *Molecular Cloning, A laboratory manual*, $2^{nd}$ Ed (1989)). The Vκ sequence for the antibody may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (*Hybridoma*, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., *Hybridoma*, 13:469 (1994)). The expression vectors can be co-transfected into an appropriate cell and supernatant fluids monitored for production of a chimeric, humanized or human antibody. Alternatively, the $V_K$ and $V_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Antibody Fragments

Antibody fragments which recognize specific epitopes can be generated by known techniques. Antibody fragments are antigen binding portions of an antibody, such as $F(ab')_2$, Fab', $F(ab)_2$, Fab, Fv, scFv and the like. $F(ab')_2$ fragments can be produced by pepsin digestion of the antibody molecule and Fab' fragments can be generated by reducing disulfide bridges of the $F(ab')_2$ fragments. Alternatively, Fab' expression libraries can be constructed (Huse et al., 1989, *Science*, 246:1274-1281) to allow rapid and easy identification of monoclonal Fab' fragments with the desired specificity. $F(ab)_2$ fragments may be generated by papain digestion of an antibody.

A single chain Fv molecule (scFv) comprises a VL domain and a VH domain. The VL and VH domains associate to form a target binding site. These two domains are further covalently linked by a peptide linker (L). Methods for making scFv molecules and designing suitable peptide linkers are described in U.S. Pat. No. 4,704,692; U.S. Pat. No. 4,946,778; Raag and Whitlow, *FASEB* 9:73-80 (1995) and Bird and Walker, *TIBTECH*, 9: 132-137 (1991).

Techniques for producing single domain antibodies (DABs or VHH) are also known in the art, as disclosed for example in Cossins et al. (2006, *Prot Express Purif* 51:253-259), incorporated herein by reference. Single domain antibodies may be obtained, for example, from camels, alpacas or llamas by standard immunization techniques. (See, e.g., Muyldermans et al., *TIBS* 26:230-235, 2001; Yau et al., *J Immunol Methods* 281:161-75, 2003; Maass et al., *J Immunol Methods* 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007). In certain embodiments, anti-pancreatic cancer VHH antibody fragments may be utilized in the claimed compositions and methods.

An antibody fragment can be prepared by proteolytic hydrolysis of the full length antibody or by expression in *E. coli* or another host of the DNA coding for the fragment. An antibody fragment can be obtained by pepsin or papain digestion of full length antibodies by conventional methods. These methods are described, for example, by Goldenberg, U.S. Pat. Nos. 4,036,945 and 4,331,647 and references contained therein. Also, see Nisonoff et al., *Arch Biochem.*

Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4.

Antibody Allotypes

Immunogenicity of therapeutic antibodies is associated with increased risk of infusion reactions and decreased duration of therapeutic response (Baert et al., 2003, *N Engl J Med* 348:602-08). The extent to which therapeutic antibodies induce an immune response in the host may be determined in part by the allotype of the antibody (Stickler et al., 2011, *Genes and Immunity* 12:213-21). Antibody allotype is related to amino acid sequence variations at specific locations in the constant region sequences of the antibody. The allotypes of IgG antibodies containing a heavy chain γ-type constant region are designated as Gm allotypes (1976, *J Immunol* 117:1056-59).

For the common IgG1 human antibodies, the most prevalent allotype is G1m1 (Stickler et al., 2011, *Genes and Immunity* 12:213-21). However, the G1m3 allotype also occurs frequently in Caucasians (Stickler et al., 2011). It has been reported that G1m1 antibodies contain allotypic sequences that tend to induce an immune response when administered to non-G1m1 (nG1m1) recipients, such as G1m3 patients (Stickler et al., 2011). Non-G1m1 allotype antibodies are not as immunogenic when administered to G1m1 patients (Stickler et al., 2011).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown for the exemplary antibodies rituximab (SEQ ID NO:85) and veltuzumab (SEQ ID NO:86).

```
Rituximab heavy chain variable region sequence
                                      (SEQ ID NO: 85)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Veltuzumab heavy chain variable region
                                      (SEQ ID NO: 86)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK
```

Jefferis and Lefranc (2009, *mAbs* 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CH1) of lysine in rituximab vs. arginine in veltuzumab. It has been reported that veltuzumab is less immunogenic in subjects than rituximab (see, e.g., Morchhauser et al., 2009, *J Clin Oncol* 27:3346-53; Goldenberg et al., 2009, *Blood* 113:1062-70; Robak & Robak, 2011, *BioDrugs* 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | |
|---|---|---|---|---|
| | Complete allotype | 214 (allotype) | 356/358 (allotype) | 431 (allotype) |
| Rituximab | G1m17,1 | K 17 | D/L 1 | A — |
| Veltuzumab | G1m3 | R 3 | E/M — | A — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Known Antibodies

Target Antigens and Exemplary Antibodies

In a preferred embodiment, antibodies are used that recognize and/or bind to antigens that are expressed at high levels on target cells and that are expressed predominantly or exclusively on diseased cells versus normal tissues. Exemplary antibodies of use for therapy of, for example, cancer include but are not limited to LL1 (anti-CD74), LL2 or RFB4 (anti-CD22), veltuzumab (hA20, anti-CD20), rituxumab (anti-CD20), obinutuzumab (GA101, anti-CD20), lambrolizumab (anti-PD1), nivolumab (anti-PD1), MK-3475 (anti-PD1), AMP-224 (anti-PD1), pidilizumab (anti-PD1), MDX-1105 (anti-PD-L1), MEDI4736 (anti-PD-L1), MPDL3280A (anti-PD-L1), BMS-936559 (anti-PD-L1), ipilimumab (anti-CTLA4), trevilizumab (anti-CTL4A), RS7 (anti-epithelial glycoprotein-1 (EGP-1, also known as TROP-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin), BWA-3 (anti-histone H2A/H4), LG2-1 (anti-histone H3), MRA12 (anti-histone H1), PR1-1 (anti-histone H2B), LG11-2 (anti-histone H2B), LG2-2 (anti-histone H2B), and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,251,164), hA19 (U.S. Pat. No. 7,109,304), hIMMU-31 (U.S. Pat. No. 7,300,655), hLL1 (U.S. Pat. No. 7,312,318), hLL2 (U.S. Pat. No. 7,074,403), hMu-9 (U.S. Pat. No. 7,387,773), hL243 (U.S. Pat. No. 7,612,180), hMN-14 (U.S. Pat. No. 6,676,924), hMN-15 (U.S. Pat. No. 7,541,440), hR1 (U.S. patent application Ser. No. 12/772,645), hRS7 (U.S. Pat. No. 7,238,785), hMN-3 (U.S. Pat. No. 7,541,440), AB-PG1-XG1-026 (U.S. patent application Ser. No. 11/983, 372, deposited as ATCC PTA-4405 and PTA-4406) and D2/B (WO 2009/130575) the text of each recited patent or application is incorporated herein by reference with respect to the Figures and Examples sections.

Other useful antigens that may be targeted using the described conjugates include carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAM5, CEACAM6, CTLA4, alpha-fetoprotein (AFP), VEGF (e.g., AVASTIN®, fibronectin splice variant), ED-B fibronectin (e.g., L19), EGP-1 (TROP-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-β, HMGB-1, hypoxia inducible factor (HIF), HM1.24, HER-2/neu, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (PlGF), PSA (prostate-specific antigen), PSMA, PAM4 antigen, PD1 receptor, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), TROP-2, VEGFR, RANTES, T101, as well as cancer stem cell antigens, complement factors C3, C3a, C3b, C5a, C5, and an oncogene product.

A comprehensive analysis of suitable antigen (Cluster Designation, or CD) targets on hematopoietic malignant cells, as shown by flow cytometry and which can be a guide to selecting suitable antibodies for immunotherapy, is Craig and Foon, *Blood* prepublished online Jan. 15, 2008; DOL 10.1182/blood-2007-11-120535.

The CD66 antigens consist of five different glycoproteins with similar structures, CD66a-e, encoded by the carcinoembryonic antigen (CEA) gene family members, BCG, CGM6, NCA, CGM1 and CEA, respectively. These CD66 antigens (e.g., CEACAM6) are expressed mainly in granulocytes, normal epithelial cells of the digestive tract and tumor cells of various tissues. Also included as suitable targets for cancers are cancer testis antigens, such as NY-ESO-1 (Theurillat et al., *Int. J. Cancer* 2007; 120(11):2411-7), as well as CD79a in myeloid leukemia (Kozlov et al., *Cancer Genet. Cytogenet.* 2005; 163(1):62-7) and also B-cell diseases, and CD79b for non-Hodgkin's lymphoma (Poison et al., *Blood* 110(2):616-623). A number of the aforementioned antigens are disclosed in U.S. Provisional Application Ser. No. 60/426,379, entitled "Use of Multi-specific, Non-covalent Complexes for Targeted Delivery of Therapeutics," filed Nov. 15, 2002. Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3):385-91), and glioblastoma (Beier et al., *Cancer Res.* 2007; 67(9):4010-5), and CD44 in colorectal cancer (Dalerba er al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8).

Anti-cancer antibodies have been demonstrated to bind to histones in some case. Kato et al. (1991, Hum Antibodies Hybridomas 2:94-101) reported that the lung cancer-specific human monoclonal antibody HB4C5 binds to histone H2B. Garzelli et al. (1994, Immunol Lett 39:277-82) observed that Epstein-Barr virus-transformed human B lymphocytes produce natural antibodies to histones. In certain embodiments, antibodies against histones may be of use in the subject combinations. Known anti-histone antibodies include, but are not limited to, BWA-3 (anti-histone H2A/H4), LG2-1 (anti-histone H3), MRA12 (anti-histone H1), PR1-1 (anti-histone H2B), LG11-2 (anti-histone H2B), and LG2-2 (anti-histone H2B) (see, e.g., Monestier et al., 1991, Eur J Immunol 21:1725-31; Monestier et al., 1993, Molec Immunol 30:1069-75).

For multiple myeloma therapy, suitable targeting antibodies have been described against, for example, CD38 and CD138 (Stevenson, Mol Med 2006; 12(11-12):345-346; Tassone et al., Blood 2004; 104(12):3688-96), CD74 (Stein et al., ibid.), CS1 (Tai et al., Blood 2008; 112(4):1329-37, and CD40 (Tai et al., 2005; Cancer Res. 65(13):5898-5906).

Macrophage migration inhibitory factor (MIF) is an important regulator of innate and adaptive immunity and apoptosis. It has been reported that CD74 is the endogenous receptor for MIF (Leng et al., 2003, J Exp Med 197:1467-76). The therapeutic effect of antagonistic anti-CD74 antibodies on MIF-mediated intracellular pathways may be of use for treatment of a broad range of disease states, such as cancers of the bladder, prostate, breast, lung, colon and chronic lymphocytic leukemia (e.g., Meyer-Siegler et al., 2004, BMC Cancer 12:34; Shachar & Haran, 2011, Leuk Lymphoma 52:1446-54). Milatuzumab (hLL1) is an exemplary anti-CD74 antibody of therapeutic use for treatment of MIF-mediated diseases.

An example of a most-preferred antibody/antigen pair is LL1, an anti-CD74 MAb (invariant chain, class II-specific chaperone, Ii) (see, e.g., U.S. Pat. Nos. 6,653,104; 7,312,318; the Examples section of each incorporated herein by reference). The CD74 antigen is highly expressed on B-cell lymphomas (including multiple myeloma) and leukemias, certain T-cell lymphomas, melanomas, colonic, lung, and renal cancers, glioblastomas, and certain other cancers (Ong et al., Immunology 98:296-302 (1999)). A review of the use of CD74 antibodies in cancer is contained in Stein et al., Clin Cancer Res. 2007 Sep. 15; 13(18 Pt 2):5556s-5563s, incorporated herein by reference. The diseases that are preferably treated with anti-CD74 antibodies include, but are not limited to, non-Hodgkin's lymphoma, Hodgkin's disease, melanoma, lung, renal, colonic cancers, glioblastome multiforme, histiocytomas, myeloid leukemias, and multiple myeloma.

In various embodiments, the claimed methods and compositions may utilize any of a variety of antibodies known in the art. Antibodies of use may be commercially obtained from a number of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. See, e.g., U.S. Pat. Nos. 7,312, 318; 7,282,567; 7,151,164; 7,074,403; 7,060,802; 7,056, 509; 7,049,060; 7,045,132; 7,041,803; 7,041,802; 7,041, 293; 7,038,018; 7,037,498; 7,012,133; 7,001,598; 6,998, 468; 6,994,976; 6,994,852; 6,989,241; 6,974,863; 6,965, 018; 6,964,854; 6,962,981; 6,962,813; 6,956,107; 6,951, 924; 6,949,244; 6,946,129; 6,943,020; 6,939,547; 6,921, 645; 6,921,645; 6,921,533; 6,919,433; 6,919,078; 6,916, 475; 6,905,681; 6,899,879; 6,893,625; 6,887,468; 6,887, 466; 6,884,594; 6,881,405; 6,878,812; 6,875,580; 6,872, 568; 6,867,006; 6,864,062; 6,861,511; 6,861,227; 6,861, 226; 6,838,282; 6,835,549; 6,835,370; 6,824,780; 6,824, 778; 6,812,206; 6,793,924; 6,783,758; 6,770,450; 6,767, 711; 6,764,688; 6,764,681; 6,764,679; 6,743,898; 6,733, 981; 6,730,307; 6,720,155; 6,716,966; 6,709,653; 6,693, 176; 6,692,908; 6,689,607; 6,689,362; 6,689,355; 6,682, 737; 6,682,736; 6,682,734; 6,673,344; 6,653,104; 6,652, 852; 6,635,482; 6,630,144; 6,610,833; 6,610,294; 6,605, 441; 6,605,279; 6,596,852; 6,592,868; 6,576,745; 6,572, 856; 6,566,076; 6,562,618; 6,545,130; 6,544,749; 6,534, 058; 6,528,625; 6,528,269; 6,521,227; 6,518,404; 6,511, 665; 6,491,915; 6,488,930; 6,482,598; 6,482,408; 6,479, 247; 6,468,531; 6,468,529; 6,465,173; 6,461,823; 6,458, 356; 6,455,044; 6,455,040, 6,451,310; 6,444,206' 6,441, 143; 6,432,404; 6,432,402; 6,419,928; 6,413,726; 6,406, 694; 6,403,770; 6,403,091; 6,395,276; 6,395,274; 6,387, 350; 6,383,759; 6,383,484; 6,376,654; 6,372,215; 6,359, 126; 6,355,481; 6,355,444; 6,355,245; 6,355,244; 6,346, 246; 6,344,198; 6,340,571; 6,340,459; 6,331,175; 6,306, 393; 6,254,868; 6,187,287; 6,183,744; 6,129,914; 6,120, 767; 6,096,289; 6,077,499; 5,922,302; 5,874,540; 5,814, 440; 5,798,229; 5,789,554; 5,776,456; 5,736,119; 5,716, 595; 5,677,136; 5,587,459; 5,443,953, 5,525,338, the Examples section of each of which is incorporated herein by reference. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art (see, e.g., U.S. Pat. Nos. 7,531,327; 7,537,930; 7,608,425 and 7,785,880, the Examples section of each of which is incorporated herein by reference).

In other embodiments, the antibody complexes bind to a MHC class I, MHC class II or accessory molecule, such as CD40, CD54, CD80 or CD86. The antibody complex also may bind to a leukocyte activation cytokine, or to a cytokine mediator, such as NF-κB.

In certain embodiments, one of the two different targets may be a cancer cell receptor or cancer-associated antigen, particularly one that is selected from the group consisting of B-cell lineage antigens (CD19, CD20, CD21, CD22, CD23, etc.), VEGF, VEGFR, EGFR, carcinoembryonic antigen (CEA), placental growth factor (PlGF), tenascin, HER-2/neu, EGP-1, EGP-2, CD25, CD30, CD33, CD38, CD40, CD45, CD52, CD74, CD80, CD138, NCA66, CEACAM1, CEACAM6 (carcinoembryonic antigen-related cellular adhesion molecule 6), MUC1, MUC2, MUC3, MUC4, MUC16, IL-6, α-fetoprotein (AFP), A3, CA125, colon-specific antigen-p (CSAp), folate receptor, HLA-DR, human chorionic gonadotropin (HCG), Ia, EL-2, insulin-like growth factor (IGF) and IGF receptor, KS-1, Le(y), MAGE, necrosis antigens, PAM-4, prostatic acid phosphatase (PAP), Pr1, prostate specific antigen (PSA), prostate specific membrane antigen (PSMA), 5100, T101, TAC, TAG72, TRAIL receptors, and carbonic anhydrase IX.

Immunoconjugates

In certain embodiments, the antibodies or fragments thereof may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., *Int. J. Cancer* 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., *Int. J. Cancer* 41: 832 (1988); Shih et al., *Int. J. Cancer* 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., *J. Immunol.* 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

In some embodiments, a chelating agent may be attached to an antibody, antibody fragment or fusion protein and used to chelate a therapeutic or diagnostic agent, such as a radionuclide. Exemplary chelators include but are not limited to DTPA (such as Mx-DTPA), DOTA, TETA, NETA or NOTA. Methods of conjugation and use of chelating agents to attach metals or other ligands to proteins are well known in the art (see, e.g., U.S. Pat. No. 7,563,433, the Examples section of which is incorporated herein by reference).

In certain embodiments, radioactive metals or paramagnetic ions may be attached to proteins or peptides by reaction with a reagent having a long tail, to which may be attached a multiplicity of chelating groups for binding ions. Such a tail can be a polymer such as a polylysine, polysaccharide, or other derivatized or derivatizable chains having pendant groups to which can be bound chelating groups such as, e.g., ethylenediaminetetraacetic acid (EDTA), diethylenetriaminepentaacetic acid (DTPA), porphyrins, polyamines, crown ethers, bis-thiosemicarbazones, polyoximes, and like groups known to be useful for this purpose.

Chelates may be directly linked to antibodies or peptides, for example as disclosed in U.S. Pat. No. 4,824,659, incorporated herein in its entirety by reference. Particularly useful metal-chelate combinations include 2-benzyl-DTPA and its monomethyl and cyclohexyl analogs, used with diagnostic isotopes in the general energy range of 60 to 4,000 keV, such as $^{125}$I, $^{131}$I, $^{123}$I, $^{124}$I, $^{62}$Cu, $^{64}$Cu, $^{18}$F, $^{111}$In, $^{67}$Ga, $^{68}$Ga, $^{99m}$Tc, $^{94m}$Tc, $^{11}$C, $^{13}$N, $^{15}$O, $^{76}$Br, for radioimaging. The same chelates, when complexed with non-radioactive metals, such as manganese, iron and gadolinium are useful for MM. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates such as macrocyclic polyethers, which are of interest for stably binding nuclides, such as $^{223}$Ra for RAIT are encompassed.

More recently, methods of $^{18}$F-labeling of use in PET scanning techniques have been disclosed, for example by reaction of F-18 with a metal or other atom, such as aluminum. The $^{18}$F-Al conjugate may be complexed with chelating groups, such as DOTA, NOTA or NETA that are attached directly to antibodies or used to label targetable constructs in pre-targeting methods. Such F-18 labeling techniques are disclosed in U.S. Pat. No. 7,563,433, the Examples section of which is incorporated herein by reference.

In specific preferred embodiments, an immunoconjugate may be an antibody-drug conjugate (ADC). Two exemplary drugs of use in ADC production are SN-38 and a prodrug form of 2-pyrrolinodoxorubicine (P2PDox). Compositions and methods of production of SN-38-conjugated ADCs are disclosed, for example, in U.S. Pat. Nos. 7,999,083; 8,080,250; 8,741,300; 8,759,496, the Figures and Examples section of each of which are incorporated herein by reference. Compositions and methods of production of P2PDox ADCs are disclosed, for example, in U.S. Pat. No. 8,877,101, the Figures and Examples section of which are incorporated herein by reference.

Methods of Producing Bispecific Antibodies

In various embodiments, the subject combination therapy may utilize one or more bispecific antibodies (bsAbs), such as a leukocyte redirecting bsAb. A bispecific antibody as used herein is an antibody that contains binding sites for two different antigens, or two different epitopes on the same antigen. An antibody that can only bind to a single epitope on a single antigen is monospecific, regardless of the number of antigen-binding sites on the antibody molecule.

Early attempts at bispecific antibody construction either utilized chemical cross-linking or hybrid hybridomas or quadromas to join the two halves of two different antibodies together (e.g., Staerz et al., 1985, Nature 314:628-31; Milstein and Cuello, *Nature* 1983; 305:537-540; Karpovsky et al., 1984, J Exp Med 160:1686-701). Although the techniques work to make bsAbs, various production problems made use of such complexes difficult, such as the production of mixed populations containing different combinations of antigen-binding sites, difficulty in protein expression, the need to purify the bsAb of interest, low yields, expense of production, etc.

More recent approaches have utilized genetically engineered constructs that are capable of producing homogeneous products of single bsAbs, without the need for extensive purification to remove unwanted byproducts. Such constructs have included tandem scFv, diabodies, tandem diabodies, dual variable domain antibodies and heterodimerization using a motif such as Ch1/Ck domain or DNL™

(Chames & Baty, 2009, Curr Opin Drug Discov Devel 12:276-83; Chames & Baty, mAbs 1:539-47).

Triomabs is a variation on the quadroma approach that use a combination of mouse IgG2a and rat IgG2b antibodies to preferentially produce the recombinant antibody, compared to the random pairing typically seen in rat/rat or mouse/mouse quadromas (Chames & Baty, mAbs 1:539-47). An anti-CD3×anti-EpCAM bsAb (catumaxomab) created by this technique was able to efficiently recruit macrophages and NK cells and to activate T cells (Chames & Baty, mAbs 1:539-47). As discussed above, catumaxomab has been approved in Europe for treatment of malignant ascites in patients with EpCAM positive carcinomas (Chames & Baty, mAbs 1:539-47). Surprisingly, the recombinant bsAb was reported to induce only moderate anti-mouse and anti-rat responses in humans (Chames & Baty, mAbs 1:539-47), probably due at least in part to the i.p. route of administration for ascites. Ertumaxomab is another triomab targeting HER2, which may be of use for metastatic breast cancer. Bi20 is another triomab that targets CD20. In vitro, Bi20 exhibited efficient lyis of B cells from CLL patients (Chames & Baty, mAbs 1:539-47).

BITE® refers to tandem scFvs that are joined by a short peptide linker (Chames & Baty, mAbs 1:539-47). Blinatumomab is an anti-CD19×anti-CD3 BITE® with reported efficacy in hematologic cancers, such as non-Hodgkin's lymphoma and ALL, at very low concentrations (Nagorsen et al., 2009, Leukemia & Lymphoma 50:886-91; Chames & Baty, mAbs 1:539-47; Topp et al., 2012, Blood 120:5185-87; Bargou et al., 2008, Science 321:974-77). Another BITE® with specificity for EpCAM has been used in gastrointestinal, ovarian, colorectal and lung cancer (Amann et al., 2009, J Immunother 32:452-64; Chames & Baty, mAbs 1:539-47). Another BITE® (MEDI-565) targeted to CEACAM5 has been proposed for use in melanoma, colorectal, lung, pancreatic, stomach, ovarian, uterine, and breast cancers (Sanders et al., 1994, J Pathol 172:343-8). BITE® has been reported to exhibit anti-tumor activity at picomolar or even femtomolar concentrations (Chames & Baty, mAbs 1:539-47).

Another method of bsAb formation, involving assembly of two heavy and two light chains derived from two different pre-existing antibodies, is based on a knobs-into-holes approach that facilitates heterodimer formation and prevents homodimer formation (Schaefer et al., 2011, Proc Natl. Acad Sci USA 108:11187-92). The "CrossMab" technique further involves the exchange of heavy and light chain domains within the Fab of one half of the bispecific antibody, making the two arms so different that light-heavy chain mispairing can not occur (Schaefer et al., 2011). The knobs-into-holes approach introduces amino acids with bulky side chains into the CH3 domain of one heavy chain that fit into appropriately designed cavities in the CH3 domain of the other heavy chain. The combination of approaches prevents mis-match of both heavy chain to heavy chain and heavy chain to light chain interactions, resulting in primarily a single product. The initial CrossMab, generated against angiopoietin-2 (Ang-2) and VEGF-A, exhibited binding characteristics comparable to the parent mAbs, with potent anti-angiogenic and anti-tumoral activity (Schaefer et al., 2011, Proc Natl. Acad Sci USA 108:11187-92; Kienast et al., Clin Cancer Res, Oct. 25, 2013, Epub ahead of print).

In addition to the DART™ technology discussed above, other approaches to bsAb production have included tetravalent IgG-scFv fusions (Dong et al., 2011, MAbs 3:273-88); dual-acting Fab (DAF) antibodies (Bostrom et al., 2009, Science 323:1610-14); Igg-like dual-variable domain antibodies (DVD-Ig) (Wu et al., 2007, Nat Biotechnol 25:1290-97); and use of dynamic exchange between IgG4 molecules (van der Neut Kolfschoten et al., 2007, Science 317:1554-57). Although the DNL™ technology discussed below is preferred for formation of leukocyte redirecting bsAbs, the person of ordinary skill will realize that other types of bsAbs may be used in the claimed methods and compositions.

DOCK-AND-LOCK™ (DNL™)

In some embodiments, a bispecific antibody, either alone or else complexed to one or more effectors such as cytokines, is formed as a DOCK-AND-LOCK™ (DNL™) complex (see, e.g., U.S. Pat. Nos. 7,521,056; 7,527,787; 7,534,866; 7,550,143; 7,666,400; 7,901,680; 7,906,118; 7,981,398; 8,003,111, the Examples section of each of which is incorporated herein by reference.) Generally, the technique takes advantage of the specific and high-affinity binding interactions that occur between a dimerization and docking domain (DDD) sequence of the regulatory (R) subunits of cAMP-dependent protein kinase (PKA) and an anchor domain (AD) sequence derived from any of a variety of AKAP proteins (Baillie et al., FEBS Letters. 2005; 579: 3264. Wong and Scott, Nat. Rev. Mol. Cell Biol. 2004; 5: 959). The DDD and AD peptides may be attached to any protein, peptide or other molecule. Because the DDD sequences spontaneously dimerize and bind to the AD sequence, the technique allows the formation of complexes between any selected molecules that may be attached to DDD or AD sequences.

Although the standard DNL™ complex comprises a trimer with two DDD-linked molecules attached to one AD-linked molecule, variations in complex structure allow the formation of dimers, trimers, tetramers, pentamers, hexamers and other multimers. In some embodiments, the DNL™ complex may comprise two or more antibodies, antibody fragments or fusion proteins which bind to the same antigenic determinant or to two or more different antigens. The DNL™ complex may also comprise one or more other effectors, such as proteins, peptides, immunomodulators, cytokines, interleukins, interferons, binding proteins, peptide ligands, carrier proteins, toxins, ribonucleases such as onconase, inhibitory oligonucleotides such as siRNA, antigens or xenoantigens, polymers such as PEG, enzymes, therapeutic agents, hormones, cytotoxic agents, anti-angiogenic agents, pro-apoptotic agents or any other molecule or aggregate.

PKA, which plays a central role in one of the best studied signal transduction pathways triggered by the binding of the second messenger cAMP to the R subunits, was first isolated from rabbit skeletal muscle in 1968 (Walsh et al., J. Biol. Chem. 1968; 243:3763). The structure of the holoenzyme consists of two catalytic subunits held in an inactive form by the R subunits (Taylor, J. Biol. Chem. 1989; 264:8443). Isozymes of PKA are found with two types of R subunits (RI and RII), and each type has α and β isoforms (Scott, Pharmacol. Ther. 1991; 50:123). Thus, the four isoforms of PKA regulatory subunits are RIα, RIβ, RIIα and RIIβ, each of which comprises a DDD moiety amino acid sequence. The R subunits have been isolated only as stable dimers and the dimerization domain has been shown to consist of the first 44 amino-terminal residues of RIIα (Newlon et al., Nat. Struct. Biol. 1999; 6:222). As discussed below, similar portions of the amino acid sequences of other regulatory subunits are involved in dimerization and docking, each located near the N-terminal end of the regulatory subunit. Binding of cAMP to the R subunits leads to the release of active catalytic subunits for a broad spectrum of serine/threonine kinase activities, which are oriented toward selected substrates through the compartmentalization of PKA via its docking with AKAPs (Scott et al., *J. Biol. Chem.* 1990; 265; 21561)

Since the first AKAP, microtubule-associated protein-2, was characterized in 1984 (Lohmann et al., *Proc. Natl. Acad. Sci USA* 1984; 81:6723), more than 50 AKAPs that localize to various sub-cellular sites, including plasma membrane, actin cytoskeleton, nucleus, mitochondria, and endoplasmic reticulum, have been identified with diverse structures in species ranging from yeast to humans (Wong and Scott, *Nat. Rev. Mol. Cell Biol.* 2004; 5:959). The AD of AKAPs for PKA is an amphipathic helix of 14-18 residues (Carr et al., *J. Biol. Chem.* 1991; 266:14188). The amino acid sequences of the AD are varied among individual AKAPs, with the binding affinities reported for Rh dimers ranging from 2 to 90 nM (Alto et al., *Proc. Natl. Acad. Sci. USA* 2003; 100:4445). AKAPs will only bind to dimeric R subunits. For human RIIα, the AD binds to a hydrophobic surface formed by the 23 amino-terminal residues (Colledge and Scott, *Trends Cell Biol.* 1999; 6:216). Thus, the dimerization domain and AKAP binding domain of human RIIα are both located within the same N-terminal 44 amino acid sequence (Newlon et al., *Nat. Struct. Biol.* 1999; 6:222; Newlon et al., *EMBO J.* 2001; 20:1651), which is termed the DDD herein.

We have developed a platform technology to utilize the DDD of human PKA regulatory subunits and the AD of AKAP as an excellent pair of linker modules for docking any two entities, referred to hereafter as A and B, into a noncovalent complex, which could be further locked into a DNL™ complex through the introduction of cysteine residues into both the DDD and AD at strategic positions to facilitate the formation of disulfide bonds. The general methodology of the approach is as follows. Entity A is constructed by linking a DDD sequence to a precursor of A, resulting in a first component hereafter referred to as a. Because the DDD sequence would effect the spontaneous formation of a dimer, A would thus be composed of $a_2$. Entity B is constructed by linking an AD sequence to a precursor of B, resulting in a second component hereafter referred to as b. The dimeric motif of DDD contained in $a_2$ will create a docking site for binding to the AD sequence contained in b, thus facilitating a ready association of $a_2$ and b to form a binary, trimeric complex composed of $a_2b$. This binding event is stabilized with a subsequent reaction to covalently secure the two entities via disulfide bridges, which occurs very efficiently based on the principle of effective local concentration because the initial binding interactions should bring the reactive thiol groups placed onto both the DDD and AD into proximity (Chmura et al., *Proc. Natl. Acad. Sci. USA* 2001; 98:8480) to ligate site-specifically. Using various combinations of linkers, adaptor modules and precursors, a wide variety of DNL™ constructs of different stoichiometry may be produced and used (see, e.g., U.S. Pat. Nos. 7,550,143; 7,521,056; 7,534,866; 7,527,787 and 7,666,400.)

By attaching the DDD and AD away from the functional groups of the two precursors, such site-specific ligations are also expected to preserve the original activities of the two precursors. This approach is modular in nature and potentially can be applied to link, site-specifically and covalently, a wide range of substances, including peptides, proteins, antibodies, antibody fragments, and other effector moieties with a wide range of activities. Utilizing the fusion protein method of constructing AD and DDD conjugated effectors described in the Examples below, virtually any protein or peptide may be incorporated into a DNL™ construct. However, the technique is not limiting and other methods of conjugation may be utilized.

A variety of methods are known for making fusion proteins, including nucleic acid synthesis, hybridization and/or amplification to produce a synthetic double-stranded nucleic acid encoding a fusion protein of interest. Such double-stranded nucleic acids may be inserted into expression vectors for fusion protein production by standard molecular biology techniques (see, e.g. Sambrook et al., MOLECULAR CLONING, A LABORATORY MANUAL, $2^{nd}$ Ed, 1989). In such preferred embodiments, the AD and/or DDD moiety may be attached to either the N-terminal or C-terminal end of an effector protein or peptide. However, the skilled artisan will realize that the site of attachment of an AD or DDD moiety to an effector moiety may vary, depending on the chemical nature of the effector moiety and the part(s) of the effector moiety involved in its physiological activity. Site-specific attachment of a variety of effector moieties may be performed using techniques known in the art, such as the use of bivalent cross-linking reagents and/or other chemical conjugation techniques.

Dock-and-Lock™ (DNL™) technology has been used to produce a variety of complexes in assorted formats (Rossi et al., 2012, *Bioconjug Chem* 23:309-23). Bispecific hexavalent antibodies (bsHexAbs) based on veltuzumab (anti-CD20) and epratuzumab (anti-CD22) were constructed by combining a stabilized (Fab)$_2$ fused to a dimerization and docking domain (DDD) with an IgG containing an anchor domain (AD) appended at the C-terminus of each heavy chain ($C_H$3-AD2-IgG) (Rossi et al., 2009, *Blood* 113, 6161-71). Compared to mixtures of their parental mAbs, these Fc-based bsHexAbs, referred to henceforth as "Fc-bsHexAbs", induced unique signaling events (Gupta et al., 2010, *Blood* 116:3258-67), and exhibited potent cytotoxicity in vitro. However, the Fc-bsHexAbs were cleared from circulation of mice approximately twice as fast as the parental mAbs (Rossi et al., 2009, *Blood* 113, 6161-71). Although the Fc-bsHexAbs are highly stable ex vivo, it is possible that some dissociation occurs in vivo, for example by intracellular processing. Further, the Fc-bsHexAbs lack CDC activity.

Fc-based immunocytokines have also been assembled as DNL™ complexes, comprising two or four molecules of interferon-alpha 2b (IFNα2b) fused to the C-terminal end of the $C_H$3-AD2-IgG Fc (Rossi et al., 2009, *Blood* 114:3864-71; Rossi et al., 2010, *Cancer Res* 70:7600-09; Rossi et al., 2011, *Blood* 118:1877-84). The Fc-IgG-IFNα maintained high specific activity, approaching that of recombinant IFNα, and were remarkably potent in vitro and in vivo against non-Hodgkin lymphoma (NHL) xenografts. The $T_{1/2}$ of the Fc-IgG-IFNα in mice was longer than PEGylated IFNα, but half as long as the parental mAbs. Similar to the Fc-bsHexAbs, the Fc-IgG-IFNα dissociated in vivo over time and exhibited diminished CDC, but ADCC was enhanced.

Structure-Function Relationships in AD and DDD Moieties

For different types of DNL™ constructs, different AD or DDD sequences may be utilized. Exemplary DDD and AD sequences are provided below.

DDD1

(SEQ ID NO: 1)
SHIQIPPGLTELLQGYTVEVLRQQPPDLVEFAVEYFTRLREARA

DDD2

(SEQ ID NO: 2)
CGHIQIPPGLTELLQGYTVEVLRQQPPDLVEFAVEYFTRLREARA

AD1

(SEQ ID NO: 3)
QIEYLAKQIVDNAIQQA

AD2

(SEQ ID NO: 4)
CGQIEYLAKQIVDNAIQQAGC

The skilled artisan will realize that DDD1 and DDD2 are based on the DDD sequence of the human RIIα isoform of protein kinase A. However, in alternative embodiments, the DDD and AD moieties may be based on the DDD sequence of the human RIα form of protein kinase A and a corresponding AKAP sequence, as exemplified in DDD3, DDD3C and AD3 below.

DDD3

(SEQ ID NO: 5)
SLRECELYVQKHNIQALLKDSIVQLCTARPERPMAFLREYFERLEKEEAK

DDD3C (SEQ ID NO: 6)
MSCGGSLRECELYVQKHNIQALLKDSIVQLCTARPERPMAFLREYFERLE
KEEAK

AD3

(SEQ ID NO: 7)
CGFEELAWKIAKMIWSDVFQQGC

In other alternative embodiments, other sequence variants of AD and/or DDD moieties may be utilized in construction of the DNL™ complexes. For example, there are only four variants of human PKA DDD sequences, corresponding to the DDD moieties of PKA RIα, RIIα, RIβ and RIIβ. The RIIα DDD sequence is the basis of DDD1 and DDD2 disclosed above. The four human PKA DDD sequences are shown below. The DDD sequence represents residues 1-44 of RIIα, 1-44 of RIIβ, 12-61 of RIα and 13-66 of RIβ. (Note that the sequence of DDD1 is modified slightly from the human PKA RIIα DDD moiety.)

PKA RIα

(SEQ ID NO: 8)
SLRECELYVQKHNIQALLKDVSIVQLCTARPERPMAFLREYFEKLEKEEA
K

PKA RIβ

(SEQ ID NO: 9)
SLKGCELYVQLHGIQQVLKDCIVHLCISKPERPMKFLREHFEKLEKEENR
QILA

PKA RIIα

(SEQ ID NO: 10)
SHIQIPPGLTELLQGYTVEVGQQPPDLVDFAVEYFTRLREARRQ

PKA RIIβ

(SEQ ID NO: 11)
SIEIPAGLTELLQGFTVEVLRHQPADLLEFALQHFTRLQQENER

The structure-function relationships of the AD and DDD domains have been the subject of investigation. (See, e.g., Burns-Hamuro et al., 2005, *Protein Sci* 14:2982-92; Carr et al., 2001, *J Biol Chem* 276:17332-38; Alto et al., 2003, *Proc Natl Acad Sci USA* 100:4445-50; Hundsrucker et al., 2006, *Biochem J* 396:297-306; Stokka et al., 2006, *Biochem J* 400:493-99; Gold et al., 2006, *Mol Cell* 24:383-95; Kinderman et al., 2006, *Mol Cell* 24:397-408, the entire text of each of which is incorporated herein by reference.)

For example, Kinderman et al. (2006, *Mol Cell* 24:397-408) examined the crystal structure of the AD-DDD binding interaction and concluded that the human DDD sequence contained a number of conserved amino acid residues that were important in either dimer formation or AKAP binding, underlined in SEQ ID NO:1 below. (See FIG. 1 of Kinderman et al., 2006, incorporated herein by reference.) The skilled artisan will realize that in designing sequence variants of the DDD sequence, one would desirably avoid changing any of the underlined residues, while conservative amino acid substitutions might be made for residues that are less critical for dimerization and AKAP binding.

(SEQ ID NO: 1)
SHIQIPPGLTELLQGYTVEVLRQQPPDLVEFAVEYFTRLREARA

As discussed in more detail below, conservative amino acid substitutions have been characterized for each of the twenty common L-amino acids. Thus, based on the data of Kinderman (2006) and conservative amino acid substitutions, potential alternative DDD sequences based on SEQ ID NO:1 are shown in Table 2. In devising Table 2, only highly conservative amino acid substitutions were considered. For example, charged residues were only substituted for residues of the same charge, residues with small side chains were substituted with residues of similar size, hydroxyl side chains were only substituted with other hydroxyls, etc. Because of the unique effect of proline on amino acid secondary structure, no other residues were substituted for proline. A limited number of such potential alternative DDD moiety sequences are shown in SEQ ID NO:12 to SEQ ID NO:31 below. The skilled artisan will realize that alternative species within the genus of DDD moieties can be constructed by standard techniques, for example using a commercial peptide synthesizer or well known site-directed mutagenesis techniques. The effect of the amino acid substitutions on AD moiety binding may also be readily determined by standard binding assays, for example as disclosed in Alto et al. (2003, *Proc Natl Acad Sci USA* 100:4445-50).

TABLE 2

Conservative Amino Acid Substitutions in DDD1 (SEQ ID NO: 1).
Consensus sequence disclosed as SEQ ID NO: 87.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T | K | N |   |   |   |   |   | A |   | S | D |   |   |   | N | A | S |   | D |   | K |
|   | R |   |   |   |   |   |   |   |   |   |   |   |   |   |   |   |   |   |   |   |   |

TABLE 2-continued

Conservative Amino Acid Substitutions in DDD1 (SEQ ID NO: 1).
Consensus sequence disclosed as SEQ ID NO: 87.

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N | N |   |   | E |   | D |   |   | L |   | D |   |   | S | K |   | K | D | L | K | L |
|   |   |   |   |   |   |   |   |   | I |   |   |   |   |   |   |   |   |   | I |   | I |
|   |   |   |   |   |   |   |   |   | V |   |   |   |   |   |   |   |   |   | V |   | V |

```
THIQIPPGLTELLQGYTVEVLRQQPPDLVEFAVEYFTRLREARA (SEQ ID NO: 12)

SKIQIPPGLTELLQGYTVEVLRQQPPDLVEFAVEYFTRLREARA (SEQ ID NO: 13)

SRIQIPPGLTELLQGYTVEVLRQQPPDLVEFAVEYFTRLREARA (SEQ ID NO: 14)

SHINIPPGLTELLQGYTVEVLRQQPPDLVEFAVEYFTRLREARA (SEQ ID NO: 15)

SHIQIPPALTELLQGYTVEVLRQQPPDLVEFAVEYFTRLREARA (SEQ ID NO: 16)

SHIQIPPGLSELLQGYTVEVLRQQPPDLVEFAVEYFTRLREARA (SEQ ID NO: 17)

SHIQIPPGLTDLLQGYTVEVLRQQPPDLVEFAVEYFTRLREARA (SEQ ID NO: 18)

SHIQIPPGLTELLNGYTVEVLRQQPPDLVEFAVEYFTRLREARA (SEQ ID NO: 19)

SHIQIPPGLTELLQAYTVEVLRQQPPDLVEFAVEYFTRLREARA (SEQ ID NO: 20)

SHIQIPPGLTELLQGYSVEVLRQQPPDLVEFAVEYFTRLREARA (SEQ ID NO: 21)

SHIQIPPGLTELLQGYTVDVLRQQPPDLVEFAVEYFTRLREARA (SEQ ID NO: 22)

SHIQIPPGLTELLQGYTVEVLKQQPPDLVEFAVEYFTRLREARA (SEQ ID NO: 23)

SHIQIPPGLTELLQGYTVEVLRNQPPDLVEFAVEYFTRLREARA (SEQ ID NO: 24)

SHIQIPPGLTELLQGYTVEVLRQNPPDLVEFAVEYFTRLREARA (SEQ ID NO: 25)

SHIQIPPGLTELLQGYTVEVLRQQPPELVEFAVEYFTRLREARA (SEQ ID NO: 26)

SHIQIPPGLTELLQGYTVEVLRQQPPDLVDFAVEYFTRLREARA (SEQ ID NO: 27)

SHIQIPPGLTELLQGYTVEVLRQQPPDLVEFLVEYFTRLREARA (SEQ ID NO: 28)

SHIQIPPGLTELLQGYTVEVLRQQPPDLVEFIVEYFTRLREARA (SEQ ID NO: 29)

SHIQIPPGLTELLQGYTVEVLRQQPPDLVEFVVEYFTRLREARA (SEQ ID NO: 30)

SHIQIPPGLTELLQGYTVEVLRQQPPDLVEFAVDYFTRLREARA (SEQ ID NO: 31)
```

Alto et al. (2003, *Proc Natl Acad Sci USA* 100:4445-50) performed a bioinformatic analysis of the AD sequence of various AKAP proteins to design an RII selective AD sequence called AKAP-IS (SEQ ID NO:3), with a binding constant for DDD of 0.4 nM. The AKAP-IS sequence was designed as a peptide antagonist of AKAP binding to PKA. Residues in the AKAP-IS sequence where substitutions tended to decrease binding to DDD are underlined in SEQ ID NO:3 below. The skilled artisan will realize that in designing sequence variants of the AD sequence, one would desirably avoid changing any of the underlined residues, while conservative amino acid substitutions might be made for residues that are less critical for DDD binding. Table 3 shows potential conservative amino acid substitutions in the sequence of AKAP-IS (AD1, SEQ ID NO:3), similar to that shown for DDD1 (SEQ ID NO:1) in Table 2 above.

A limited number of such potential alternative AD moiety sequences are shown in SEQ ID NO:32 to SEQ ID NO:49 below. Other species within the genus of possible AD moiety sequences could be made, tested and used by the skilled artisan, based on the data of Alto et al. (2003). It is noted that FIG. 2 of Alto (2003) shows a number of amino acid substitutions that may be made, while retaining binding activity to DDD moieties, based on actual binding experiments.

AKAP-IS (SEQ ID NO: 3)

QIEYLAKQIVDNAIQQA

TABLE 3

Conservative Amino Acid Substitutions in AD1 (SEQ ID NO: 3). Consensus sequence disclosed as SEQ ID NO: 88.

| Q | I | E | Y | L | A | K | Q | I | V | D | N | A | I | Q | Q | A |
|---|---|---|---|---|---|---|---|---|---|---|---|---|---|---|---|---|
| N | L | D | F | I | | | R | N | | E | Q | | | N | N | L |

TABLE 3-continued Conservative Amino Acid Substitutions in AD1 (SEQ ID NO: 3). Consensus sequence disclosed as SEQ ID NO: 88.

| V | T | V |   |   |   | I |
|   | S |   |   |   |   | V |

NIEYLAKQIVDNAIQQA (SEQ ID NO: 32)

QLEYLAKQIVDNAIQQA (SEQ ID NO: 33)

QVEYLAKQIVDNAIQQA (SEQ ID NO: 34)

QIDYLAKQIVDNAIQQA (SEQ ID NO: 35)

QIEFLAKQIVDNAIQQA (SEQ ID NO: 36)

QIETLAKQIVDNAIQQA (SEQ ID NO: 37)

QIESLAKQIVDNAIQQA (SEQ ID NO: 38)

QIEYIAKQIVDNAIQQA (SEQ ID NO: 39)

QIEYVAKQIVDNAIQQA (SEQ ID NO: 40)

QIEYLARQIVDNAIQQA (SEQ ID NO: 41)

QIEYLAKNIVDNAIQQA (SEQ ID NO: 42)

QIEYLAKQIVENAIQQA (SEQ ID NO: 43)

QIEYLAKQIVDQAIQQA (SEQ ID NO: 44)

QIEYLAKQIVDNAINQA (SEQ ID NO: 45)

QIEYLAKQIVDNAIQNA (SEQ ID NO: 46)

QIEYLAKQIVDNAIQQL (SEQ ID NO: 47)

QIEYLAKQIVDNAIQQI (SEQ ID NO: 48)

QIEYLAKQIVDNAIQQV (SEQ ID NO: 49)

Gold et al. (2006, *Mol Cell* 24:383-95) utilized crystallography and peptide screening to develop a SuperAKAP-IS sequence (SEQ ID NO:50), exhibiting a five order of magnitude higher selectivity for the RII isoform of PKA compared with the RI isoform. Underlined residues indicate the positions of amino acid substitutions, relative to the AKAP-IS sequence, which increased binding to the DDD moiety of RIIα. In this sequence, the N-terminal Q residue is numbered as residue number 4 and the C-terminal A residue is residue number 20. Residues where substitutions could be made to affect the affinity for RIIα were residues 8, 11, 15, 16, 18, 19 and 20 (Gold et al., 2006). It is contemplated that in certain alternative embodiments, the SuperAKAP-IS sequence may be substituted for the AKAP-IS AD moiety sequence to prepare DNL™ constructs. Other alternative sequences that might be substituted for the AKAP-IS AD sequence are shown in SEQ ID NO:51-53. Substitutions relative to the AKAP-IS sequence are underlined. It is anticipated that, as with the AD2 sequence shown in SEQ ID NO:4, the AD moiety may also include the additional N-terminal residues cysteine and glycine and C-terminal residues glycine and cysteine.

SuperAKAP-IS (SEQ ID NO: 50)

QIEY<u>V</u>AKQIVD<u>Y</u>AI<u>H</u>QA

-continued

Alternative AKAP sequences (SEQ ID NO: 51)

QIEY<u>K</u>AKQIVD<u>H</u>AI<u>H</u>QA (SEQ ID NO: 52)

QIEY<u>H</u>AKQIVD<u>H</u>AI<u>H</u>QA (SEQ ID NO: 53)

QIEY<u>V</u>AKQIVD<u>H</u>AI<u>H</u>QA

FIG. 2 of Gold et al. disclosed additional DDD-binding sequences from a variety of AKAP proteins, shown below.

RII-Specific AKAPs

AKAP-KL (SEQ ID NO: 54)

PLEYQAGLLVQNAIQQAI

AKAP79

(SEQ ID NO: 55)

LLIETASSLVKNAIQLSI

AKAP-Lbc (SEQ ID NO: 56)

LIEEAASRIVDAVIEQVK

RI-Specific AKAPs

AKAPce

```
                                                    (SEQ ID NO: 57)
alyqfadrfselviseal riad
                                                    (SEQ ID NO: 58)
leqvanqladqiikeat pv38
                                                    (SEQ ID NO: 59)
feelawkiakmiwsdvf Dual-Specificity AKAPs
akap7
                                                    (SEQ ID NO: 60)
elvrlskrlvenavlkav map2d
                                                    (SEQ ID NO: 61)
taeevsarivqvvtaeav dakap1
                                                    (SEQ ID NO: 62)
qikqaafqlisqvileat Dakap2
                                                    (SEQ ID NO: 63)
lawkiakmivsdvmqq
```

Stokka et al. (2006, *Biochem J* 400:493-99) also developed peptide competitors of AKAP binding to PKA, shown in SEQ ID NO:64-66. The peptide antagonists were designated as Ht31 (SEQ ID NO:64), RIAD (SEQ ID NO:65) and PV-38 (SEQ ID NO:66). The Ht-31 peptide exhibited a greater affinity for the RII isoform of PKA, while the RIAD and PV-38 showed higher affinity for RI.

```
Ht31
                                                    (SEQ ID NO: 64)
DLIEEAASRIVDAVIEQVKAAGAY

RIAD
                                                    (SEQ ID NO: 65)
LEQYANQLADQIIKEATE

PV-38
                                                    (SEQ ID NO: 66)
FEELAWKIAKMIWSDVFQQC
```

Hundsrucker et al. (2006, *Biochem J* 396:297-306) developed still other peptide competitors for AKAP binding to PKA, with a binding constant as low as 0.4 nM to the DDD of the RII form of PKA. The sequences of various AKAP antagonistic peptides are provided in Table 1 of Hundsrucker et al., reproduced in Table 4 below. AKAPIS represents a synthetic RII subunit-binding peptide. All other peptides are derived from the RII-binding domains of the indicated AKAPs.

TABLE 4

| AKAP Peptide sequences | |
|---|---|
| | Peptide Sequence |
| AKAPIS | QIEYLAKQIVDNAIQQA (SEQ ID NO: 3) |
| AKAPIS-P | QIEYLAKQIPDNAIQQA (SEQ ID NO: 67) |
| Ht31 | KGADLIEEAASRIVDAVIEQVKAAG (SEQ ID NO: 68) |
| Ht31-P | KGADLIEEAASRIPDAPIEQVKAAG (SEQ ID NO: 69) |

TABLE 4-continued

| AKAP Peptide sequences | |
|---|---|
| | Peptide Sequence |
| AKAP7δ-wt-pep | PEDAELVRLSKRLVENAVLKAVQQY (SEQ ID NO: 70) |
| AKAP7δ-L304T-pep | PEDAELVRTSKRLVENAVLKAVQQY (SEQ ID NO: 71) |
| AKAP7δ-L308D-pep | PEDAELVRLSKRDVENAVLKAVQQY (SEQ ID NO: 72) |
| AKAP7δ-P-pep | PEDAELVRLSKRLPENAVLKAVQQY (SEQ ID NO: 73) |
| AKAP7δ-PP-pep | PEDAELVRLSKRLPENAPLKAVQQY (SEQ ID NO: 74) |
| AKAP7δ-L314E-pep | PEDAELVRLSKRLVENAVEKAVQQY (SEQ ID NO: 75) |
| AKAP1-pep | EEGLDRNEEIKRAAFQIISQVISEA (SEQ ID NO: 76) |
| AKAP2-pep | LVDDPLEYQAGLLVQNAIQQAIAEQ (SEQ ID NO: 77) |
| AKAP5-pep | QYETLLIETASSLVKNAIQLSIEQL (SEQ ID NO: 78) |
| AKAP9-pep | LEKQYQEQLEEEVAKVIVSMSIAFA (SEQ ID NO: 79) |
| AKAP10-pep | NTDEAQEELAWKIAKMIVSDIMQQA (SEQ ID NO: 80) |
| AKAP11-pep | VNLDKKAVLAEKIVAEAIEKAEREL (SEQ ID NO: 81) |
| AKAP12-pep | NGILELETKSSKLVQNIIQTAVDQF (SEQ ID NO: 82) |
| AKAP14-pep | TQDKNYEDELTQVALALVEDVINYA (SEQ ID NO: 83) |
| Rab32-pep | ETSAKDNINIEEAARFLVEKILVNH (SEQ ID NO: 84) |

Residues that were highly conserved among the AD domains of different AKAP proteins are indicated below by underlining with reference to the AKAP IS sequence (SEQ ID NO:3). The residues are the same as observed by Alto et al. (2003), with the addition of the C-terminal alanine residue. (See FIG. 4 of Hundsrucker et al. (2006), incorporated herein by reference.) The sequences of peptide antagonists with particularly high affinities for the RII DDD sequence were those of AKAP-IS, AKAP7δ-wt-pep, AKAP7δ-L304T-pep and AKAP7δ-L308D-pep.

```
AKAP-IS
                                                    (SEQ ID NO: 3)
QIEYLAKQIVDNAIQQA
```

Carr et al. (2001, *J Biol Chem* 276:17332-38) examined the degree of sequence homology between different AKAP-binding DDD sequences from human and non-human proteins and identified residues in the DDD sequences that appeared to be the most highly conserved among different DDD moieties. These are indicated below by underlining with reference to the human PKA RIIα DDD sequence of SEQ ID NO:1. Residues that were particularly conserved are further indicated by italics. The residues overlap with, but are not identical to those suggested by Kinderman et al.

(2006) to be important for binding to AKAP proteins. The skilled artisan will realize that in designing sequence variants of DDD, it would be most preferred to avoid changing the most conserved residues (italicized), and it would be preferred to also avoid changing the conserved residues (underlined), while conservative amino acid substitutions may be considered for residues that are neither underlined nor italicized.

(SEQ ID NO: 1)
SHIQIPPGLTELLQGYTVEVLRQQPPDLVEFAVEYFTRLREARA

A modified set of conservative amino acid substitutions for the DDD1 (SEQ ID NO:1) sequence, based on the data of Carr et al. (2001) is shown in Table 5. Even with this reduced set of substituted sequences, there are over 65,000 possible alternative DDD moiety sequences that may be produced, tested and used by the skilled artisan without undue experimentation. The skilled artisan could readily derive such alternative DDD amino acid sequences as disclosed above for Table 2 and Table 3.

TABLE 5

Conservative Amino Acid Substitutions in DDD1 (SEQ ID NO: 1).
Consensus sequence disclosed as SEQ ID NO: 89.

| S | H | I | Q | I | P | P | G | L | T | E | L | L | Q | G | Y | T | V | E | V | L | R |
|---|---|---|---|---|---|---|---|---|---|---|---|---|---|---|---|---|---|---|---|---|---|
| T |   | N |   |   |   |   |   |   | S |   |   |   |   |   |   |   | I |   |   |   |   |
|   |   |   |   |   |   |   |   |   |   |   |   |   |   |   |   |   | L |   |   |   |   |
|   |   |   |   |   |   |   |   |   |   |   |   |   |   |   |   |   | A |   |   |   |   |

| Q | Q | P | P | D | L | V | E | F | A | V | E | Y | F | T | R | L | R | E | A | R | A |
|---|---|---|---|---|---|---|---|---|---|---|---|---|---|---|---|---|---|---|---|---|---|
| N |   |   |   |   |   |   |   |   |   | I | D |   |   | S | K |   | K |   | L |   | L |
|   |   |   |   |   |   |   |   |   |   | L |   |   |   |   |   |   |   |   | I |   | I |
|   |   |   |   |   |   |   |   |   |   | A |   |   |   |   |   |   |   |   | V |   | V |

The skilled artisan will realize that these and other amino acid substitutions in the DDD or AD amino acid sequences may be utilized to produce alternative species within the genus of AD or DDD moieties, using techniques that are standard in the field and only routine experimentation.

Amino Acid Substitutions

In alternative embodiments, the disclosed methods and compositions may involve production and use of proteins or peptides with one or more substituted amino acid residues. For example, the DDD and/or AD sequences used to make DNL™ constructs may be modified as discussed above.

The skilled artisan will be aware that, in general, amino acid substitutions typically involve the replacement of an amino acid with another amino acid of relatively similar properties (i.e., conservative amino acid substitutions). The properties of the various amino acids and effect of amino acid substitution on protein structure and function have been the subject of extensive study and knowledge in the art.

For example, the hydropathic index of amino acids may be considered (Kyte & Doolittle, 1982, *J. Mol. Biol.*, 157: 105-132). The relative hydropathic character of the amino acid contributes to the secondary structure of the resultant protein, which in turn defines the interaction of the protein with other molecules. Each amino acid has been assigned a hydropathic index on the basis of its hydrophobicity and charge characteristics (Kyte & Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5). In making conservative substitutions, the use of amino acids whose hydropathic indices are within ±2 is preferred, within ±1 are more preferred, and within ±0.5 are even more preferred.

Amino acid substitution may also take into account the hydrophilicity of the amino acid residue (e.g., U.S. Pat. No. 4,554,101). Hydrophilicity values have been assigned to amino acid residues: arginine (+3.0); lysine (+3.0); aspartate (+3.0); glutamate (+3.0); serine (+0.3); asparagine (+0.2); glutamine (+0.2); glycine (0); threonine (−0.4); proline (−0.5.+−0.1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). Replacement of amino acids with others of similar hydrophilicity is preferred.

Other considerations include the size of the amino acid side chain. For example, it would generally not be preferred to replace an amino acid with a compact side chain, such as glycine or serine, with an amino acid with a bulky side chain, e.g., tryptophan or tyrosine. The effect of various amino acid residues on protein secondary structure is also a consideration. Through empirical study, the effect of different amino acid residues on the tendency of protein domains to adopt an alpha-helical, beta-sheet or reverse turn secondary structure has been determined and is known in the art (see, e.g., Chou & Fasman, 1974, *Biochemistry*, 13:222-245; 1978, *Ann. Rev. Biochem.*, 47: 251-276; 1979, *Biophys. J.*, 26:367-384).

Based on such considerations and extensive empirical study, tables of conservative amino acid substitutions have been constructed and are known in the art. For example: arginine and lysine; glutamate and aspartate; serine and threonine; glutamine and asparagine; and valine, leucine and isoleucine. Alternatively: Ala (A) leu, ile, val; Arg (R) gln, asn, lys; Asn (N) his, asp, lys, arg, gln; Asp (D) asn, glu; Cys (C) ala, ser; Gln (Q) glu, asn; Glu (E) gln, asp; Gly (G) ala; His (H) asn, gln, lys, arg; Ile (I) val, met, ala, phe, leu; Leu (L) val, met, ala, phe, ile; Lys (K) gln, asn, arg; Met (M) phe, ile, leu; Phe (F) leu, val, ile, ala, tyr; Pro (P) ala; Ser (S), thr; Thr (T) ser; Trp (W) phe, tyr; Tyr (Y) trp, phe, thr, ser; Val (V) ile, leu, met, phe, ala.

Other considerations for amino acid substitutions include whether or not the residue is located in the interior of a protein or is solvent exposed. For interior residues, conservative substitutions would include: Asp and Asn; Ser and Thr; Ser and Ala; Thr and Ala; Ala and Gly; Ile and Val; Val and Leu; Leu and Ile; Leu and Met; Phe and Tyr; Tyr and Trp. (See, e.g., PROWL website at rockefeller.edu) For solvent exposed residues, conservative substitutions would include: Asp and Asn; Asp and Glu; Glu and Gln; Glu and Ala; Gly and Asn; Ala and Pro; Ala and Gly; Ala and Ser; Ala and Lys; Ser and Thr; Lys and Arg; Val and Leu; Leu and Ile; Ile and Val; Phe and Tyr. (Id.) Various matrices have been constructed to assist in selection of amino acid substitutions, such as the PAM250 scoring matrix, Dayhoff matrix, Grantham matrix, McLachlan matrix, Doolittle matrix, Henikoff matrix, Miyata matrix, Fitch matrix, Jones matrix, Rao matrix, Levin matrix and Risler matrix (Idem.)

In determining amino acid substitutions, one may also consider the existence of intermolecular or intramolecular bonds, such as formation of ionic bonds (salt bridges) between positively charged residues (e.g., His, Arg, Lys) and negatively charged residues (e.g., Asp, Glu) or disulfide bonds between nearby cysteine residues.

Methods of substituting any amino acid for any other amino acid in an encoded protein sequence are well known and a matter of routine experimentation for the skilled artisan, for example by the technique of site-directed mutagenesis or by synthesis and assembly of oligonucleotides encoding an amino acid substitution and splicing into an expression vector construct.

Therapeutic Agents

In alternative embodiments, therapeutic agents such as cytotoxic agents, anti-angiogenic agents, pro-apoptotic agents, antibiotics, hormones, hormone antagonists, chemokines, drugs, prodrugs, toxins, enzymes or other agents may be used, either conjugated to the subject bsAbs, ADCs and/or antibodies or separately administered before, simultaneously with, or after the bsAbs, ADCs and/or antibodies. Drugs of use may possess a pharmaceutical property selected from the group consisting of antimitotic, antikinase, alkylating, antimetabolite, antibiotic, alkaloid, anti-angiogenic, pro-apoptotic agents and combinations thereof.

Exemplary drugs of use may include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, *vinca* alkaloids and ZD1839.

Toxins of use may include ricin, abrin, alpha toxin, saporin, ribonuclease (RNase), e.g., onconase, DNase I, Staphylococcal enterotoxin-A, pokeweed antiviral protein, gelonin, diphtheria toxin, *Pseudomonas* exotoxin, and *Pseudomonas* endotoxin.

Chemokines of use may include RANTES, MCAF, MIP1-alpha, MIP1-Beta and IP-10.

In certain embodiments, anti-angiogenic agents, such as angiostatin, baculostatin, canstatin, maspin, anti-VEGF antibodies, anti-PlGF peptides and antibodies, anti-vascular growth factor antibodies, anti-Flk-1 antibodies, anti-Flt-1 antibodies and peptides, anti-Kras antibodies, anti-cMET antibodies, anti-MIF (macrophage migration-inhibitory factor) antibodies, laminin peptides, fibronectin peptides, plasminogen activator inhibitors, tissue metalloproteinase inhibitors, interferons, interleukin-12, IP-10, Gro-β, thrombospondin, 2-methoxyoestradiol, proliferin-related protein, carboxiamidotriazole, CM101, Marimastat, pentosan polysulphate, angiopoietin-2, interferon-alpha, herbimycin A, PNU145156E, 16K prolactin fragment, Linomide (roquinimex), thalidomide, pentoxifylline, genistein, TNP-470, endostatin, paclitaxel, accutin, angiostatin, cidofovir, vincristine, bleomycin, AGM-1470, platelet factor 4 or minocycline may be of use.

Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β or -λ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-13, IL-14, IL-15, IL-16, IL-17, IL-18, IL-21, IL-25, LIF, kit-ligand or FLT-3, angiostatin, thrombospondin, endostatin, tumor necrosis factor and LT.

Radionuclides of use include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{211}$Pb, and $^{227}$Th. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5, 000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like. Some useful diagnostic nuclides may include $^{18}$F, $^{52}$Fe, $^{62}$Cu, $^{64}$Cu, $^{67}$Cu, $^{67}$Ga, $^{68}$Ga, $^{86}$Y, $^{89}$Zr, $^{94}$Tc, $^{94m}$Tc, $^{99m}$Tc, or, $^{111}$In.

Therapeutic agents may include a photoactive agent or dye. Fluorescent compositions, such as fluorochrome, and other chromogens, or dyes, such as porphyrins sensitive to visible light, have been used to detect and to treat lesions by directing the suitable light to the lesion. In therapy, this has been termed photoradiation, phototherapy, or photodynamic therapy. See Joni et al. (eds.), PHOTODYNAMIC THERAPY OF TUMORS AND OTHER DISEASES (Libreria Progetto 1985); van den Bergh, Chem. Britain (1986), 22:430. Moreover, monoclonal antibodies have been coupled with photoactivated dyes for achieving phototherapy. See Mew et al., *J. Immunol.* (1983), 130:1473; idem., *Cancer Res.* (1985), 45:4380; Oseroff et al., *Proc. Natl. Acad. Sci. USA* (1986), 83:8744; idem., *Photochem. Photobiol.* (1987), 46:83; Hasan et al., *Prog. Clin. Biol. Res.* (1989), 288:471; Tatsuta et al., *Lasers Surg. Med.* (1989), 9:422; Pelegrin et al., *Cancer* (1991), 67:2529.

Other useful therapeutic agents may comprise oligonucleotides, especially antisense oligonucleotides that preferably are directed against oncogenes and oncogene products, such as bcl-2 or p53. A preferred form of therapeutic oligonucleotide is siRNA. The skilled artisan will realize that any siRNA or interference RNA species may be attached to an antibody or fragment thereof for delivery to a targeted tissue. Many siRNA species against a wide variety of targets are known in the art, and any such known siRNA may be utilized in the claimed methods and compositions.

Known siRNA species of potential use include those specific for IKK-gamma (U.S. Pat. No. 7,022,828); VEGF, Flt-1 and Flk-1/KDR (U.S. Pat. No. 7,148,342); Bcl2 and EGFR (U.S. Pat. No. 7,541,453); CDC20 (U.S. Pat. No. 7,550,572); transducin (beta)-like 3 (U.S. Pat. No. 7,576,196); KRAS (U.S. Pat. No. 7,576,197); carbonic anhydrase II (U.S. Pat. No. 7,579,457); complement component 3 (U.S. Pat. No. 7,582,746); interleukin-1 receptor-associated kinase 4 (IRAK4) (U.S. Pat. No. 7,592,443); survivin (U.S. Pat. No. 7,608,7070); superoxide dismutase 1 (U.S. Pat. No. 7,632,938); MET proto-oncogene (U.S. Pat. No. 7,632,939); amyloid beta precursor protein (APP) (U.S. Pat. No. 7,635,771); IGF-1R (U.S. Pat. No. 7,638,621); ICAM1 (U.S. Pat. No. 7,642,349); complement factor B (U.S. Pat. No. 7,696,344); p53 (U.S. Pat. No. 7,781,575), and apolipoprotein B (U.S. Pat. No. 7,795,421), the Examples section of each referenced patent incorporated herein by reference.

Additional siRNA species are available from known commercial sources, such as Sigma-Aldrich (St Louis, Mo.), Invitrogen (Carlsbad, Calif.), Santa Cruz Biotechnology (Santa Cruz, Calif.), Ambion (Austin, Tex.), Dharmacon (Thermo Scientific, Lafayette, Colo.), Promega (Madison, Wis.), Minis Bio (Madison, Wis.) and Qiagen (Valencia, Calif.), among many others. Other publicly available sources of siRNA species include the siRNAdb database at the Stockholm Bioinformatics Centre, the MIT/ICBP siRNA Database, the RNAi Consortium shRNA Library at the Broad Institute, and the Probe database at NCBI. For example, there are 30,852 siRNA species in the NCBI Probe database. The skilled artisan will realize that for any gene of interest, either a siRNA species has already been designed, or one may readily be designed using publicly available software tools. Any such siRNA species may be delivered using the subject DNL™ complexes.

Methods of Therapeutic Treatment

Various embodiments concern methods of treating a cancer in a subject, such as a mammal, including humans, domestic or companion pets, such as dogs and cats, comprising administering to the subject a therapeutically effective amount of a combination of cytotoxic and/or immunomodulatory agents.

The administration of the cytotoxic bsAbs, ADCs and/or checkpoint inhibitor antibodies can be supplemented by administering concurrently or sequentially a therapeutically effective amount of another antibody that binds to or is reactive with another antigen on the surface of the target cell. Preferred additional MAbs comprise at least one humanized, chimeric or human MAb selected from the group consisting of a MAb reactive with CD4, CD5, CD8, CD14, CD15, CD16, CD19, IGF-1R, CD20, CD21, CD22, CD23, CD25, CD30, CD32b, CD33, CD37, CD38, CD40, CD40L, CD45, CD46, CD52, CD54, CD70, CD74, CD79a, CD79b, CD80, CD95, CD126, CD133, CD138, CD154, CEACAM5, CEACAM6, B7, AFP, PSMA, EGP-1, EGP-2, carbonic anhydrase IX, PAM4 antigen, MUC1, MUC2, MUC3, MUC4, MUC5, Ia, MIF, HM1.24, HLA-DR, tenascin, Flt-3, VEGFR, PlGF, ILGF, IL-6, IL-25, tenascin, TRAIL-R1, TRAIL-R2, complement factor C5, oncogene product, or a combination thereof. Various antibodies of use, such as anti-CD19, anti-CD20, and anti-CD22 antibodies, are known to those of skill in the art. See, for example, Ghetie et al., *Cancer Res.* 48:2610 (1988); Hekman et al., *Cancer Immunol. Immunother.* 32:364 (1991); Longo, *Curr. Opin. Oncol.* 8:353 (1996), U.S. Pat. Nos. 5,798,554; 6,187,287; 6,306,393; 6,676,924; 7,109,304; 7,151,164; 7,230,084; 7,230,085; 7,238,785; 7,238,786; 7,282,567; 7,300,655; 7,312,318; 7,501,498; 7,612,180; 7,670,804; and U.S. Patent Application Publ. Nos. 20080131363; 20070172920; 20060193865; and 20080138333, the Examples section of each incorporated herein by reference.

The combination therapy can be further supplemented with the administration, either concurrently or sequentially, of at least one therapeutic agent. For example, "CVB" (1.5 g/m$^2$ cyclophosphamide, 200-400 mg/m$^2$ etoposide, and 150-200 mg/m$^2$ carmustine) is a regimen used to treat non-Hodgkin's lymphoma. Patti et al., *Eur. J. Haematol.* 51: 18 (1993). Other suitable combination chemotherapeutic regimens are well-known to those of skill in the art. See, for example, Freedman et al., "Non-Hodgkin's Lymphomas," in CANCER MEDICINE, VOLUME 2, 3rd Edition, Holland et al. (eds.), pages 2028-2068 (Lea & Febiger 1993). As an illustration, first generation chemotherapeutic regimens for treatment of intermediate-grade non-Hodgkin's lymphoma (NHL) include C-MOPP (cyclophosphamide, vincristine, procarbazine and prednisone) and CHOP (cyclophosphamide, doxorubicin, vincristine, and prednisone). A useful second generation chemotherapeutic regimen is m-BACOD (methotrexate, bleomycin, doxorubicin, cyclophosphamide, vincristine, dexamethasone and leucovorin), while a suitable third generation regimen is MACOP-B (methotrexate, doxorubicin, cyclophosphamide, vincristine, prednisone, bleomycin and leucovorin). Additional useful drugs include phenyl butyrate, bendamustine, and bryostatin-1.

The combinations of therapeutic agents can be formulated according to known methods to prepare pharmaceutically useful compositions, whereby the bsAb, ADC, interferon and/or checkpoint inhibitor antibody is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The subject bsAbs, ADCs, interferons and/or antibodies can be formulated for intravenous administration via, for example, bolus injection or continuous infusion. Preferably, the bsAb, ADC and/or antibody is infused over a period of less than about 4 hours, and more preferably, over a period of less than about 3 hours. For example, the first bolus could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic combinations. Control release preparations can be prepared through the use of polymers to complex or adsorb the agents to be administered. For example, biocompatible polymers include matrices of poly(ethylene-co-vinyl acetate) and matrices of a polyanhydride copolymer of a stearic acid dimer and sebacic acid. Sherwood et al., *Bio/Technology* 10: 1446 (1992). The rate of release from such a matrix depends upon the molecular weight of the therapeutic agent, the amount of agent within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

The bsAbs, interferons and/or checkpoint inhibitor antibodies may be administered to a mammal subcutaneously or even by other parenteral routes, such as intravenously, intramuscularly, intraperitoneally or intravascularly. ADCs may be administered intravenously, intraperitoneally or intravascularly. Moreover, the administration may be by continuous infusion or by single or multiple boluses. Preferably, the bsAb, ADC, interferon and/or checkpoint inhibitor antibody is infused over a period of less than about 4 hours, and more preferably, over a period of less than about 3 hours.

More generally, the dosage of an administered bsAb, ADC, interferon and/or checkpoint inhibitor antibody for humans will vary depending upon such factors as the patient's age, weight, height, sex, general medical condition and previous medical history. It may be desirable to provide the recipient with a dosage of bsAb, ADC and/or antibody that is in the range of from about 1 mg/kg to 25 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy.

Alternatively, a bsAb, ADC, and/or checkpoint inhibitor antibody may be administered as one dosage every 2 or 3 weeks, repeated for a total of at least 3 dosages. Or, the combination may be administered twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 20 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

The person of ordinary skill will realize that while the dosage schedules discussed above are relevant for ADCs, bsAbs and/or mAbs, the interferon agents should be administered at substantially lower dosages to avoid systemic toxicity. Dosages of interferons (such as PEGINTERFERON) for humans are more typically in the microgram range, for example 180 μg s.c. once per week, or 100 to 180 μg, or 135 μg, or 135 μg/1.73 m$^2$, or 90 μg/1.73 m$^2$, or 250 μg s.c. every other day may be of use, depending on the type of interferon.

While the bsAbs, interferons, ADCs and/or checkpoint inhibitor antibodies may be administered as a periodic bolus injection, in alternative embodiments the bsAbs, ADCs, interferons and/or checkpoint inhibitor antibodies may be administered by continuous infusion. In order to increase the Cmax and extend the PK of the therapeutic agents in the blood, a continuous infusion may be administered for example by indwelling catheter. Such devices are known in the art, such as HICKMAN®, BROVIAC® or PORT-A-CATH® catheters (see, e.g., Skolnik et al., *Ther Drug Monit* 32:741-48, 2010) and any such known indwelling catheter may be used. A variety of continuous infusion pumps are also known in the art and any such known infusion pump may be used. The dosage range for continuous infusion may be between 0.1 and 3.0 mg/kg per day. More preferably, the bsAbs, ADCs, interferons and/or checkpoint inhibitor antibodies can be administered by intravenous infusions over relatively short periods of 2 to 5 hours, more preferably 2-3 hours.

In preferred embodiments, the combination of agents is of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor). Cancers conducive to treatment methods of the present invention involves cells which express, over-express, or abnormally express IGF-1R.

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational TROPhoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, TROPhoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenstrom's Macroglobulinemia, Wilms' Tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, BASIC PATHOLOGY, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis *punctata*, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis.

In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Expression Vectors

Still other embodiments may concern DNA sequences comprising a nucleic acid encoding an antibody, antibody fragment, cytokine or constituent fusion protein of a bsAb, such as a DNL™ construct. Fusion proteins may comprise an antibody or fragment or cytokine attached to, for example, an AD or DDD moiety.

Various embodiments relate to expression vectors comprising the coding DNA sequences. The vectors may contain sequences encoding the light and heavy chain constant regions and the hinge region of a human immunoglobulin to which may be attached chimeric, humanized or human variable region sequences. The vectors may additionally contain promoters that express the encoded protein(s) in a selected host cell, enhancers and signal or leader sequences. Vectors that are particularly useful are pdHL2 or GS. More preferably, the light and heavy chain constant regions and hinge region may be from a human EU myeloma immunoglobulin, where optionally at least one of the amino acid in the allotype positions is changed to that found in a different IgG1 allotype, and wherein optionally amino acid 253 of the heavy chain of EU based on the EU number system may be replaced with alanine. See Edelman et al., *Proc. Natl. Acad. Sci USA* 63: 78-85 (1969). In other embodiments, an IgG1 sequence may be converted to an IgG4 sequence.

The skilled artisan will realize that methods of genetically engineering expression constructs and insertion into host cells to express engineered proteins are well known in the art and a matter of routine experimentation. Host cells and methods of expression of cloned antibodies or fragments have been described, for example, in U.S. Pat. Nos. 7,531,327, 7,537,930, 7,785,880, 8,076,410, 8,153,433 and 8,372,603, the Examples section of each incorporated herein by reference.

Kits

Various embodiments may concern kits containing components suitable for treating or diagnosing diseased tissue in a patient. Exemplary kits may contain one or more bsAbs, ADCs, interferons, and/or checkpoint inhibitor antibodies as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used. In certain embodiments, a therapeutic agent may be provided in the form of a prefilled syringe or autoinjection pen containing a sterile, liquid formulation or lyophilized preparation.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The following examples are provided to illustrate, but not to limit, the claims of the present invention.

Example 1

T-Cell Redirecting Bispecific Antibody DOCK-AND-LOCK™ (DNL™) Complexes

Several species of exemplary leukocyte redirecting bispecific antibodies were made as DNL™ complexes, as described below. The complexes were effective to induce an immune response against appropriate target cells including, but not limited to, Trop-2$^+$ cancer cells.

Materials and Methods

General techniques for making and using DOCK-AND-LOCK™ (DNL™) complexes are described in the Examples below. An exemplary leukocyte redirecting bispecific antibody with binding sites for CD3 and CD19 was made as a DNL™ complex, referred to as (19)-3s (FIG. 1). An anti-CD19 F(ab)₂ DNL module was constructed by recombinant fusion of a dimerization and docking domain (DDD2) at the carboxyl terminal end of the Fd chain. An anti-CD3-scFv module was designed from Okt3 mAb with addition of an anchor domain (AD2) and assembled in the format $V_H$-L1-$V_K$-L2-6H-L3-AD2 ("6H" disclosed as SEQ ID NO:105), where the V domains were fused via a flexible peptide linker and the AD2 peptide was preceded by a 6-His linker (SEQ ID NO:105). The sequences of the anti-CD3 variable regions, linkers and AD2 were as shown below.

```
VH sequence of anti-CD3 scFv
                                      (SEQ ID NO: 96)
QVQLQQSGAELARPGASVKMSCKASGYTFTRYTMHWVKQRPGQGLEWIGY
INPSRGYTNYNQKFKDKATLTTDKSSSTAYMQLSSLTSEDSAVYYCARYY
DDHYSLDYWGQGTTLTVSS L1 Linker
                                      (SEQ ID NO: 97)
GGGGSGGGGSGGGGS VK sequence of anti-CD3 scFv
                                      (SEQ ID NO: 98)
DIVLTQSPAIIVISASPGEKVTMTCSASSSVSYMNWYQQKSGTSPKRWIY
DTSKLASGVPAHFRGSGSGTSYSLTISGMEAEDAATYYCQQWSSNPFTFG
SGTKLEIKR L2 Linker
                                      (SEQ ID NO: 99)
GGGGS Poly-His-L3 Linker
                                      (SEQ ID NO: 100)
HHHHHHGGGSG AD2
                                      (SEQ ID NO: 101)
CGQIEYLAKQIVDNAIQQAGC
```

Expression Vectors and DNL™ Modules—

DNL™ complexes were constructed comprising antibody moieties against various disease-associated antigens, linked to an anti-CD3 antibody moiety, generally abbreviated as (X)-3s bsAbs. Independent production cell lines were developed in SpESFX-10 mouse myeloma cells (Rossi et al., 2011, *Biotechnol Prog* 27:766-75) for each of the DNL™ modules used to make the (X)-3s bsAbs. A cDNA sequence encoding the Okt3scFv-AD2 polypeptide (SEQ ID NOs:96-101) was synthesized and cloned into the pdHL2 expression vector via 5′ Xba I and 3′ Eag I restriction sites. The construct comprised the $V_H$ domain fused to the $V_L$ in an scFv with the structure $V_H$-L1-$V_K$-L2-6H-L3-AD2 ("6H" disclosed as SEQ ID NO:105). The expressed protein had two amino acid substitutions from the original Okt3 mAb. A cysteine residue in the CDR-H3 was changed to serine (Kipryanov, 1997, *J Immunol Methods* 200:69-77). The penultimate residue of the $V_L$ was changed from aspartate to lysine.

The Okt3scFv-AD2 module was combined with various $C_H1$-DDD2-Fab modules to generate a panel of (X)-3s trivalent bsAbs (Table 6). The $C_H1$-DDD2-Fab-pdHL2 expression vectors were constructed as described previously for similar constructs (Rossi et al., 2008, *Cancer Res* 68:8384-92). Briefly, expression vectors encoding $C_H1$-DDD2-Fab were generated from the corresponding IgG-pdHL2 expression vectors by excising the coding sequence for the $C_H1$-Hinge-$C_H2$-$C_H3$ domains with Sac II and Eag I restriction enzymes and replacing it with a 507 bp sequence encoding $C_H1$-DDD2, which was excised from the $C_H1$-DDD2-Fab-hA20-pdHL2 expression vector (Rossi et al., 2008, *Cancer Res* 68:8384-92) with the same enzymes. $C_H1$-DDD2-Fab modules were derived from the humanized mAbs hA19 (anti-CD19), labetuzumab (hMN-14, anti-CEACAM5), clivatuzumab (hPAM4, anti-mucin), hMN-15 (anti-CEACAM6), hRS7 (anti-TROP-2), veltuzumab (hA20, anti-CD20), hL243 (anti-HLA-DR) and epratuzumab (hLL2, anti-CD22). The mAb designated hA19 was humanized from the mouse anti-CD19 mAb B43 (Uckun et al., 1988, *Blood* 71:13-29). Each expression vector was linearized by digestion with Sal I restriction enzyme and used to transfect SpESFX-10 cells by electroporation.

Clones were selected in media containing 0.2 μM methotrexate (MTX) and screened for protein expression by ELISA. Okt3scFv-AD2 was captured on Ni-NTA HisSorb plates (Qiagen) and detected with an anti-AD2 mAb. $C_H1$-DDD2-Fab modules were captured with goat-anti-human-kappa chain and detected with goat-anti-human-F(ab′)₂-HRP. Productivity of protein-expression was amplified by stepwise increases in MTX concentration up to 3 μM. Okt3scFv-AD2 and $C_H1$-DDD2-Fab modules were purified to homogeneity from the broth of roller bottle cultures by affinity chromatography using Ni-SEPHAROSE® and Kappa-Select resins, respectively. The DNL™ method was used to assemble (X)-3s bsAbs via the site-specific conjugation of mole equivalents of Okt3scFv-AD2 and $C_H1$-DDD2-Fab modules. For example, approximately 100 mg of (19)-3s were produced by combining 22 mg of Okt3scFv-AD2 with 80 mg of $C_H1$-DDD2-Fab-hA19. The mixture was reduced overnight at room temperature with 1 mM reduced glutathione prior to the addition of 2 mM oxidized glutathione. The (19)-3s was purified from the reaction mixture by sequential affinity chromatography with Kappa-Select and Ni-SEPHAROSE®. Additional (X)-3s constructs were assembled at various scales following a similar process.

TABLE 6

| (X)-3s DNL ™ Constructs | | | |
|---|---|---|---|
| Code | Target | $C_H1$-DDD2-Fab | AD2-anti-CD3 |
| (19)-3s | CD19 | $C_H1$-DDD2-Fab-hA19 | scFv-AD2-Okt3 |
| (20)-3s | CD20 | $C_H1$-DDD2-Fab-hA20 | scFv-AD2-Okt3 |
| (22)-3s | CD22 | $C_H1$-DDD2-Fab-hLL2 | scFv-AD2-Okt3 |
| (C2)-3s | HLA-DR | $C_H1$-DDD2-Fab-hL243 | scFv-AD2-Okt3 |
| (M1)-3s | MUC5AC | $C_H1$-DDD2-Fab-hPAM4 | scFv-AD2-Okt3 |
| (14)-3s | CEACAM5 | $C_H1$-DDD2-Fab-hMN-14 | scFv-AD2-Okt3 |
| (15)-3s | CEACEAM6 | $C_H1$-DDD2-Fab-hMN-15 | scFv-AD2-Okt3 |
| (E1)-3s | TROP-2 | $C_H1$-DDD2-Fab-hRS7 | scFv-AD2-Okt3 |

Analytical Methods—

Size-exclusion high-performance liquid chromatography (SE-HPLC) was performed with an Alliance HPLC System with a BIOSUITE™ 250, 4-μm UHR SEC column (Waters Corp). Electrospray ionization time of flight (ESI-TOF) liquid chromatography/mass spectrometry (LC-MS) was performed with a 1200-series HPLC coupled with a 6210 TOF MS (Agilent Technologies, Santa Clara, Calif.). The (19)-3s was resolved by reversed phase HPLC (RP-HPLC) at 60° C., using a 14-min gradient of 30-80% acetonitrile in 0.1% aqueous formic acid with an *Aeris* widepore 3.6 μm C4 column (Phenomenex). For the TOF MS, the capillary and fragmentor voltages were set to 5500 and 300 V, respectively.

Cell Lines and Reagents—

Raji, Ramos, Daudi, LS174T and Capan-1 cell lines were purchased from the American Type Cell Culture Collection (ATCC, Manassas, Md.) and Nalm-6 cells were purchased from Deutsche Sammlung von Mikroorganismen and Zellinien (DSMZ, Braunchweig, Germany). All cell lines, except Capan-1, were maintained in RPMI-1640 containing 10% FBS, 1% L-glutamine, 1% penicillin-streptomycin and 1% MEM nonessential amino acids. Capan-1 cells were maintained with 20% FBS. All cell culture media and supplements were purchased from Life Technologies (Carlsbad, Calif.).

PBMCs and T Cell Isolation—

Human peripheral blood mononuclear cells (PBMC) were purified from whole donor blood (Blood Center of NJ, East Orange, N.J.) using UNI-SEP$_{MAXI}$ tubes (Novamed, Ltd, Jerusalem, Israel). CD3-positive T cells were isolated from PBMCs by negative selection using the Pan T Cell Isolation Kit (Miltenyi Biotec, Auburn, Calif.), according to the manufacturer's protocol. Efficiency of T cell isolation was assessed by FACS after staining the enriched T cells with anti-CD3-PE antibody. In some cases, further staining with CD-19 and CD-14 was performed as well to identify contaminating cells.

T Cell Activation—

Isolated T cells were plated in 6-well tissue culture plates at a final density of $2.25 \times 10^6$ cells/well. Daudi cells were added to some wells at a final density of $1.5 \times 10^6$ cells/well, other wells were left to contain only T cells. Alternatively, PBMCs were added to 6-well tissue culture plates at a final cell density of $6 \times 10^6$ cells/well. The volume of each well was brought up to 3 mL. To the appropriate wells, 3 ng/mL of (19)-3s, (M1)-3s or (19)-DDD2 was added. After incubation overnight at 37° C., 1 mL of each sample was removed. The cells were pelleted and labeled on ice with CD69-APC and CD3-PE for 20 minutes. Cells were washed 2 times with 1% BSA in PBS and analyzed using a FACSCALIBER™ flow cytometer (BD Biosciences, San Jose, Calif.).

T-Cell Proliferation—

PBMCs were seeded in T25 flasks at a concentration of $1 \times 10^6$ cells/mL containing the specified reagents. For B cell-depleted flasks, B cells were removed by negative selection using a B-cell isolation kit from Miltenyi according to manufacturer's protocol. On select days, 100 μL of media was removed from each flask, labeled with anti-CD7-APC for 20 minutes on ice, washed once and resuspended in 300 μL of 1% BSA/PBS containing 7-AAD. For each sample, the entire volume is analyzed using a FACSCALIBER™ flow cytometer. Each sample is counted in duplicate. Analysis is performed using FlowJo Software. For each sample, dead (7-AAD+) cells, and debris (based on forward vs. side scatter) was removed. Finally, live CD7+ cells were selected and plotted using Prism software.

Cell Binding Assays (Jurkat/Capan-1)—

Jurkat cells were stained with PKH26 Red Fluorescent Cell Linker Kit (Sigma) according to manufacturer's protocol. Capan-1 cells were stained with 5 μM CFSE (carboxyfluorescein diacetate succinimidyl ester, Life Technologies) according to manufacturer's protocol. Labeled Capan-1 cells were added to 8-well chamber slides (ThermoWaltham, Mass.) and allowed to attach overnight. The following day, media was removed and PKH26-labeled Jurkat cells were added in media containing 0.1 μg/mL of (E1)-3s, (M1)-3s or (19)-3s. Following a 1-hour incubation at 37° C., slides were washed with PBS to remove any unbound cells and observed by fluorescence microscopy.

Cell Binding Assays (Jurkat/Daudi)—

Jurkat and Daudi cells were labeled with anti-CD3-PE and anti-CD20-FITC, respectively. Labeled cells were then coincubated at a 2.5:1 ratio with 0.1 μg/mL (19)-3s for 30 minutes at room temperature. Aliquots of cells were then observed by fluorescence microscopy.

Cytotoxicity Assay (Hematologic Tumor Cell Lines)—

Target cells were labeled with PKH67 Green Fluorescent Cell Linker Kit (Sigma) according to the manufacturer's protocol. Briefly, $5 \times 10^6$ target cells were resuspended in 250 μL of diluent C. In a second tube 1 μL of PKH26 dye is added to 250 μL of diluent C. The cell suspension is then added to the dye solution, mixed thoroughly and incubated at RT for 2 minutes. The reaction was quenched by adding an equal volume of FBS. The labeled cells were then washed 3 times with complete RPMI. Unstimulated, isolated T cells were used as effector cells. Effector cells and PKH67-labeled target cells were combined at a 10:1 ratio and plated in 48-well plates containing serial dilutions of (19)-3s or (14)-3s. Each well contained $5 \times 10^4$ target cells and $5 \times 10^5$ effector cells. Jeko-1 assays were performed in 20% RPMI. Plates were incubated for 18-24 hours in a 37° C. incubator containing 5% $CO_2$. Following incubation, all cells were removed from 48-well plates into flow cytometer tubes and resuspended in 1% BSA/PBS containing 1 ug/mL of 7AAD, to distinguish live from dead cells, and 30,000 COUNTBRIGHT™ Absolute Counting Beads (Life Technologies). Cells were analyzed on a FACSCALIBER™ flow cytometer. For each sample, 8,000 COUNTBRIGHT™ beads were counted as a normalized reference. Data were analyzed using FlowJo software (Treestar, Inc., Ashland, Oreg.). For each sample, dead cells and debris were excluded and total live target cells were counted.

Cytotoxicity Assay (Solid Tumor Cell Lines)—

Target cells were labeled with PKH67 Green Fluorescent Cell Linker Kit (Sigma) following the same procedure as for staining with PKH23. Effector cells used were as follows: For Capan-1 assays, CD8+ enriched T cells were used, following purification from a CD8+ enrichment column (R&D Systems, Minneapolis, Minn.). For LS174T cells: Stimulated T cells were used after incubation of PBMC for 5 days in media containing 25 U/mL IL-2 and 50 ng/mL Okt3 Mab, followed by 2 days incubation in media containing 25 U/mL IL-2 alone. Effector cells and PKH67-labeled target cells were combined at a 3:1 ratio ($5 \times 10^4$ target cells and $1.5 \times 10^5$ effector cells/well) and plated over 48-well plates containing serial dilutions of (E1)-3s, (14)-3s or (19)-3s. Capan-1 assays were performed in 20% RPMI. Plates were incubated for 42-48 hours in a 37° C. incubator containing 5% $CO_2$. Following incubation, suspension cells were combined with trypsinized attached cells from all wells and transferred into flow cytometer tubes. Cells were washed one time and resuspended in 1% BSA/PBS containing 1 ug/mL of 7AAD, to distinguish live from dead cells, and 30,000 COUNTBRIGHT™ Absolute Counting Beads. Cells were analyzed on a FACSCALIBER™ flow cytometer. For each sample, 8,000 COUNTBRIGHT™ beads were counted as a normalized reference. Data were analyzed using FlowJo software (Treestar, Inc., Ashland, Oreg.). For each sample, dead cells and debris were excluded and total live target cells were counted.

In Vivo Efficacy—

Female NOD/SCID mice, 8 weeks old, were purchased from Charles River (Wilmington, Mass.). Mice were injected s.c. with a mixture of Raji ($1 \times 10^6$) and human PBMCs ($5 \times 10^6$ cells) mixed 1:1 with matrigel. Therapy began 1 hour later. Treatment regimens, dosages, and number of animals in each experiment are described in the Results. Animals were monitored daily for signs of tumor out-growth. Once tumors appeared, they were measured twice weekly. Tumor volume (TV) was determined by measurements in two dimensions using calipers, with volumes defined as: L×w²/2, where L is the longest dimension of the tumor and w the shortest. Efficacy was determined by a log-rank test using Prism GraphPad software (v5; LaJolla, Calif.) on Kaplan-Meier curves using survival surrogate endpoints as time for tumor progression (TTP) to 1.0 cm³. Significance was considered at P<0.05.

Results

Construction and Biochemical Analysis of Leukocyte Redirecting Bispecific Antibodies.

The DNL™ method was used to generate a panel of (X)-3s, leukocyte redirecting bsAbs for targeting of various tumor-associated antigens including CD19, CD20, HLA-DR, TROP-2, CEACAM5 and MUC5AC. The purity of these structures was demonstrated by SE-HPLC and SDS-PAGE analysis, where only bands representing the three constituent polypeptides (Okt3scFv-AD2, hA19-Fd-DDD2 and hA19 kappa) were evident (data not shown). LC-MS analysis identified a single RP-HPLC peak having a deconvoluted mass spectrum consistent (mass accuracy=11 ppm) with the calculated mass (137432.37 Da) of (19)-3s from its deduced amino acid sequence, including the predicted amino-terminal pyroglutamates on the Okt3scFv-AD2 and each of the two $C_H1$-DDD2-hA19 Fd chains (data not shown). No additional post-translational modifications, including glycosylation were indicated.

Immune Synapse Formation Between Daudi Burkitt Lymphoma and T Cells, Mediated by (19)-3s.

Figure 2A:
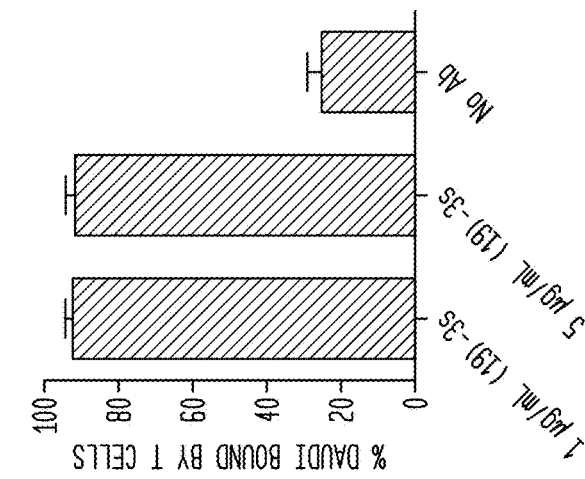
FIG. 2A. Immune synapse formation between Daudi Burkitt lymphoma and T cells, mediated by (19)-3s. Freshly isolated T cells were combined with Daudi cells at an E:T ratio of 2.5:1. Cells were treated with 0, 1 or 5 μg/mL of (19)-3s for 30 min at room temperature prior to analysis by flow cytometry. Anti-CD20-FITC and anti-CD7-APC were used to identify Daudi and T cells, respectively. Co-binding was indicated as the % of CD20$^+$/CD7$^+$ events. After treatment with (19)-3s, 45.5% of flow events were CD20/CD7 dual-positive, indicating synapsed Daudi and T cells.
Figure 2B:
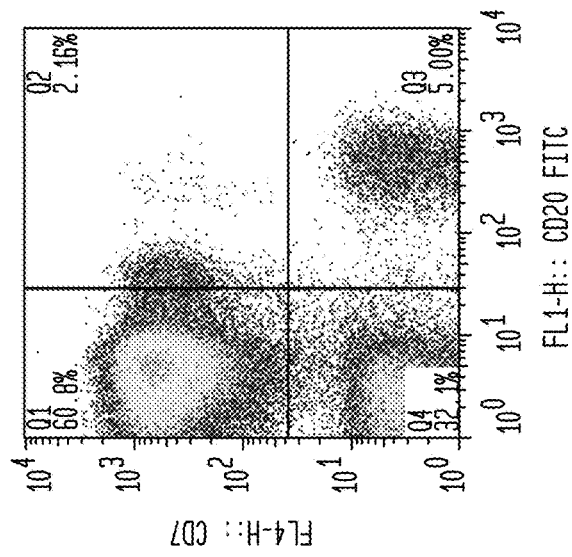
FIG. 2B. Conditions were as in FIG. 2(A), except for the absence of (19)-3s antibody. Compared to FIG. 2(A), only 2% of flow events were CD20/CD7 dual-positive without antibody.
Figure 2C:
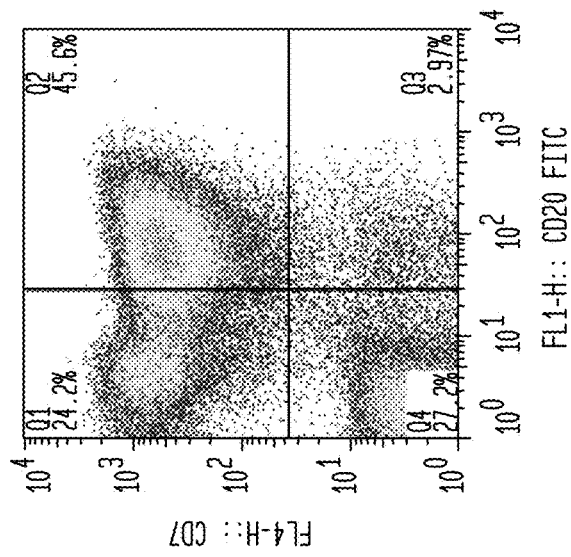
FIG. 2C. Addition of (19)-3s resulted in association of >90% of the Daudi with T cells.

The effects of the leukocyte redirecting (19)-3s DNL™ complex on targeting effector T cells to CD19⁺ lymphoma cells was examined (FIG. 2). Freshly isolated T cells were combined with Daudi cells at an E:T ratio of 2.5:1. Cells were treated with 0, 1 or 5 µg/mL of (19)-3s DNL™ complex for 30 min at room temperature prior to analysis by flow cytometry. Anti-CD20-FITC and anti-CD7-APC were used to identify Daudi and T cells, respectively. Co-binding was indicated as the % of CD20⁺/CD7⁺ events. After treatment with (19)-3s, 45.5% of flow events were CD20/CD7 dual-positive, indicating synapsed Daudi and T cells (FIG. 2A), compared to 2% measured for the mixed cells without antibody (FIG. 2B). Addition of (19)-3s resulted in association of >90% of the Daudi with T cells (FIG. 2C). These results show that the (19)-3s DNL™ complex was effective to direct T cells to the targeted antigen-expressing lymphoma cells.

Synapse formation between T cells and target lymphoma cells was demonstrated by fluorescence microscopy (FIG. 3) Jurkat (T cells) and Daudi (B cells) were combined at a 1:1 ratio, treated with 0.1 µg/mL of the (19)-3s DNL™ complex for 30 minutes and stained with anti-CD20-FITC (FIG. 3A) and anti-CD3-PE (FIG. 3B), prior to analysis by fluorescence microscopy. The merged image (FIG. 3C) reveals synapse formation between green-stained Daudi and red-stained Jurkat cells. Synapse formation was not evident in the absence of (19)-3s (FIG. 3D). FIG. 3C demonstrates that the target lymphoma cells are in direct contact with the targeted T cells.

Figure 4:
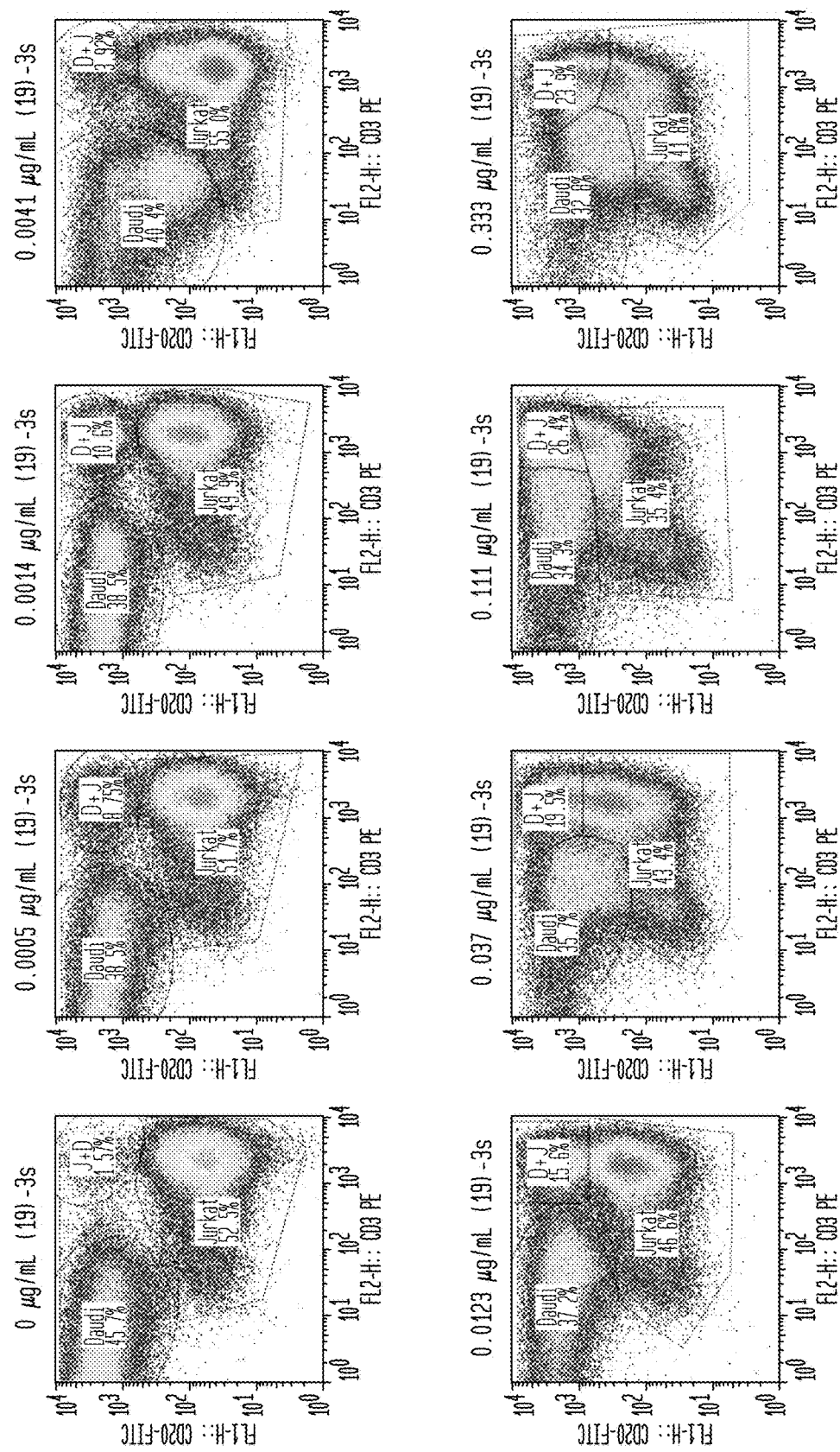
FIG. 4. Dose response analysis of (19)-3s mediated cell-to-cell association of Daudi and Jurkat cells as a function of increasing concentrations of (19)-3s.

A dose-response series was performed for (19)-3s mediated association of T cells to an exemplary B-cell lymphoma line (FIG. 4). As shown in FIG. 4, under the conditions of this experiment, saturation of (19)-3s-mediated cell-to-cell association of T cells to target cells was reached at a concentration between 0.037 and 0.111 µg/ml of the DNL™ complex.

Figures 5A, 5B:
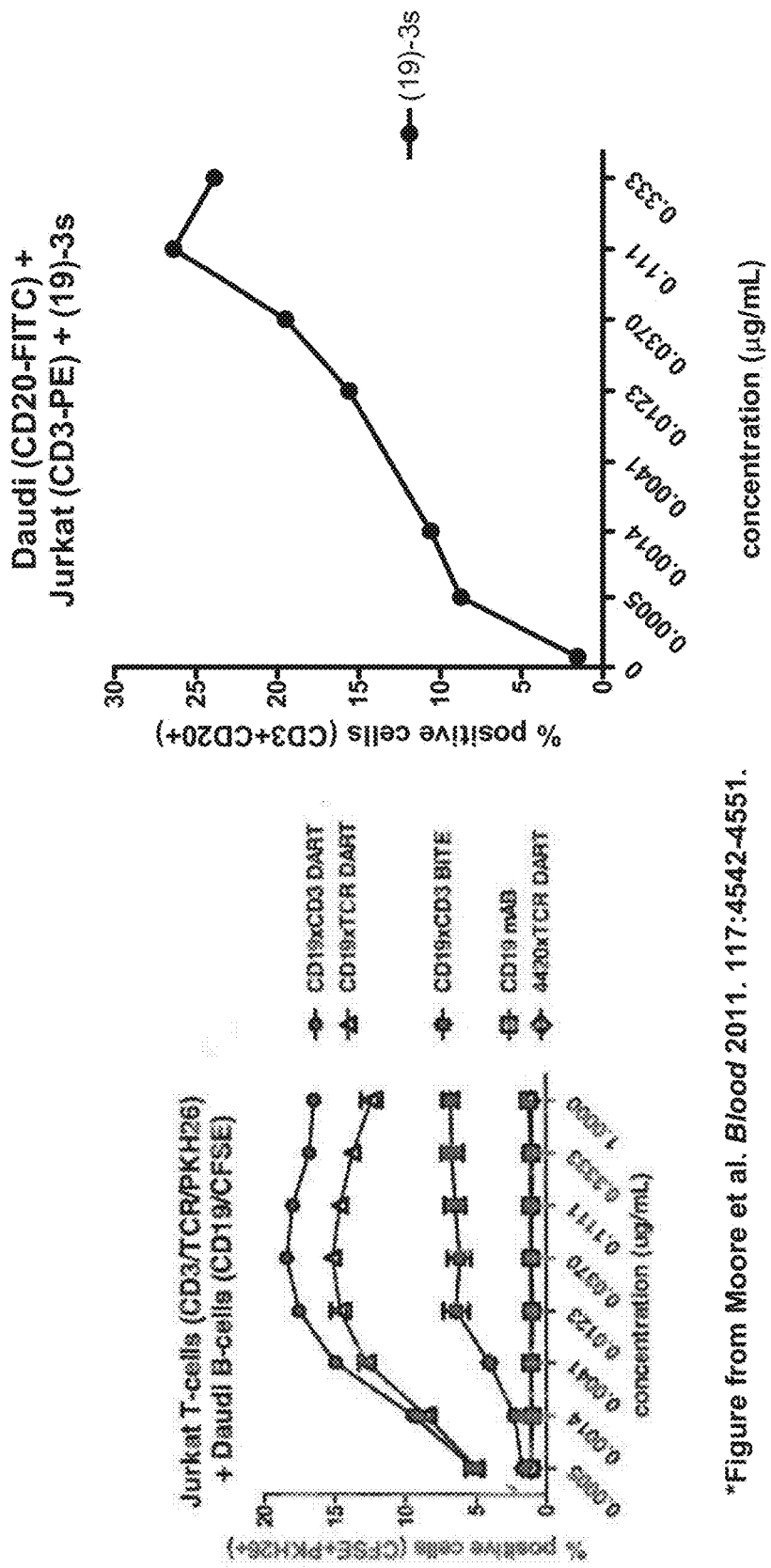
FIG. 5A. Comparison of cell-to-cell association mediated by BITE® and DART™. The data for BITE® and DART™ was taken from Moore et al. (2011, *Blood* 117:4542-4551.
FIG. 5B. Comparison of cell-to-cell association mediated by (19)-3s.

FIG. 5 shows a comparison of the relative efficacies of BITE® (FIG. 5A), DART™ (FIG. 5A) and DNL™ (FIG. 5B) anti-CD3×anti-CD19 complexes for redirecting T cells to targeted CD19⁺ B cells. The data for BITE® and DART™ was obtained from Moore et al. (2011, *Blood* 117:4542-51). At the lowest concentration tested of 0.0005 µg/ml, the (19)-3s DNL™ complex was more effective than BITE® or DART™ at targeting T cells to B-cell lymphoma (FIG. 5). The (19)-3s DNL™ complex also induced a slightly higher maximum level of cell-to-cell association than the comparable BITE® and DART™ complexes (FIG. 5A). Although difficult to extrapolate from the single data points generated for the (19)-3s DNL™ complex, the $EC_{50}$ levels appeared to be similar for BITE®, DART™ and DNL™ (FIG. 5).

(19)-3s, (E1)-3s and (M1)-3s-Mediated Cell-Cell Association of T Cells to Target Tumor Cells.

To evaluate the ability of the T-cell redirecting BsAbs to facilitate the association of T cells to their target tumor cells, Jurkat T cells were coincubated with target tumor cells containing (X)-3s and evaluated by flow cytometry and fluorescence microscopy. Jurkat T cells are a CD4+ T cell leukemia line, chosen for their ability to demonstrate T cell binding without depletion of the FITC labeled Daudi cells in the presence of various concentrations of (19)-3s and analyzed by flow cytometry for the detection of double positive (CD3+CD20+) populations indicating T cell-B cell associated complexes. An apparent cell-cell association was seen following treatment with 0.5 ng/mL of (19)-3s and after treatment with 0.1 µg/mL over 25% of the cell population existed in a cell-cell association (FIG. 5). Fluorescent microscopy supports this data, as immune synapses are evident following treatment with 0.1 µg/mL (19)-3s (FIG. 4). No synapse formation was seen in the absence of (19)-3s (data not shown).

This cell-cell association was observed in the pancreatic tumor line Capan-1 as well (FIG. 6). Capan-1 expresses high levels of TROP2 and moderate levels of MUC5AC. Therefore, both the TROP2-targeting bsAb, (E1)-3s (FIG. 6C), and MUC5AC-targeting bsAb, (M1)-3s (FIG. 6B) were compared to the non-targeting control bsAb, (19)-3s (FIG. 6A). CF SE-labeled Capan-1 cells were coincubated with PKH26-labeled Jurkat in the presence of these bsAbs. Fluorescent microscopy revealed, as expected, large T-cell/Capan complexes mediated by (E1)-3s, followed by smaller, yet substantial complexes mediated by (M1)-3s and relatively low complex formation following (19)-3s treatment (FIG. 6).

(19)-3s Specifically Induces T Cell Activation and Proliferation.

The ability of (19)-3s to activate T cells was evaluated either in PBMCs (FIG. 7A), or T cells coincubated with Daudi B cells (FIG. 7B), by measuring the expression levels of CD69, an early marker of T cell activation. Treatment with 3 ng/mL of (19)-3s induced T cell activation in T cells coincubated with Daudi B cells as indicated by a >50-fold increase in CD69 expression compared with non-targeting control antibodies, (19)-DDD2 and (M1)-3s, as well as T cells treated with (19)-3s without Daudi target cells (FIG. 7B). Similar results were observed when the antibodies were incubated with PBMCs, containing both T and B cells; (19)-3s stimulated CD69 expression levels >20-fold higher than non-targeting controls (FIG. 7A). In the absence of target cells, purified T cells treated with (19)-3s did not show activation (FIG. 7C).

T cell proliferation, as another indication of T cell activation, was evaluated after treatment of PBMCs with various CD3-targeting antibodies. (19)-3s at 3 nM or 30 pM induced T cell proliferation similar to that of the positive control IL-2/PHA (FIG. 8A). Non-targeting control antibody, (14)-3s, shows some non-specific T cell proliferation at the highest (3 nM) concentration (FIG. 8A). However, T cell proliferation was not observed in PBMCs depleted of B cells (FIG. 8B), suggesting that target cells are necessary for specific (19)-3s induced T cell proliferation.

(X)-3s Re-Directed T-Cell Mediated Killing of Malignant Cell Lines.

The cytotoxicity of each leukocyte targeting molecule was evaluated by its ability to mediate lysis of specific tumor target cells. For the hematologic tumor cell lines, a 10:1 E:T ratio using an unstimulated, enriched T cell population as the effector cells in an 18-24 hour assay demonstrated the optimal assay conditions. The CD19-targeting bsAb, (19)-3s induced the most potent specific killing of the relatively low CD19-expressing cell lines Ramos ($IC_{50}$=0.17 pM, $Lysis_{Max}$=79%) Daudi ($IC_{50}$=1 pM, $Lysis_{Max}$=60%), and Nalm6 ($IC_{50}$=6 pM, $Lysis_{Max}$=93%) (FIG. 9A). Interestingly, the high CD19-expressing cell lines, Namalwa ($IC_{50}$=63 pM, $Lysis_{Max}$=60%) and Raji ($IC_{50}$=3 nM, $Lysis_{Max}$=41%) were the least sensitive to (19)-3s (FIG. 9A). The non-targeting (14)-3s DNL™ construct had little cytotoxic effect in any of the cell lines tested (FIG. 9B). Consistent cytotoxic effects of the (19)-3s construct on the Nalm-6 ALL cell line were obtained with PBMCs obtained from two different donors (FIG. 9C).

and acute lymphoblastic leukemia (Nalm-6) (Table 7). A non-tumor binding control, (14)-3s, induced only moderate T-cell killing at >10 nM. The nature of the antigen/epitope, particularly its size and proximity to the cell surface, appears to be more important than antigen density for T-cell retargeting potency (Table 7). It is likely that (20)-3s is consistently more potent than (19)-3s and (C2)-3s, even when the expression of CD19 or HLA-DR is considerably higher than CD20, as seen with Namalwa and Jeko-1, respectively (Table 7). This is likely because the CD20 epitope comprises a small extracellular loop having close proximity to the cell surface. When compared directly using Daudi, (22)-3s was the least potent. Compared to CD19 and CD20, CD22 is expressed at the lowest density, is a rapidly internalizing antigen, and its epitope is further away from the cell surface. Each of these factors may contribute to its reduced potency. Finally, sensitivity to T-cell retargeted killing is cell-line-dependent, as observed using (19)-3s, where Raji ($IC_{50}$>3 nM) is largely unresponsive yet Ramos ($IC_{50}$=2 pM) is highly sensitive, even though the former expresses higher CD19 antigen density (Table 7).

In conclusion, (19)-3s, (20)-3s, (22)-3s and (C2)-3s bind to T cells and target B cells simultaneously and induce T-cell-mediated killing in vitro. The modular nature of the DNL method allowed the rapid production of several related conjugates for redirected leukocyte killing of various B cell malignancies, without the need for additional recombinant engineering and protein production. The close proximity of the CD20 extracellular epitope to the cell surface resulted in the highest potency for (20)-3s.

TABLE 7

Ex vivo re-directed T-cell killing

| Cell Line | Type[1] | Antigen Expression[2] | | | | $IC_{50}$[4] (pM) | | | |
|---|---|---|---|---|---|---|---|---|---|
| | | CD19 | CD20 | CD22 | HLA- | (19)-3s | (20)- | (22)-3s | (C2)- |
| Daudi | BL | 1.00 | 1.00 | 1.00 | 1.00 | 1 | 0.3 | 6 | N.D. |
| Ramos | BL | 0.76 | 0.65 | 0.26 | 0.36 | 2 | 0.4 | N.D. | 2 |
| Nalm-6 | ALL | 1.63 | 0.05 | 0.19 | 0.17 | 6 | N.D. | N.D. | N.D. |
| Namalwa | BL | 0.76 | 0.11 | 0.05 | 0.40 | 63 | 30 | >3000 | N.D. |
| Raji | BL | 1.41 | 0.69 | 0.59 | 0.84 | >3000 | N.D. | N.D. | N.D. |
| Jeko-1 | MCL | 0.89 | 1.02 | 0.05 | 1.06 | 3000 | 1 | N.D. | 20 |

[1]BL, Burkitt lymphoma; ALL, acute lymphoblastic leukemia; MCL, mantle cell lymphoma.
[2]Expression level determined by flow cytometry and normalized to that of Daudi.
[3]$IC_{50}$, the picomolar concentration that achieved 50% target cell killing.

Figure 10A:
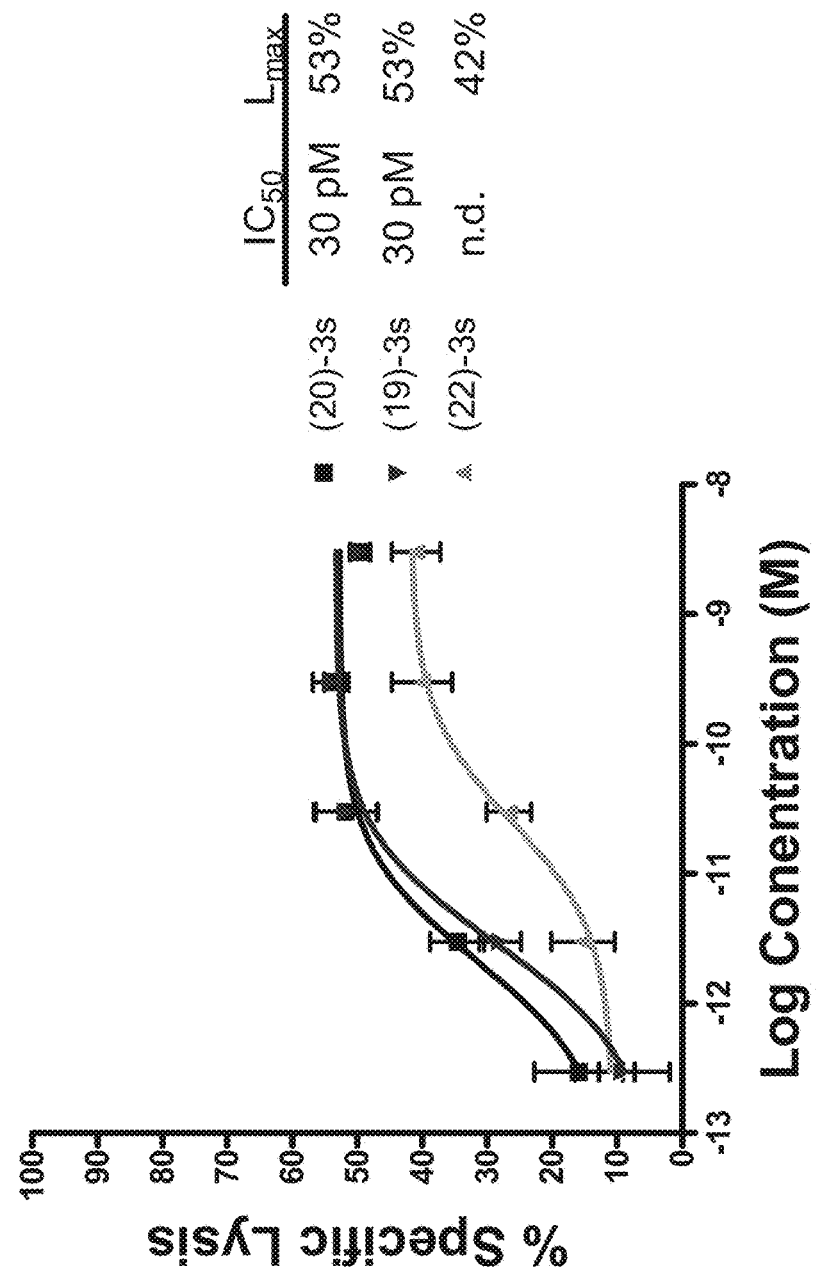
FIG. 10A. In vitro cytotoxicity of (20)-3s, (22)-3s and (C2)-3s T-cell redirecting bsAbs. Dose-response curves were determined for cytotoxicity to Namalwa cells induced by (20)-3s, (22)-3s and (C2)-3s T-cell redirecting bsAbs.
Figure 10B:
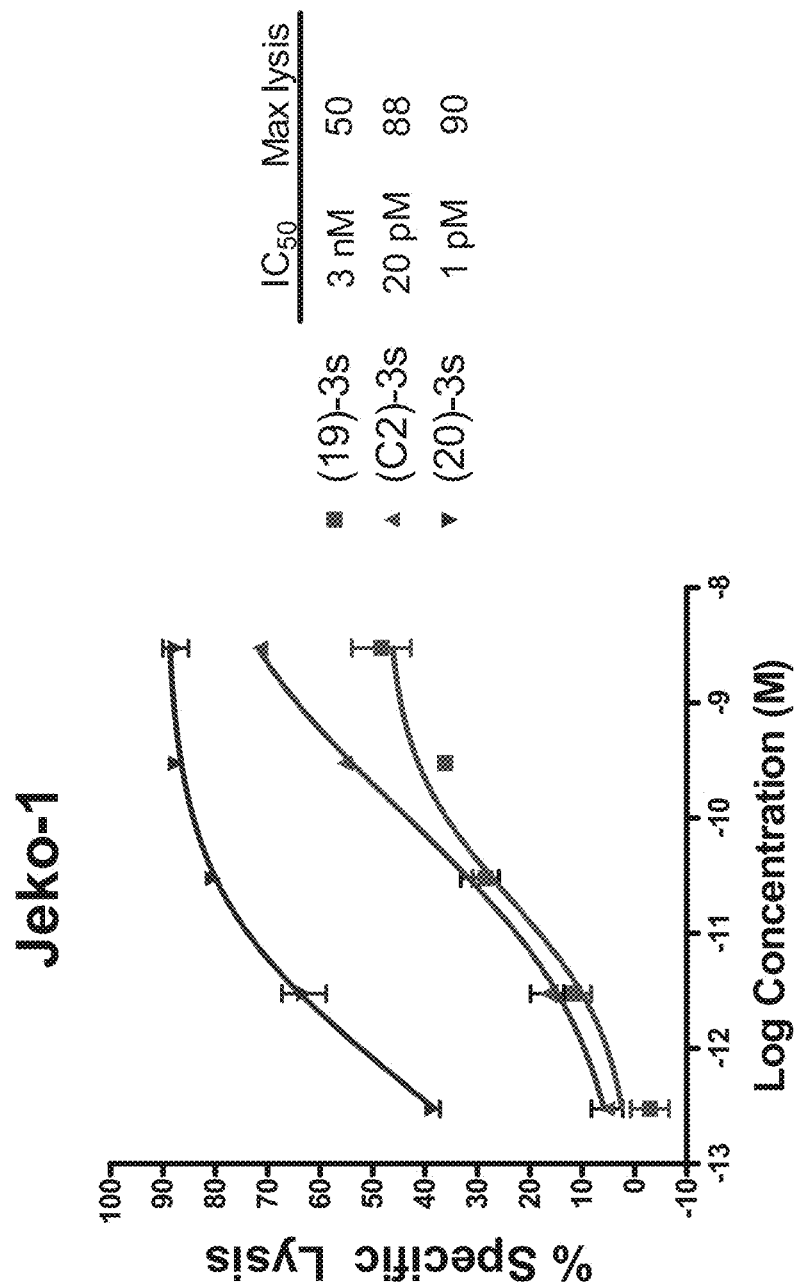
FIG. 10B. In vitro cytotoxicity of (20)-3s, (22)-3s and (C2)-3s T-cell redirecting bsAbs. Dose-response curves were determined for cytotoxicity to Jeko cells induced by (20)-3s, (22)-3s and (C2)-3s T-cell redirecting bsAbs.
Figure 10C:
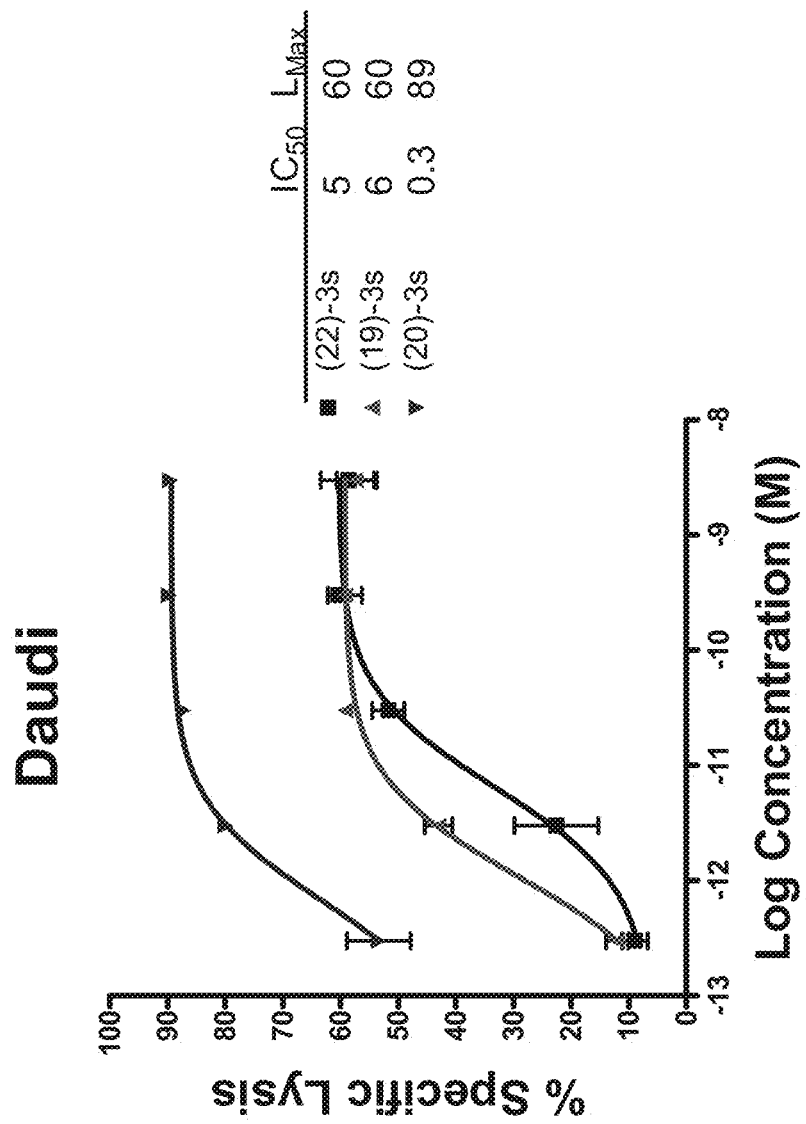
FIG. 10C. In vitro cytotoxicity of (20)-3s, (22)-3s and (C2)-3s T-cell redirecting bsAbs. Dose-response curves were determined for cytotoxicity to Daudi cells induced by (20)-3s, (22)-3s and (C2)-3s T-cell redirecting bsAbs.

The in vitro cytotoxic effects of (20)-3s, (22)-3s and (C2)-3s T-cell redirecting bsAbs were determined in several cell lines (FIG. 10). The CD22-targeting bsAb, (22)-3s, demonstrated potent ($IC_{50}$=5 pM, $Lysis_{Max}$=60%) specific T-cell mediated lysis in the CD22-positive Daudi cell line (FIG. 10C), but not in the CD22-negative Namalwa cells (FIG. 10A).

The CD20-targeting bsAb, (20)-3s demonstrated the highest potency in the higher-expressing CD20 cell lines, Daudi ($IC_{50}$=<0.3 pM, $Lysis_{Max}$=90%) (FIG. 10C) and Jeko ($IC_{50}$=1 pM, $Lysis_{Max}$=90%) (FIG. 10B), compared to the lower CD20-expressing Namalwa cell line ($IC_{50}$=30 pM, $Lysis_{Max}$=53%) (FIG. 10A).

The HLA-DR-targeting bsAb, (C2)-3s was tested in the HLA-DR expressing Jeko-1 cell line ($IC_{50}$=20 pM, $Lysis_{Max}$=88%) (FIG. 10B).

At an E:T ratio of 10:1, using isolated T cells as effector cells, the bsAbs induced potent T cell-mediated cytotoxicity in various B cell malignancies, including Burkitt lymphoma (Daudi, Ramos, Namalwa) mantle cell lymphoma (Jeko-1)

Figure 11A:
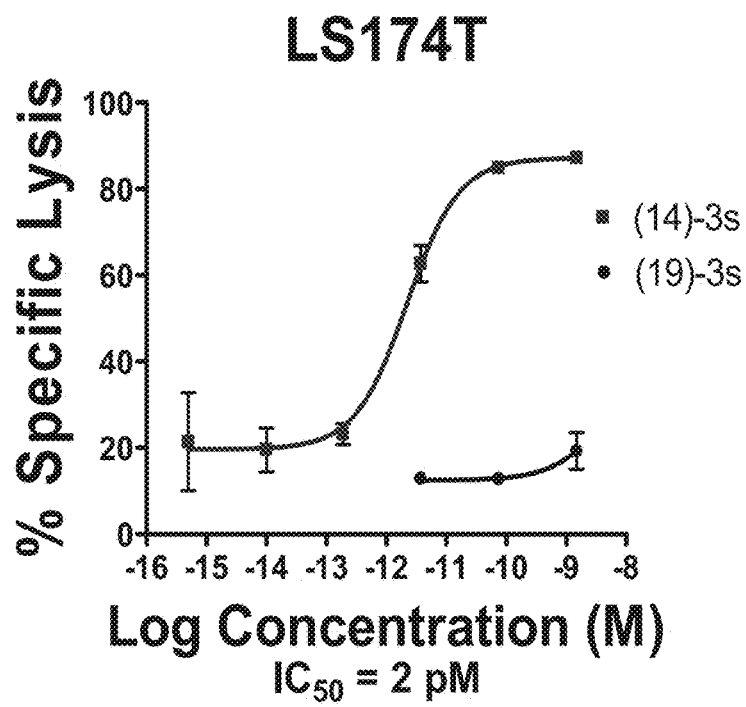
FIG. 11A. In vitro cytotoxicity of T-cell redirecting bsAbs in solid tumor cell lines. Dose-response curves were determined for cytotoxicity to the LS174T colon adenocarcinoma cell line for the (14)-3s bsAb, compared to non-targeting (19)-3s bsAb.
Figure 11B:
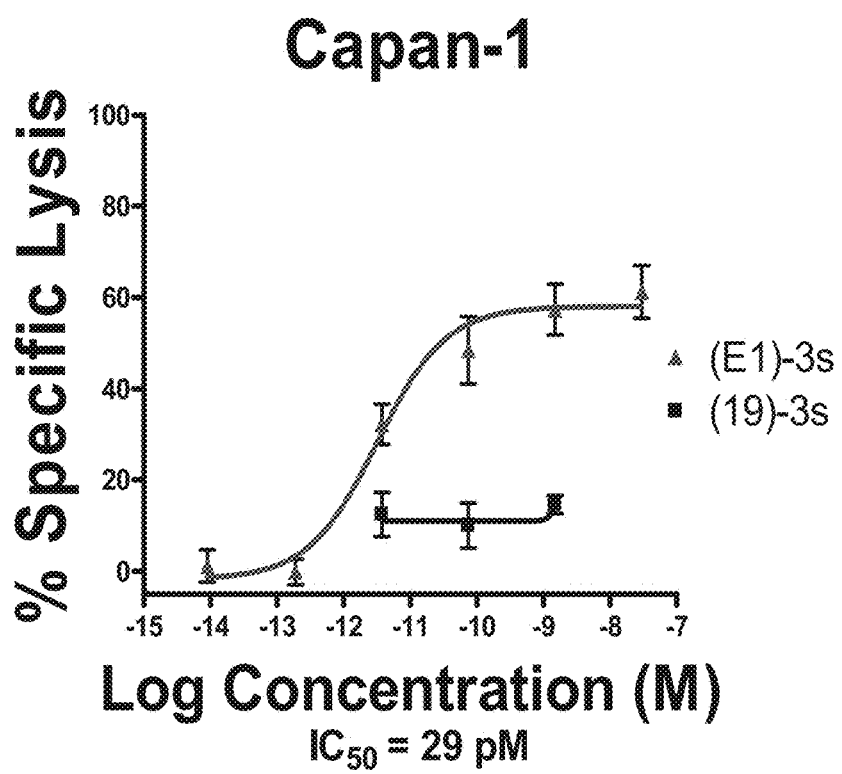
FIG. 11B. In vitro cytotoxicity of T-cell redirecting bsAbs in solid tumor cell lines. Dose-response curves were determined for cytotoxicity to the Capan-1 pancreatic adenocarcinoma cell line for the (E1)-3s bsAb, compared to non-targeting (19)-3s bsAb.
Figure 11C:
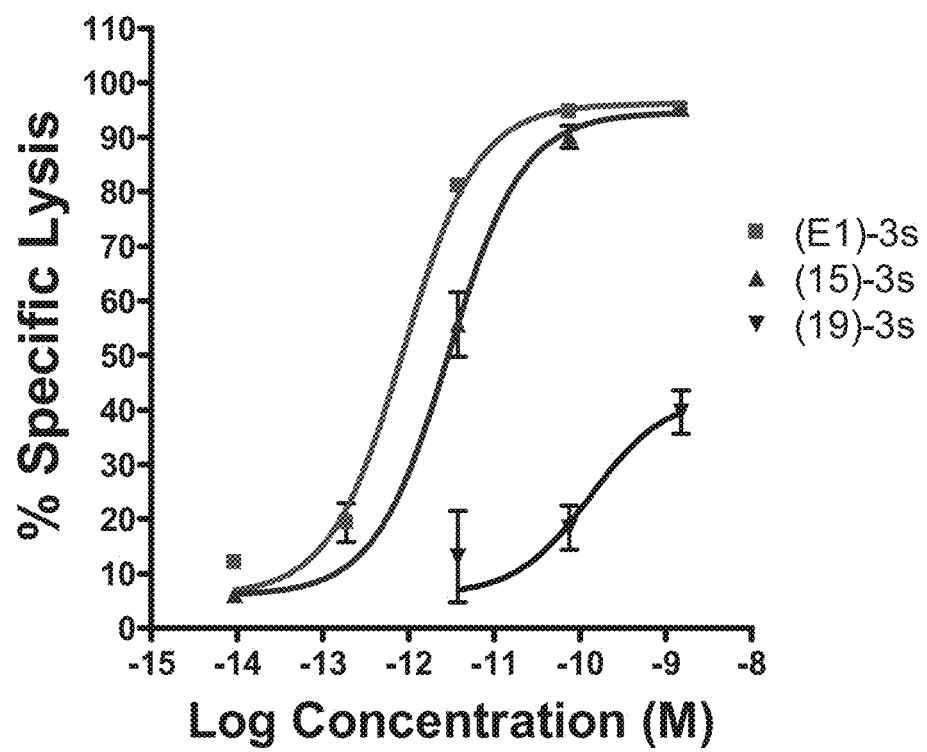
FIG. 11C. In vitro cytotoxicity of T-cell redirecting bsAbs in solid tumor cell lines. Dose-response curves were determined for cytotoxicity to the NCI-N87 gastric carcinoma cell line for the (E1)-3s and (15)-3s bsAbs, compared to non-targeting (19)-3s bsAb.
Figure 13B:
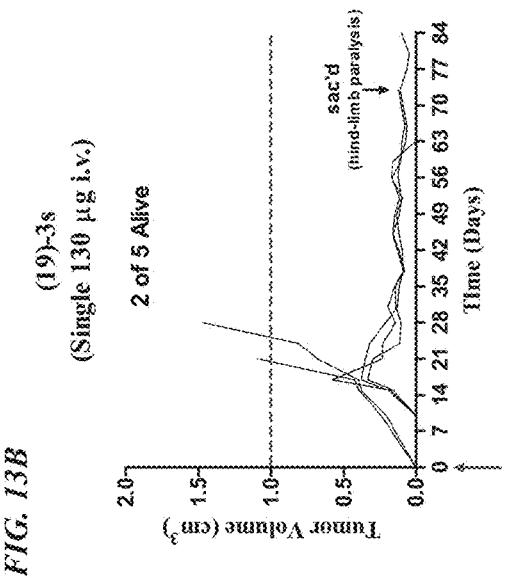
FIG. 13B. In vivo retargeting of Raji lymphoma xenografts using (19)-3s bsAb. NOD/SCID mice bearing Raji Burkitt lymphoma (1×10$^6$ cells) xenografts, reconstituted with human PBMCs (5×10$^6$ cells) and treated with (19)-3s for only 1 week, administered as indicated by the arrows. Cells were treated with a single dose of 130 µg.
Figure 13D:
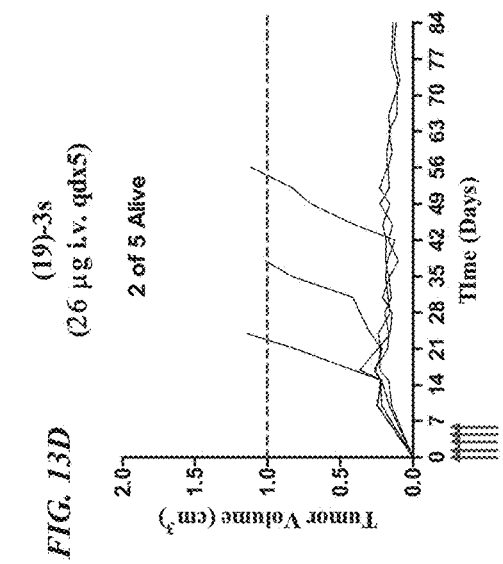
FIG. 13D. In vivo retargeting of Raji lymphoma xenografts using (19)-3s bsAb. NOD/SCID mice bearing Raji Burkitt lymphoma (1×10$^6$ cells) xenografts, reconstituted with human PBMCs (5×10$^6$ cells) and treated with (19)-3s for only 1 week, administered as indicated by the arrows. Cells were treated 5× with 26 µg per dose.
Figure 13A:
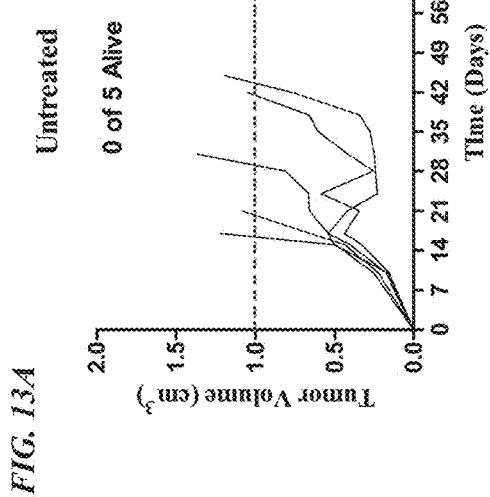
FIG. 13A. In vivo retargeting of Raji lymphoma xenografts using (19)-3s bsAb. NOD/SCID mice bearing Raji Burkitt lymphoma (1×10$^6$ cells) xenografts, reconstituted with human PBMCs (5×10$^6$ cells) and treated with (19)-3s for only 1 week, administered as indicated by the arrows. Control with untreated cells.
Figure 13C:
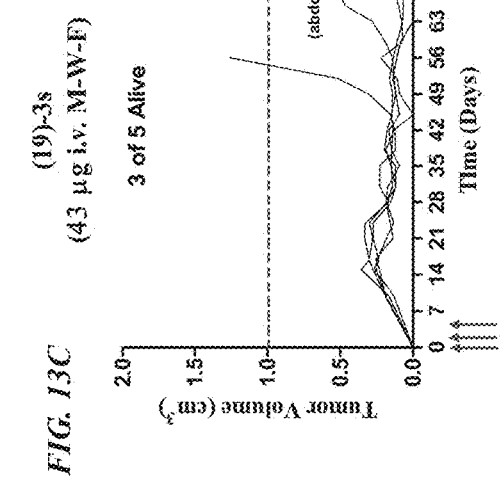
FIG. 13C. In vivo retargeting of Raji lymphoma xenografts using (19)-3s bsAb. NOD/SCID mice bearing Raji Burkitt lymphoma (1×10$^6$ cells) xenografts, reconstituted with human PBMCs (5×10$^6$ cells) and treated with (19)-3s for only 1 week, administered as indicated by the arrows. Cells were treated 3× with 43 µg per dose.
Figure 15A:
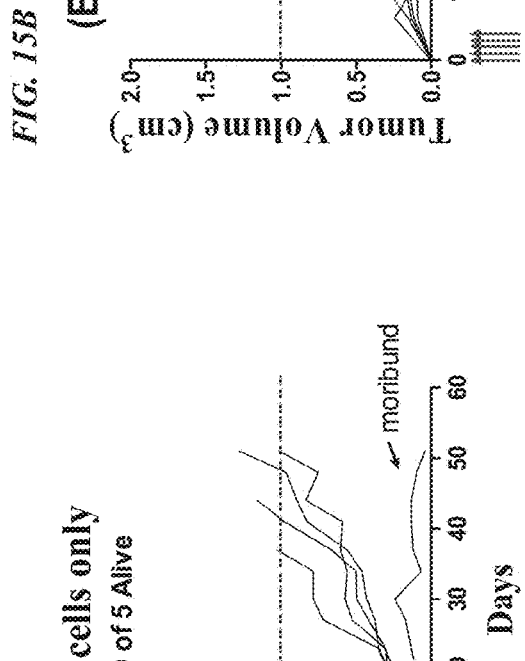
FIG. 15A. In vivo efficacy of T-cell retargeting bsAbs in solid tumor xenografts. NOD/SCID mouse xenografts were prepared with LS174T colon adenocarcinoma. Mice were administered T cells only without bsAb.
Figure 15B:
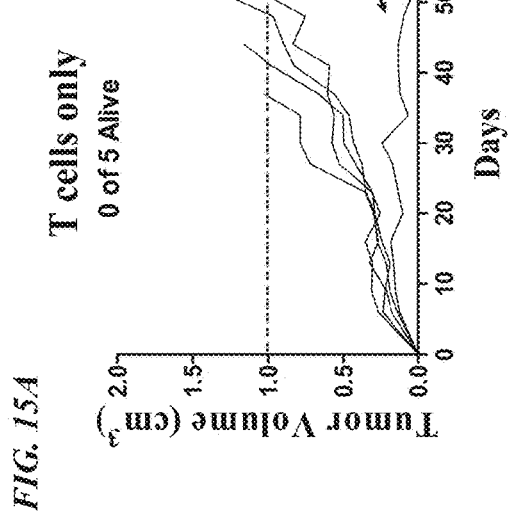
FIG. 15B. In vivo efficacy of T-cell retargeting bsAbs in solid tumor xenografts. NOD/SCID mouse xenografts were prepared with LS174T colon adenocarcinoma. Mice were treated with (E1)-3s bsAb as indicated.
Figure 15C:
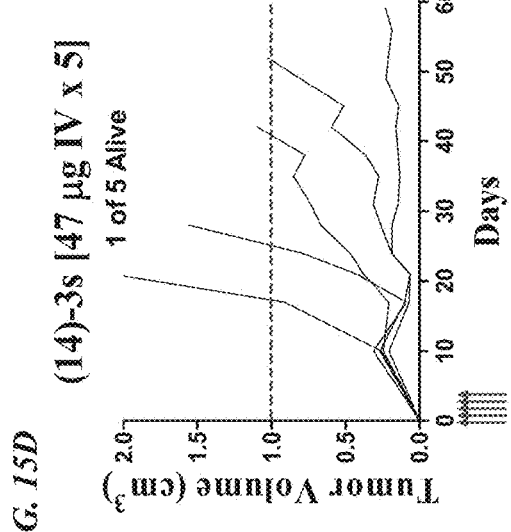
FIG. 15C. In vivo efficacy of T-cell retargeting bsAbs in solid tumor xenografts. NOD/SCID mouse xenografts were prepared with Capan-1 pancreatic carcinoma. Mice were administered PBMCs only without bsAb.
Figure 15D:
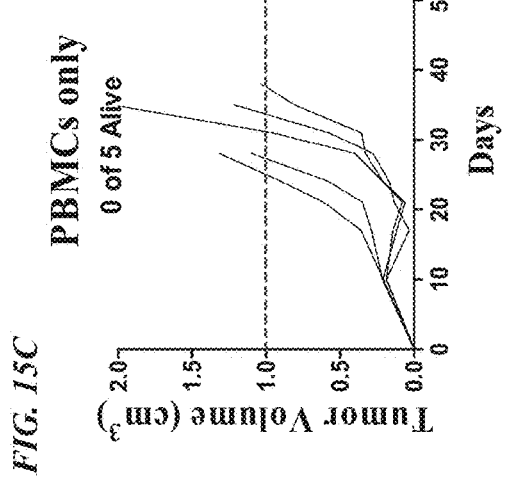
FIG. 15D. In vivo efficacy of T-cell retargeting bsAbs in solid tumor xenografts. NOD/SCID mouse xenografts were prepared with Capan-1 pancreatic carcinoma. Mice were treated with (14)-3s bsAb as indicated.

The in vitro cytotoxic effects of leukocyte redirecting bsAbs were also determined in solid tumor cells (FIG. 11). For the solid tumor cell lines, optimal assay conditions were determined to be a 3:1 E:T ratio using stimulated T cells in a 42-48 hour assay. Each bsAb induced specific T-cell mediated lysis of the tumor target cells. The CEACAM5-expressing human colon adenocarcinoma cell line, LS-174T, demonstrated potent specific lysis ($IC_{50}$=2 pM) following treatment with (14)-3s (FIG. 11A). (E1)-3s mediated potent specific lysis of the TROP2 expressing Capan-1 human pancreatic adenocarcinoma cell line ($IC_{50}$=29 pM) (FIG. 11B). The gastric carcinoma cell line NCI-N87, which expresses high levels of both CEACAM6 and TROP 2 demonstrated very potent specific lysis to both T-cell targeting molecules, (15)-3s and (E1)-3s ($IC_{50}$=3 pM and 0.85 pM respectively) (FIG. 11C). The non-targeting control antibody, (19)-3s, induced low (<20%) non-specific lysis at concentrations >1 nM for Capan-1 and LS174T, and moderate (~40%) non-specific lysis in NCI-N87 cells (FIG. 11A-C). A summary of the in vitro cytotoxicity data for various leukocyte redirecting bsAbs in a variety of tumor cell lines is shown in FIG. 12. The various constructs showed a maximal cell lysis of up to 90% or more of the targeted tumor cells, with $IC_{50}$ values for cell lines expressing the targeted antiben that were generally in the low picomolar range (FIG. 12).

Example 2

In Vivo Studies of Leukocyte Redirecting DNL™ Complex

One potential limitation of small (<60 kDa) scFv-based constructs, such as BITE® and DART™, is the requirement for administration by long-term continuous infusion, due to their toxicity and rapid clearance from circulation. Because the molecular size of DNL™ bsAbs is above the threshold typically associated with renal clearance, it should exhibit slower clearance from circulation. We measured the pharmacokinetic parameters in mice following a single bolus i.v. injection of 5 mg/kg of the (19)-3s bsAb (data not shown). A biphasic clearance was observed with a t1/2α and t1/2β of 1.1 and 5.1 h, respectively, resulting in an area under the curve of 1880 pmol*h/mL (data not shown), which was nearly 6-fold greater than that reported for MT103 (anti-CD19×anti-CD3 BITE®) administered at the same molar concentration (US Patent US2010/0303827A1). The major difference is apparently a longer t1/2α for (19)-3s (data not shown). Because of the potentially advantageous properties of (19)-3s, we evaluated the possibility of using less frequent dosing schedules rather than daily dosing, which is typically used for BITE® in animal studies.

A pilot study was performed using Raji human Burkitt lymphoma xenografts in NOD/SCID mice reconstituted with human PBMCs (FIG. 13, FIG. 14). Raji cells ($1 \times 10^6$ cells/mouse) were combined with freshly isolated PBMCs ($5 \times 10^6$ cells/mouse) from a single healthy donor, mixed 1:1 with matrigel, and injected SC into all of the animals in the study on Day 0. Groups of 5 mice received i.v. injections of (19)-3s totaling 130 µg as a single dose on Day 0 (FIG. 13B), three doses of 43 µg (Days 0, 2 and 4) (FIG. 13C) or five daily doses of 26 µg (Days 0-5) (FIG. 13D). The untreated group (FIG. 13A), which was inoculated with the same cell mixture but did not receive (19)-3s, had a median survival time (MST) of 31 days. Each therapy regimen improved survival (P≤0.05), with the three dose (every other day) schedule providing the greatest survival benefit (MST=91 days; P=0.0018 by log-rank analysis).

A follow-up study was begun to determine the efficacy of less frequent dosing (FIG. 14). Groups of 9 NOD/SCID mice were inoculated with Raji and PBMCs in a similar fashion as above. In this study, therapy was extended to two weeks, compared to one week in the first study. Groups received i.v. injections of (19)-3s totaling 360 µg as 2×130-µg (FIG. 14B), 4×65-µg (FIG. 14D) or 6×43-µg doses over two weeks (FIG. 14E). An additional group was administered 2×130-µg doses SC, instead of i.v. (FIG. 14C). For comparison, control groups of untreated mice (FIG. 14A) or mice treated with non-targeting (M1)-3s antibody (FIG. 14F) were prepared. As of Day 28, each of the (19)-3s treatment groups had significantly smaller AUC than the untreated control (P<0.05). Surprisingly, two weekly doses via the SC route was apparently as effective as greater frequency i.v. dosing.

In vivo studies were also performed using solid tumors (FIG. 15). NOD/SCID mouse xenografts were prepared as described above, for the LS174T colon adenocarcinoma (FIG. 15A, FIG. 15B) or Capan-1 pancreatic carcinoma (FIG. 15C, FIG. 15D). In each case, mice administered the targeting (E1)-3s (FIG. 15B) or (14)-3s (FIG. 15D) bsAb DNL™ constructs showed improved survival compared to controls.

In conclusion, the leukocyte-retargeting bsAbs, including (19)-3s, (E1)-3s and (M1)-3s DNL™ constructs, mediated synapse formation between T cells and B cells, colon adenocarcinoma or pancreatic carcinoma cells, respectively, via monovalent and bivalent binding to CD3 and CD19, respectively. T-cell activation, proliferation and target cell killing were induced by the DNL™ bsAbs at pM concentrations in an ex vivo setting. Advantageous properties of the DNL™ bsAbs, including bivalent tumor binding and slower clearance, would allow for less frequent dosing and possibly SC administration, compared to BITE® or DART™ constructs, which are administered i.v. daily in animal models and as a continuous infusion in the clinic. The modular nature of the DNL™ method allows the rapid production of a large number of related conjugates for redirected leukocyte killing of various malignancies, without the need for additional recombinant engineering and protein production.

The person of ordinary skill in the art will realize that other antibodies that bind to CD3 or other leukocyte antigens, as well as other antibodies that bind to Trop-2 or other disease-associated antigens are known in the art and any such antibody can be used to make $F(ab)_2$, scFv or other antibody fragments using techniques well known in the art. Such alternative antibodies or fragments thereof may be utilized in the instant methods and compositions. As discussed below, methods of making DOCK-AND-LOCK™ (DNL™) complexes may be applied to incorporate any known antibodies or antibody fragments into a stable, physiologically active complex.

Example 3

Interferon-α Enhances the Cytotoxic Effect of Anti-Trop-2×Anti-CD3 Bispecific Antibodies The therapeutic efficacy of an anti-human Trop-2×anti-human CD3 bispecific antibody ((E1)-3s), made from hRS7 and OKT3 as a DNL™ complex, was tested for its ability to delay tumor outgrowth of Capan-1 human pancreatic adenocarcinoma tumor cells when mixed with human T-cells and injected into mice. The effect of interferon-α (either in the form of E1*-2b or PEGASYS®) when combined with this therapy was also evaluated.

Methods

Five week-old female NOD/SCID mice were injected s.c. with a mixture of Capan-1 ($5 \times 10^6$) and human T-cells ($2.5 \times 10^6$ cells) mixed 1:1 with matrigel (E:T ratio of 1:2). There were six different treatment groups of 8 mice each. Treatment consisted of one group receiving 47 µg (E1)-3s i.v. every day for five days starting 1 hour after the administration of the Capan-1/T-cell mixture. Two groups were treated with equimolar amounts of IFN, one received the DNL molecule made from IFN-α2b-DDD2-CK-hRS7 IgG1 (E1*-2b; 2.5 µg s.c. weekly×4 wks) while another received PEGASYS® (Roche; 0.6 µg s.c. weekly×4 wks). Two other groups received a combination of (E1)-3s plus E1*2b or (E1)-3s plus PEGASYS®. The final group control group remained untreated. Table 8 summarizes the various treatment groups.

TABLE 8

Treatment Groups for (E1)-3s Therapy
(E1)-3s Therapy of a Human Pancreatic Carcinoma Xenograft (Capan-1)
in NOD/SCID Mice

| Group | (N) | Amount Injected | Schedule |
|---|---|---|---|
| 1 | 8 | Untreated | N.A. |
| 2 | 8 | (E1)-3s (47 µg i.v.) | qdx5 |
| 3 | 8 | E1*-2b (2.5 µg s.c.) | qwkx4 |
| 4 | 8 | PEGASYS ® (0.6 µg s.c.) | qwkx4 |
| 5 | 8 | (E1)-3s + E1*-2b | qdx5 + qwkx4 |
| 6 | 8 | (E1)-3s + PEGASYS | qdx5 + qwkx4 |

Mice were monitored daily for signs of tumor out-growth. All animals had their tumors measured twice weekly once tumors began to come up. Mice were euthanized for disease progression if their tumor volumes exceeded 1.0 cm$^3$ in size.

Results

Figure 16A:
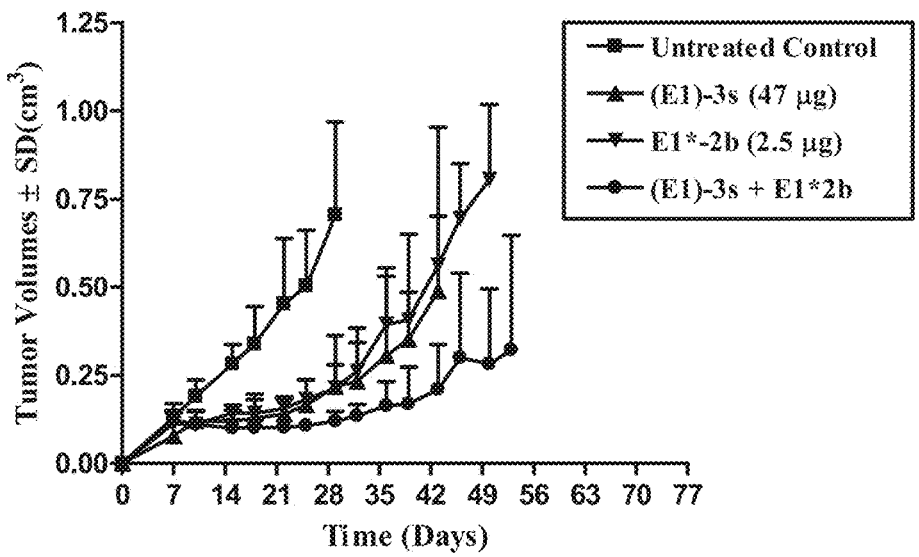
FIG. 16A. In vivo inhibition of tumor growth by (E1)-3s DNL™ complex in the presence or absence of interferon-α. Capan-1 pancreatic carcinoma xenografts in NOD/SCID mice were treated with anti-TROP-2×anti-CD3 bsAb with or without added interferon-α. The interferon-α was added in the form of a TROP-2 targeting DNL™ complex.
Figure 16B:
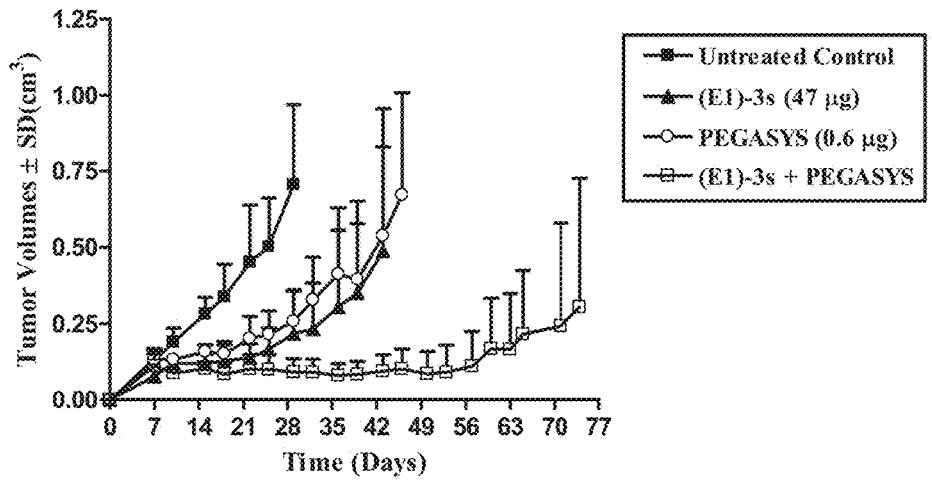
FIG. 16B. In vivo inhibition of tumor growth by (E1)-3s DNL™ complex in the presence or absence of interferon-α. Capan-1 pancreatic carcinoma xenografts in NOD/SCID mice were treated with anti-TROP-2×anti-CD3 bsAb with or without added interferon-α. The interferon-α was added as the commercially available PEGASYS® (peginterferon alfa-2a).

Mean tumor volumes for the various groups are shown in FIG. 16. The data containing PEGASYS® groups (FIG. 16B) are shown on a separate graph from the E1*2b groups (FIG. 16A) for clarity. All treatments were significantly better at controlling tumor growth in terms of area-under-the-curve (AUC) when compared to the untreated mice out to day 29, which was when the first mouse in the untreated group was euthanized for disease progression (P<0.0009; AUC$_{29\ days}$). Combining (E1)-3s with PEGASYS® resulted in the best anti-tumor response overall in terms of tumor out-growth (FIG. 16B). This treatment was significantly better than any of the individual treatments (P<0.042; AUC) as well as superior to the combination of (E1)-3s plus E1*-2b (P=0.0312; AUC$_{53\ days}$) (FIG. 16A). The combination of (E1)-3s plus E1*2b could significantly control tumor growth when compared to E1*2b or PEGASYS® alone (P<0.0073; AUC$_{46\ days}$) but not (E1)-3s alone (FIG. 16A-B). There were no significant differences between mice treated with (E1)-3s, PEGASYS®, or E1*-2b (FIG. 16A-B).

Figure 17:
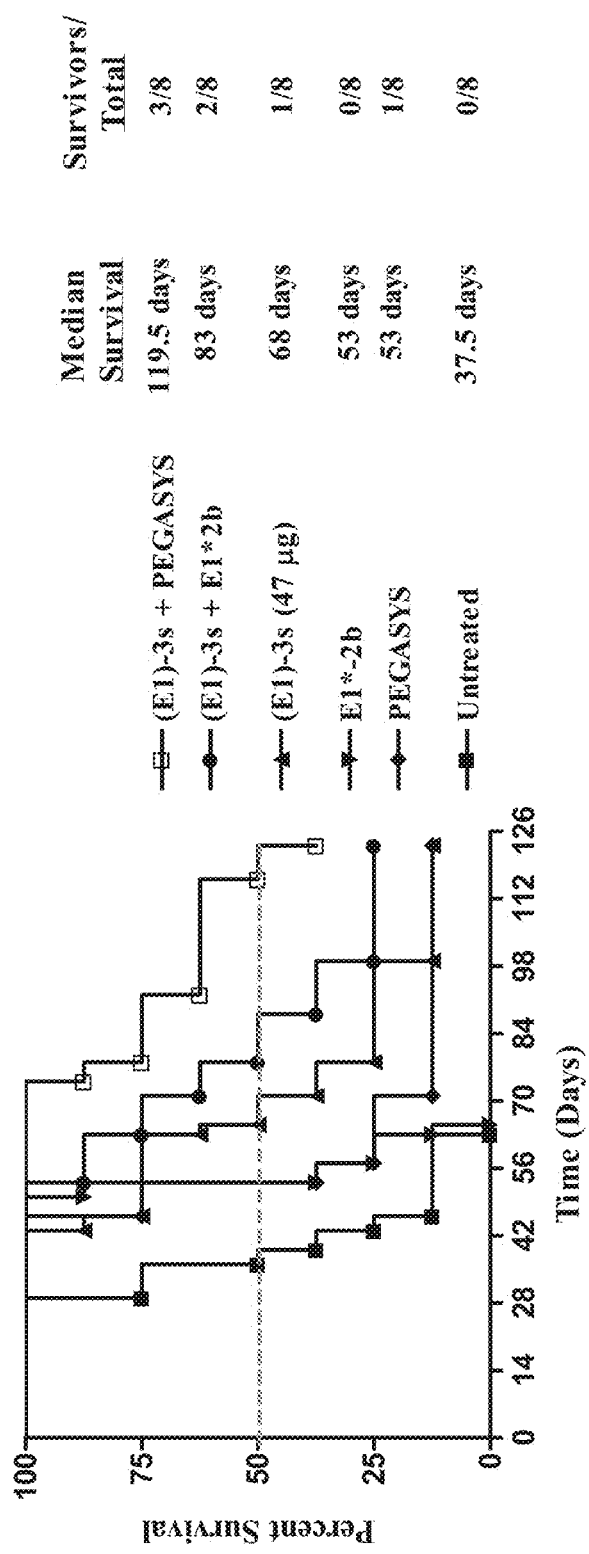
FIG. 17. Survival curves for NOD/SCID mice treated with (E1)-3s with or without interferon-α. Controls were untreated or treated with interferon-α alone.

In terms of survival, all treatments provide a significant survival benefit when compared to the untreated mice (P<0.0112; log-rank) (FIG. 17). As of day 81, there was no significant difference in median survival times (MST) between mice treated with the combination of (E1)-3s plus E1*-2b and those treated (E1)-3s plus PEGASYS® (MST=79.5 and >81 days, respectively) (FIG. 17). The mice treated with (E1)-3s plus PEGASYS® had a significantly improved survival outcome than any of the individual treatments (P<0.0237) (FIG. 17). Mice treated with (E1)-3s plus E1*2b had a survival benefit when compared to mice treated with E1*-2b alone (MST=53 days; P<0.0311) but not when compared to mice treated with just (E1)-3s or PEGASYS® alone (MST=68 and 53 days, respectively) (FIG. 17). Treatment with (E1)-3s provided a significant improvement in survival when compared to mice treated with E1*-2b (P=0.0406) but not when compared to mice treated with PEGASYS® alone (FIG. 17). There was no significant differences between mice treated with only E1*2b and those treated with PEGASYS® alone (FIG. 17).

The results demonstrate that addition of interferon-α provides a substantial increase in survival and decrease in tumor growth when combined with a leukocyte redirecting bsAb. The person of ordinary skill will realize that the improved efficacy observed with addition of type I or type III interferons (interferon-α, interferon-β, or interferon-λ) is not limited to the specific (E1)-3s bsAb, but will be observed with other leukocyte redirecting bsAbs, made either as DNL™ complexes or in other forms, such as BITE® or DART™.

Example 4

Further Studies on Interferon-α Combination Therapy with Leukocyte-Redirecting Bispecific Antibodies In the Example above, the combination of (E1)-3s plus PEGASYS® proved to be a very effective treatment in the control of tumor growth. In order to confirm these results and extend them, a study was performed in which two new groups were added. First, a control group for (E1)-3s was included in which an equimolar amount of TF12 was administered to animals. TF12 consists of two hRS7-Fab molecules linked to one non-targeting 679 Fab (anti-HSG). Additionally, since Capan-1 is sensitive to IFN, another group was added in which the effect of PEGASYS® on Capan-1 tumor growth was assessed without the benefit of T cells.

After the mice (40) were injected with the Capan-1/T-cell mixture, they were randomized into five treatment groups. One hour later, one group of 11 mice received 47 µg (E1)-3s i.v. every day starting 1 h post-tumor cell injection and continued for four more consecutive days (qdx5). One group of 7 animals received interferon in the form of PEGASYS® s.c. on a weekly basis for four weeks. Another group received a combination of (E1)-3s i.v. plus PEGASYS® s.c. Untreated control animals receive Capan-1/T cells but no treatment. A further control group received TF12 at amounts equivalent to the (E1)-3s in terms of moles (57 µg qdx5). Group 6 mice (8 animals) received a separate injection of only Capan-1 cells (i.e., no T cells) and was treated with PEGASYS®. All therapy injections were in a volume of 100 µL. Table 9 summarizes the various groups

TABLE 9

Treatment Groups for (E1)-3s and TF12 Therapy
(E1)-3s Therapy of a Human Pancreatic Carcinoma Xenograft (Capan-1)
in NOD/SCID Mice

| Group | (N) | Amount Injected | Schedule |
|---|---|---|---|
| 1 | 7 | Untreated (Capan-1 + T cells only) | N.A. |
| 2 | 11 | (E1)-3s (47 µg i.v.) | qdx5 |
| 3 | 7 | TF12 (57 µg i.v.) | qdx5 |
| 4 | 7 | PEGASYS ® (0.6 µg s.c.) | qwkx4 |
| 5 | 8 | (E1)-3s + PEGASYS ® | qdx5 + qwkx4 |
| 6 | 8 | PEGASYS ® (0.6 µg s.c.) (Capan-1 cells only) | qwkx4 |

Mice were monitored daily for signs of tumor out-growth. All animals had their tumors measured twice weekly once tumors began to come up. Mice were euthanized for disease progression if their tumor volumes exceeded 1.0 cm$^3$ in size.

Results

Mean tumor growth (FIG. 18) and survival curves (FIG. 19) are shown. While not different from each other, mice treated with (E1)-3s, PEGASYS®, or PEGASYS® (without T cells), demonstrated significant anti-tumor effects when compared to TF12 and untreated control groups (P<0.0102; AUC). On the day this experiment ended (day 59), the mean tumor volume for the mice treated with the combination of (E1)-3s plus PEGASYS® was 0.083±0.048 cm$^3$. Overall, this treatment group demonstrated a significant anti-tumor effect when compared to all the other treatment groups (P<0.0072; AUC).

Figure 18:
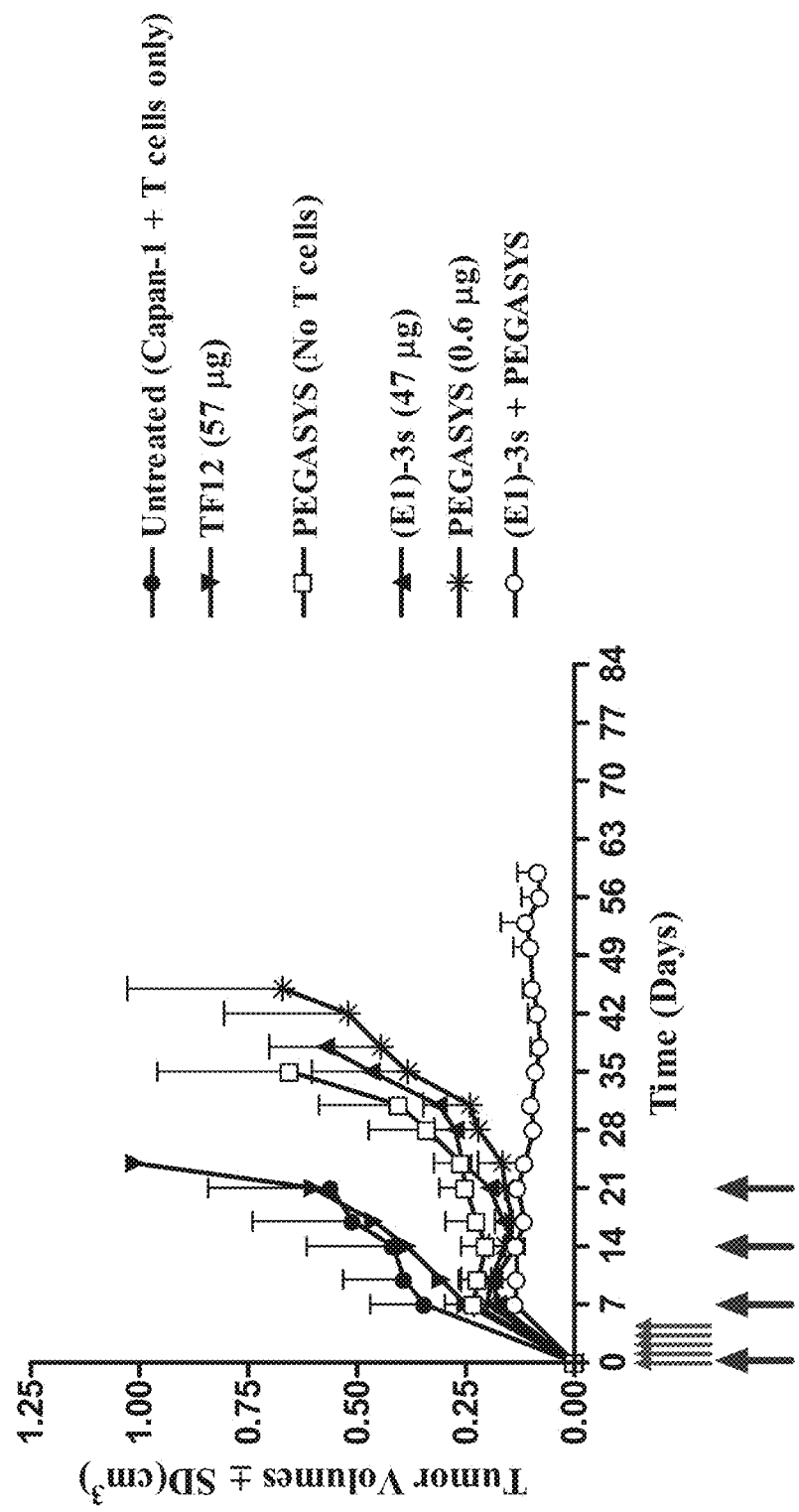
FIG. 18. In vivo inhibition of tumor growth by (E1)-3s DNL™ complex in the presence or absence of interferon-α, compared to TF12 control. Capan-1 pancreatic carcinoma xenografts in NOD/SCID mice were treated with anti-TROP-2×anti-CD3 bsAb with or without added interferon-α, added as PEGASYS®, compared to untreated control, TF12 control or PEGASYS® alone.
Figure 19:
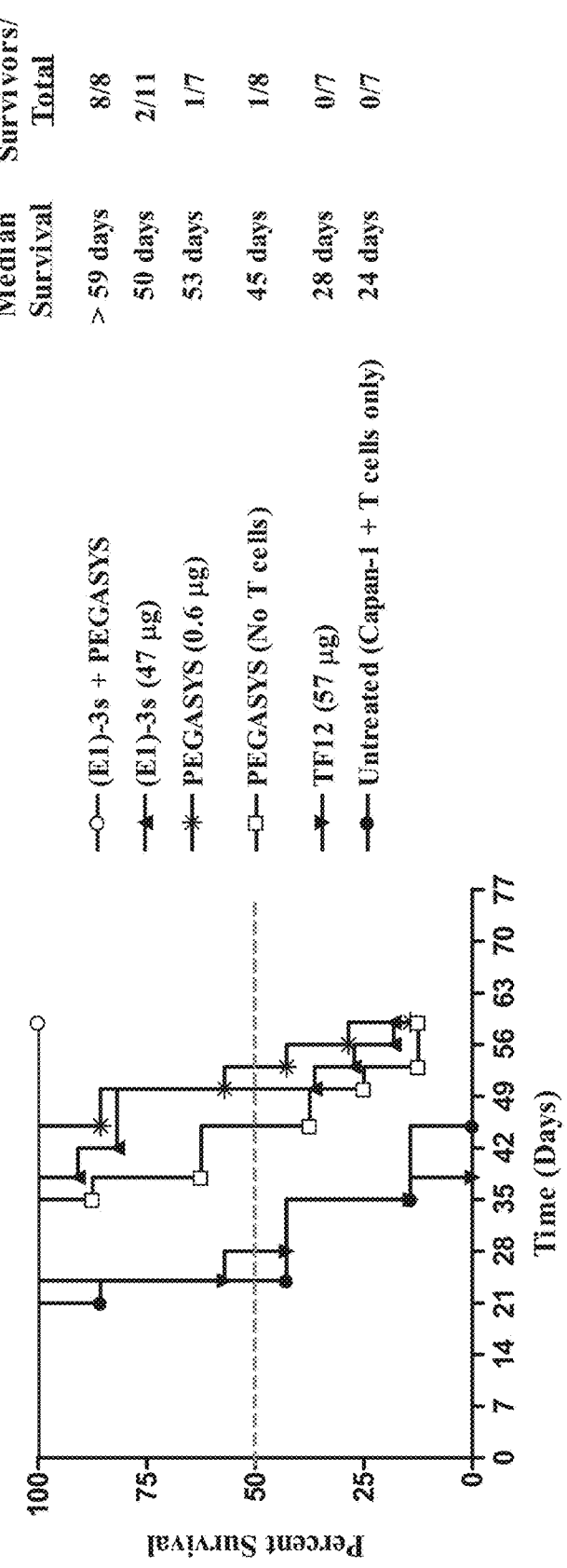
FIG. 19. Survival curves for NOD/SCID mice treated with (E1)-3s with or without interferon-α (PEGASYS®). Controls were untreated or treated with PEGASYS® alone or TF12 alone.

Each individual treatment (PEGASYS®, PEGASYS® without T cells, and (E1)-3s) significantly improved survival in comparison to both the TF12 and untreated control groups (P<0.0059; log-rank) (FIG. 18, FIG. 19). All the groups except the combination of (E1)-3s plus PEGASYS® reached their respective MSTs. No animals were euthanized for disease progression (TV>1.0 cm$^3$) in this combination group. Importantly, the combination of (E1)-3s plus PEGASYS® provided a significant survival benefit when compared to all other treatments (P<0.0007; log-rank) (FIG. 18, FIG. 19).

Example 5

Effect of Interferon-α Combination Therapy with T-Cell-Redirecting Bispecific Antibodies in Human Gastric Cancer The methods and compositions disclosed in the preceding two Examples were used to study the effects of leukocyte redirecting bsAbs alone or in combination with interferon-α (PEGASYS®) in the IFN-refractory NCI-N87 human gastric tumor line. Groups of mice (N=8 each group) were injected s.c. with 5×10$^6$ NCI-N87 cells+2.5×10$^6$ T Cells (1:2 E:T ratio) mixed with matrigel and therapy started 1 h later. The treatment groups are shown in Table 10.

TABLE 10

Treatment Groups for (E1)-3s and TF12 Therapy
(E1)-3s Therapy of a Human Gastric Carcinoma Xenograft (NCI-N87) in NOD-SCID Mice

| Group | Amount Injected | Schedule |
| --- | --- | --- |
| 1 | Untreated (NCI-N87 + T cells only) | N.A. |
| 2 | (E1)-3s (47 µg i.v.) | qdx5 |
| 3 | TF12 (57 µg i.v.) | qdx5 |
| 4 | PEGASYS ® (0.6 µg s.c.) | qwkx4 |
| 5 | TF12 + PEGASYS ® | qdx5 + qwkx4 |
| 6 | (E1)-3s + PEGASYS ® | qdx5 + qwkx4 |

Figure 20:
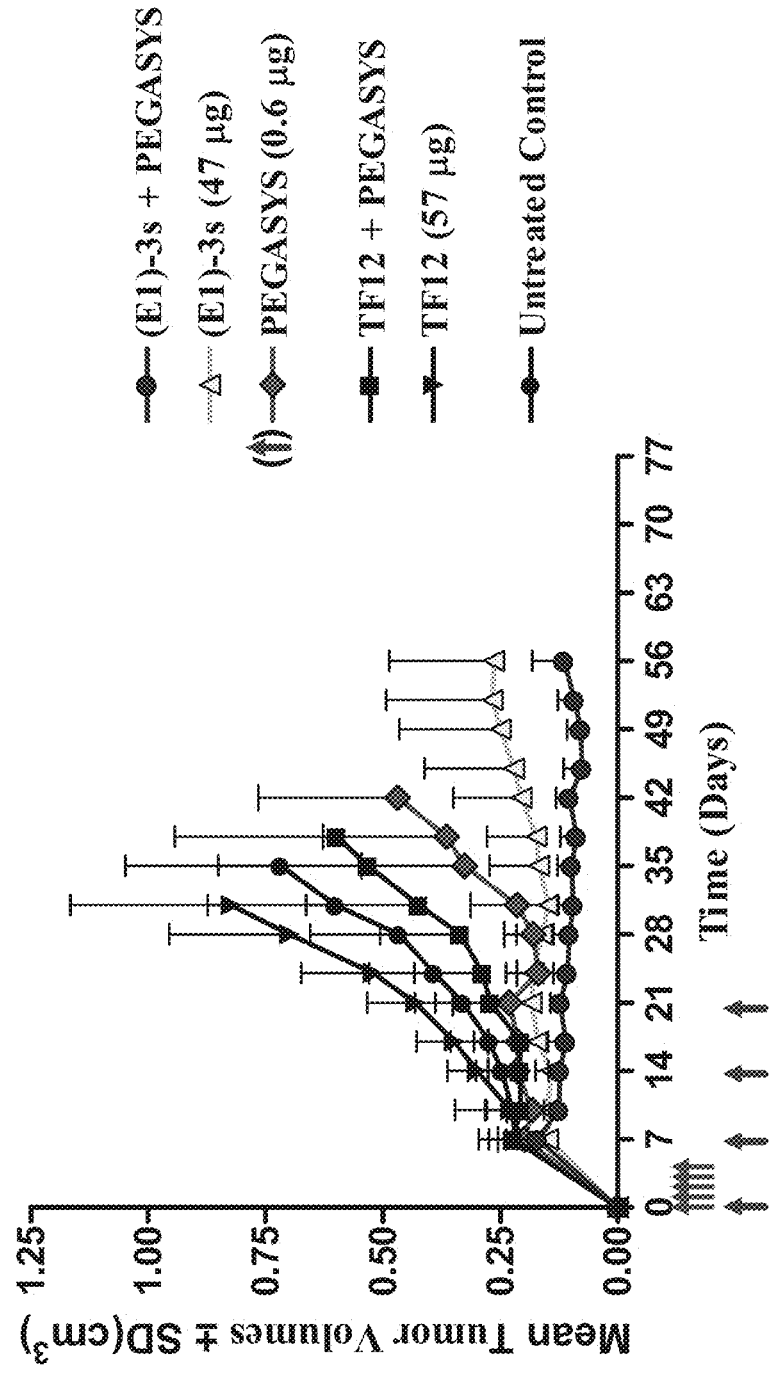
FIG. 20. In vivo inhibition of tumor growth by (E1)-3s DNL™ complex in the presence or absence of interferon-α, compared to TF12 control. NCI-N87 human gastric cancer xenografts in NOD/SCID mice were treated with anti-TROP-2×anti-CD3 bsAb with or without added interferon-α, added as PEGASYS®, compared to untreated control, TF12 control or PEGASYS® alone.
Figure 21:
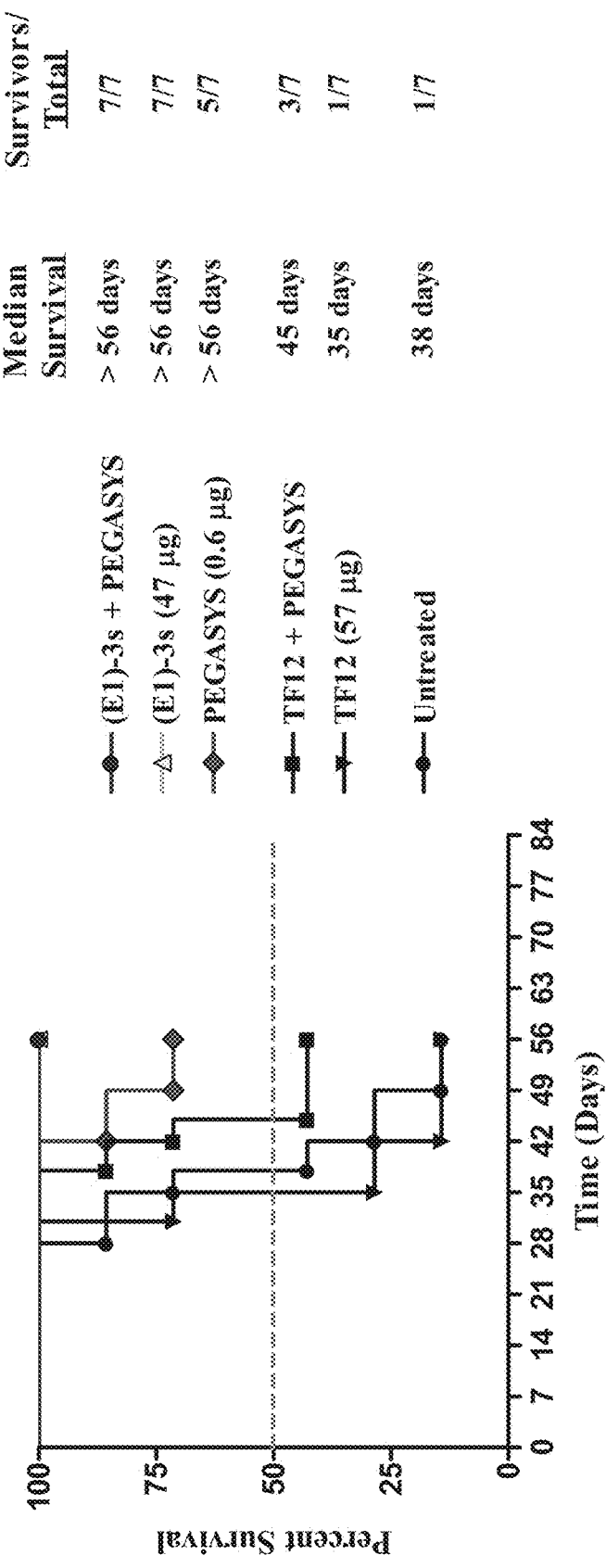
FIG. 21. Survival curves for NOD/SCID mice with NCI-N87 gastric cancer xenografts treated with (E1)-3s with or without interferon-α (PEGASYS®). Controls were untreated or treated with PEGASYS® alone or TF12 alone.

The effects of leukocyte redirecting bsAb (E1)-3s alone or in combination with interferon are shown in FIG. 20 and FIG. 21. The (E1)-3s bsAb was effective to reduce tumor growth and increase survival in gastric cancer. Significantly, the combination with interferon-α enhanced the effect of leukocyte redirecting bsAb, even in an interferon resistant tumor. The combination therapy was more effective than either agent added alone. Controls with mice treated with TF12 bsAb alone or in combination with interferon-α showed little effect on tumor growth or mortality, compared to untreated animals.

Example 6

In Vivo Therapeutic Use of Antibody-Drug Conjugates (ADCs) in Preclinical Models of Human Pancreatic or Colon Carcinoma CL2A-SN-38-antibody conjugates were prepared as previously described (see, e.g., U.S. Pat. Nos. 7,999,083 and 8,080,250). Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. In a Capan 1 pancreatic tumor model, specific CL2A-SN-38 conjugates of hRS7 (anti-TROP2), hPAM4 (anti-MUC5ac), and hMN-14 (anti-CEACAM5) antibodies showed better efficacies than control hA20-CL2A-SN-38 conjugate (anti-CD20) and untreated control (not shown). Similarly in a BXPC3 model of human pancreatic cancer, the specific hRS7-CL2A-SN-38 showed better therapeutic efficacy than control treatments (not shown). Likewise, in an aggressive LS174T model of human colon carcinoma, treatment with specific hMN-14-CL2A-SN-38 was more efficacious than non-treatment (not shown).

Example 7

In Vivo Therapy of Lung Metastases of GW-39 Human Colonic Tumors in Nude Mice Using ADC hMN-14-[CL2-SN-38], IMMU-130

A lung metastatic model of colonic carcinoma was established in nude mice by i.v. injection of GW-39 human colonic tumor suspension, and therapy was initiated 14 days later. Specific anti-CEACAM5 antibody conjugate, hMN14-CL2-SN-38, as well as nontargeting anti-CD22 MAb control conjugate, hLL2-CL2-SN-38 and equidose mixtures of hMN14 and SN-38 were injected at a dose schedule of q4d×8, using different doses. Selective therapeutic effects were observed with the hMN-14 ADC (not shown). At a dosage of 250 µg, the mice treated with hMN14-CL2-SN-38 showed a median survival of greater than 107 days. Mice treated with the control conjugated antibody hLL2-CL2-SN-38, which does not specifically target lung cancer cells, showed median survival of 77 days, while mice treated with unconjugated hMN14 IgG and free SN-38 showed a median survival of 45 days, comparable to the untreated saline control of 43.5 days. A significant and surprising increase in effectiveness of the conjugated, cancer cell targeted antibody-SN-38 conjugate, which was substantially more effective than unconjugated antibody and free chemotherapeutic agent alone, was clearly seen (not shown). The dose-responsiveness of therapeutic effect of conjugated antibody was also observed (not shown). These results demonstrate the clear superiority of the SN-38-antibody conjugate compared to the combined effect of both unconjugated antibody and free SN-38 in the same in vivo human lung cancer system.

Example 8

Use of ADC (IMMU-132 or hRS7-SN-38) to Treat Therapy-Refractive Metastatic Colonic Cancer (mCRC)

The patient was a 62-year-old woman with mCRC who originally presented with metastatic disease in January 2012. She had laparoscopic ileal transverse colectomy as the first therapy a couple of weeks after diagnosis, and then received 4 cycles of FOLFOX (leucovorin, 5-fluorouracil, oxaliplatin) chemotherapy in a neoadjuvant setting prior to right hepatectomy in March 2012 for removal of metastatic lesions in the right lobe of the liver. This was followed by an adjuvant FOLFOX regimen that resumed in June, 2012, for a total of 12 cycles of FOLFOX. In August, oxaliplatin was dropped from the regimen due to worsening neurotoxicity. Her last cycle of 5-FU was on 09/25/12.

CT done in January 2013 showed metastases to liver. She was then assessed as a good candidate for enrollment to IMMU-132 (hRS7-SN-38) investigational study. Comorbidities in her medical history include asthma, diabetes mellitus, hypertension, hypercholesteremia, heart murmur, hiatal hernia, hypothyroidism, carpel tunnel syndrome, glaucoma, depression, restless leg syndrome, and neuropathy. Her surgical history includes tubo-ligation (1975), thyroidectomy (1983), cholescystectomy (2001), carpel tunnel release (2008), and glaucoma surgery.

At the time of entry into this therapy, her target lesion was a 3.1-cm tumor in the left lobe of the liver. Non-target lesions included several hypo-attenuated masses in the liver. Her baseline CEA was 781 ng/mL.

IMMU-132 was given on a once-weekly schedule by infusion for 2 consecutive weeks, then a rest of one week, this constituting a treatment cycle. These cycles were repeated as tolerated. The first infusion of IMMU-132 (8 mg/kg) was started on Feb. 15, 2013, and completed without notable events. She experienced nausea (Grade 2) and fatigue (Grade 2) during the course of the first cycle and has been continuing the treatment since then without major adverse events. She reported alopecia and constipation in March 2013. The first response assessment done (after 6 doses) on Apr. 8, 2013 showed a shrinkage of target lesion by 29% by computed tomography (CT). Her CEA level decreased to 230 ng/mL on Mar. 25, 2013. In the second response assessment (after 10 doses) on May 23, 2013, the target lesion shrank by 39%, thus constituting a partial response by RECIST criteria. She has been continuing treatment, receiving 6 cycles constituting 12 doses of hRS7-SN-38 (IMMU-132) at 8 mg/kg. Her overall health and clinical symptoms improved considerably since starting this investigational treatment.

Example 9

ADC Therapy with IMMU-132 for Metastatic Solid Cancers

IMMU-132 is an ADC comprising the active metabolite of CPT-11, SN-38, conjugated by a pH-sensitive linker (average drug-antibody ratio=7.6) to the hRS7 anti-Trop-2 humanized monoclonal antibody, which exhibits rapid internalization when bound to Trop-2. IMMU-132 targets Trop-2, a type I transmembrane protein expressed in high prevalence and specificity by many carcinomas. This Example reports a Phase I clinical trial of 25 patients with different metastatic cancers (pancreatic, 7; triple-negative breast [TNBC], 4; colorectal [CRC], 3; gastric, 3, esophageal, prostatic, ovarian, non-small-cell lung, small-cell lung [SCLC], renal, tonsillar, urinary bladder, 1 each) after failing a median of 3 prior treatments (some including topoisomerase-I and -II inhibiting drugs).

IMMU-132 was administered in repeated 21-day cycles, with each treatment given on days 1 and 8. Dosing started at 8 mg/kg/dose (i.e., 16 mg/kg/cycle), and escalated to 18 mg/kg before encountering dose-limiting neutropenia, in a 3+3 trial design. Fatigue, alopecia, and occasional mild to moderate diarrhea were some of the more common non-hematological toxicities, with 2 patients also reporting a rash. Over 80% of 24 assessable patients had stable disease or tumor shrinkage (SD and PR) among the various metastatic cancers as best response by CT. Three patients (CRC, TNBC, SCLC) have PRs by RECIST; median TTP for all patients, excluding those with pancreatic cancer, is >18 weeks. Neutropenia has been controlled by dose reduction to 8-10 mg/kg/dose (16-20 mg/kg/cycle).

Immunohistochemistry showed strong expression of Trop-2 in most archived patient tumors, but it is not detected in serum. Corresponding reductions in blood tumor marker titers (e.g., CEA, CA19-9) reflected tumor responses. No anti-antibody or anti-SN-38 antibodies have been detected despite repeated dosing. Peak and trough assessments of IMMU-132 concentrations in the serum show that the conjugate clears completely within 7 days, an expected finding based on in vitro studies showing 50% of the SN-38 is released in the serum every day. These results indicate that this novel ADC, given in doses ranging from 16-24 mg/kg per cycle, shows a high therapeutic index in diverse metastatic solid cancers.

Example 10

IMMU-130, an SN-38 ADC that Targets CEACAM5, is Therapeutically Active in Metastatic Colorectal Cancer (mCRC)

IMMU-130, an ADC of SN-38 conjugated by a pH-sensitive linker (7.6 average drug-antibody ratio) to the humanized anti-CEACAM5 antibody (labetuzumab), is completing two Phase I trials. In both, eligible patients with advanced mCRC were required to have failed/relapsed standard treatments, one being the topoisomerase-I inhibiting drug, CPT-11 (irinotecan), and an elevated plasma CEA (>5 ng/mL).

IMMU-130 was administered every 14 days (EOW) at doses starting from 2.0 mg/kg in the first protocol (IMMU-130-01). Febrile neutropenia occurred in 2 of 3 patients at 24 mg/kg; otherwise at ≤16 mg/kg, neutropenia (≥Grade 2) was observed in 7 patients, with one also experiencing thrombocytopenia. One patient [of 8 who received ≥4 doses (2 cycles)] showed a 40.6% decrease in liver (starting at 7 cm) and lung target lesions (PR by RECIST) for 4.7 months, with no major toxicity, tolerating a total of 18 doses at 16 mg/kg. The study is continuing at 12 mg/kg EOW.

Since SN-38 is most effective in S-phase cells, a more protracted exposure could improve efficacy. Thus, in a second Phase I trial (IMMU-130-02), dosing was intensified to twice-weekly, starting at 6 mg/kg/dose for 2 weeks (4 doses) with 1 week off, as a treatment cycle, in a 3+3 trial design. Neutropenia and manageable diarrhea were the major side effects, until dose reduction to 4.0 mg/kg twice-weekly, with early results indicating multiple cycles are well-tolerated. Currently, tumor shrinkage occurred in 3 patients, with 1 in continuing PR (−46%) by RECIST, among 6 patients who completed ≥4 doses (1 cycle). In both trials, CEA blood titers correlated with tumor response, and high levels did not interfere with therapy. There have been no anti-antibody or anti-SN-38 antibody reactions, based on ELISA tests. In each study, the ADC was cleared by 50% within the first 24 h, which is much longer exposure than with typical doses of the parental molecule, CPT-11. These results indicate that this novel ADC, given in different regimens averaging ~16-24 mg/kg/cycle, shows a high therapeutic index in advanced mCRC patients. Since CEACAM5 has elevated expression in breast and lung cancers, as well as other epithelial tumors, it may be a useful target in other cancers as well.

Example 11

Antitumor Activity of Checkpoint Inhibitor Antibody Alone or Combined with Anti-Trop-2×anti-CD3 bsAb, IFN-α or Anti-Trop-2 ADC To determine if the antitumor activity of the exemplary checkpoint inhibitor antibody, ipilimumab (anti-CTLA4) is synergistic with or inhibited by the addition of other therapeutic agents, CTLA4 mAb is evaluated alone or in combination with the exemplary T-cell redirecting bsAb (E1)-3s, with interferon-α (PEGINTERFERON®), or with the exemplary ADC hRS7-SN-38 (IMMU-132) in murine tumor models. M109 lung carcinoma, SA1N fibrosarcoma, and CT26 colon carcinoma models are chosen based on different sensitivity to the various agents and CTLA4 blockade. Human T cells are co-administered with the antibodies.

All compounds are tested at their optimal dose and schedule. When used in combination, CTLA4 mAb is initiated one day after the first dose of IMMU-132, (E1)-3s or interferon-α. Percent tumor growth inhibition and number of days to reach target tumor size are used to evaluate efficacy. Antitumor activity is scored as: complete regression (CR; non-palpable tumor) or partial regression (PR; 50% reduction in tumor volume). Synergy is defined as antitumor activity significantly superior ($p<0.05$) to the activity of monotherapy with each agent.

In the SA1N fibrosarcoma tumor model, which is sensitive to CTLA4 blockade and modestly sensitive to (E1)-3s, interferon-α, and IMMU-132, borderline synergy is evident with the combination of CTLA4 mAb and (E1)-3s, whereas no effect is observed with interferon-α. IMMU-132 monotherapy does not produce significant SA1N antitumor activity. However, combining IMMU-132 with CTLA4 mAb results in synergy. In the M109 lung metastasis model and CT26 colon carcinoma model, synergy is detected for CTLA4 mAb combined with each of IMMU-132, (E1)-3s and interferon-α.

In summary, addition of CTLA4 mAb to interferon-α, IMMU-132, or (E1)-3s results in model-dependent synergistic activities. Synergy is observed regardless of the immunogenicity of the tumor and only when at least one of the therapies is active. All combination regimens are well-tolerated and the combination therapies do not appear to inhibit CTLA4 mAb activity. Synergy is observed in tumors unresponsive to CTLA4 mAb alone, suggesting that the other therapeutic agents might induce immunogenic cell death.

Example 12

Combination Therapy with Anti-Trop-2 ADC (IMMU-132) and Interferon-α (PEGINTERFERON®) to Treat Refractory, Metastatic, Non-Small Cell Lung Cancer The patient is a 60-year-old man diagnosed with non-small cell lung cancer. The patient is given chemotherapy regimens of carboplatin, bevacizumab for 6 months and shows a response, and then after progressing, receives further courses of chemotherapy with carboplatin, etoposide, TAXOTERE®, gemcitabine over the next 2 years, with occasional responses lasting no more than 2 months. The patient then presents with a left mediastinal mass measuring 6.5×4 cm and pleural effusion.

After signing informed consent, the patient is given IMMU-132 at a dose of 18 mg/kg every other week. After the first week of treatment, the patient is given combination therapy with IMMU-132 and PEGINTERFERON®. During the first two injections, brief periods of neutropenia and diarrhea are experienced, with 4 bowel movements within 4 hours, but these resolve or respond to symptomatic medications within 2 days. After a total of 6 infusions of IMMU-132 and 5 infusions of PEGINTERFERON®, CT evaluation of the index lesion shows a 22% reduction, just below a partial response but definite tumor shrinkage. The patient continues with this therapy for another two months, when a partial response of 45% tumor shrinkage of the sum of the diameters of the index lesion is noted by CT, thus constituting a partial response by RECIST criteria. The combination therapy appears to provide a synergistic response, compared to the two agents administered separately.

Example 13

Combination Therapy with ADC (IMMU-130) and T-Cell Redirecting bsAb (MT100) to Treat Advanced Colonic Cancer The patient is a 75-year-old woman initially diagnosed with metastatic colonic cancer (Stage IV). She has a right partial hemicolectomy and resection of her small intestine and then receives FOLFOX, FOLFOX+bevacizumab, FOLFIRI+ramucirumab, and FOLFIRI+cetuximab therapies for a year and a half, when she shows progression of disease, with spread of disease to the posterior cul-de-sac, omentum, with ascites in her pelvis and a pleural effusion on the right side of her chest cavity. Her baseline CEA titer just before this therapy is 15 ng/mL. She is given 6 mg/kg IMMU-130 (anti-CEACAM5-SN-38) twice weekly for 2 consecutive weeks, and then one week rest (3-week cycle). After the first cycle, the patient is given combination therapy with IMMU-132 and the leukocyte redirecting bsAb MT110, which is administered by continuous infusion on the same 3-week cycle. After 5 cycles, which are tolerated very well, without any major hematological or non-hematological toxicities, her plasma CEA titer shrinks modestly to 1.3 ng/mL, but at the 8-week evaluation she shows a 21% shrinkage of the index tumor lesions, which increases to a 27% shrinkage at 13 weeks. Surprisingly, the patient's ascites and pleural effusion both decrease (with the latter disappearing) at this time, thus improving the patient's overall status remarkably. The combination therapy appears to provide a synergistic response, compared to the two agents administered separately.

Example 14

Combination Therapy with ADC (IMMU-130), Anti-Trop-2×Anti-CD3 bsAb ((E1)-3s) and Interferon-α to Treat Gastric Cancer Patient with Stage IV Metastatic Disease The patient is a 52-year-old male who sought medical attention because of gastric discomfort and pain related to eating for about 6 years, and with weight loss during the past 12 months. Palpation of the stomach area reveals a firm lump which is then gastroscoped, revealing an ulcerous mass at the lower part of his stomach. This is biopsied and diagnosed as a gastric adenocarcinoma. Laboratory testing reveals no specific abnormal changes, except that liver function tests, LDH, and CEA are elevated, the latter being 10.2 ng/mL. The patent then undergoes a total-body PET scan, which discloses, in addition to the gastric tumor, metastatic disease in the left axilla and in the right lobe of the liver (2 small metastases). The patient has his gastric tumor resected, and then has baseline CT measurements of his metastatic tumors. Four weeks after surgery, he receives 3 courses of combination chemotherapy consisting of a regimen of cisplatin and 5-fluorouracil (CF), but does not tolerate this well, so is switched to treatment with docetaxel. It appears that the disease is stabilized for about 4 months, based on CT scans, but then the patient's complaints of further weight loss, abdominal pain, loss of appetite, and extreme fatigue cause repeated CT studies, which show increase in size of the metastases by a sum of 20% and a suspicious lesion at the site of the original gastric resection.

The patient is then given experimental therapy with IMMU-130 (anti-CEACAM5-SN-38) on a weekly schedule of 8 mg/kg. After the first week, combination therapy with IMMU-130, (E1)-3s and interferon-α is initiated. The patient exhibits no evidence of diarrhea or neutropenia over the following 4 weeks. The patient then undergoes a CT study to measure his metastatic tumor sizes and to view the original area of gastric resection. The radiologist measures, according to RECIST criteria, a decrease of the sum of the metastatic lesions, compared to baseline prior to therapy, of 23%. There does not seem to be any clear lesion in the area of the original gastric resection. The patient's CEA titer at this time is 7.2 ng/mL, which is much reduced from the baseline value of 14.5 ng/mL. The patient continues on weekly combination therapy, and after a total of 13 infusions, his CT studies show that one liver metastasis has disappeared and the sum of all metastatic lesions is decreased by 41%, constituting a partial response by RECIST. The patient's general condition improves and he resumes his usual activities while continuing to receive maintenance therapy every third week. At the last measurement of blood CEA, the value is 4.8 ng/mL, which is within the normal range for a smoker, which is the case for this patient.

Example 15

General Techniques for Dock-And-Lock™

The general techniques discussed below may be used to generate DNL™ complexes with AD or DDD moieties attached to any antibodies or antigen-binding antibody fragments, using the disclosed methods and compositions.

Expression Vectors

The plasmid vector pdHL2 has been used to produce a number of antibodies and antibody-based constructs. See Gillies et al., *J Immunol Methods* (1989), 125:191-202; Losman et al., Cancer (Phila) (1997), 80:2660-6. The di-cistronic mammalian expression vector directs the synthesis of the heavy and light chains of IgG. The vector sequences are mostly identical for many different IgG-pdHL2 constructs, with the only differences existing in the variable domain ($V_H$ and $V_L$) sequences. Using molecular biology tools known to those skilled in the art, these IgG expression vectors can be converted into Fab-DDD or Fab-AD expression vectors.

To generate Fab-DDD expression vectors, the coding sequences for the hinge, CH2 and CH3 domains of the heavy chain were replaced with a sequence encoding the first 4 residues of the hinge, a 14 residue linker and a DDD moiety, such as the first 44 residues of human RIIα (referred to as DDD1, SEQ ID NO:1). To generate Fab-AD expression vectors, the sequences for the hinge, CH2 and CH3 domains of IgG were replaced with a sequence encoding the first 4 residues of the hinge, a 15 residue linker and an AD moiety, such as a 17 residue synthetic AD called AKAP-IS (referred to as AD1, SEQ ID NO:3), which was generated using bioinformatics and peptide array technology and shown to bind RIIα dimers with a very high affinity (0.4 nM). See Alto, et al. *Proc. Natl. Acad. Sci., U.S.A* (2003), 100:4445-50. Two shuttle vectors were designed to facilitate the conversion of IgG-pdHL2 vectors to either Fab-DDD1 or Fab-AD1 expression vectors, as described below.

Preparation of CH1

The CH1 domain was amplified by PCR using the pdHL2 plasmid vector as a template. The left PCR primer consisted of the upstream (5') end of the CH1 domain and a SacII restriction endonuclease site, which is 5' of the CH1 coding sequence. The right primer consisted of the sequence coding for the first 4 residues of the hinge (PKSC, SEQ ID NO:102) followed by four glycines and a serine, with the final two codons (GS) comprising a Bam HI restriction site. The 410 bp PCR amplimer was cloned into the PGEMT® PCR cloning vector (PROMEGA®, Inc.) and clones were screened for inserts in the T7 (5') orientation.

A duplex oligonucleotide was synthesized to code for the amino acid sequence of DDD1 preceded by 11 residues of the linker peptide, with the first two codons comprising a BamHI restriction site. A stop codon and an EagI restriction site are appended to the 3'end. The encoded polypeptide sequence is shown below.

(SEQ ID NO: 103)
GSGGGGSGGGGSHIQIPPGLTELLQGYTVEVLRQQPPDLVEFAVEYFTRL
REARA

Two oligonucleotides, designated RIIA1-44 top and RIIA1-44 bottom, which overlap by 30 base pairs on their 3' ends, were synthesized and combined to comprise the central 154 base pairs of the 174 bp DDD1 sequence. The oligonucleotides were annealed and subjected to a primer extension reaction with Taq polymerase. Following primer extension, the duplex was amplified by PCR. The amplimer was cloned into PGEMT® and screened for inserts in the T7 (5') orientation.

A duplex oligonucleotide was synthesized to code for the amino acid sequence of AD1 preceded by 11 residues of the linker peptide with the first two codons comprising a BamHI restriction site. A stop codon and an EagI restriction site are appended to the 3'end. The encoded polypeptide sequence is shown below.

(SEQ ID NO: 104)
GSGGGGSGGGGSQIEYLAKQIVDNAIQQA

Two complimentary overlapping oligonucleotides encoding the above peptide sequence, designated AKAP-IS Top and AKAP-IS Bottom, were synthesized and annealed. The duplex was amplified by PCR. The amplimer was cloned into the PGEMT® vector and screened for inserts in the T7 (5') orientation.

Ligating DDD1 with CH1

A 190 bp fragment encoding the DDD1 sequence was excised from PGEMT® with BamHI and NotI restriction enzymes and then ligated into the same sites in CH1-PGEMT® to generate the shuttle vector CH1-DDD1-PGEMT®.

Ligating AD1 with CH1

A 110 bp fragment containing the AD1 sequence was excised from PGEMT® with BamHI and NotI and then ligated into the same sites in CH1-PGEMT® to generate the shuttle vector CH1-AD1-PGEMT®.

With this modular design either CH1-DDD1 or CH1-AD1 can be incorporated into any IgG construct in the pdHL2 vector. The entire heavy chain constant domain is replaced with one of the above constructs by removing the SacII/EagI restriction fragment (CH1-CH3) from pdHL2 and replacing it with the SacII/EagI fragment of CH1-DDD1 or CH1-AD1, which is excised from the respective PGEMT® shuttle vector.

C-DDD2-Fd-hMN-14-pdHL2

C-DDD2-Fd-hMN-14-pdHL2 is an expression vector for production of C-DDD2-Fab-hMN-14, which possesses a dimerization and docking domain sequence of DDD2 (SEQ ID NO:2) appended to the carboxyl terminus of the Fd of hMN-14 via a 14 amino acid residue Gly/Ser peptide linker. The fusion protein secreted is composed of two identical copies of hMN-14 Fab held together by non-covalent interaction of the DDD2 domains.

The expression vector was engineered as follows. Two overlapping, complimentary oligonucleotides, which comprise the coding sequence for part of the linker peptide and residues 1-13 of DDD2, were made synthetically. The oligonucleotides were annealed and phosphorylated with T4 PNK, resulting in overhangs on the 5' and 3' ends that are compatible for ligation with DNA digested with the restriction endonucleases BamHI and PstI, respectively.

The duplex DNA was ligated with the shuttle vector CH1-DDD1-PGEMT®, which was prepared by digestion with BamHI and PstI, to generate the shuttle vector CH1-DDD2-PGEMT®. A 507 bp fragment was excised from CH1-DDD2-PGEMT® with SacII and EagI and ligated with the IgG expression vector hMN-14(I)-pdHL2, which was prepared by digestion with SacII and EagI. The final expression construct was designated C-DDD2-Fd-hMN-14-pdHL2. Similar techniques have been utilized to generated DDD2-fusion proteins of the Fab fragments of a number of different humanized antibodies.

h679-Fd-AD2-pdHL2 h679-Fab-AD2, was designed to pair to C-DDD2-Fab-hMN-14. h679-Fd-AD2-pdHL2 is an expression vector for the production of h679-Fab-AD2, which possesses an anchoring domain sequence of AD2 (SEQ ID NO:4) appended to the carboxyl terminal end of the CH1 domain via a 14 amino acid residue Gly/Ser peptide linker. AD2 has one cysteine residue preceding and another one following the anchor domain sequence of AD1.

The expression vector was engineered as follows. Two overlapping, complimentary oligonucleotides (AD2 Top and AD2 Bottom), which comprise the coding sequence for AD2 and part of the linker sequence, were made synthetically. The oligonucleotides were annealed and phosphorylated with T4 PNK, resulting in overhangs on the 5' and 3' ends that are compatible for ligation with DNA digested with the restriction endonucleases BamHI and SpeI, respectively.

The duplex DNA was ligated into the shuttle vector CH1-AD1-PGEMT®, which was prepared by digestion with BamHI and SpeI, to generate the shuttle vector CH1-AD2-PGEMT®. A 429 base pair fragment containing CH1 and AD2 coding sequences was excised from the shuttle vector with SacII and EagI restriction enzymes and ligated into h679-pdHL2 vector that prepared by digestion with those same enzymes. The final expression vector is h679-Fd-AD2-pdHL2.

Generation of TF2 DNL™ Construct

A trimeric DNL™ construct designated TF2 was obtained by reacting C-DDD2-Fab-hMN-14 with h679-Fab-AD2. A pilot batch of TF2 was generated with >90% yield as follows. Protein L-purified C-DDD2-Fab-hMN-14 (200 mg) was mixed with h679-Fab-AD2 (60 mg) at a 1.4:1 molar ratio. The total protein concentration was 1.5 mg/ml in PBS containing 1 mM EDTA. Subsequent steps involved TCEP reduction, HIC chromatography, DMSO oxidation, and IMP 291 affinity chromatography. Before the addition of TCEP, SE-HPLC did not show any evidence of $a_2b$ formation. Addition of 5 mM TCEP rapidly resulted in the formation of $a_2b$ complex consistent with a 157 kDa protein expected for the binary structure. TF2 was purified to near homogeneity by IMP 291 affinity chromatography (not shown). IMP 291 is a synthetic peptide containing the HSG hapten to which the 679 Fab binds (Rossi et al., 2005, Clin Cancer Res 11:7122s-29s). SE-HPLC analysis of the IMP 291 unbound fraction demonstrated the removal of $a_4$, $a_2$ and free kappa chains from the product (not shown).

The functionality of TF2 was determined by BIACORE® assay. TF2, C-DDD1-hMN-14+h679-AD1 (used as a control sample of noncovalent $a_2b$ complex), or C-DDD2-hMN-14+ h679-AD2 (used as a control sample of unreduced $a_2$ and b components) were diluted to 1 µg/ml (total protein) and passed over a sensorchip immobilized with HSG. The response for TF2 was approximately two-fold that of the two control samples, indicating that only the h679-Fab-AD component in the control samples would bind to and remain on the sensorchip. Subsequent injections of WI2 IgG, an anti-idiotype antibody for hMN-14, demonstrated that only TF2 had a DDD-Fab-hMN-14 component that was tightly associated with h679-Fab-AD as indicated by an additional signal response. The additional increase of response units resulting from the binding of WI2 to TF2 immobilized on the sensorchip corresponded to two fully functional binding sites, each contributed by one subunit of C-DDD2-Fab-hMN-14. This was confirmed by the ability of TF2 to bind two Fab fragments of WI2 (not shown).

Production of TF10 DNL™ Construct

A similar protocol was used to generate a trimeric TF10 DNL™ construct, comprising two copies of a C-DDD2-Fab-hPAM4 and one copy of C-AD2-Fab-679. The TF10 bispecific ([hPAM4]$_2$×h679) antibody was produced using the method disclosed for production of the (anti CEA)$_2$×anti HSG bsAb TF2, as described above. The TF10 construct bears two humanized PAM4 Fabs and one humanized 679 Fab.

The two fusion proteins (hPAM4-DDD2 and h679-AD2) were expressed independently in stably transfected myeloma cells. The tissue culture supernatant fluids were combined, resulting in a two-fold molar excess of hPAM4-DDD2. The reaction mixture was incubated at room temperature for 24 hours under mild reducing conditions using 1 mM reduced glutathione. Following reduction, the reaction was completed by mild oxidation using 2 mM oxidized glutathione. TF10 was isolated by affinity chromatography using IMP291-affigel resin, which binds with high specificity to the h679 Fab.

Example 16

Production of AD- and DDD-Linked Fab and IgG Fusion Proteins from Multiple Antibodies Using the techniques described in the preceding Example, the IgG and Fab fusion proteins shown in Table 11 were constructed and incorporated into DNL™ constructs. The fusion proteins retained the antigen-binding characteristics of the parent antibodies and the DNL™ constructs exhibited the antigen-binding activities of the incorporated antibodies or antibody fragments.

TABLE 11

Fusion proteins comprising IgG or Fab

| Fusion Protein | Binding Specificity |
|---|---|
| C-AD1-Fab-h679 | HSG |
| C-AD2-Fab-h679 | HSG |
| C-(AD)$_2$-Fab-h679 | HSG |
| C-AD2-Fab-h734 | Indium-DTPA |
| C-AD2-Fab-hA20 | CD20 |
| C-AD2-Fab-hA20L | CD20 |
| C-AD2-Fab-hL243 | HLA-DR |
| C-AD2-Fab-hLL2 | CD22 |
| N-AD2-Fab-hLL2 | CD22 |
| C-AD2-IgG-hMN-14 | CEACAM5 |
| C-AD2-IgG-hR1 | IGF-1R |
| C-AD2-IgG-hRS7 | EGP-1 |
| C-AD2-IgG-hPAM4 | MUC |
| C-AD2-IgG-hLL1 | CD74 |
| C-DDD1-Fab-hMN-14 | CEACAM5 |
| C-DDD2-Fab-hMN-14 | CEACAM5 |
| C-DDD2-Fab-h679 | HSG |
| C-DDD2-Fab-hA19 | CD19 |
| C-DDD2-Fab-hA20 | CD20 |
| C-DDD2-Fab-hAFP | AFP |
| C-DDD2-Fab-hL243 | HLA-DR |
| C-DDD2-Fab-hLL1 | CD74 |
| C-DDD2-Fab-hLL2 | CD22 |
| C-DDD2-Fab-hMN-3 | CEACAM6 |
| C-DDD2-Fab-hMN-15 | CEACAM6 |
| C-DDD2-Fab-hPAM4 | MUC |
| C-DDD2-Fab-hR1 | IGF-1R |
| C-DDD2-Fab-hRS7 | EGP-1 |
| N-DDD2-Fab-hMN-14 | CEACAM5 |

Example 17

Use of NK-Targeted Leukocyte-Redirecting bsAbs

The use of bsAbs to retarget leukocytes is not limited to antibodies against T cells. In alternative embodiments, bsAbs that bind to monocytes, NK cells or neutrophils may also be used for retargeting purposes.

CD16 is an activating low-affinity Fc-γ receptor for IgG, which is highly expressed by the CD56$^{dim}$ subset of NK cells (Gleason et al., 2012, Mol Cancer Ther 11:2674-84). In addition to their use in NK cell retargeting, bsAbs comprising an anti-CD16 antibody component have the ability to activate NK-mediated cytotoxicity through direct signaling of CD16, inducing directed secretion of lytic granules and target cell death (Gleason et al., 2012).

A CD16/CD19 bispecific killer cell engager (BiKE) and a CD16/CD19/CD22 trispecific killer cell engager (TriKe) are prepared according to (Gleason et al., 2012, Mol Cancer Ther 11:2674-84), using DNA shuffling and ligation techniques as previously reported (Vallera et al., 2005, Clin Cancer Res 11:3879-88). The expressed BiKE and TriKE are purified by sequential ion exchange and size-exclusion column chromatography. Resting PBMCs are exposed to primary ALL and CLL tumor cells in the presence of CD16/CD19 BiKE or CD16/CD19/CD22 TriKE (10 µg/mL). A significant increase in cytotoxicity to tumor cells is observed in the presence of the BiKE or TriKE, compared to cells without retargeting antibody. No effect is observed on tumor cells exposed to BiKE or TriKE in the absence of PBMCs. The TriKE has a greater effect on tumor cell toxicity relative to the BiKE, indicating that binding to an additional tumor cell antigen may enhance the retargeting effect. Similar results are obtained using purified NK cells instead of PBMCs.

A CD16/CD33 BiKE is prepared as disclosed in Wiernik et al. (2013, Clin Cancer Res 19:3844-55. The BiKE is administered to nude mice injected with human HL60 promyelocytic leukemia xenograft cells, co-administered with human PBMCs. The BiKE treated mice show a decreased mortality and tumor growth rate compared to mice treated with control bsAbs. Addition of an anti-CD33-SN-38 ADC further enhances the cytotoxic effect of the BiKE.

Example 18

Trivalent Antibodies for Therapeutic Use

A trivalent, trispecific cell targeting construct is made as described in patent EP1309795B1 comprising: (i) chimerizing or humanizing a mouse anti-CD16 mab as described in U.S. Pat. No. 618,728 from which the Fab of Claim 1 of EP1309795 is derived; (ii) constructing a single chain antibody comprised of the Fv of the humanized anti-Trop-2 antibody described in U.S. Pat. No. 7,238,785, and joining the scFv by a linker to the carboxyl terminal of the light chain of the anti-CD16 Fab of (i); and (iii) constructing a single chain of the Fv of the humanized anti-CD19 described in U.S. Pat. No. 8,486,395 and joining the scFv by a linker to the carboxyl terminal of the CH1 of the anti-CD16 Fab of (ii).

The trivalent construct is administered to a subject with metastatic pancreatic cancer, in combination with IMMU-132. A partial response is observed and the tumor shows a regression in size that lasts for 12 months.

Example 19

Anti-Trop-2×Anti-CD3 Bispecific Antibody

A bispecific antibody (bsAb) was produced as a tandem single-chain variable fragment (scFv) for redirecting T cells via CD3 binding to tumor cells, particularly carcinomas, via Trop-2 targeting. Trop-2 is a tumor-associated antigen (TAA) that could be highly effective for targeting various epithelial cancers. However, it has yet to be investigated in any bsAb format for T-cell-redirected therapy. Trop-2 is a 35 kDa transmembrane glycoprotein that is overexpressed relative to normal tissues in a variety of human cancers, including pancreatic and gastric carcinomas, where increased expression correlates with poor prognosis (Fong et al., 2008, Br J Cancer 99:1290-5; Iacobuzio-Donahue et al., 2002, Am J Pathol 160:1239-49; Kapoor, 2013, Tumour Biol 34:1967-8; Muhlmann et al., 2009, J Clin Pathol 62:152-8; Stein et al., 1993, Int J Cancer 55:938-46; Stein et al., 1993, Int J Cancer 55:938-46). Variable domains (VH and VK) derived from hRS7, the humanized version of the original murine anti-Trop-2 mAb, RS7, were combined with the variable domains of the murine anti-CD3 mAb, Okt3, to generate the E1-3 bsAb.

Construction of a Plasmid Vector for Expression of E1-3 in Mammalian Cells

A double stranded DNA sequence (SEQ ID NO:106) was synthesized and assembled into the pUC57 plasmid vector.

Figure 22:
FIG. 22. Schematic representation of the nascent E1-3 polypeptide. LP, leader peptide that is removed in mature protein; VH, heavy chain variable domain, VK, kappa light chain variable domain, L1, linker peptide 1; L2, linker peptide 2; L3, linker peptide 3; 6H, hexa-histidine.

SEQ ID NO:106 was excised from pUC57 by digestion with Xba I and Eag I restriction endonucleases, and ligated into the pdHL2 mammalian expression vector, which was prepared by digestion with the same enzymes. The coding sequence directs the synthesis of a single polypeptide (SEQ ID NO:107) comprising a leader peptide, hRS7VK (SEQ ID NO:108), L1 (SEQ ID NO:109), hRS7VH (SEQ ID NO:110), L2 (SEQ ID NO:111), Okt3VH (SEQ ID NO:112), L3 (SEQ ID NO:113), Okt3VK (SEQ ID NO:114), and 6-His (SEQ ID NO:105). A schematic representation of the tandem scFv E1-3 is shown in FIG. 22.

```
Synthetic DNA sequence comprising E1-3 insert
                              (SEQ ID NO: 106)
tctagacacaggccgccatcatgggatggagctgtatcatcctcttctt ggtagcaacagctacaggtgtccactccgacattcagctgacccagtct ccatcctccctgtctgcatctgtaggagacagagtcagcatcacctgca aggccagtcaggatgtgagtattgctgtagcctggtatcagcagaaacc agggaaagcccctaagctcctgatctactcggcatcctaccggtacact ggagtccctgataggttcagtggcagtggatctgggacagatttcactc tcaccatcagcagtctgcaacctgaagattttgcagrnattactgtcag caacattatattactccgctcacgttcggtgctgggaccaaggtggaga tcaaaggtggaggagggtccggtgaggagggtctggtggaggagggag ccaggtccagctgcagcaatctgggtctgagttgaagaagcctgggcc tcagtgaaggrncctgcaaggcttctggatacaccttcacaaactatgg aatgaactgggtgaagcaggcccctggacaagggcttaaatggatggc tggataaacacctacactggagagccaacatatactgatgacttcaagg gacggtttgccttctccttggacacctctgtcagcacggcatatctcca gatcagcagcctaaaggctgacgacactgccgtgtatttctgtgcaaga ggggggttcggtagtagctactggtacttcgatgtctggggccaagggt ccctggtcaccgtctcctcaggtggcggagggtccgatatcaagctgca gcagtctggagcagagctcgctcgaccaggagctagtgtgaagatgtca tgtaaaacaagtggctatacttccccggtacactatgcactgggtca agcagcgcccaggacagggtctggaatggatcggctacattaacccag cagggatataccaactacaatcagaagttcaaggataaagccaccctg actaccgacaagtcctctagtacagcttatatgcagctgtcaagcctca cttccgaggactctgcagtgtattactgcgccagatattacgacgatca ttattgtctggattactggggccagggaacaactctcacagtgtcctct gtcgaaggtggcagtggaggtcaggtggcagcggagggtccggtggag tggacgatatccagctgacccagtctcctgccattatgagcgcttcccc aggcgagaaggtgacaatgacttgccgggccagttcaagcgtcagctat atgaattggtatcagcagaagtctggaaccagtcctaaacgatggatct atgacacatctaaagtggcaagcggggtcccatacaggttctctgggag tggttcaggcactagctattccctgacctttcctctatggaggccgaa gatgcagccacctattactgtcagcagtggagttcaaatccactcacct tcggagcaggcactaaactggaactcaagcaccaccaccaccaccacta aggcggccg Deduced amino acid sequence of E1-3
                              (SEQ ID NO: 107)
DIQLTQSPSSLSASVGDRVSITCKASQDVSIAVAWYQQKPGKAPKLLIY

SASYRYTGVPDRFSGSGSGTDFTLTISSLQPEDFAVYYCQQHYITPLTF

GAGTKVEIKGGGGSGGGGSGGGGSQVQLQQSGSELKKPGASVKVSCKAS

GYTFTNYGMNWVKQAPGQGLKWMGWINTYTGEPTYTDDFKGRFAFSLDT

SVSTAYLQISSLKADDTAVYFCARGGFGSSYWYFDVWGQGSLVTVSSGG

GGSDIKLQQSGAELARPGASVKMSCKTSGYTFTRYTMHWVKQRPGQGLE

WIGYINPSRGYTNYNQKFKDKATLTTDKSSSTAYMQLSSLTSEDSAVYY

CARYYDDHYCLDYWGQGTTLTVSSVEGGSGGSGGSGGSGGVDDIQLTQS

PAIMSASPGEKVTMTCRASSSVSYMNWYQQKSGTSPKRWIYDTSKVASG

VPYRFSGSGSGTSYSLTISSMEAEDAATYYCQQWSSNPLTFGAGTKLEL

KHHHHHH

Amino acid sequence of hRS7 VK
                              (SEQ ID NO: 108)
DIQLTQSPSSLSASVGDRVSITCKASQDVSIAVAWYQQKPGKAPKLLIY
SASYRYTGVPDRFSGSGSGTDFTLTISSLQPEDFAVYYCQQHYITPLTF
GAGTKVEIK Amino acid sequence of linker L1
                              (SEQ ID NO: 109)
GGGGSGGGGSGGGGS Amino acid sequence hRS7 VH
                              (SEQ ID NO: 110)
QVQLQQSGSELKKPGASVKVSCKASGYTFTNYGMNWVKQAPGQGLKWMG
WINTYTGEPTYTDDFKGRFAFSLDTSVSTAYLQISSLKADDTAVYFCAR
GGFGSSYWYFDVWGQGSLVTVSS Amino acid sequence of linker L2
                              (SEQ ID NO: 111)
GGGGS Amino acid sequence of Okt3 VH
                              (SEQ ID NO: 112)
DIKLQQSGAELARPGASVKMSCKTSGYTFTRYTMHWVKQRPGQGLEWIGY
INPSRGYTNYNQKFKDKATLTTDKSSSTAYMQLSSLTSEDSAVYYCARYY
DDHYCLDYWGQGTTLTVSS Amino acid sequence of linker L3
                              (SEQ ID NO: 113)
VEGGSGGSGGSGGSGGVD Amino acid sequence of Okt3 VK
                              (SEQ ID NO: 114)
DIQLTQSPAIMSASPGEKVTMTCRASS SVSYMNWYQQKSGTSPKRWIYD
TSKVASGVPYRFSGSGSGTSYSLTISSMEAEDAATYYCQQWSSNPLTFGA
GTKLE
```

Development of a Stable Production Clone in SpESF Myeloma Cells

The E1-3-pdHL2 vector was linearized by digestion with Sal I restriction endonuclease and 30 µg was used to stably transfect $1 \times 10^7$ SpESFX myeloma cells (Rossi et al., 2011, Biotechnol Prog 27:766-75) by electroporation using two pulses at 850 V and 10 µF. Selection and production media was supplemented with 0.2 µM methotrexate (MTX). Transfectant clones were selected in 96-well tissue culture plates and screened for E1-3 expression by ELISA using Ni-NTA 96-well plates. The E1-3 protein was purified from the culture broth of roller bottle cultures by immobilized metal affinity chromatography (IMAC) using Nickel-SEPHAROSE® resin, followed by size exclusion high performance liquid chromatography (SE-HPLC). The purified product resolved as a single SE-HPLC peak (not shown) and a single polypeptide band by SDS-PAGE (not shown), with relative mobilities consistent with its calculated molecular size of 53,423 Da.

Example 20

Redirected T Cell Killing of Trop-2-Expressing Solid Tumor Cells Ex Vivo

Peripheral blood mononuclear cells (PBMCs) were prepared from the buffy coat of blood specimens of two healthy donors (Blood Center of NJ), and used for the isolation of CD8$^+$ T cells (Miltenyi). Capan-1 (pancreatic cancer, 157,000 Trop-2/cell), BxPC3 (pancreatic cancer, 500,000 Trop-2/cell) and NCI-N87 (gastric cancer, 247,000 Trop-2/cell) cell lines (ATCC) were used as target cells expressing low-, high- and mid-levels of Trop-2. BxPC3 and NCI-N87 were maintained in RPMI1640 media supplemented with 10% FBS, while Capan-1 cells were maintained in 20% FBS/RPMI1640. CD8$^+$ T cells ($1.2 \times 10^5$ cells/well) were combined with target cells ($2 \times 10^4$ cells/well) at a 6:1 ratio in 96-well tissue culture plates. Titrations of E1-3 and (E1)-3s were added to the assay plates. Following a 48-hour incubation at 37° C., plates were washed twice with PBS to remove the T cells, and then 150 µL of fresh media supplemented with 30% MTS reagent (CELLTITER 96® Aqueous One Solution, Promega) was added to each well. Absorbance at 490 nm was measured after 1-2 h at 37° C. with an ENVISION plate Reader®.

Figure 23:
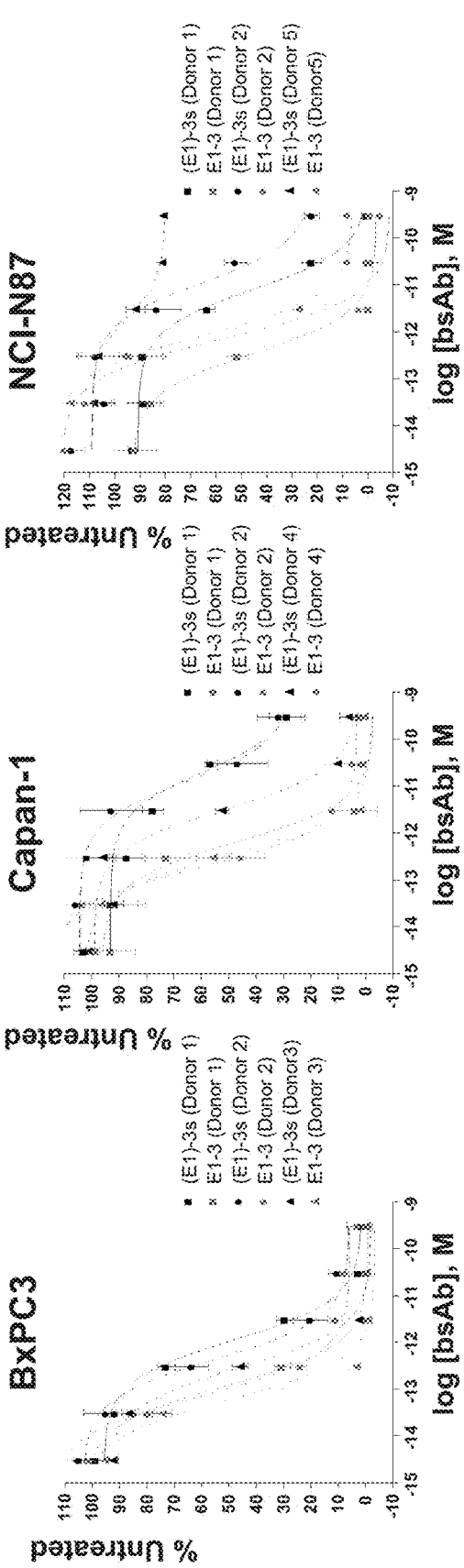
FIG. 23A. Ex vivo T cell redirected killing of BxPC3 human pancreatic cancer solid tumor cell line.
FIG. 23B. Ex vivo T cell redirected killing of Capan-1 human pancreatic cancer solid tumor cell line.
FIG. 23C. Ex vivo T cell redirected killing of NCI-N87 human gastric cancer solid tumor cell line.
Figure 24:
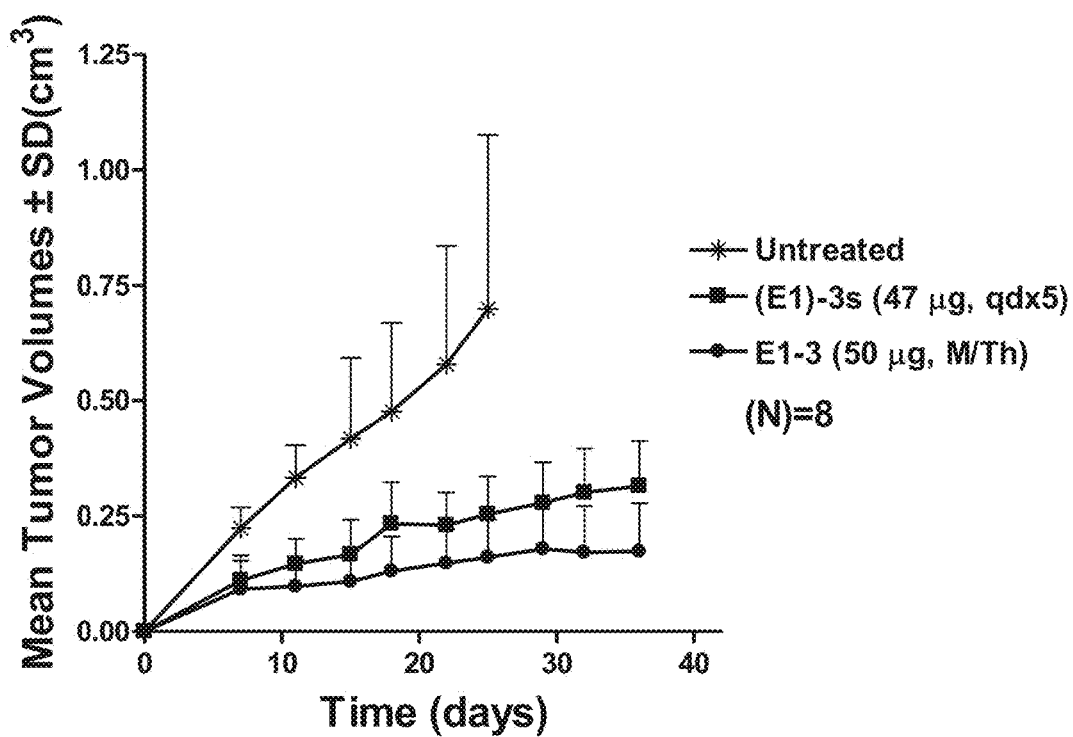
FIG. 24. In vivo T cell redirected therapy of NCI-N87 gastric carcinoma in NOD-SCID mice.

The in vitro potency of the E1-3 bispecific antibody was compared with that of the equivalent DNL construct, (E1)-3s, in three Trop-2-expressing cell lines (BxPC3, Capan-1 and NCI-N87) using T cells from three donors for each cell line (FIG. 23). Based on the IC$_{50}$ values (Table 12), E1-3 is at least 5-fold more potent than (E1)-3s in all three cell lines, whose relative sensitivity to E1-3 appears to correlate with the Trop-2-antigen density, when compared with T cells from the same donor. However, potency was varied among the donor T cells used. In vitro, E1-3 mediated a highly potent T-cell lysis of BxPC3 [IC$_{50}$=0.09(±0.04) pM], Capan-1 [IC$_{50}$=1.2(±1.1) pM] and NCI-N87 [IC$_{50}$=1.2 (±1.2) pM] target cells.

through 5. The untreated group received the mixture of NCI-N87 and PBMCs without bsAb. Tumor volume (TV) was determined twice weekly by measurements in two dimensions using calipers, with volumes defined as: $L \times W^2/2$, where L is the longest dimension of the tumor and W the shortest (FIG. 24). Statistical analysis of tumor growth was based on area under the curve (AUC). Profiles of individual tumor growth were obtained through linear-curve modeling. An F-test was employed to determine equality of variance between groups prior to statistical analysis of growth curves. A Critical Z test on the survival data identified any outliers within a given treatment group with P<0.05 censored from the final data analysis. A two-tailed t-test was used to assess statistical significance between the various treatment groups and controls, except for the untreated control, where a one-tailed t-test was used. Additionally, efficacy was determined by log-rank using Prism software on Kaplan-Meier curves using survival surrogate endpoints as time for tumor progression (TTP) to 1.0 cm3. Significance was considered at P≤0.05 for all comparisons.

Both E1-3 (P) and (E1)-3s delayed growth of NCI-N87 tumors significantly (P≤0.001; AUC$_{day25}$) (FIG. 24). The E1-3 was superior to (E1)-3s (P=0.0324, AUC$_{day36}$) (FIG. 24). In vivo, two 50-µg doses of E1-3 given three days apart cured all of the mice (N=8) bearing NCI-N87 xenografts (P=0.0005; Log-Rank). Tumors in the control group (PBMCs only) reached the endpoint (TV>1 cm$^3$) at 39.5 days. All mice were tumor-free in the E1-3 group after 78 days.

Example 22

Trogocytosis Induced by Anti-CD3×Anti-Trop-2 Bispecific Antibodies

Trop-2 has limited presence on normal tissues but is highly expressed in diverse epithelial cancers. As discussed in the Examples above, (E1)-3s is a T-cell-redirecting trivalent bispecific antibody (bsAb) DNL® complex, comprising an anti-CD3 scFv covalently linked to a stabilized dimer of a Trop-2-targeting Fab. We show herein for the first time that bsAb-mediated bidirectional trogocytosis occurs between target cells and T cells and involves formation of immunologic synapses.

TABLE 12

| IC$_{50}$ values for ex vivo T cell redirected killing of Trop-2$^+$ cancer cell lines with E1-3 and (E1)-3s. | | | | | | | | |
|---|---|---|---|---|---|---|---|---|
| | BxPC3 500,000/cell | | | Capan-1 157,000/cell | | | NCI-N87 247,000/cell | | |
| Trop-2 | Donor 1 | Donor 2 | Donor 3 | Donor 1 | Donor 2 | Donor 4 | Donor 1 | Donor 2 | Donor 5 |
| E1-3 | 0.12 | 0.10 | 0.05 | 0.58 | 2.7 | 0.47 | 0.29 | 0.76 | 2.50 |
| (E1)-3s | 1.06 | 0.56 | 0.32 | 35.6 | 248 | 8.51 | 6.76 | 34 | NA* |

IC$_{50}$ values = pM concentration resulting in 50% killing.
*Did not achieve 50% killing. Donors 1 and 2 were the same for each donor. Donors 3, 4 and 5 were independent donors.

Example 21

In Vivo Therapy of Solid Tumors with E1-3 vs. (E1)-3s

Female 4-8-week old NOD/SCID mice were administered subcutaneous injections of a mixture of PBMCs and NCI-N87 (2:1) mixed with an equal volume of MATRIGEL®. Therapy consisted of i.v. injections of 50 µg of E1-3 on days 1 and 4, or daily injections with 47 µg of (E1)-3s on days 1

Methods

BxPC3 cells were detached with trypsin (which does not affect Trop-2) and mixed with purified T cells. Cell mixtures were treated with 0.1 nmol/L bsAbs at 37° C. for 1 hour. Cells were stained with either: (i) anti-Trop-2 MABC518 followed by GAM-FITC, or (ii) anti-Trop-2-PE clone MR54 and anti-CD4-APC. Single BxPC3 and T cells were gated from cell conjugates by forward and side scattering, as well as Trop-2 and CD4 fluorescence.

Results (E1)-3s induces the formation of immunologic synapses between T cells and target cells. This was shown using Capan-1 pancreatic carcinoma cells (Rossi et al., 2013, MAbs 6:381-91). Here, addition of 0.1 μg/mL (E1)-3s to a mixture of purified $CD8^+$ T cells and NCI-N87 gastric carcinoma cells, which were membrane-labeled with red and green fluorescence, respectively, resulted in the formation of conjugates evident by fluorescence microscopy (not shown). No conjugates were observed in the presence of (19)-3s (not shown) or TF12 (not shown), which bind only T cells or NCI-N87, respectively. Dunking the slides in saline washed off the vast majority of T cells in wells containing (19)-3s or TF12, whereas many T cells remained bound to the adherent NCI-N87 cells in the wells treated with (E1)-3s.

Figure 25:
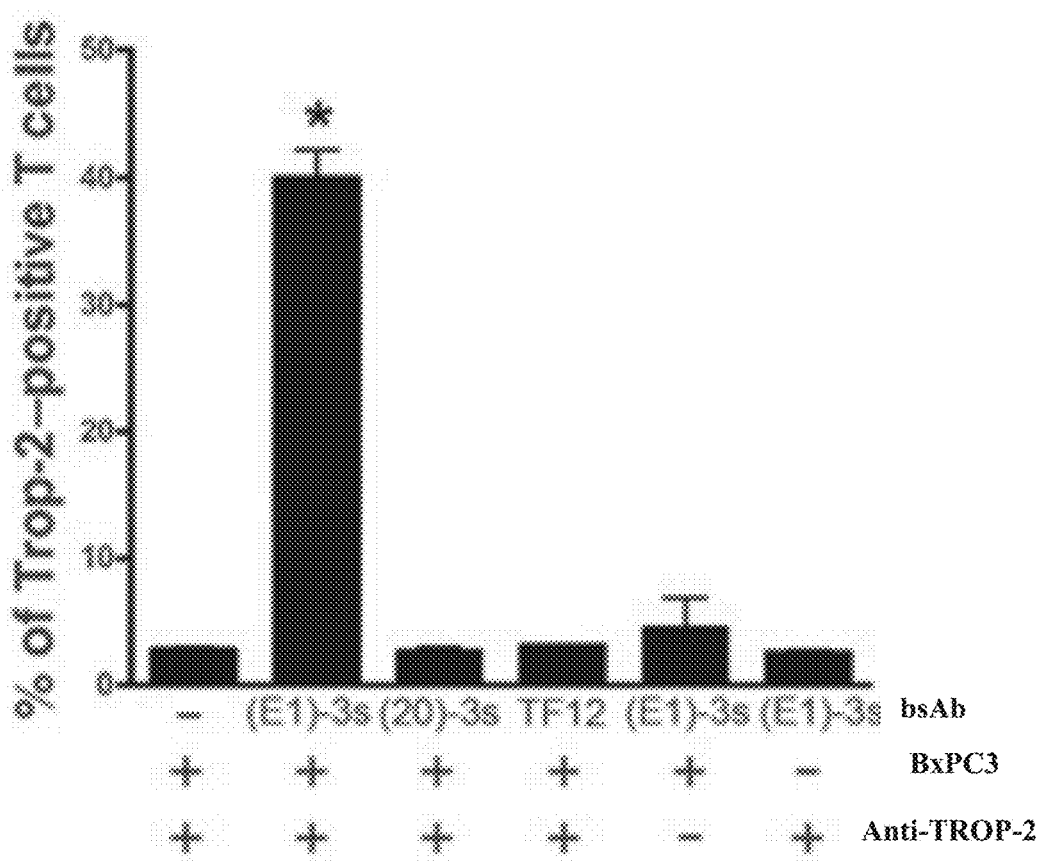
FIG. 25. Immunologic synapse formation and bidirectional trogocytosis mediated by (E1)-3s. Purified T cells were mixed with BxPC3 cells at a 5:1 ratio and incubated for 60 minutes with 0.1 nmol/L of the indicated bsAb before staining with anti-Trop-2 MAb C518 and GAM-Fc-FITC. The cells were analyzed by flow cytometry, with nonconjugated T cells and BxPC3 cells first gated by forward versus side scattering. Trogocytosis of Trop-2 from BxPC3 cells to T cells was evident by detection of Trop-2 on T cells, specifically in cell mixtures with (E1)-3s, shown as the percentage of Trop-2-positive unconjugated T cells.
Figure 26:
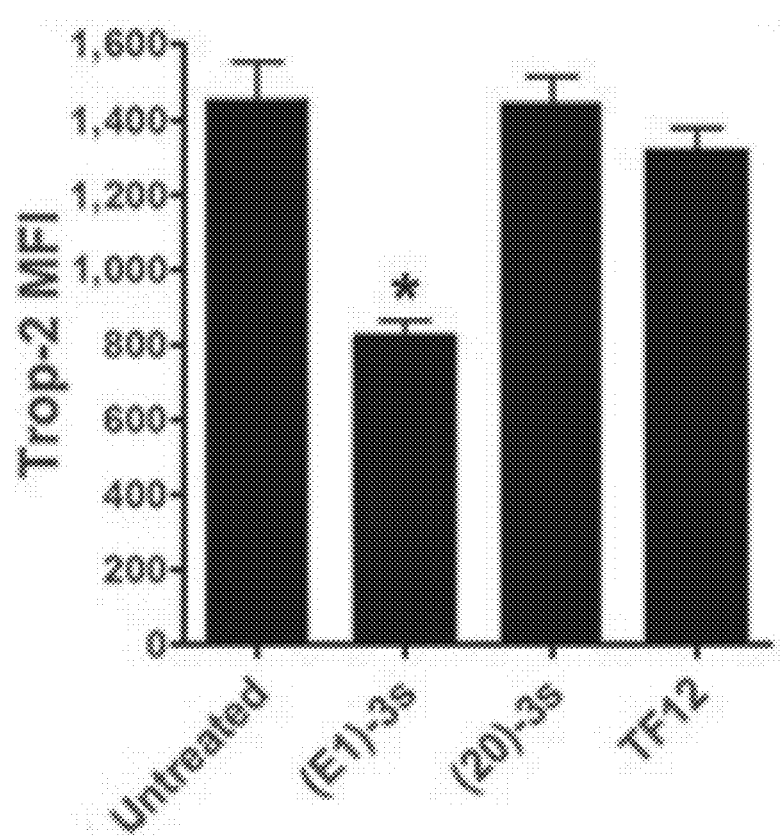
FIG. 26. Immunologic synapse formation and bidirectional trogocytosis mediated by (E1)-3s. Purified T cells were mixed with BxPC3 cells at a 5:1 ratio and incubated for 60 minutes with 0.1 nmol/L of the indicated bsAb before staining with anti-Trop-2 MAb C518 and GAM-Fc-FITC. The cells were analyzed by flow cytometry, with nonconjugated T cells and BxPC3 cells first gated by forward versus side scattering. Trogocytosis resulted in a reduction of Trop-2 on BxPC3 cells, shown as the geometric MFI.

Treatment of BxPC3 (500,000 Trop-2/cell) and purified T-cell mixtures with (E1)-3s specifically induced trogocytosis, whereby Trop-2 was transferred from BxPC3 to T cells (FIG. 25). Whereas (E1)-3s treatment resulted in 40% Trop-$2^+$ T cells, <5% of the T cells were counted in the Trop-$2^+$ gate following treatment with control bsAbs binding only Trop-2 (TF12) or CD3 [(20)-3s], or with (E1)-3s in the absence of BxPC3 cells. The uptake of Trop-2 by T cells coincided with its reduction on BcPC3 cells (FIG. 26). During the short incubation time, the T cells (97.5% live) and BxPC3 (94.5% live) remained at high viability, indicating that the T cells acquired the tumor antigens by trogocytosis and not by adhering to membrane fragments of dead cells (not shown). Trogocytosis mediated by (E1)-3s was bidirectional, because T-cell membrane components were transferred to BxPC3 cells, as demonstrated for CD4 (data not shown).

Example 23

Bispecific Anti-CD3×Anti-Trop-2 Antibodies and Cytokine Release

As discussed in the Examples above, we studied the effects of interferon-α(IFNα) on (E1)-3s-mediated T-cell killing of human gastric and pancreatic cancer cell lines. T-cell activation, cytokine induction, and cytotoxicity were evaluated ex vivo using peripheral blood mononuclear cells (PBMC) or T cells with NCI-N87 gastric cancer as target cells. In the presence of target cells and PBMCs, (E1)-3s did not cause excess cytokine production. When combined with (E1)-3s, peginterferonalfa-2a—which alone did not increase T-cell activation or raise cytokine levels over baseline—increased CD69 expression but did not significantly increase cytokine induction. IFNα enhanced the therapeutic efficacy of (E1)-3s without increasing the production of other cytokines to levels that could induce cytokine release syndrome (CRS). Adjuvant therapy with IFNα, or other cytokines, might be universally applicable for enhanced efficacy of T-cell immunotherapy.

Methods

Cytokine release was measured ex vivo using $5\times10^5$ cells/0.5 mL/well of either NCI-N87, which were allowed to attach overnight, or Raji. Freshly isolated PBMCs ($5\times10^6$ cells/0.4 mL/well) were added to each well. Treatments (100 μL, 10×) comprising (19)-3s, 19-3 BiTE, (E1)-3s, peginterferonalfa-2a, or (E1)-3s plus peginterferonalfa-2a were added to 0.1 nmol/L for each reagent. Alternatively, titrations ranging from 1 pmol/L to 10 nmol/L were used for dose-response studies. Following a 20-hour incubation at 37° C. with gentle shaking, the supernatant fluid was diluted 1:2 (or greater when necessary) and the concentrations of TNFα, IFNg, IL2, IL6, and IL10 measured using Single-Analyte ELISArray kits (Qiagen), following the manufacturer's protocol.

Results

A Trop-2×CD3 BiTE (or equivalent) was not available for comparison with (E1)-3s. However, the availability of both (19)-3s, which has the same (X)-3s molecular configuration as (E1)-3s, and 19-3 BiTE, which has the identical amino acid sequence as the CD19×CD3 BiTE, blinatumomab, enabled a head-to-head comparison to evaluate the relative cytokine-inducing potency of the two bsAb formats.

Initially, titrations of (19)-3s and 19-3 BiTE were added to mixtures of PBMCs (two independent donors), and Raji NHL cells and the levels of TNFα, IFNγ, and IL6 were measured after 20 hours (not shown). Minimal cytokine levels were detected from PBMCs alone, even with the addition of a bsAb. However, because of a mixed lymphocyte reaction occurring between Raji and the donor PBMCs (stronger for donor A), cytokine levels in untreated cell mixtures were elevated for each of TNFα (200 and 50 pg/mL), IFNγ (600 and 200 pg/mL), and IL6 (190 and 220 pg/mL). The levels of TNFα and IL6 were increased above those of untreated only at ≥1 nmol/L (19)-3s. Apparently, (19)-3s inhibited TNFα and IL6 production at lower concentrations. In comparison, TNFα and IL6 were elevated to >1,000 pg/mL at all concentrations of 19-3 BiTE tested (≥1 pmol/L). The levels of IFNγ were not increased significantly by (19)-3s, whereas 19-3 BiTE showed a dose-dependent increase to >2,000 pg/mL.

Figure 27A:
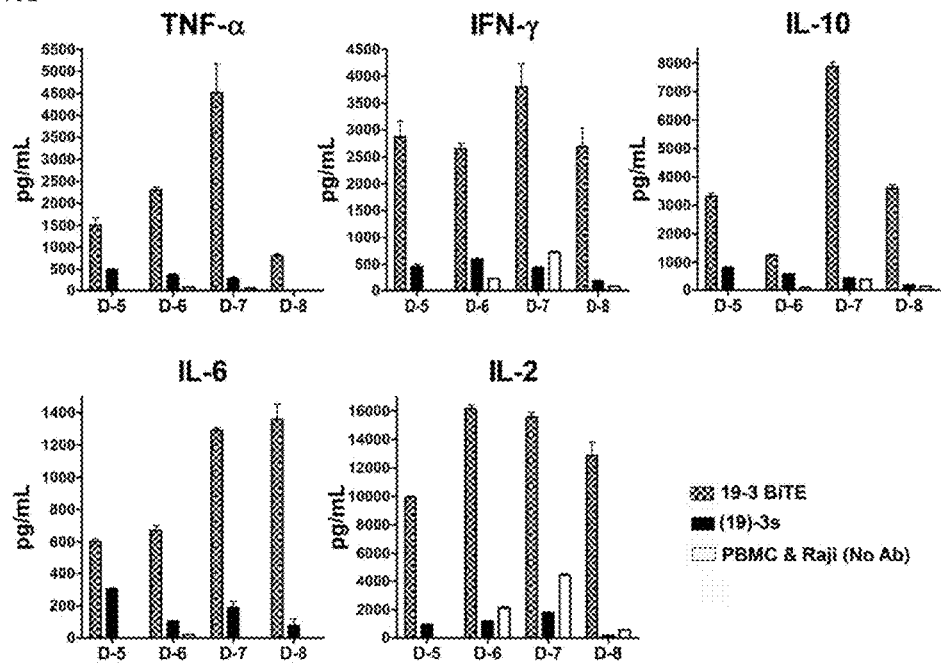
FIG. 27A. Cytokine induction. (A) PBMCs ($6\times10^6$ cells/well) were combined with Raji ($5\times10^5$ cells/well) and treated for 20 h with 0.1 nM 19-3 BiTE (checkered), (19)-3s (black), or incubated without bsAb (white, not tested for D-5). Concentrations of TNF-α, IFN-γ, IL-2, IL-6, and IL-10 in the supernatant fluids were determined using commercial ELISA kits. D-1 through D-8 are independent blood donors, where only D-5 was used in both A and B at the same time.

For all further comparisons, agents were tested at 0.1 nmol/L, which is approximately what has been used in similar studies with BiTE (Brandl et al., Cancer Immunol Immunother 2007, 56:1551-63). We compared the levels of TNFα, IFNγ, IL2, IL6, and IL10 induced by 0.1 nmol/L (19)-3s or 19-3 BiTE from Raji mixed with PBMCs, using 4 different donors (FIG. 27A). With each of the 4 donors, the levels of each of the five cytokines were significantly higher with 19-3 BiTE, compared with (19)-3s. The mean TNFα concentration with 19-3 BiTE (2,284±1,483 pg/mL) was 8-fold higher (P=0.0001) than that with (19)-3s (280±188 pg/mL). Treatment with 19-3 BiTE, compared with (19)-3s, resulted in levels of IFNγ (3,002±560 pg/mL vs. 416±169 pg/mL), IL2 (13,635±2,601 pg/mL vs. 1,024±598 pg/mL), IL6 (981±364 pg/mL vs. 168±96 pg/mL), and IL10 (4,006±2,520 pg/mL vs. 493±242 pg/mL) that were 7-, 13-, 6-, and 8-fold higher for 19-3 BiTE, respectively (P<0.0001 for each). These results indicate that the (X)-3s bsAb format is a considerably less potent inducer of cytokine release, compared with the BiTE format.

Figure 27B:
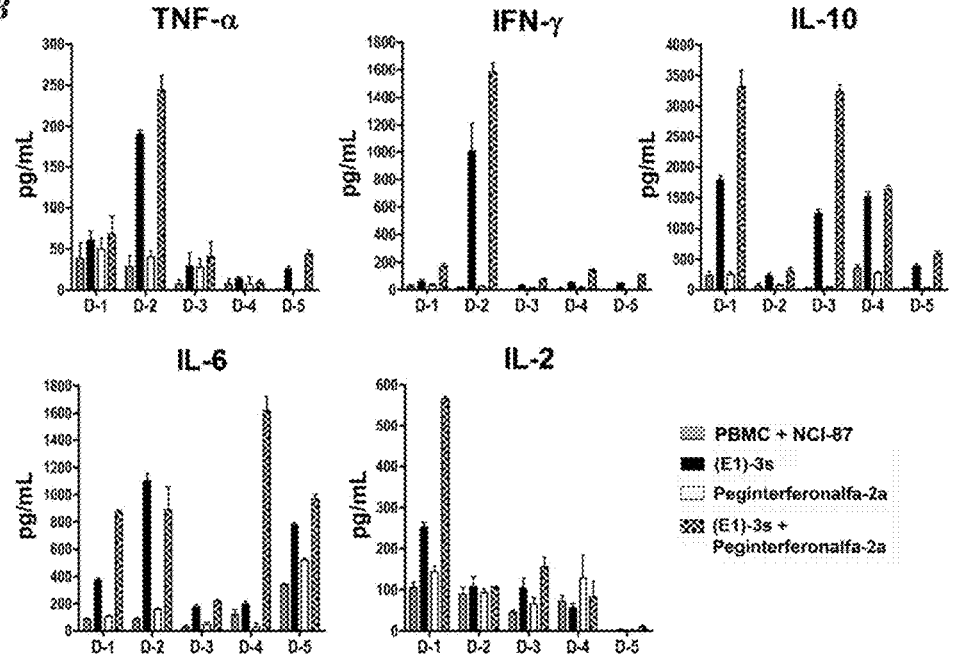
FIG. 27B. NCI-N87 cells ($5\times10^5$ cells/0.5 mL/well) were cultured overnight in 24-well plates to allow cell attachment. PBMCs were added to wells containing attached NCI-N87 cells (10:1 ratio) and treated for 20 h with 0.1 nM of (E1)-3s (black), peginterferonalfa-2a (white), (E1)-3s plus peginterferonalfa-2a (checkered), or untreated (gray). Concentrations of TNF-α, IFN-γ, IL-2, IL-6, and IL-10 in the supernatant fluids were determined using commercial ELISA kits. D-1 through D-8 are independent blood donors, where only D-5 was used in both A and B at the same time.

In general, (E1)-3s in the presence of PBMCs and target cells caused even less cytokine production than (19)-3s, because there is no mixed lymphocyte reaction to elevate the baseline levels (FIG. 27B). Levels remained low for the proinflammatory cytokines IFNγ (<100 pg/mL), TNFα (<100 pg/mL), and IL2 (<250 pg/mL) with 4 of 5 donors. IL6 was low (<400 pg/mL) in 3 of 5 donors, and moderate (800-1,100 pg/mL) in donors D-2 and D-5. Donor D-2 also responded to the (E1)-3s more than the others for IFNγ (1,000 pg/mL) and TNFα (190 pg/mL). IL10, an anti-inflammatory cytokine, was significantly (P<0.0001) elevated by (E1)-3s to >1,200 pg/mL in 3 of 5 donors. Of note, donor D-2, who had a uniquely potent proinflammatory response, produced relatively low levels of IL10 (230 pg/mL) after treatment with (E1)-3s. Peginterferonalfa-2a alone did not increase the level of any cytokine over background. Addition of peginterferonalfa-2a to (E1)-3s consistently increased IFNγ (~1.5-3-fold) over (E1)-3s alone. For the rest of the cytokines, there was an apparent trend for a
moderately increased production with the combination; however, a consistent effect was not observed.

Example 24

In Vitro Cytotoxicity Induced by Bispecific Anti-CD3×Anti-Trop-2 Antibodies

Figures 28A, 28B:
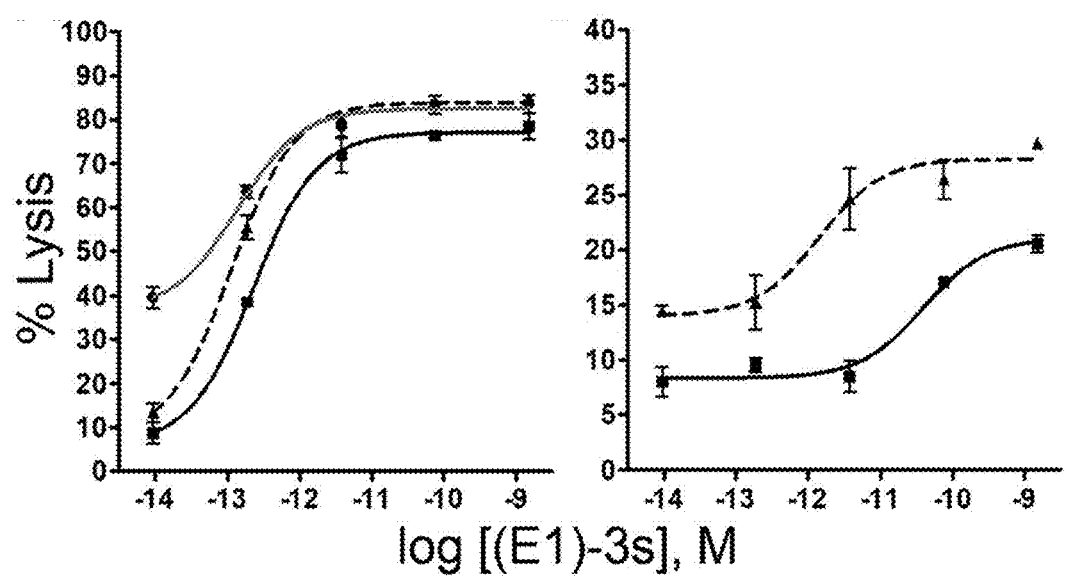
FIG. 28A. In-vitro cytotoxicity. Purified $CD8^+$ T cells isolated from a first donor were pre-treated for 24 h with 0.1 nM peginterferonalfa-2a (▲, dashed), 0.1 nM 20*-2b (●, grey) or media (■, black) before combining with PKH-67 green fluorescent labeled NCI-N87 cells at a 5:1 ratio. The cell mixtures were treated with titrations of (E1)-3s for two days before counting the number of live NCI-N87 cells by flow cytometry. Non-linear regression analysis (sigmoidal dose-response) of the percent lysis, which was calculated for each sample using the formula: $[1-(A_1/A_2)]\times100$, where $A_1$ and $A_2$ represent the number of viable target cells in the test and untreated samples, respectively, vs the log of the molar concentration of (E1)-3s.
FIG. 28B. In-vitro cytotoxicity. Purified $CD8^+$ T cells isolated from a second donor were pre-treated for 24 h with 0.1 nM peginterferonalfa-2a (▲, dashed), 0.1 nM 20*-2b (●, grey) or media (■, black) before combining with PKH-67 green fluorescent labeled NCI-N87 cells at a 5:1 ratio. The cell mixtures were treated with titrations of (E1)-3s for two days before counting the number of live NCI-N87 cells by flow cytometry. Non-linear regression analysis (sigmoidal dose-response) of the percent lysis, which was calculated for each sample using the formula: $[1-(A_1/A_2)]\times100$, where $A_1$ and $A_2$ represent the number of viable target cells in the test and untreated samples, respectively, vs the log of the molar concentration of (E1)-3s.

Further studies were performed to examine in vitro cytotoxicity induced by anti-CD3×anti-Trop-2 bispecific antibodies.
Methods
Freshly-isolated CD8$^+$ T cells were incubated for 24 h with 0.1 nM peginterferonalfa-2a, 0.1 nM 20*-2b, or media only. Treated or untreated T cells and PKH67 green fluorescent-labeled NCI-N87 cells were combined at a 5:1 ratio ($5 \times 10^4$ target cells and $2.5 \times 10^5$ effector cells/well) in 48-well plates containing serial dilutions of (E1)-3s in triplicate. Peginterferonalfa-2a or 20*-2b were maintained at 0.1 nM in the appropriate cell mixtures. Plates were incubated for 48 h at 37° C. Suspension cells were removed and the attached cells were detached with trypsin-EDTA and combined with the corresponding suspension. Cells were washed and resuspended in 1% BSA-PBS containing 30,000 COUNTBRIGHT™ Absolute Counting Beads (Life Technologies) and 1 μg/mL of 7-AAD. Total live target cells (7-AAD$^-$/PKH67$^+$) were counted by flow cytometry. For each sample, 8,000 COUNTBRIGHT™ beads were counted as a normalized reference. The specific lysis (%) was calculated using the formula: $[1-(A_1/A_2)] \times 100$, where $A_1$ and $A_2$ represent the number of viable target cells in the test and untreated samples, respectively. Statistical significance (P≤0.05) was determined for IC$_{50}$ (the concentration resulting in 50% lysis), EC$_{50}$ (50% effective concentration) and lysis$^{max}$ (maximal target cell lysis) by F-test on non-linear regression (sigmoidal dose-response) curves with Prism software.
Results
To evaluate redirected T-cell killing of Trop-2-expressing tumor cells, CD8$^+$ T cells were mixed with NCI-N87 cells in the presence or absence of IFN-α2 (0.1 nM peginterferonalfa-2a or 20*-2b) along with titrations of (E1)-3s (FIG. 28). Considerable variability in T-cell potency was observed among donors (FIG. 28A, FIG. 28B). With a donor of very active T cells, (E1)-3s mediated a highly potent (IC$_{50}$=0.37 pM; lysis$^{max}$=77.1%) T-cell lysis of NCI-N87 cells, and inclusion of peginterferonalfa-2a enhanced its activity, improving the IC$_{50}$ (0.14 pM; P=0.0001) by more than 2.5 fold and increasing lysis$^{max}$ (84.0%; P<0.0001) (FIG. 28A). NCI-N87 was only weakly sensitive to the direct actions of IFN-α (peginterferonalfa-2a IC$_{50}$=>10 nM, data not shown), and inhibited <10% by 0.1 nM peginterferonalfa-2a in the absence of (E1)-3s. The more potent form of IFNα, 20*-2b, consisting of 4 IFN-α molecules fused to a bivalent anti-CD20 mAb by DNL®, enhanced the potency of (E1)-3s by more than 7-fold (IC$_{50}$=0.05 pM; P<0.0001). At 0.1 nM, 20*-2b inhibited NCI-N87 by 12.6% in the absence of (E1)-3s. The 20*-2b was included only to show enhanced activity with another (more potent) form IFN-α, and that the effect is not restricted to peginterferonalfa-2a. The anti-CD20 mAb moiety is not functional in this experiment. In a similar assay using very weak donor T cells, (E1)-3s was considerably less potent (EC$_{50}$=39 pM; lysis$^{max}$=21%); however, addition of peginterferonalfa-2a enhanced the potency by >25 fold (EC$_{50}$=1.4 pM; P=0.0008) (FIG. 28B). Potent (E1)-3s-mediated T-cell killing also was observed for the human pancreatic cancer line, BxPC3 (IC$_{50}$=0.4 pM); however, the effect of adding IFN-α was not evaluated with this cell line (not shown).

Example 25

Figure 29A:
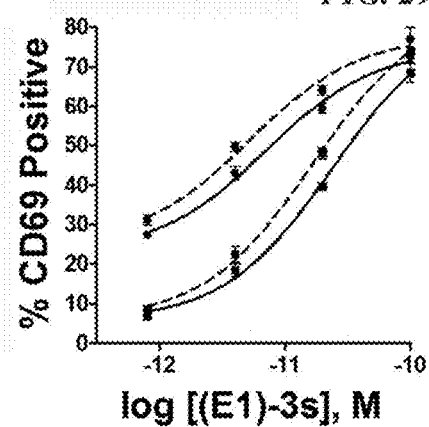
Figure 29B:
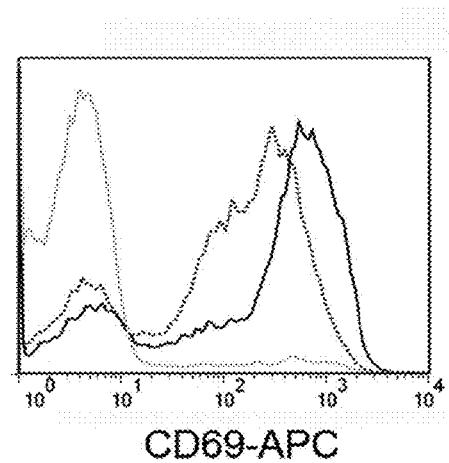
FIG. 29B. T-cell activation. Purified T cells were mixed 5:1 with NCI-N87 cells and treated for 18 h with (E1)-3s before measuring CD69 expression by flow cytometry. Histogram showing anti-CD69-APC staining of $CD8^+$ T cells following treatment with 0.1 nM (E1)-3s (dotted), 0.1 nM peginterferonalfa-2a (gray), or a combination of both agents (black), in the presence of NCI-N87 cells.
Figure 29C:
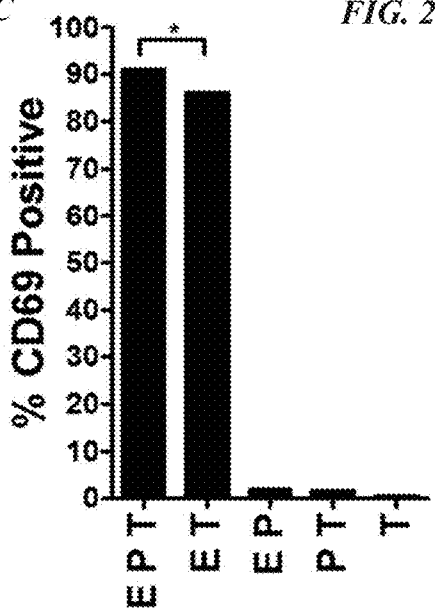
FIG. 29C. T-cell activation. Purified T cells were mixed 5:1 with NCI-N87 cells and treated for 18 h with (E1)-3s before measuring CD69 expression by flow cytometry. Percent CD69-positive $CD8^+$ T cells after incubation with 0.1 nM (E1)-3s (E) and/or 0.1 nM peginterferonalfa-2a (P), in the absence or presence of NCI-N87 target cells (T). Each treatment was assayed in triplicate. Error bars, S.D. *, $P<0.001$.
Figure 29D:
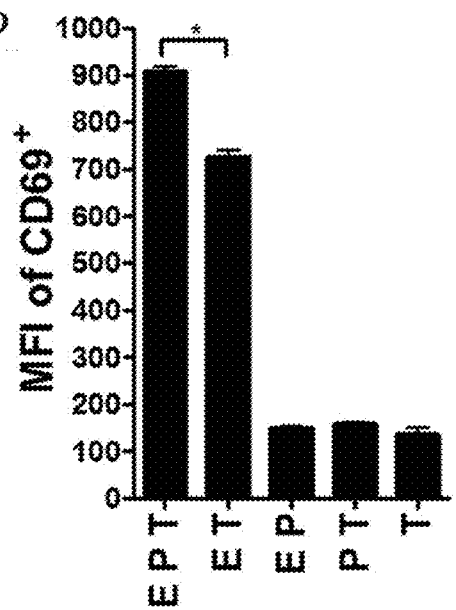
FIG. 29D. T-cell activation. Purified T cells were mixed 5:1 with NCI-N87 cells and treated for 18 h with (E1)-3s before measuring CD69 expression by flow cytometry. Geometric mean fluorescence of the $CD69^+$ cells after incubation with 0.1 nM (E1)-3s (E) and/or 0.1 nM peginterferonalfa-2a (P), in the absence or presence of NCI-N87 target cells (T). Each treatment was assayed in triplicate. Error bars, S.D. *, $P<0.001$.

Dose-Response Curves for T Cell Activation by Anti-CD3×Anti-Trop-2 Bispecific Antibodies Addition of 0.1 nM peginterferonalfa-2a increased CD69 upregulation on T cells treated with (E1)-3s moderately, but significantly. For (E1)-3s dose-response experiments measuring % CD69$^+$ T cells, the EC$_{50}$ was lowered from 26 pM to 16 pM (P<0.0001) for CD4$^+$ T cells, and from 11 pM to 6 pM (P=0.0204) for CD8$^+$ T cells in the presence of IFN-α (FIG. 29A). Peginterferonalfa-2a combined with (E1)-3s resulted in more CD69$^+$ cells (FIG. 29B, FIG. 29C, P<0.0001), and also, the activated cells had significantly higher CD69 expression with IFN-α (FIG. 29B, FIG. 29D; MFI=907 vs 726; P<0.0001). Peginterferonalfa-2a induced minimal CD69 expression in the absence of (E1)-3s. Likewise, (E1)-3, either alone or in combination with peginterferonalfa-2a, did not activate T cells in the absence of target cells.

Example 26

Extended In Vivo Survival with (E1)-3s is Augmented with IFN-α

The preliminary data on in vivo survival reported in Example 3 above were further extended to as long as 126 days. As shown below, the combination of (E1)-3s with IFN-α provided the greatest benefit for animals bearing Trop-2$^+$ xenograft tumors.
Methods
Female 4-8-week old NOD/SCID mice (Charles River, Wilmington, Mass.) were injected s.c. with a mixture of $5 \times 10^6$ tumor cells (Capan-1 or NCI-N87) and T cells ($2.5 \times 10^6$) combined with an equal volume of matrigel. Therapy began 1 h later by i.v. injection, as per the BiTE methodology (Dreier et al., 2003, J Immunol 170:4397-402). Treatment regimens, dosages, and number of animals in each experiment are described in the figure legends. Tumor volume was determined twice weekly by measurements in two dimensions using calipers, with volumes defined as: $L \times w^2/2$, where L is the longest dimension of the tumor and w the shortest.
Statistical analysis of tumor growth was based on area under the curve (AUC). Profiles of individual tumor growth were obtained through linear-curve modeling. An F-test was employed to determine equality of variance between groups prior to statistical analysis of growth curves. A Critical Z test on the survival data identified any outliers within a given treatment group with P≤0.05 censored from the final data analysis. A two-tailed t-test was used to assess statistical significance between the various treatment groups and controls, except for the untreated control, where a one-tailed t-test was used. Additionally, efficacy was determined by log-rank using Prism software on Kaplan-Meier curves using survival surrogate endpoints as time for tumor progression to 1.0 cm$^3$. Significance was considered at P≤0.05 for all comparisons.

Results

In vivo efficacy with human pancreatic cancer was evaluated with Capan-1 xenografts. In the first study, treatment with a combination of (E1)-3s and peginterferonalfa-2a [median survival time (MST) >59 days] was superior to all other treatments (P<0.0007, log-rank), including (E1)-3s (MST=50 days) or peginterferonalfa-2a (MST=53 days) alone (FIG. 30A). Even with the omission of T cells, peginterferonalfa-2a extended survival (MST=45 days, P=0.0059 vs saline, log-rank), indicating direct action on the tumor cells. However, peginterferonalfa-2a was more effective in the presence of T cells (P=0.0260, AUC), suggesting stimulation of T cells by IFN-α. TF12, which binds target but not T cells, did not affect tumor growth or survival. A repeat experiment, using T cells from a different donor, confirmed the results of the first study (FIG. 30B). The second study continued until all groups reached their MST. As in the initial experiment, the combination of (E1)-3s and peginterferonalfa-2a (MST=119.5 days) was superior to all other groups in terms of both tumor growth inhibition and overall survival (P=0.0475 vs (E1)-3s alone; P<0.0001 vs all other groups; log-rank). (E1)-3s (MST=68 days) was superior (P=0.0373, AUC over 29 days) to peginterferonalfa-2a with T cells (MST=53 days) and to T cells alone (MST=37.5 days; P=0.0014 log-rank).

For the NCI-N87 gastric cancer xenograft model (FIG. 30C), the combination of (E1)-3s and peginterferonalfa-2a (MST>88 days) was superior to (E1)-3s alone (MST=49 days; P=0.0007, log-rank). Compared to the control group with only T cells (MST=32 days), peginterferonalfa-2a alone with T cells provided only a minor, but significant, survival advantage (MST=35 days; P=0.0276). (E1)-3s plus peginterferonalfa-2a without T cells did not improve survival significantly.

The antigen density measured for NCI-N87 [247,000 (±65,000) Trop-2/cell] and Capan-1 [157,000 (±37,000) Trop-2/cell] was not significantly different. Compared to NCI-N87, Capan-1 cells were >5-fold more sensitive ($IC_{50}$=2 nM vs.>10 nM) to direct inhibition by peginterferonalfa-2a in vitro (not shown). (E1)-3s does not cross-react with mouse Trop-2 or CD3 (not shown), and NOD-SCID mice are T-cell deficient.

Discussion

This section discusses results presented in Examples 23-26. We described in Examples 1 and 2 above the use of the (X)-3s bsAb format for redirecting T cell-mediated therapy of both hematopoietic and solid tumors using several example constructs, including (E1)-3s, (19)-3s and (20)-3s. In one in vivo experiment from that study, where Capan-1 xenografts were treated with (E1)-3s, we included groups with peginterferonalfa-2a, because prior (unpublished) data showed that Capan-1 was inhibited by IFN-α. The striking enhancement observed with the addition of IFN-α spurred further investigation, leading to the current studies. The results of studies with T cell redirecting bispecific antibodies, in combination with peginterferonalfa-2a are reported herein. The studies were extended until all groups reached their MST, confirming that IFN-α can enhance the in-vivo efficacy of T-cell killing of an IFN-α-sensitive cell line. IFN-α also can enhance T-cell-mediated killing of a cell line that is weakly sensitive to the direct actions of IFN-α. These in vivo studies were performed following methods, including dosing and schedules, typically used with BiTE constructs.

Flieger and colleagues demonstrated that in-vitro killing by $CD3^+CD56^+$ NK-T cells, which were expanded ex vivo and redirected with an EpCAM×CD3 BiTE (MT110), was enhanced with either IFN-α or IL-2 (Flieger et al., 2000, Cancer Immunol Immunother 49:441-8). However, even in the absence of the bsAb, IFN-α significantly inhibited the target cells. Since a control to evaluate potential direct effects of IFN-α on target cells was lacking, the extent to which the enhanced cytotoxicity was due to IFN-α stimulating NK-T cells, compared to direct inhibition of target cells, could not be determined. Therefore, we measured the sensitivity to IFN-α for both target cells and included groups with peginterferonalfa-2a only, both in the presence and absence of pan-T cells. For Capan-1 tumors, which were more sensitive to IFN-α in vitro, peginterferonalfa-2a improved survival in the absence of T cells, and even more so in the presence of T cells, indicating that IFN-α acted on both Capan-1 as well as T cells in this model. In the absence of T cells, peginterferonalfa-2a did not improve survival of mice bearing NCI-N87 xenografts, which were weakly sensitive to IFN-α in vitro, indicating that the enhancement with IFN-α was due primarily to its actions on T cells. The mechanism of the observed T-cell enhancement by IFN-α is unclear. The increase in CD69 expression attributed to IFN-α was moderate, but significant, suggesting that the cytokine may potentiate T-cell activation induced with the bsAb. Additionally, IFN-α specifically increased (up to 3-fold) the release of IFN-γ, which is considered the chief cytotoxic cytokine produced by cytotoxic T cells, whereas none of the other cytokines measured increased consistently.

Combination therapy with IFN-α and a T-cell-redirecting bsAb has not been investigated clinically, or even in animal models. However, IL-2 was combined with a $F(ab')_2$ fragment of an anti-CD3/EpCAM quadroma in a clinical trial (Kroesen et al., 1997, Cancer Immunol Immunother 45:203-6), but treatment was limited due to considerable toxicity most likely caused by induction of secondary cytokines, known as CRS or cytokine storm. Systemic administration of IL-2 is known to induce a cytokine storm (Panelli et al., 2004, J Transl Med 2:17), and the severity of adverse events associated with CRS, such as with the TGN1412 catastrophic trial, are correlated with IL-2 release (Eastwood et al., 2013, Br J Clin Pharmacol 76:299-315). Although it is not without side effects, immunotherapy with IFN-α, which is not produced by T cells, is not typically associated with cytokine storm.

CRS is a risk associated with immunotherapy using any T-cell directed mAb (e.g., Okt3) or bsAb, including BiTE (Klinger et al., 2012, Blood 119:6226-33). However, not all bsAb formats necessarily have the same risk. Brandl et al. reported cytokine induction with blinatumomab, where response levels of IL-2, IL-6, IFN-γ, and TNF-α were variable among donors and typically peaked at >1 ng/mL, with some donors reaching levels as high as 5 ng/mL (Brandl et al., 2007, Cancer Immunol Immunother 56:1551-63). We lacked a suitable BiTE, or equivalent construct, for direct comparison with (E1)-3s. However, we were able to compare the relative cytokine-inducing potency between the (X)-3s and BiTE formats, using a CD19×CD3 BiTE (identical sequence as blinatumomab) and (19)-3s made by DNL®. The 19-3 BiTE induced similar cytokine levels as reported by Brandl and colleagues under similar conditions. The levels of the five cytokines measured were 7-13-fold higher for 19-3 BiTE, compared to those of (19)-3s. The use of foreign lymphoma cells (Raji) caused a mixed lymphocyte reaction, which increased the baseline cytokine levels, particularly for IL-2. BiTE, but not (19)-3s, increased the cytokine levels well above the mixed lymphocyte baseline level. Using NCI-N87 gastric carcinoma cells as the target for (E1)-3s did not increase baseline cytokine levels. We observed an expected variability in donor response to (E1)-3s; however, the resulting cytokine levels were even lower than those induced by (19)-3s, particularly for TNF-α and IFN-γ, which were <100 pg/mL. Nevertheless, one of five donors had elevated levels (~1 ng/mL) of IFN-γ and IL-6. Addition of IFN-α (peginterferonalfa-2a) to (E1)-3s increased IFN-γ 2-3-fold, but did not consistently affect the levels of the other cytokines. These results suggest that compared to other constructs, such as BiTE, the (X)-3s bsAb format is less likely to induce CRS, and the addition of IFN-α to a therapeutic regimen does not increase this risk.

We observed considerable variability in the potency of donor T cells. The in vitro results shown in FIG. 28 represent the most and least active T cells that we have tested, with a 100-fold difference in potency ($IC_{50}$=0.37 pM vs. 39 pM) for killing NCI-N87; however, an $IC_{50}$=1-5 pM is most representative (>10 donors) and the low-activity T cells was atypical. Notably, lysis with the weaker T cells was augmented by IFN-α more than with the potent T cells.

EpCAM is a widely exploited TAA that is overexpressed in many carcinomas. However, the heterogeneous expression of EpCAM in carcinomas and the fact that EpCAM is not tumor-specific, since it is expressed on most normal epithelia, raise concerns that immunotherapy directed towards EpCAM could have severe side effects (Balzar et al., 1999, J Mol Med (Berl) 77:699-712; Momburg et al., 1987, Cancer Res 47:2883-91). Like EpCAM, Trop-2 is highly expressed in diverse carcinomas, but its expression in normal tissues is under debate. Several reports indicate that, in contrast to tumor cells, somatic adult tissues show little or no Trop-2 expression, which is invariably upregulated in tumors, regardless of baseline expression in normal tissues (Wang et al., 2008, Mol Cancer Ther 7:280-5; Zhang et al., 1997, Science 276:1268-72). However, recent evidence indicates expression of Trop-2 on epithelia of several normal tissues (Trerotola et al., 2013, Oncogene 32:222-33). Nonetheless, expression of Trop-2 in Cynomolgus monkeys did not result in toxicities after administrations of reasonably high doses of hRS7 (humanized anti-Trop-2) conjugated with SN-38 as an antibody-drug conjugate (ADC) (Cardillo et al., 2011, Clin Cancer Res 17:3157-69). Further, in clinical studies with this anti-Trop-2 ADC, no increased normal organ toxicity other than manageable neutropenia and diarrhea, expected from the drug (a metabolite of irinotecan), was observed at therapeutic doses (Starodub et al., Proceedings of the 105th Annual Meeting of the American Association for Cancer Research. 2014 (abstr CT206)). Thus, immunotherapy, including T-cell-redirected therapy, using Trop-2 for tumor targeting, is expected to have a similar, or greater, therapeutic index compared to similar regimens targeting EpCAM.

This is the first report of trogocytosis between target tumor and T cells mediated by a bsAb. This finding demonstrates that the target/T-cell conjugates induced with (E1)-3s have functional immunologic synapses. We observed a similar bi-directional trogocytosis between B cells and T cells, which was mediated by (19)-3s (unpublished data), and believe this is likely a common phenomenon with T-cell redirecting bsAbs.

Example 27

Further Studies with E1-3 Bispecific Antibodies

Summary

A T-cell redirecting bispecific tandem scFv, E1-3, was produced as described in Example 19 above, using the variable domains of hRS7 (humanized anti-Trop-2 mAb) and Okt-3 (anti-CD3 mAb). The studies reported in this Example continue and expand on the results shown in Examples 20-25. Any discrepancies between the instant reported results and those shown in Examples 20-25 are based on the collection of additional data. T-cell activation, proliferation, cytokine induction and cytotoxicity were evaluated ex vivo using PBMCs or purified T cells with human pancreatic (Capan-1 and BxPC-3) and gastric (NCI-N87) cancer cell lines as target cells. In vivo activity was assayed with NCI-N87 xenografts that were inoculated s.c. in a mixture with twice the number of human PBMCs and matrigel.

Results

In the presence of target cells and PBMCs, E1-3 potently induced T-cell activation, proliferation and a dose-dependent cytokine production of IL-2 (>2 ng/mL), IL-6 (>1 ng/mL), IL-10 (>7 ng/mL), TNF-α (>1 ng/mL) and IFN-γ (>50 ng/mL). Using 3-5 different T cell donors, E1-3 mediated a highly potent T-cell lysis of BxPC-3 [$IC_{50}$=0.09(±0.04) pM], Capan-1 [$IC_{50}$=1.2(±1.1) pM] and NCI-N87 [$IC_{50}$=1.2 (±1.2) pM] target cells in vitro. In vivo, two 50-μg doses of E1-3 given three days apart cured 6 of 8 mice bearing NCI-N87 xenografts (P<0.0001; Log-Rank). Tumors in the control group (PBMCs only) reached the endpoint (TV>1 cm³) with a median of 39.5 days. Seven of 8 animals had not reached the endpoint, with six of the mice remaining tumor-free in the E1-3 group when the experiment was terminated after 176 days.

T-Cell Activation and Proliferation—

Purified CD8⁺ T cells were mixed 5:1 with NCI-N87 cells, treated for 18 h with 0.01 nM E1-3 and analyzed by flow cytometry. CD69 was upregulated by E1-3 in the presence of target cells (not shown). Treatments with omission of E1-3 or NCI-N87 target cells did not induce CD69 expression (not shown). Additionally, T cells experienced an increase in forward (FSC) and side scattering (SSC) after culture in the presence of E1-3 and target cells (not shown). T-cell proliferation was evident after three days (P<0.005, data not shown).

Cytokine Release—

Figure 31:
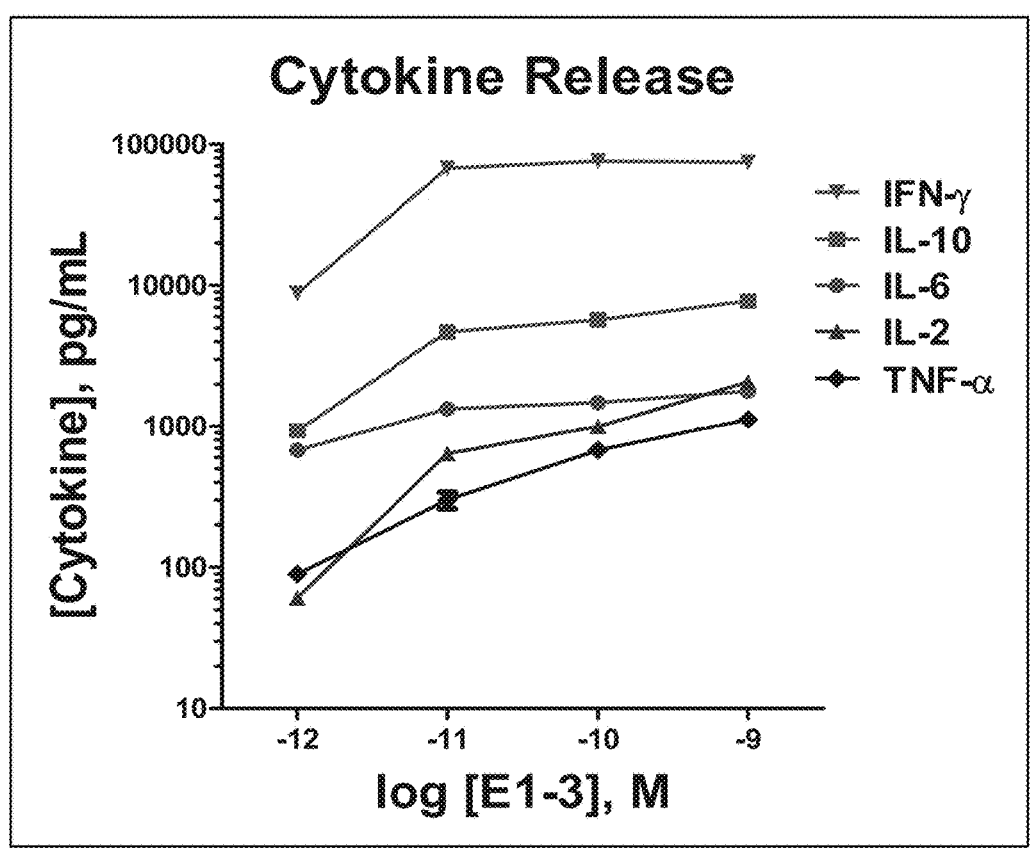
FIG. 31. Cytokine production induced by E1-3. PBMCs were combined at a 5:1 ratio with BxPC-3 cells and treated with a titration of E1-3 for 24 h. Cytokine concentrations were measured using Single-Analyte ELISArray kits (Qiagen). All cytokine levels were <10 pg/mL in the absence of E1-3.

The ability of E1-3 bispecific tandem scFv to induce release of cytokines IFN-γ, TNF-α, IL-2, IL-6 and IL-10 as a function of dosage was determined. As shown in FIG. 31, the E1-3 bispecific antibody effectively induced cytokine release in the picomolar concentration range.

In Vitro T-Cell Mediated Killing—

Figure 32:
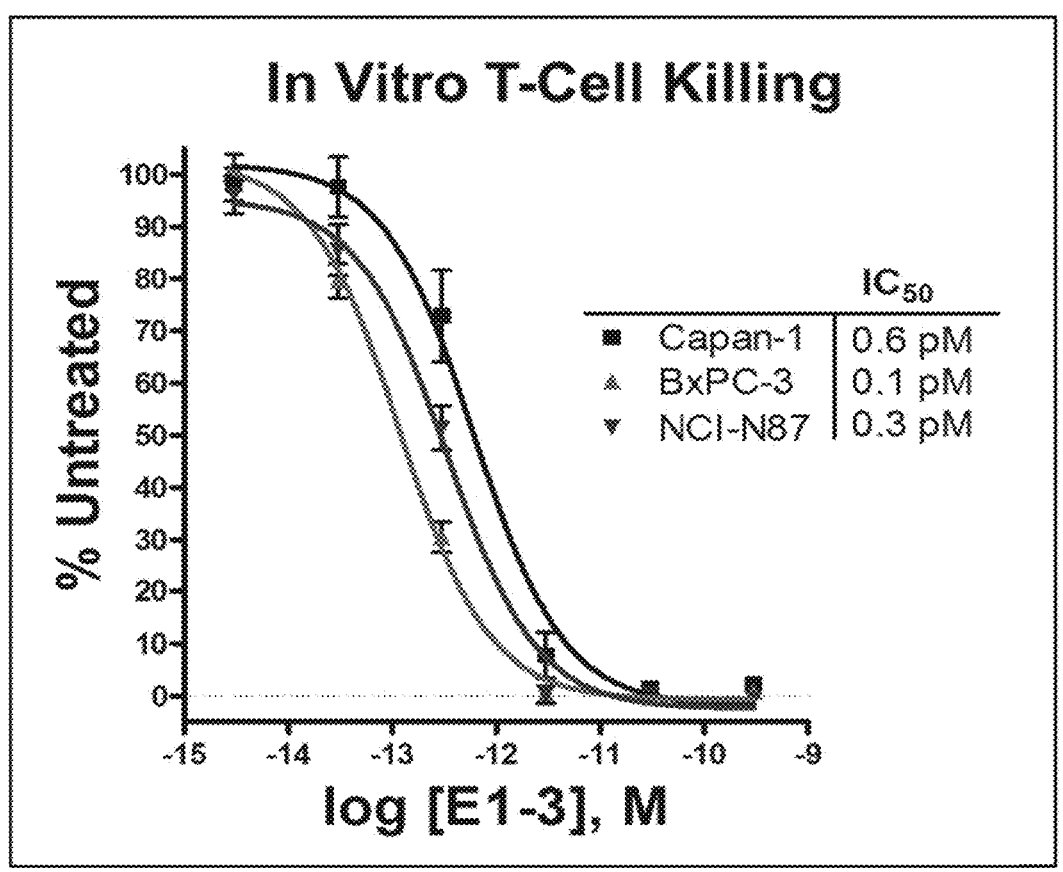
FIG. 32. In vitro redirected T cell killing of pancreatic and gastric cancer cell lines. Purified CD8$^+$ T cells ($1.2 \times 10^5$/well) were mixed 6:1 with target cells ($2 \times 10^4$/well) and treated with titrations of E1-3 in a 96-well plate. After 48 h, wells were washed to remove T cells and the viable target cell densities were determined with an MTS assay. Example of results for one of several T cell donors.

The ability of E1-3 to induce T-cell mediated killing of target pancreatic and gastric cancer cells was determined in the presence of purified CD8⁺ T cells ($1.2 \times 10^5$/well). An exemplary dose-response curve using T-cells from a representative donor are shown in FIG. 32. In this experiment, the $IC_{50}$ values for E1-3 were 0.6 pM for Capan-1, 0.1 pM for BxPC-3 and 0.3 pM for NCI-N87.

In Vivo Anti-Tumor Effects of E1-3—

Figure 33A:
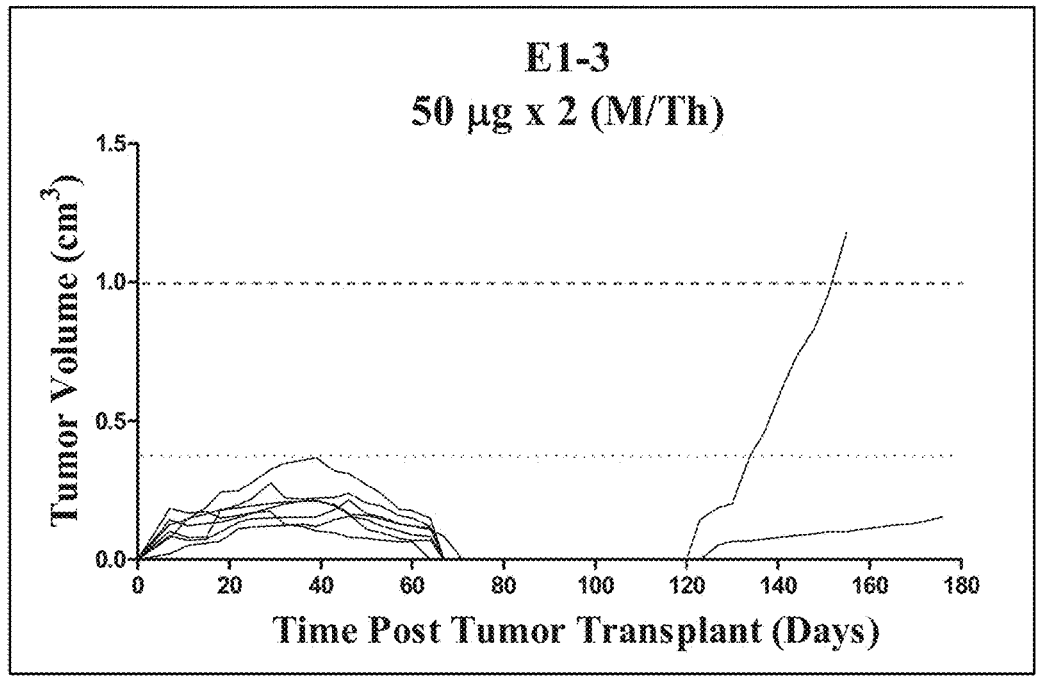
FIG. 33A. In vivo therapy of human gastric tumor xenografts. PBMCs were mixed 2:1 with NCI-N87 cells and injected s.c. with matrigel in NOD-SCID mice. Animals were given 50 µg E1-3 i.v. on Days 0 and 3. Mice were monitored daily for signs of tumor out-growth, after which tumors were measured twice weekly with an endpoint measurement of >1.0 cm$^3$. After 176 days, 7 of 8 mice in the E1-3 treatment group had not reached the endpoint with 6 animals remaining tumor free.
Figure 33B:
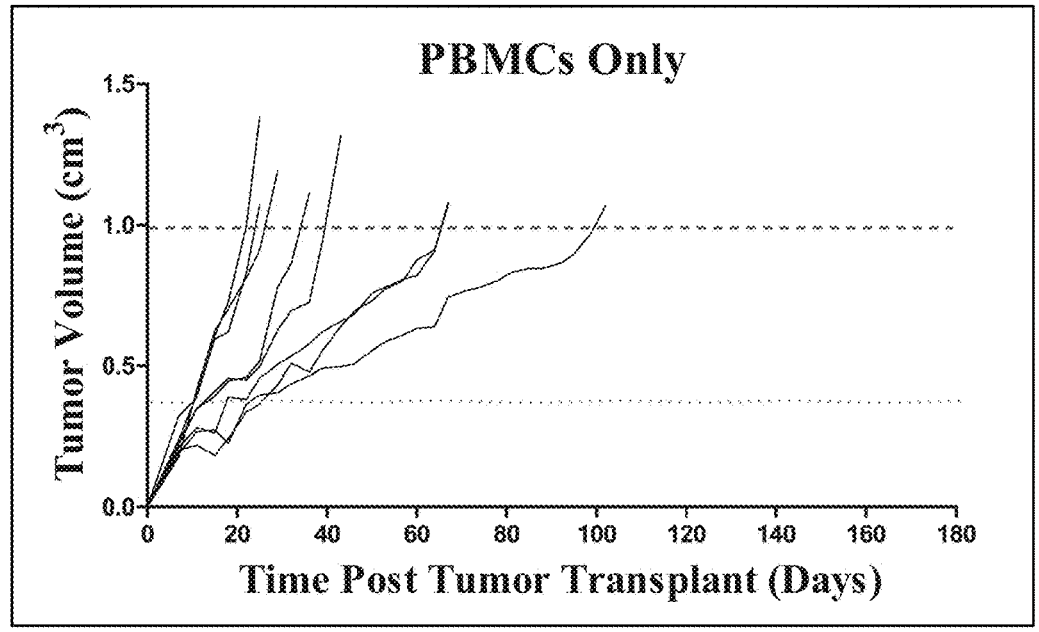
FIG. 33B. In vivo therapy of human gastric tumor xenografts. PBMCs were mixed 2:1 with NCI-N87 cells and injected s.c. with matrigel in NOD-SCID mice. Animals were given 50 µg E1-3 i.v. on Days 0 and 3. Mice were monitored daily for signs of tumor out-growth, after which tumors were measured twice weekly with an endpoint measurement of >1.0 cm$^3$. Tumors in the control group comprising only PBMCs and NCI-87 reached the end point with a median time of 39.5 days.

Nude mice bearing NCI-N87 xenografts were treated with two 50-μg doses of E1-3 given three days apart. The treatment (FIG. 33A) cured 6 of 8 mice bearing the human gastric cancer xenografts (P<0.0001; Log-Rank). In comparison with tumors in the control group (treated with PBMCs only) reached the endpoint (TV>1 cm³) with a median of 39.5 days (FIG. 33B). When the study was terminated after 176 days, seven of eight animals in the E1-3 group had not reached the endpoint.

Conclusions

The studies above show that Trop-2 is an attractive target for T-cell-mediated killing of pancreatic, gastric and other epithelial cancers. The E1-3 anti-Trop-2×anti-CD3 bispecific antibody induced potent T-cell activation and cytokine production. E1-3 was highly effective at killing solid tumors in vitro and in vivo.

All of the COMPOSITIONS and METHODS disclosed and claimed herein can be made and used without undue experimentation in light of the present disclosure. While the compositions and methods have been described in terms of preferred embodiments, it is apparent to those of skill in the art that variations maybe applied to the COMPOSITIONS and METHODS and in the steps or in the sequence of steps of the METHODS described herein without departing from the concept, spirit and scope of the invention. More specifically, certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of inducing an immune response to a Trop-2 expressing cancer comprising:
   a) administering to a subject with a Trop-2 expressing cancer a bispecific antibody that comprises (i) at least one anti-Trop-2 antibody or antigen-binding fragment thereof and one anti-CD3 antibody or antigen-binding fragment thereof, wherein the at least one anti-Trop-2 antibody or fragment thereof binds to the same epitope as an anti-Trop-2 antibody comprising the light chain CDR sequences CDR1 (KASQDVSIAVA, SEQ ID NO:115); CDR2 (SASYRYT, SEQ ID NO:116); and CDR3 (QQHYITPLT, SEQ ID NO:117) and the heavy chain CDR sequences CDR1 (NYGMN, SEQ ID NO:118); CDR2 (WINTYTGEPTYTDDFKG, SEQ ID NO:119) and CDR3 (GGFGSSYWYFDV, SEQ ID NO:120); and
   b) administering to the subject at least one therapeutic agent selected from the group consisting of (i) interferon α; and (ii) a checkpoint inhibitor antibody.

2. The method of claim 1, wherein the checkpoint inhibitor antibody is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirilumab, IPH2101 and tremelimumab.

3. The method of claim 1, wherein the checkpoint inhibitor antibody binds to an antigen selected from the group consisting of CTLA4, PD1, PD-L1, LAG3, B7-H3, B7-H4, KIR and TIM3.

4. The method of claim 1, wherein the bispecific antibody and the therapeutic agent are administered simultaneously.

5. The method of claim 1, wherein the interferon-α is administered as free interferon, PEGylated interferon, an interferon fusion protein or interferon conjugated to an antibody.

6. The method of claim 1, wherein the bispecific antibody comprises at least one antibody fragment selected from the group consisting of a scFv, a Fab and a dAb.

7. The method of claim 1, wherein the Trop-2 expressing cancer is a carcinoma of the esophagus, pancreas, lung, stomach, colon, rectum, urinary bladder, breast, ovary, uterus, kidney or prostate.

8. The method of claim 1, further comprising administering to the subject an anti-cancer agent selected from the group consisting of a second antibody or antigen-binding fragment thereof, a drug, a toxin, an enzyme, an anti-angiogenic agent, a pro-apoptotic agent, an antibiotic, a hormone, an immunomodulator, a cytokine, a boron compound and a radioisotope.

9. The method of claim 1, wherein the bispecific antibody comprises a humanized RS7 (anti-Trop-2) antibody or antigen-binding fragment thereof.

10. The method of claim 1, wherein the bispecific antibody comprises an Okt3 (anti-CD3) antibody or antigen-binding fragment thereof.

11. The method of claim 1, wherein the bispecific antibody comprises the amino acid sequence of SEQ ID NO:107.

12. The method of claim 1, wherein the bispecific antibody induces an immune response to a Trop-2 expressing cancer without increasing cytokine production to levels capable of inducing cytokine release syndrome (CRS).

13. The method of claim 1, wherein the bispecific antibody induces trogocytosis of cell surface antigens between Trop-2 expressing cancer cells and T cells.

14. The method of claim 1, wherein the bispecific antibody and the therapeutic agent are administered sequentially.

* * * * *